(12) United States Patent
Lindquist et al.

(10) Patent No.: US 11,047,848 B2
(45) Date of Patent: Jun. 29, 2021

(54) CELLULAR DISCOVERY PLATFORM FOR NEURODEGENERATIVE DISEASES

(71) Applicant: Whitehead Institute for Biomedical Research, Cambridge, MA (US)

(72) Inventors: Susan L. Lindquist, Cambridge, MA (US); Vikram Khurana, Cambridge, MA (US); Chee-Yeun Chung, Cambridge, MA (US)

(73) Assignee: Whitehead Institute for Biomedical Research, Cambridge, MA (US)

(*) Notice: Subject to any disclaimer, the term of this patent is extended or adjusted under 35 U.S.C. 154(b) by 0 days.

(21) Appl. No.: 14/777,013

(22) PCT Filed: Mar. 17, 2014

(86) PCT No.: PCT/US2014/030838
§ 371 (c)(1),
(2) Date: Sep. 15, 2015

(87) PCT Pub. No.: WO2014/145975
PCT Pub. Date: Sep. 18, 2014

(65) Prior Publication Data
US 2016/0041149 A1 Feb. 11, 2016
US 2017/0153226 A9 Jun. 1, 2017

Related U.S. Application Data

(60) Provisional application No. 61/895,274, filed on Oct. 24, 2013, provisional application No. 61/857,648, filed on Jul. 23, 2013, provisional application No. 61/794,870, filed on Mar. 15, 2013.

(51) Int. Cl.
*G01N 33/50* (2006.01)
*G01N 33/68* (2006.01)
*C12Q 1/6883* (2018.01)

(52) U.S. Cl.
CPC ....... *G01N 33/5058* (2013.01); *C12Q 1/6883* (2013.01); *G01N 33/6896* (2013.01); *C12Q 2600/136* (2013.01); *C12Q 2600/156* (2013.01); *G01N 2500/10* (2013.01)

(58) Field of Classification Search
CPC .......... G01N 33/5058; G01N 33/6896; G01N 2500/10; C12Q 2600/136
See application file for complete search history.

(56) References Cited

U.S. PATENT DOCUMENTS

| | | |
|---|---|---|
| 5,843,780 A | 12/1998 | Thomson |
| 6,200,806 B1 | 3/2001 | Thomson |
| 7,029,913 B2 | 4/2006 | Thomson |
| 7,045,290 B2 | 5/2006 | Lindquist et al. |
| 2004/0115774 A1 | 6/2004 | Kochendoerfer et al. |
| 2005/0255450 A1 | 11/2005 | Muchowski et al. |
| 2008/0261953 A1 | 10/2008 | Lindquist et al. |
| 2009/0010894 A1 | 1/2009 | Langston |
| 2009/0099069 A1 | 4/2009 | Lindquist et al. |
| 2009/0186407 A1 | 7/2009 | Mitalipova et al. |
| 2009/0227032 A1 | 9/2009 | Yamanaka et al. |
| 2009/0304664 A1 | 12/2009 | Lindquist et al. |
| 2010/0021437 A1 | 1/2010 | Isacson et al. |
| 2010/0273776 A1 | 10/2010 | Lindquist et al. |
| 2010/0310525 A1 | 12/2010 | Chevalier et al. |
| 2011/0027235 A1 | 2/2011 | Gregory et al. |
| 2011/0053857 A1 | 3/2011 | Lindquist et al. |
| 2011/0064722 A1 | 3/2011 | Lindquist et al. |
| 2011/0076678 A1 | 3/2011 | Jaenisch et al. |
| 2011/0088107 A1 | 4/2011 | Hanna et al. |
| 2011/0300533 A1 | 12/2011 | Lindquist et al. |
| 2012/0192301 A1 | 7/2012 | Jaenisch et al. |
| 2012/0237499 A1 | 9/2012 | Gitler et al. |
| 2013/0022988 A1 | 1/2013 | Matlack et al. |
| 2013/0045483 A1 | 2/2013 | Treusch et al. |

FOREIGN PATENT DOCUMENTS

| | | |
|---|---|---|
| JP | 2004-537973 A | 12/2004 |
| WO | WO 1993/001275 A1 | 1/1993 |
| WO | WO 2010/042669 A2 | 4/2010 |
| WO | WO 2011/097036 A1 | 8/2011 |
| WO | WO 2011/130624 A2 | 10/2011 |
| WO | WO 2011/142832 A2 | 11/2011 |
| WO | WO 2012/112737 A2 | 8/2012 |
| WO | WO 2012/117245 A1 | 9/2012 |

OTHER PUBLICATIONS

An et al., Introduction: cell-based assays for high-throughput screening. Methods Mol Biol. 2009;486:1-12. doi: 10.1007/978-1-60327-545-3_1.

Byers et al., SNCA triplication Parkinson's patient's iPSC-derived DA neurons accumulate α-synuclein and are susceptible to oxidative stress. PLoS One. 2011;6(11):e26159. doi: 10.1371/journal.pone.0026159. Epub Nov. 16, 2011.

Carey et al., Reprogramming of murine and human somatic cells using a single polycistronic vector. Proc Natl Acad Sci U S A. Jan. 6, 2009;106(1):157-62. doi: 10.1073/pnas.0811426106. Epub Dec. 24, 2008. Erratum in: Proc Natl Acad Sci U S A. Mar. 31, 2009;106(13):5449. Proc Natl Acad Sci U S A. Jul. 14, 2009;106(28):11818.

Chambers et al., Highly efficient neural conversion of human ES and iPS cells by dual inhibition of SMAD signaling. Nat Biotechnol. Mar. 2009;27(3):275-80. doi: 10.1038/nbt.1529. Epub Mar. 1, 2009.

Colla et al., Endoplasmic reticulum stress is important for the manifestations of α-synucleinopathy in vivo. J Neurosci. Mar. 7, 2012;32(10):3306-20. doi:10.1523/JNEUROSCI.5367-11.2012.

Cooper et al., Alpha-synuclein blocks ER-Golgi traffic and Rab1 rescues neuron loss in Parkinson's models. Science. Jul. 21, 2006;313(5785):324-8. Epub Jun. 22, 2006.

(Continued)

*Primary Examiner* — Gregory S Emch

(74) *Attorney, Agent, or Firm* — Wolf, Greenfield & Sacks, P.C.

(57) ABSTRACT

In some aspects, a cross-species platform useful for drug discovery in neurodegenerative diseases is described.

20 Claims, 36 Drawing Sheets

Specification includes a Sequence Listing.

(56) References Cited

OTHER PUBLICATIONS

Cooper et al., Pharmacological rescue of mitochondrial deficits in iPSC-derived neural cells from patients with familial Parkinson's disease. Sci Transl Med. Jul. 4, 2012;4(141):141ra90. doi:10.1126/scitranslmed.3003985.
Dimos et al., Induced pluripotent stem cells generated from patients with ALS can be differentiated into motor neurons. Science. Aug. 29, 2008;321(5893):1218-21. doi:10.1126/science.1158799. Epub Jul. 31, 2008.
Egawa et al., Drug screening for ALS using patient-specific induced pluripotent stem cells. Sci Transl Med. Aug. 1, 2012;4(145):145ra104. doi:10.1126/scitranslmed.3004052.
Gafni et al., Derivation of novel human ground state naive pluripotent stem cells. Nature. Dec. 12, 2013;504(7479):282-6. doi: 10.1038/nature12745. Epub Oct. 30, 2013.
Hermjakob et al., IntAct: an open source molecular interaction database. Nucleic Acids Res. Jan. 1, 2004;32(Database issue):D452-5.
Hockemeyer et al., A drug-inducible system for direct reprogramming of human somatic cells to pluripotency. Cell Stem Cell. Sep. 11, 2008;3(3):346-53. doi: 10.1016/j.stem.2008.08.014.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Israel et al., Probing sporadic and familial Alzheimer's disease using induced pluripotent stem cells. Nature. Jan. 25, 2012;482(7384):216-20. doi:10.1038/nature10821.
Ju et al., A yeast model of FUS/TLS-dependent cytotoxicity. PLoS Biol. Apr. 2011;9(4):e1001052. doi:10.1371/journal.pbio.1001052. Epub Apr. 26, 2011.
Khurana et al., Modelling neurodegeneration in *Saccharomyces cerevisiae*: why cook with baker's yeast? Nat Rev Neurosci. Jun. 2010;11(6):436-49. doi: 10.1038/nrn2809. Epub Apr. 28, 2010.
Kim et al., Investigating synapse formation and function using human pluripotent stem cell-derived neurons. Proc Natl Acad Sci USA. Feb. 15, 2011;108(7):3005-10. doi: 10.1073/pnas.1007753108. Epub Jan. 28, 2011.
Li et al., A kinase inhibitor screen identifies small-molecule enhancers of reprogramming and iPS cell generation. Nat Commun. 2012;3:1085. doi:10.1038/ncomms2059.
Li et al., Identification of Oct4-activating compounds that enhance reprogramming efficiency. Proc Natl Acad Sci U S A. Dec. 18, 2012;109(51):20853-8. doi: 10.1073/pnas.1219181110. Epub Dec. 3, 2012.
Lyssiotis et al., Reprogramming of murine fibroblasts to induced pluripotent stem cells with chemical complementation of Klf4. Proc Natl Acad Sci U S A. Jun. 2, 2009;106(22):8912-7. doi: 10.1073/pnas.0903860106. Epub May 15, 2009.
Maekawa et al., Direct reprogramming of somatic cells is promoted by maternal transcription factor Glis1. Nature. Jun. 8, 2011;474(7350):225-9. doi: 10.1038/nature10106.
Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Mitalipova et al., Human embryonic stem cell lines derived from discarded embryos. Stem Cells. 2003;21(5):521-6.
Nguyen et al., LRRK2 mutant iPSC-derived DA neurons demonstrate increased susceptibility to oxidative stress. Cell Stem Cell. Mar. 4, 2011;8(3):267-80. doi: 10.1016/j.stem.2011.01.013.
Obokata et al., Bidirectional developmental potential in reprogrammed cells with acquired pluripotency. Nature. Jan. 30, 2014;505(7485):676-80. doi: 10.1038/nature12969. Retraction in: Obokata et al., Nature. Jul. 3, 2014;511(7507):112.
Obokata et al., Stimulus-triggered fate conversion of somatic cells into pluripotency. Nature. Jan. 30, 2014;505(7485):641-7. doi: 10.1038/nature12968. Retraction in: Obokata H, Wakayama T, Sasai Y, Kojima K, Vacanti MP, Niwa H,Yamato M, Vacanti CA. Nature. Jul. 3, 2014;511(7507):112.
Outeiro et al., Yeast cells provide insight into alpha-synuclein biology and pathobiology. Science. Dec. 5, 2003;302(5651):1772-5.
Ring et al., Direct reprogramming of mouse and human fibroblasts into multipotent neural stem cells with a single factor. Cell Stem Cell. Jul. 6, 2012;11(1):100-9. doi: 10.1016/j.stem.2012.05.018. Epub Jun. 7, 2012.
Shi et al., Directed differentiation of human pluripotent stem cells to cerebral cortex neurons and neural networks. Nat Protoc. Oct. 2012;7(10):1836-46. doi: 10.1038/nprot.2012.116. Epub Sep. 13, 2012.
Soldner et al., Parkinson's disease patient-derived induced pluripotent stem cells free of viral reprogramming factors. Cell. Mar. 6, 2009;136(5):964-77. doi: 10.1016/j.cell.2009.02.013.
Stadtfeld et al., Induced pluripotency: history, mechanisms, and applications. Genes Dev. Oct. 15, 2010;24(20):2239-63. doi: 10.1101/gad.1963910.
Su et al., Compounds from an unbiased chemical screen reverse both ER-to-Golgi trafficking defects and mitochondrial dysfunction in Parkinson's disease models. Dis Model Mech. Mar.-Apr. 2010;3(3-4):194-208. doi: 10.1242/dmm.004267. Epub Dec. 28, 2009.
Sundstrom et al., Organotypic cultures as tools for functional screening in the CNS. Drug Discov Today. Jul. 15, 2005;10(14):993-1000.
Tardiff et al., Yeast reveal a "druggable" Rsp5/Nedd4 network that ameliorates α-synuclein toxicity in neurons. Science. Nov. 22, 2013;342(6161):979-83. doi:10.1126/science.1245321. Epub Oct. 24, 2013.
Treusch et al., Functional links between Aβ toxicity, endocytic trafficking, and Alzheimer's disease risk factors in yeast. Science. Dec. 2, 2011;334(6060):1241-5. doi: 10.1126/science.1213210. Epub Oct. 27, 2011.
Warren et al., Highly efficient reprogramming to pluripotency and directed differentiation of human cells with synthetic modified mRNA. Cell Stem Cell. Nov. 5, 2010;7(5):618-30. doi: 10.1016/j.stem.2010.08.012. Epub Sep. 30, 2010.
Zhang et al., Rapid single-step induction of functional neurons from human pluripotent stem cells. Neuron. Jun. 5, 2013;78(5):785-98. doi: 10.1016/j.neuron.2013.05.029.
Chamberlain et al., Induced pluripotent stem (iPS) cells as in vitro models of human neurogenetic disorders. Neurogenetics. Oct. 2008;9(4):227-35. doi: 10.1007/s10048-008-0147-z.
Lee et al., Open innovation for phenotypic drug discovery: The PD2 assay panel. J Biomol Screen. Jul. 2011;16(6):588-602. doi: 10.1177/1087057111405379.
Park et al., Disease-specific induced pluripotent stem cells. Cell. Sep. 5, 2008;134(5):877-86. doi: 10.1016/j.cell.2008.07.041.
Tardiff et al., Phenotypic screens for compounds that target the cellular pathologies underlying Parkinson's disease. Drug Discov Today Technol. 2013 Spring;10(1):e121-8. doi: 10.1016/j.ddtec.2012.02.003.
Kritzer et al., Rapid selection of cyclic peptides that reduce alpha-synuclein toxicity in yeast and animal models. Nat Chem Biol. Sep. 2009;5(9):655-63. doi: 10.1038/nchembio.193. Epub Jul. 13, 2009.
Floto et al., Small molecule enhancers of rapamycin-induced TOR inhibition promote autophagy, reduce toxicity in Huntington's disease models and enhance killing of mycobacteria by macrophages. Autophagy. Nov.-Dec. 2007;3(6):620-2. Epub Aug. 16, 2007.
Sarkar et al., Small molecules enhance autophagy and reduce toxicity in Huntington's disease models. Nat Chem Biol. Jun. 2007;3(6):331-8. Epub May 7, 2007. Author Manuscript.
Scott et al., Production of cyclic peptides and proteins in vivo. Proc Natl Acad Sci U S A. Nov. 23, 1999;96(24):13638-43. doi: 10.1073/pnas.96.24.13638.

Deletion of Vps35 enhances toxicity

Mutant hVps35 does not restore viability like the WT gene

SEQUENCE LISTING

<160> NUMBER OF SEQ ID NOS: 14

<210> SEQ ID NO 1

```
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 414
<212> TYPE: PRT
<213> ORGANISM: Homo sapiens

<400> SEQUENCE: 2

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205
```

-continued

```
Glu Phe Phe Ser Gln Tyr Gly Asp Val Met Asp Val Phe Ile Pro Lys
    210                 215                 220
Pro Phe Arg Ala Phe Ala Phe Val Thr Phe Ala Asp Asp Gln Ile Ala
225                 230                 235                 240
Gln Ser Leu Cys Gly Glu Asp Leu Ile Ile Lys Gly Ile Ser Val His
                245                 250                 255
Ile Ser Asn Ala Glu Pro Lys His Asn Ser Asn Arg Gln Leu Glu Arg
            260                 265                 270
Ser Gly Arg Phe Gly Gly Asn Pro Gly Gly Phe Gly Asn Gln Gly Gly
        275                 280                 285
Phe Gly Asn Ser Arg Gly Gly Gly Ala Gly Leu Gly Asn Asn Gln Gly
    290                 295                 300
Ser Asn Met Gly Gly Gly Met Asn Phe Gly Ala Phe Ser Ile Asn Pro
305                 310                 315                 320
Ala Met Met Ala Ala Ala Gln Ala Ala Leu Gln Ser Ser Trp Gly Met
                325                 330                 335
Met Gly Met Leu Ala Ser Gln Asn Gln Ser Gly Pro Ser Gly Asn
            340                 345                 350
Asn Gln Asn Gln Gly Asn Met Gln Arg Glu Pro Asn Gln Ala Phe Gly
        355                 360                 365
Ser Gly Asn Asn Ser Tyr Ser Gly Ser Asn Ser Gly Ala Ala Ile Gly
    370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met
                405                 410

<210> SEQ ID NO 3
<211> LENGTH: 526
<212> TYPE: PRT
<213> ORGANISM: Homo sapiens

<400> SEQUENCE: 3

Met Ala Ser Asn Asp Tyr Thr Gln Gln Ala Thr Gln Ser Tyr Gly Ala
1               5                   10                  15
Tyr Pro Thr Gln Pro Gly Gln Gly Tyr Ser Gln Gln Ser Ser Gln Pro
            20                  25                  30
Tyr Gly Gln Gln Ser Tyr Ser Gly Tyr Ser Gln Ser Thr Asp Thr Ser
        35                  40                  45
Gly Tyr Gly Gln Ser Ser Tyr Ser Ser Tyr Gly Gln Ser Gln Asn Thr
    50                  55                  60
Gly Tyr Gly Thr Gln Ser Thr Pro Gln Gly Tyr Gly Ser Thr Gly Gly
65                  70                  75                  80
Tyr Gly Ser Ser Gln Ser Ser Gln Ser Ser Tyr Gly Gln Gln Ser Ser
                85                  90                  95
Tyr Pro Gly Tyr Gly Gln Gln Pro Ala Pro Ser Ser Thr Ser Gly Ser
            100                 105                 110
Tyr Gly Ser Ser Ser Gln Ser Ser Tyr Gly Gln Pro Gln Ser Gly
        115                 120                 125
Ser Tyr Ser Gln Gln Pro Ser Tyr Gly Gly Gln Gln Ser Tyr Gly
        130                 135                 140
Gln Gln Gln Ser Tyr Asn Pro Pro Gln Gly Tyr Gly Gln Gln Asn Gln
145                 150                 155                 160
Tyr Asn Ser Ser Ser Gly Gly Gly Gly Gly Gly Gly Gly Gly Gly Asn
```

```
                    165                 170                 175
Tyr Gly Gln Asp Gln Ser Ser Met Ser Ser Gly Gly Ser Gly Gly
            180                 185                 190
Gly Tyr Gly Asn Gln Asp Gln Ser Gly Gly Gly Ser Gly Gly Tyr
            195                 200                 205
Gly Gln Gln Asp Arg Gly Gly Arg Gly Arg Gly Ser Gly Gly Gly
            210                 215                 220
Gly Gly Gly Gly Gly Gly Tyr Asn Arg Ser Ser Gly Gly Tyr Glu
225                 230                 235                 240
Pro Arg Gly Arg Gly Gly Gly Arg Gly Gly Arg Gly Met Gly Gly
            245                 250                 255
Ser Asp Arg Gly Gly Phe Asn Lys Phe Gly Gly Pro Arg Asp Gln Gly
            260                 265                 270
Ser Arg His Asp Ser Glu Gln Asp Asn Ser Asp Asn Asn Thr Ile Phe
            275                 280                 285
Val Gln Gly Leu Gly Glu Asn Val Thr Ile Glu Ser Val Ala Asp Tyr
            290                 295                 300
Phe Lys Gln Ile Gly Ile Ile Lys Thr Asn Lys Lys Thr Gly Gln Pro
305                 310                 315                 320
Met Ile Asn Leu Tyr Thr Asp Arg Glu Thr Gly Lys Leu Lys Gly Glu
            325                 330                 335
Ala Thr Val Ser Phe Asp Asp Pro Pro Ser Ala Lys Ala Ala Ile Asp
            340                 345                 350
Trp Phe Asp Gly Lys Glu Phe Ser Gly Asn Pro Ile Lys Val Ser Phe
            355                 360                 365
Ala Thr Arg Arg Ala Asp Phe Asn Arg Gly Gly Gly Asn Gly Arg Gly
            370                 375                 380
Gly Arg Gly Arg Gly Gly Pro Met Gly Arg Gly Gly Tyr Gly Gly Gly
385                 390                 395                 400
Gly Ser Gly Gly Gly Gly Arg Gly Gly Phe Pro Ser Gly Gly Gly
            405                 410                 415
Gly Gly Gly Gln Gln Arg Ala Gly Asp Trp Lys Cys Pro Asn Pro Thr
            420                 425                 430
Cys Glu Asn Met Asn Phe Ser Trp Arg Asn Glu Cys Asn Gln Cys Lys
            435                 440                 445
Ala Pro Lys Pro Asp Gly Pro Gly Gly Pro Gly Gly Ser His Met
            450                 455                 460
Gly Gly Asn Tyr Gly Asp Asp Arg Arg Gly Gly Arg Gly Gly Tyr Asp
465                 470                 475                 480
Arg Gly Gly Tyr Arg Gly Arg Gly Gly Asp Arg Gly Gly Phe Arg Gly
            485                 490                 495
Gly Arg Gly Gly Gly Asp Arg Gly Gly Phe Gly Pro Gly Lys Met Asp
            500                 505                 510
Ser Arg Gly Glu His Arg Gln Asp Arg Arg Glu Arg Pro Tyr
            515                 520                 525

<210> SEQ ID NO 4
<211> LENGTH: 43
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                  10                  15
```

```
Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40
```

<210> SEQ ID NO 5
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 5

```
Met Phe Phe Asn Arg Leu Ser Ala Gly Lys Leu Leu Val Pro Leu Ser
1               5                   10                  15

Val Val Leu Tyr Ala Leu Phe Val Ile Leu Pro Leu Gln Asn Ser
            20                  25                  30

Phe His Ser Ser Asn Val Leu Val Arg Gly Asp Ala Glu Phe Arg His
            35                  40                  45

Asp Ser Gly Tyr Glu Val His His Gln Lys Leu Val Phe Phe Ala Glu
        50                  55                  60

Asp Val Gly Ser Asn Lys Gly Ala Ile Ile Gly Leu Met Val Gly Gly
65                  70                  75                  80

Val Val Ile Ala
```

<210> SEQ ID NO 6
<211> LENGTH: 2527
<212> TYPE: PRT
<213> ORGANISM: Homo sapiens

<400> SEQUENCE: 6

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
            35                  40                  45

Glu His Ala Ser Lys Leu Phe Gln Gly Lys Asn Ile His Val Pro Leu
        50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
            115                 120                 125

Val Asn Leu Ser Val Ile Gly Leu Lys Thr Leu Asp Leu Leu Leu Thr
        130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
            195                 200                 205
```

-continued

Leu Ser Ala Leu Thr Asn Phe Lys Asp Glu Glu Ile Val Leu His
            210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
            245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
            275                 280                 285

Asn Glu Val His Glu Phe Val Val Lys Ala Val Gln Gln Tyr Pro Glu
            290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
            325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
            355                 360                 365

Ala Ala Cys Trp Ala Leu Asn Asn Leu Leu Met Tyr Gln Asn Ser Leu
            370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
            405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
            435                 440                 445

Met Gln Lys His Ile His Ser Pro Glu Val Ala Glu Ser Gly Cys Lys
            450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
            485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
            515                 520                 525

Lys Leu Asn Met Val Lys Lys Gln Cys Phe Lys Asn Asp Ile His Lys
530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
            565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
            595                 600                 605

Leu Ile Gly Tyr Leu Ile Thr Lys Lys Asn Val Phe Ile Gly Thr Gly
610                 615                 620

His Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
            645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
            675                 680                 685

Gln Gln Phe Leu Asn Leu Cys Cys Lys Cys Phe Ala Lys Val Ala Met
690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
            725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Asn Ser Gly Ser Arg Glu
            755                 760                 765

Gln Asp Val Arg Lys Ala Leu Thr Ile Ser Ile Gly Lys Gly Asp Ser
770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
            805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
            835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
            885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
            965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu Ser Gln Lys Cys Cys Ile Ser Val
            995                 1000                1005

His Leu Glu His Leu Glu Lys Leu Glu Leu His Gln Asn Ala Leu
        1010                1015                1020

Thr Ser Phe Pro Gln Gln Leu Cys Glu Thr Leu Lys Ser Leu Thr
        1025                1030                1035

His Leu Asp Leu His Ser Asn Lys Phe Thr Ser Phe Pro Ser Tyr

-continued

```
                1040                1045                1050
Leu Leu Lys Met Ser Cys Ile Ala Asn Leu Asp Val Ser Arg Asn
        1055                1060                1065

Asp Ile Gly Pro Ser Val Val Leu Asp Pro Thr Val Lys Cys Pro
        1070                1075                1080

Thr Leu Lys Gln Phe Asn Leu Ser Tyr Asn Gln Leu Ser Phe Val
        1085                1090                1095

Pro Glu Asn Leu Thr Asp Val Val Glu Lys Leu Glu Gln Leu Ile
        1100                1105                1110

Leu Glu Gly Asn Lys Ile Ser Gly Ile Cys Ser Pro Leu Arg Leu
        1115                1120                1125

Lys Glu Leu Lys Ile Leu Asn Leu Ser Lys Asn His Ile Ser Ser
        1130                1135                1140

Leu Ser Glu Asn Phe Leu Glu Ala Cys Pro Lys Val Glu Ser Phe
        1145                1150                1155

Ser Ala Arg Met Asn Phe Leu Ala Ala Met Pro Phe Leu Pro Pro
        1160                1165                1170

Ser Met Thr Ile Leu Lys Leu Ser Gln Asn Lys Phe Ser Cys Ile
        1175                1180                1185

Pro Glu Ala Ile Leu Asn Leu Pro His Leu Arg Ser Leu Asp Met
        1190                1195                1200

Ser Ser Asn Asp Ile Gln Tyr Leu Pro Gly Pro Ala His Trp Lys
        1205                1210                1215

Ser Leu Asn Leu Arg Glu Leu Leu Phe Ser His Asn Gln Ile Ser
        1220                1225                1230

Ile Leu Asp Leu Ser Glu Lys Ala Tyr Leu Trp Ser Arg Val Glu
        1235                1240                1245

Lys Leu His Leu Ser His Asn Lys Leu Lys Glu Ile Pro Pro Glu
        1250                1255                1260

Ile Gly Cys Leu Glu Asn Leu Thr Ser Leu Asp Val Ser Tyr Asn
        1265                1270                1275

Leu Glu Leu Arg Ser Phe Pro Asn Glu Met Gly Lys Leu Ser Lys
        1280                1285                1290

Ile Trp Asp Leu Pro Leu Asp Glu Leu His Leu Asn Phe Asp Phe
        1295                1300                1305

Lys His Ile Gly Cys Lys Ala Lys Asp Ile Ile Arg Phe Leu Gln
        1310                1315                1320

Gln Arg Leu Lys Lys Ala Val Pro Tyr Asn Arg Met Lys Leu Met
        1325                1330                1335

Ile Val Gly Asn Thr Gly Ser Gly Lys Thr Thr Leu Leu Gln Gln
        1340                1345                1350

Leu Met Lys Thr Lys Lys Ser Asp Leu Gly Met Gln Ser Ala Thr
        1355                1360                1365

Val Gly Ile Asp Val Lys Asp Trp Pro Ile Gln Ile Arg Asp Lys
        1370                1375                1380

Arg Lys Arg Asp Leu Val Leu Asn Val Trp Asp Phe Ala Gly Arg
        1385                1390                1395

Glu Glu Phe Tyr Ser Thr His Pro His Phe Met Thr Gln Arg Ala
        1400                1405                1410

Leu Tyr Leu Ala Val Tyr Asp Leu Ser Lys Gly Gln Ala Glu Val
        1415                1420                1425

Asp Ala Met Lys Pro Trp Leu Phe Asn Ile Lys Ala Arg Ala Ser
        1430                1435                1440
```

```
Ser Ser Pro Val Ile Leu Val Gly Thr His Leu Asp Val Ser Asp
1445                1450                1455

Glu Lys Gln Arg Lys Ala Cys Met Ser Lys Ile Thr Lys Glu Leu
1460                1465                1470

Leu Asn Lys Arg Gly Phe Pro Ala Ile Arg Asp Tyr His Phe Val
1475                1480                1485

Asn Ala Thr Glu Glu Ser Asp Ala Leu Ala Lys Leu Arg Lys Thr
1490                1495                1500

Ile Ile Asn Glu Ser Leu Asn Phe Lys Ile Arg Asp Gln Leu Val
1505                1510                1515

Val Gly Gln Leu Ile Pro Asp Cys Tyr Val Glu Leu Glu Lys Ile
1520                1525                1530

Ile Leu Ser Glu Arg Lys Asn Val Pro Ile Glu Phe Pro Val Ile
1535                1540                1545

Asp Arg Lys Arg Leu Leu Gln Leu Val Arg Glu Asn Gln Leu Gln
1550                1555                1560

Leu Asp Glu Asn Glu Leu Pro His Ala Val His Phe Leu Asn Glu
1565                1570                1575

Ser Gly Val Leu Leu His Phe Gln Asp Pro Ala Leu Gln Leu Ser
1580                1585                1590

Asp Leu Tyr Phe Val Glu Pro Lys Trp Leu Cys Lys Ile Met Ala
1595                1600                1605

Gln Ile Leu Thr Val Lys Val Glu Gly Cys Pro Lys His Pro Lys
1610                1615                1620

Gly Ile Ile Ser Arg Arg Asp Val Glu Lys Phe Leu Ser Lys Lys
1625                1630                1635

Arg Lys Phe Pro Lys Asn Tyr Met Ser Gln Tyr Phe Lys Leu Leu
1640                1645                1650

Glu Lys Phe Gln Ile Ala Leu Pro Ile Gly Glu Tyr Leu Leu
1655                1660                1665

Val Pro Ser Ser Leu Ser Asp His Arg Pro Val Ile Glu Leu Pro
1670                1675                1680

His Cys Glu Asn Ser Glu Ile Ile Ile Arg Leu Tyr Glu Met Pro
1685                1690                1695

Tyr Phe Pro Met Gly Phe Trp Ser Arg Leu Ile Asn Arg Leu Leu
1700                1705                1710

Glu Ile Ser Pro Tyr Met Leu Ser Gly Arg Glu Arg Ala Leu Arg
1715                1720                1725

Pro Asn Arg Met Tyr Trp Arg Gln Gly Ile Tyr Leu Asn Trp Ser
1730                1735                1740

Pro Glu Ala Tyr Cys Leu Val Gly Ser Glu Val Leu Asp Asn His
1745                1750                1755

Pro Glu Ser Phe Leu Lys Ile Thr Val Pro Ser Cys Arg Lys Gly
1760                1765                1770

Cys Ile Leu Leu Gly Gln Val Val Asp His Ile Asp Ser Leu Met
1775                1780                1785

Glu Glu Trp Phe Pro Gly Leu Leu Glu Ile Asp Ile Cys Gly Glu
1790                1795                1800

Gly Glu Thr Leu Leu Lys Lys Trp Ala Leu Tyr Ser Phe Asn Asp
1805                1810                1815

Gly Glu Glu His Gln Lys Ile Leu Leu Asp Asp Leu Met Lys Lys
1820                1825                1830
```

```
Ala Glu Gly Asp Leu Leu Val Asn Pro Asp Gln Pro Arg Leu
    1835                1840                1845

Thr Ile Pro Ile Ser Gln Ile Ala Pro Asp Leu Ile Leu Ala Asp
    1850                1855                1860

Leu Pro Arg Asn Ile Met Leu Asn Asn Asp Glu Leu Glu Phe Glu
    1865                1870                1875

Gln Ala Pro Glu Phe Leu Leu Gly Asp Gly Ser Phe Gly Ser Val
    1880                1885                1890

Tyr Arg Ala Ala Tyr Glu Gly Glu Glu Val Ala Val Lys Ile Phe
    1895                1900                1905

Asn Lys His Thr Ser Leu Arg Leu Leu Arg Gln Glu Leu Val Val
    1910                1915                1920

Leu Cys His Leu His His Pro Ser Leu Ile Ser Leu Leu Ala Ala
    1925                1930                1935

Gly Ile Arg Pro Arg Met Leu Val Met Glu Leu Ala Ser Lys Gly
    1940                1945                1950

Ser Leu Asp Arg Leu Leu Gln Gln Asp Lys Ala Ser Leu Thr Arg
    1955                1960                1965

Thr Leu Gln His Arg Ile Ala Leu His Val Ala Asp Gly Leu Arg
    1970                1975                1980

Tyr Leu His Ser Ala Met Ile Ile Tyr Arg Asp Leu Lys Pro His
    1985                1990                1995

Asn Val Leu Leu Phe Thr Leu Tyr Pro Asn Ala Ala Ile Ile Ala
    2000                2005                2010

Lys Ile Ala Asp Tyr Gly Ile Ala Gln Tyr Cys Cys Arg Met Gly
    2015                2020                2025

Ile Lys Thr Ser Glu Gly Thr Pro Gly Phe Arg Ala Pro Glu Val
    2030                2035                2040

Ala Arg Gly Asn Val Ile Tyr Asn Gln Gln Ala Asp Val Tyr Ser
    2045                2050                2055

Phe Gly Leu Leu Leu Tyr Asp Ile Leu Thr Thr Gly Gly Arg Ile
    2060                2065                2070

Val Glu Gly Leu Lys Phe Pro Asn Glu Phe Asp Glu Leu Glu Ile
    2075                2080                2085

Gln Gly Lys Leu Pro Asp Pro Val Lys Glu Tyr Gly Cys Ala Pro
    2090                2095                2100

Trp Pro Met Val Glu Lys Leu Ile Lys Gln Cys Leu Lys Glu Asn
    2105                2110                2115

Pro Gln Glu Arg Pro Thr Ser Ala Gln Val Phe Asp Ile Leu Asn
    2120                2125                2130

Ser Ala Glu Leu Val Cys Leu Thr Arg Arg Ile Leu Leu Pro Lys
    2135                2140                2145

Asn Val Ile Val Glu Cys Met Val Ala Thr His His Asn Ser Arg
    2150                2155                2160

Asn Ala Ser Ile Trp Leu Gly Cys Gly His Thr Asp Arg Gly Gln
    2165                2170                2175

Leu Ser Phe Leu Asp Leu Asn Thr Glu Gly Tyr Thr Ser Glu Glu
    2180                2185                2190

Val Ala Asp Ser Arg Ile Leu Cys Leu Ala Leu Val His Leu Pro
    2195                2200                2205

Val Glu Lys Glu Ser Trp Ile Val Ser Gly Thr Gln Ser Gly Thr
    2210                2215                2220

Leu Leu Val Ile Asn Thr Glu Asp Gly Lys Lys Arg His Thr Leu
```

```
                  2225                2230                2235

Glu Lys Met Thr Asp Ser Val Thr Cys Leu Tyr Cys Asn Ser Phe
        2240                2245                2250

Ser Lys Gln Ser Lys Gln Lys Asn Phe Leu Leu Val Gly Thr Ala
    2255                2260                2265

Asp Gly Lys Leu Ala Ile Phe Glu Asp Lys Thr Val Lys Leu Lys
        2270                2275                2280

Gly Ala Ala Pro Leu Lys Ile Leu Asn Ile Gly Asn Val Ser Thr
    2285                2290                2295

Pro Leu Met Cys Leu Ser Glu Ser Thr Asn Ser Thr Glu Arg Asn
        2300                2305                2310

Val Met Trp Gly Gly Cys Gly Thr Lys Ile Phe Ser Phe Ser Asn
    2315                2320                2325

Asp Phe Thr Ile Gln Lys Leu Ile Glu Thr Arg Thr Ser Gln Leu
        2330                2335                2340

Phe Ser Tyr Ala Ala Phe Ser Asp Ser Asn Ile Ile Thr Val Val
    2345                2350                2355

Val Asp Thr Ala Leu Tyr Ile Ala Lys Gln Asn Ser Pro Val Val
        2360                2365                2370

Glu Val Trp Asp Lys Lys Thr Glu Lys Leu Cys Gly Leu Ile Asp
    2375                2380                2385

Cys Val His Phe Leu Arg Glu Val Met Val Lys Glu Asn Lys Glu
        2390                2395                2400

Ser Lys His Lys Met Ser Tyr Ser Gly Arg Val Lys Thr Leu Cys
    2405                2410                2415

Leu Gln Lys Asn Thr Ala Leu Trp Ile Gly Thr Gly Gly Gly His
        2420                2425                2430

Ile Leu Leu Leu Asp Leu Ser Thr Arg Arg Leu Ile Arg Val Ile
    2435                2440                2445

Tyr Asn Phe Cys Asn Ser Val Arg Val Met Met Thr Ala Gln Leu
        2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
        2480                2485                2490

Thr Val Trp Asp Ile Asn Leu Pro His Glu Val Gln Asn Leu Glu
    2495                2500                2505

Lys His Ile Glu Val Arg Lys Glu Leu Ala Glu Lys Met Arg Arg
        2510                2515                2520

Thr Ser Val Glu
    2525

<210> SEQ ID NO 7
<211> LENGTH: 796
<212> TYPE: PRT
<213> ORGANISM: Homo sapiens

<400> SEQUENCE: 7

Met Pro Thr Thr Gln Gln Ser Pro Gln Asp Glu Gln Glu Lys Leu Leu
1               5                   10                  15

Asp Glu Ala Ile Gln Ala Val Lys Val Gln Ser Phe Gln Met Lys Arg
            20                  25                  30

Cys Leu Asp Lys Asn Lys Leu Met Asp Ala Leu Lys His Ala Ser Asn
        35                  40                  45
```

-continued

```
Met Leu Gly Glu Leu Arg Thr Ser Met Leu Ser Pro Lys Ser Tyr Tyr
     50                  55                  60
Glu Leu Tyr Met Ala Ile Ser Asp Glu Leu His Tyr Leu Glu Val Tyr
 65                  70                  75                  80
Leu Thr Asp Glu Phe Ala Lys Gly Arg Lys Val Ala Asp Leu Tyr Glu
                 85                  90                  95
Leu Val Gln Tyr Ala Gly Asn Ile Ile Pro Arg Leu Tyr Leu Leu Ile
                100                 105                 110
Thr Val Gly Val Val Tyr Val Lys Ser Phe Pro Gln Ser Arg Lys Asp
                115                 120                 125
Ile Leu Lys Asp Leu Val Glu Met Cys Arg Gly Val Gln His Pro Leu
    130                 135                 140
Arg Gly Leu Phe Leu Arg Asn Tyr Leu Leu Gln Cys Thr Arg Asn Ile
145                 150                 155                 160
Leu Pro Asp Glu Gly Glu Pro Thr Asp Glu Thr Thr Gly Asp Ile
                165                 170                 175
Ser Asp Ser Met Asp Phe Val Leu Leu Asn Phe Ala Glu Met Asn Lys
                180                 185                 190
Leu Trp Val Arg Met Gln His Gln Gly His Ser Arg Asp Arg Glu Lys
                195                 200                 205
Arg Glu Arg Glu Arg Gln Glu Leu Arg Ile Leu Val Gly Thr Asn Leu
    210                 215                 220
Val Arg Leu Ser Gln Leu Glu Gly Val Asn Val Glu Arg Tyr Lys Gln
225                 230                 235                 240
Ile Val Leu Thr Gly Ile Leu Glu Gln Val Val Asn Cys Arg Asp Ala
                245                 250                 255
Leu Ala Gln Glu Tyr Leu Met Glu Cys Ile Ile Gln Val Phe Pro Asp
                260                 265                 270
Glu Phe His Leu Gln Thr Leu Asn Pro Phe Leu Arg Ala Cys Ala Glu
                275                 280                 285
Leu His Gln Asn Val Asn Val Lys Asn Ile Ile Ala Leu Ile Asp
    290                 295                 300
Arg Leu Ala Leu Phe Ala His Arg Glu Asp Gly Pro Gly Ile Pro Ala
305                 310                 315                 320
Asp Ile Lys Leu Phe Asp Ile Phe Ser Gln Gln Val Ala Thr Val Ile
                325                 330                 335
Gln Ser Arg Gln Asp Met Pro Ser Glu Asp Val Val Ser Leu Gln Val
                340                 345                 350
Ser Leu Ile Asn Leu Ala Met Lys Cys Tyr Pro Asp Arg Val Asp Tyr
                355                 360                 365
Val Asp Lys Val Leu Glu Thr Thr Val Glu Ile Phe Asn Lys Leu Asn
    370                 375                 380
Leu Glu His Ile Ala Thr Ser Ser Ala Val Ser Lys Glu Leu Thr Arg
385                 390                 395                 400
Leu Leu Lys Ile Pro Val Asp Thr Tyr Asn Asn Ile Leu Thr Val Leu
                405                 410                 415
Lys Leu Lys His Phe His Pro Leu Phe Glu Tyr Phe Asp Tyr Glu Ser
                420                 425                 430
Arg Lys Ser Met Ser Cys Tyr Val Leu Ser Asn Val Leu Asp Tyr Asn
                435                 440                 445
Thr Glu Ile Val Ser Gln Asp Gln Val Asp Ser Ile Met Asn Leu Val
    450                 455                 460
Ser Thr Leu Ile Gln Asp Gln Pro Asp Gln Pro Val Glu Asp Pro Asp
```

```
                    465                 470                 475                 480
Pro Glu Asp Phe Ala Asp Glu Gln Ser Leu Val Gly Arg Phe Ile His
                    485                 490                 495
Leu Leu Arg Ser Glu Asp Pro Asp Gln Gln Tyr Leu Ile Leu Asn Thr
                500                 505                 510
Ala Arg Lys His Phe Gly Ala Gly Asn Gln Arg Ile Arg Phe Thr
            515                 520                 525
Leu Pro Pro Leu Val Phe Ala Ala Tyr Gln Leu Ala Phe Arg Tyr Lys
530                 535                 540
Glu Asn Ser Lys Val Asp Asp Lys Trp Glu Lys Lys Cys Gln Lys Ile
545                 550                 555                 560
Phe Ser Phe Ala His Gln Thr Ile Ser Ala Leu Ile Lys Ala Glu Leu
                565                 570                 575
Ala Glu Leu Pro Leu Arg Leu Phe Leu Gln Gly Ala Leu Ala Ala Gly
            580                 585                 590
Glu Ile Gly Phe Glu Asn His Glu Thr Val Ala Tyr Glu Phe Met Ser
        595                 600                 605
Gln Ala Phe Ser Leu Tyr Glu Asp Glu Ile Ser Asp Ser Lys Ala Gln
        610                 615                 620
Leu Ala Ala Ile Thr Leu Ile Ile Gly Thr Phe Glu Arg Met Lys Cys
625                 630                 635                 640
Phe Ser Glu Glu Asn His Glu Pro Leu Arg Thr Gln Cys Ala Leu Ala
                645                 650                 655
Ala Ser Lys Leu Leu Lys Lys Pro Asp Gln Gly Arg Ala Val Ser Thr
            660                 665                 670
Cys Ala His Leu Phe Trp Ser Gly Arg Asn Thr Asp Lys Asn Gly Glu
        675                 680                 685
Glu Leu His Gly Gly Lys Arg Val Met Glu Cys Leu Lys Lys Ala Leu
        690                 695                 700
Lys Ile Ala Asn Gln Cys Met Asp Pro Ser Leu Gln Val Gln Leu Phe
705                 710                 715                 720
Ile Glu Ile Leu Asn Arg Tyr Ile Tyr Phe Tyr Glu Lys Glu Asn Asp
                725                 730                 735
Ala Val Thr Ile Gln Val Leu Asn Gln Leu Ile Gln Lys Ile Arg Glu
            740                 745                 750
Asp Leu Pro Asn Leu Glu Ser Ser Glu Glu Thr Glu Gln Ile Asn Lys
        755                 760                 765
His Phe His Asn Thr Leu Glu His Leu Arg Leu Arg Arg Glu Ser Pro
    770                 775                 780
Glu Ser Glu Gly Pro Ile Tyr Glu Gly Leu Ile Leu
785                 790                 795

<210> SEQ ID NO 8
<211> LENGTH: 536
<212> TYPE: PRT
<213> ORGANISM: Homo sapiens

<400> SEQUENCE: 8

Met Glu Phe Ser Ser Pro Ser Arg Glu Glu Cys Pro Lys Pro Leu Ser
1               5                   10                  15
Arg Val Ser Ile Met Ala Gly Ser Leu Thr Gly Leu Leu Leu Leu Gln
                20                  25                  30
Ala Val Ser Trp Ala Ser Gly Ala Arg Pro Cys Ile Pro Lys Ser Phe
            35                  40                  45
```

```
Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
            115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
            195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
450                 455                 460

Phe Ile Pro Glu Gly Ser Gln Arg Val Gly Leu Val Ala Ser Gln Lys
```

```
                465                 470                 475                 480
Asn Asp Leu Asp Ala Val Ala Leu Met His Pro Asp Gly Ser Ala Val
                    485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
    530                 535
```

<210> SEQ ID NO 9
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 9
tgtcccctcc accccacagt ggggccacta gggacaggat tggtgacaga aaagc        55

<210> SEQ ID NO 10
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 10
gcttttctgt caccaatcct gtccctagtg gccccactgt ggggtggagg ggaca        55

<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

His His His His His His
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 12

Gln Gly Ser Tyr
1

<210> SEQ ID NO 13
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 13
gctaatcagc aatttaaggc tag                                           23

<210> SEQ ID NO 14
<211> LENGTH: 22

```
<212> TYPE: DNA
<213> ORGANISM: Artificial Sequence
<220> FEATURE:
<223> OTHER INFORMATION: Synthetic Polynucleotide

<400> SEQUENCE: 14
gatatgttct tagaatgctc ag                                          22
```

CELLULAR DISCOVERY PLATFORM FOR NEURODEGENERATIVE DISEASES

RELATED APPLICATIONS

The present application is a national stage filing under 35 U.S.C. § 371 of international PCT application, PCT/US2014/030838, filed Mar. 17, 2014, which claims priority under 35 U.S.C. § 119(e) to U.S. provisional patent applications, U.S. Ser. No. 61/794,870, filed Mar. 15, 2013, U.S. Ser. No. 61/857,648, filed Jul. 23, 2013, and U.S. Ser. No. 61/895,274, filed Oct. 24, 2013, each of which is incorporated herein by reference.

BACKGROUND

Neurodegenerative diseases encompass a variety of disorders that involve progressive loss of structure and/or function of neurons in affected regions of the nervous system, often accompanied by neuronal loss. Many of the neurodegenerative diseases that affect the brain can lead to dementia, a devastating condition in which the loss of cognitive abilities detrimentally affects daily living and social functioning. There are more than 35 million people with dementia worldwide, and this number is predicted to double within 20 years.

Major causes of dementia include Parkinson's disease, Alzheimer's disease, and frontotemporal lobar degeneration. These and a number of other neurodegenerative diseases are characterized by accumulation in the nervous system of particular polypeptides that misfold and associate, leading to formation of aggregates that can be detected as intracellular or extracellular inclusions or deposits on histopathological examination of nervous system tissue using suitable techniques such as optical microscopy with appropriate stains and/or immunohistochemical detection using antibodies that bind to proteins present in the aggregates.

Parkinson's disease is pathologically characterized by the presence of cytoplasmic Lewy bodies, major components of which are filaments composed of the neuronal protein alpha-synuclein, in neurons within the brain. Alpha-synuclein aggregates have been associated with several neurological diseases. A number of dominant point mutations in alpha-synuclein that cause familial early onset Parkinson's disease have been described. Duplication and triplication of the alpha-synuclein gene, leading to overproduction of alpha-synuclein, have also been linked to familial early-onset Parkinson's disease. In vitro studies have demonstrated that recombinant alpha-synuclein can form Lewy body-like fibrils that recapitulate the ultrastructural features of alpha-synuclein aggregates isolated from patients with Parkinson's disease. Certain Parkinson's disease-linked alpha-synuclein mutations have been shown to accelerate the aggregation process. Parkinson's disease is clinically characterized by bradykinesia, rigidity, resting tremor, and postural rigidity, a constellation of symptoms commonly referred to as "parkinsonism". Patients frequently develop cognitive impairment and depression as the disease progresses. Most motor symptoms can be attributed to the degeneration of dopaminergic neurons within the substantia nigra pars compacta, a key regulatory nucleus of the basal ganglia circuitry. However, several other nondopaminergic neuronal populations may also degenerate, including various autonomic nuclei and the locus ceruleus as well as glutamatergic neurons throughout the cerebral cortex.

Alzheimer's disease is a neurodegenerative disorder characterized by neurofibrillary tangles and plaques containing an amyloid beta peptide. Patients with Alzheimer's disease exhibit progressive dementia, which may manifest with impairment in memory and cognitive abilities. Proteolytic cleavage of the amyloid precursor protein (APP) results in the generation of an amyloid beta peptide ranging typically from 38 to 43 amino acids long. The amyloid beta 1-42 peptide is particularly prone to self-aggregation and is strongly linked to development of Alzheimer's disease, the most common cause of dementia.

Frontotemporal dementia results from degeneration of the cortex of the frontal and temporal lobes, often in conjunction with the degeneration of subcortical brain regions. Frontotemporal lobar degeneration (FTLD) is the pathological term corresponding to this clinical syndrome. TDP-43 (TAR DNA-Binding Protein 43) was identified as a protein that binds to human immunodeficiency virus type 1 TAR DNA sequence motifs and represses transcription of viral RNA. Hyperphosphorylated, ubiquitinated, C-terminal fragments of TDP-43 have been recovered from the central nervous systems of patients with FTLD with ubiquitin-positive inclusions. TDP-43-containing inclusions are also found in central nervous system in a subgroup of patients with amyotrophic lateral sclerosis, a disease characterized by degeneration of motor neurons and, in some cases, also frontotemporal lobar degeneration.

There is an urgent need for effective therapies for neurodegenerative diseases, such as those associated with protein aggregation. There is a particular need for disease-modifying therapies, e.g., therapies effective in modifying the course of neurodegenerative diseases, such as those associated with protein aggregation.

SUMMARY

In some aspects, the invention provides compositions and methods useful for drug discovery for neurodegenerative diseases. In some aspects, the invention provides compositions and methods useful for drug discovery for neurodegenerative diseases characterized by protein misfolding and/or dysfunction. In some embodiments the disease is characterized by abnormal accumulation of a protein, e.g., protein aggregation or a gain-of-function mutation that results in detrimental effects in neurons or glial cells. In some embodiments the disease is characterized by a loss-of-function mutation that results in detrimental effects in neurons or glial cells. In some aspects, the invention makes use of the tractability of yeast in combination with the disease-relevance of neurons derived from human subjects. In some aspects, the yeast express a neurodegeneration associated protein that induces toxicity in yeast. In some embodiments the neurodegeneration associated protein comprises an alpha-synuclein, Abeta, TDP-43, FUS, or polyglutamine expanded protein. In some aspects, the yeast have a loss of function of a yeast homolog of a human gene characterized in that loss-of-function mutations in the human gene cause a neurodegenative disease. In some embodiments the yeast, in addition to expressing a neurodegeneration associated protein or having a loss of function of a yeast homolog of a human gene characterized in that loss-of-function mutations in the human gene cause a neurodegenative disease, also overexpress or have a mutation or deletion or otherwise disabled yeast homolog of a human genetic modifier of the neurodegenerative disease. In some embodiments of any aspect the human neurons are induced neurons. In some embodiments of any aspect the neurons are derived from pluripotent human cells, e.g., human induced pluripotent stem (iPS) cells or human embryonic stem (ES)

cels. In some embodiments of any aspect the neurons are derived from human subjects suffering from a neurodegenerative disease, e.g., a neurodegenerative disease associated with protein misfolding and/or aggregation or associated with a loss-of-function mutation. In some embodiments of any aspect the neurons are derived from a human subject who has a familial form of the disease. In some embodiments of any aspect the neurons are derived from a human subject who has a sporadic form of the disease. In some embodiments of any aspect the neurons are derived from a human subject who does not or is not known to have a mutation associated with a familial form of the disease, e.g., a form with a dominant or recessive inheritance pattern. In some embodiments of any aspect the disease is a synucleinopathy, Alzheimer's disease, a TDP-43 proteinopathy, a FUS-opathy, or a polyglutamine expansion disease. In some embodiments of any aspect the disease is characterized by parkinsonism.

In some aspects, described herein is a method of identifying a candidate therapeutic agent for treatment of a neurodegenerative disease comprising: (a) contacting a human neuron that has a genotype associated with the neurodegenerative disease with an agent that reduces toxicity of a neurodegeneration associated protein associated with the disease in a yeast cell that expresses the neurodegeneration associated protein; (b) measuring the level of a phenotype associated with the disease in the neuron; and (c) identifying the agent as a candidate therapeutic agent for treatment of the neurodegenerative disease if the level of the phenotype is reduced as compared with the level of the phenotype in the absence of the agent. In some embodiments the neurodegeneration associated protein comprises an alpha-synuclein protein, TDP-43 protein, FUS protein, A-beta protein, or polyglutamine-expanded protein. In some embodiments the neurodegenerative disease is a synucleinopathy, TDP-43 proteinopathy, FUS-opathy, Alzheimer's disease, or a polyglutamine expansion disease. In some embodiments the neuron is not engineered to have an extra copy of a gene encoding the neurodegeneration associated protein and has not been derived or cultured in the presence of an agent that enhances the phenotype (phenotype enhancer). In some embodiments the phenotype is detectable in the yeast cell in the absence of the agent. In some embodiments the phenotype is detectable in a neuron derived from an iPS cell derived from a human subject who has the disease, wherein the neuron is not engineered to have an extra copy of a gene encoding the neurodegeneration associated protein and has not been derived or cultured in the presence of an agent that enhances the phenotype. In some embodiments the neurodegeneration associated protein comprises an alpha-synuclein protein and the phenotype comprises nitrosative stress, mitochondrial dysfunction, defective endoplasmic reticulum-associated degradation (ERAD), or impaired ER-to-Golgi trafficking. In some embodiments the neurodegeneration associated protein comprises an Abeta protein and the phenotype comprises a defect in endocytosis. In some embodiments the neurodegeneration associated protein comprises a TDP-43 protein and the phenotype comprises an increase in stress granule formation or a defect in endocytosis. In some embodiments the neuron is derived from a human subject who has the neurodegenerative disease. In some embodiments the neuron is derived from an iPS cell or ES cell. In some embodiments the neuron is derived from a subject who has a mutation in or at least one extra copy of a gene that encodes the neurodegeneration associated protein. In some embodiments the neuron is derived from an iPS cell derived from a human subject who has the neurodegenerative disease. In some embodiments the neuron is derived from an iPS cell derived from a human subject who has a mutation in or at least one extra copy of a gene that encodes the neurodegeneration associated protein. In some embodiments the neuron is derived from an iPS cell or ES cell and is genetically engineered to have a mutation in or at least one extra copy of a gene that encodes the neurodegenerative disease associated protein. In some embodiments the neuron has a disease-associated mutation in the gene encoding the neurodegeneration associated protein, and wherein the phenotype is not detectable in an isogenic mutation-corrected neuron. In some embodiments contacting the neuron with the agent comprises contacting a central nervous system (CNS) cell culture comprising the neuron with the agent. In some embodiments the neuron is a cortical neuron. In some embodiments the neuron is a midbrain neuron. In some embodiments the neuron is a dopaminergic neuron. In some embodiments the neuron is an excitatory neuron. In some embodiments the neuron is a motor neuron. In some embodiments the agent is a small molecule. In some embodiments step (b) comprises measuring the level of at least two phenotypes associated with the disease in the neuron and step (c) comprises determining that the agent inhibits at least two of the phenotypes. In some embodiments the method further comprises (d) generating an analog of a candidate therapeutic agent identified in step (c). In some embodiments the method further comprises (d) generating an analog of a candidate therapeutic agent identified in step (c); (e) testing the ability of the analog to reduce toxicity induced by the protein in a yeast cell or testing the ability of the analog to inhibit the phenotype in a neuron that has a genotype associated with the disease, wherein the analog is identified as a candidate therapeutic agent for treating the disease if the analog reduces toxicity induced by the protein in the yeast cell or inhibits the phenotype in the neuron. In some embodiments the method comprises identifying the agent by screening a small molecule library to identify a small molecule that reduces toxicity induced by the neurodegeneration associated protein in yeast cells. In some embodiments the method comprises deriving the neuron from a non-neuronal cell, e.g., a pluripotent stem cell, e.g., an iPS cell or ES cell. In some embodiments the method comprises administering a candidate therapeutic agent identified in step (c) or an analog thereof to a mammalian subject that has the disease or is at increased risk of developing the disease, e.g., a human subject. In some embodiments the mammalian subject is a human subject from whom the neuron was derived. In some embodiments wherein the neuron was derived from a human subject in need of treatment for the disease, and step (c) comprises identifying the agent as a candidate therapeutic agent for treatment of that subject if the level of the phenotype is reduced as compared with the level of the phenotype in the absence of the agent, and in some embodiments further comprising administering a candidate agent identified in step (c) to the subject.

In some aspects described herein is a method of confirming the activity of an agent that modulates toxicity associated with a neurodegeneration associated protein comprising: (a) contacting a human neuron that has a genotype associated with a neurodegenerative disease with an agent that modulates toxicity induced by the protein in a yeast cell that expresses the protein; (b) measuring the level of a phenotype associated with the disease in the neuron; and (c) determining that the level of the phenotype is altered as compared with the level of the phenotype in the absence of the agent, thereby confirming the activity of the agent. In some embodiments step (c) comprises determining that the level of the phenotype is reduced as compared with the level of the phenotype in the absence of the agent, thereby confirming that the agent inhibits toxicity associated with the protein. In some embodiments the neuron is not engineered to have an extra copy of a gene encoding the protein and has not been derived or cultured in the presence of an agent that enhances the phenotype. In some embodiments the phenotype is detectable in a yeast cell that expresses the protein at a level that is sufficient to induce toxicity in the cell. In some embodiments the agent reduces toxicity induced by the protein in a yeast cell that expresses the protein at a level that, in the absence of the agent, is sufficient to induce toxicity in the cell. In some embodiments the neuron is derived from an iPS cell or ES cell. In some embodiments wherein the neuron is derived from a subject who has a mutation in or at least one extra copy of a gene that encodes the protein. In some embodiments the neuron is derived from an iPS cell derived from a human subject who has the neurodegenerative disease. In some embodiments the neuron is derived from an iPS cell derived from a human subject who has a mutation in or at least one extra copy of a gene that encodes the neurodegeneration associated protein. In some embodiments the neuron is derived from an iPS cell or ES cell and is genetically engineered to have a mutation in or at least one extra copy of the protein. In some embodiments the neuron is a midbrain neuron. In some embodiments the neuron is a dopaminergic neuron. In some embodiments the neuron is an excitatory neuron. In some embodiments the neuron is a motor neuron. In some embodiments the neurodegeneration associated protein comprises an alpha-synuclein protein, TDP-43 protein, FUS protein, A-beta protein, or polyglutamine-expanded protein. In some embodiments the neurodegeneration associated protein comprises an alpha-synuclein protein, and the phenotype comprises nitrosative stress, mitochondrial dysfunction, defective endoplasmic reticulum-associated degradation (ERAD), or impaired ER-to-Golgi trafficking. In some embodiments the neurodegeneration associated protein comprises an Abeta protein and the phenotype comprises a defect in endocytosis. In some embodiments the neurodegeneration associated protein comprises a TDP-43 protein and the phenotype comprises an increase in stress granule formation or a defect in endocytosis.

In some aspects, described herein is a method of identifying a phenotype associated with a neurodegenerative disease characterized by abnormal accumulation of a neurodegeneration associated protein comprising steps of: (a) providing a yeast cell that expresses the protein at a level sufficient to induce toxicity in the cell; (b) detecting a phenotype in the yeast cell associated with expression of the protein; (c) providing a human neuron that has a genotype associated with the disease; and (d) detecting the phenotype in the neuron, thereby identifying a phenotype associated with the neurodegenerative disease. In some embodiments the neuron has a mutation in at least one copy of a gene encoding the protein. In some embodiments the neuron has a mutation in at least one copy of a gene encoding the protein, and wherein the phenotype is not detectable in an isogenic mutation-corrected neuron. In some embodiments the neurodegeneration associated protein comprises an alpha-synuclein protein, TDP-43 protein, FUS protein, A-beta protein, or polyglutamine-expanded protein. In some embodiments the method further comprises (e) providing a rodent neuron engineered to express the protein; and (f) detecting the phenotype in the rodent neuron. In some embodiments the method further comprises optimizing an assay for detecting the phenotype for use in mammalian neurons using rodent neurons engineered to express the protein. In some embodiments the yeast cell overexpresses at least one gene whose overexpression modulates toxicity induced by the protein or has reduced or absent expression of at least one gene whose deletion modulates toxicity induced by the protein. In some embodiments of the method neuron is not engineered to have an extra copy of a gene encoding a protein associated with the disease and has not been derived or cultured in the presence of an agent that enhances the phenotype. In some embodiments the method further comprises (c) contacting a human neuron having a genotype associated with the disease with an agent; and (d) determining whether the agent inhibits the phenotype in the neuron. In some embodiments the method further comprises (c) contacting a human neuron having a genotype associated with the disease with an agent that reduces toxicity induced by the protein in the yeast cell; and (d) determining that the agent inhibits the phenotype in the neuron.

In some aspects, described herein is a method of identifying a candidate therapeutic agent for treating a synucleinopathy comprising: (a) contacting a human neuron having a genotype associated with a synucleinopathy with an agent; (b) measuring the level of a phenotype comprising nitrosative stress, mitochondrial dysfunction, defective endoplasmic reticulum-associated degradation (ERAD), or impaired ER-to-Golgi trafficking in the neuron; and (c) determining that the agent reduces the level of the phenotype, thereby identifying a candidate therapeutic agent for treatment of a synucleinopathy. In some embodiments the phenotype is detectable in a yeast cell that expresses an alpha-synuclein protein at a level that is sufficient to induce toxicity in the cell. In some embodiments the agent reduces toxicity induced by an alpha-synuclein protein in a yeast cell that expresses the protein at a level that, in the absence of the agent, is sufficient to induce toxicity in the cell. In some embodiments the neuron is derived from an iPS cell or ES cell. In some embodiments the neuron is derived from a subject who has a mutation in or at least one extra copy of a gene that encodes the neurodegeneration associated protein. In some embodiments the neuron is derived from an iPS cell derived from a human subject who has the neurodegenerative disease. In some embodiments the neuron is derived from an iPS cell derived from a human subject who has a mutation in or at least one extra copy of a gene that encodes the neurodegeneration associated protein. In some embodiments the neuron is derived from an iPS cell or ES cell and is genetically engineered to have a mutation in or at least one extra copy of a gene that encodes the neurodegeneration associated protein. In some embodiments the neuron is a central nervous system neuron. In some embodiments the neuron is a cortical neuron. In some embodiments the neuron is a midbrain neuron. In some embodiments the neuron is a dopaminergic neuron. In some embodiments the neuron is an excitatory neuron. In some embodiments the neuron is a motor neuron. In some embodiments the neuron is not engineered to have an extra copy of a gene encoding alpha-synuclein and has not been derived or cultured in the presence of an agent that enhances the phenotype. In some embodiments the neuron is derived from a subject who has a mutation associated with autosomal dominant Parkinson's disease. In some embodiments the neuron is derived from a subject who has a mutation in at least one copy of the gene that encodes alpha-synuclein. In some embodiments the neuron is derived from a subject who has a mutation associated with autosomal dominant Parkinson's disease in the gene encoding alpha-synuclein. In some embodiments the neuron is derived from a subject who has at least one extra copy of the gene encoding alpha-synuclein. In some embodiments the agent reduces toxicity of alpha-synuclein in a yeast cell that expresses alpha-synuclein. In some embodiments the method comprises administering a candidate therapeutic agent identified in step (c) or an analog thereof to a mammalian subject that has a synucleinopathy or is at increased risk of developing a synucleinopathy. In some embodiments the mammalian subject is a human subject. In some embodiments the mammalian subject is the human subject from whom the neuron was derived. In some embodiments the human subject is a patient in need of treatment for a synucleinopathy, and step (c) comprises identifying the agent as a candidate therapeutic agent for treatment of that patient if the level of the phenotype is reduced as compared with the level of the phenotype in the absence of the agent. In some embodiments the method further comprises administering a candidate agent identified in step (c) to the patient.

In some aspects, described herein is a method of identifying a candidate therapeutic agent for treatment of a synucleinopathy comprising steps of: (a) contacting a human neuron having a genotype associated with a synucleinopathy with an agent; (b) measuring the level of a phenotype associated with the synucleinopathy in the neuron, wherein the neuron is not engineered to have an extra copy of a gene encoding alpha-synuclein and has not been derived or cultured in the presence of an agent that enhances the phenotype; and (c) determining that the agent inhibits the phenotype, thereby identifying a candidate therapeutic agent for treating the synucleinopathy. In some embodiments the phenotype is detectable in a yeast cell that expresses an alpha-synuclein protein at a level sufficient to induce toxicity in the cell. In some embodiments the agent reduces toxicity of an alpha-synuclein protein in a yeast cell that expresses the protein at a level sufficient to induce toxicity in the cell. In some embodiments the neuron is derived from an iPS cell or ES cell. In some embodiments the neuron is derived from a subject who has a mutation in or at least one extra copy of a gene that encodes the neurodegenerative disease associated protein. In some embodiments the neuron is derived from an iPS cell derived from a human subject who has the neurodegenerative disease. In some embodiments the neuron is derived from an iPS cell derived from a human subject who has a mutation in or at least one extra copy of a gene that encodes the neurodegeneration associated protein. In some embodiments the neuron is derived from an iPS cell or ES cell and is genetically engineered to have a mutation in or at least one extra copy of a gene that encodes the neurodegeneration associated protein. In some embodiments the neuron is a central nervous system neuron. In some embodiments the neuron is a cortical neuron. In some embodiments the neuron is a midbrain neuron. In some embodiments the neuron is a dopaminergic neuron. In some embodiments the neuron is an excitatory neuron. In some embodiments the neuron is a motor neuron. In some embodiments the agent is a small molecule. In some embodiments the neuron is not engineered to have an extra copy of a gene encoding alpha-synuclein and has not been derived or cultured in the presence of an agent that enhances the phenotype. In some embodiments the subject has a mutation associated with autosomal dominant Parkinson's disease. In some embodiments the subject has a mutation in at least one copy of the gene that encodes alpha-synuclein. In some embodiments the subject has a mutation associated with autosomal dominant Parkinson's disease in the gene encoding alpha-synuclein. In some embodiments the subject has at least one extra copy of the gene encoding alpha-synuclein. In some embodiments the phenotype comprises nitrosative stress, mitochondrial dysfunction, defective endoplasmic reticulum-associated degradation (ERAD), or impaired ER-to-Golgi trafficking. In some embodiments the agent reduces toxicity of an alpha-synuclein protein in a yeast cell that expresses the protein at a level that, in the absence of the agent, is sufficient to induce toxicity in the cell. In some embodiments the method comprises administering a candidate therapeutic agent identified in step (c) or an analog thereof to a mammalian subject that has a synucleinopathy or is at increased risk of developing a synucleinopathy. In some embodiments the mammalian subject is a human subject. In some embodiments the mammalian subject is the human subject from whom the neuron was derived. In some embodiments the human subject is a patient in need of treatment for a synucleinopathy, and step (c) comprises identifying the agent as a candidate therapeutic agent for treatment of that patient if the level of the phenotype is reduced as compared with the level of the phenotype in the absence of the agent. In some embodiments the method further comprises administering a candidate agent identified in step (c) to the patient.

In some aspects described herein is a method of confirming that a human gene is a genetic modifier of a neurodegenerative disease characterized by abnormal accumulation of a neurodegeneration associated protein comprising: (a) contacting a human neuron that has a genotype associated with the neurodegenerative disease with an agent that increases or reduces the level or activity of a gene product of a human homolog of a yeast gene that is a genetic modifier of toxicity associated with the neurodegeneration associated protein in yeast; (b) measuring the level of a phenotype associated with the disease in the neuron; and (c) determining that the level of the phenotype is altered as compared with the level of the phenotype in the absence of the agent, thereby confirming that the human homolog of the yeast gene is a genetic modifier of the neurodegenerative disease. In some embodiments the yeast gene is a genetic enhancer of toxicity associated with the neurodegeneration associated protein. In some embodiments the yeast gene is a genetic enhancer of toxicity associated with the neurodegeneration associated protein and the agent reduces the level or activity of a gene product of the human homolog. In some embodiments the yeast gene is a genetic suppressor of toxicity associated with the neurodegeneration associated protein. In some embodiments the yeast gene is a genetic suppressor of toxicity associated with the neurodegeneration associated protein, and the agent reduces the level or activity of a gene product of the human homolog. In some embodiments the agent comprises a nucleic acid that encodes a protein encoded by the human homolog, and the method comprises introducing the agent into the neuron or a precursor of the neuron, so that the neuron expresses the protein. In some embodiments the agent comprises an RNAi agent that inhibits expression of the human homolog, and the method comprises introducing the agent into the neuron or a precursor of the neuron, so that expression of the human homolog is inhibited. In some embodiments the neurodegeneration associated protein comprises an alpha-synuclein protein, TDP-43 protein, FUS protein, A-beta protein, or polyglutamine-expanded protein. In some embodiments the neurodegeneration associated protein comprises an alpha-synuclein protein, and the phenotype comprises nitrosative stress, mitochondrial dysfunction, defective endoplasmic reticulum-associated degradation (ERAD), or impaired ER-to-Golgi trafficking. In some embodiments the neurodegeneration associated protein comprises an Abeta protein and the phenotype comprises a defect in endocytosis. In some embodiments the neurodegeneration associated protein comprises a TDP-43 protein and the phenotype comprises an increase in stress granule formation or a defect in endocytosis. In some embodiments neuron is derived from an iPS cell or ES cell. In some embodiments the neuron is derived from a subject who has a mutation in or at least one extra copy of a gene that encodes the neurodegeneration associated protein. In some embodiments the neuron is derived from an iPS cell derived from a human subject who has the neurodegenerative disease. In some embodiments the neuron is derived from an iPS cell derived from a human subject who has a mutation in or at least one extra copy of a gene that encodes the neurodegeneration associated protein. In some embodiments the neuron is derived from an iPS cell or ES cell and is genetically engineered to have a mutation in or at least one extra copy of a gene that encodes the neurodegeneration associated protein. In some embodiments the neuron is a central nervous system neuron. In some embodiments the neuron is a cortical neuron. In some embodiments the neuron is a midbrain neuron. In some embodiments the neuron is a dopaminergic neuron. In some embodiments the neuron is an excitatory neuron. In some embodiments the neuron is a motor neuron. In some embodiments the method comprises performing a screen to identify the agent.

In some aspects, described herein is a method of identifying an agent that modulates a phenotype associated with a neurodegenerative disease characterized by abnormal accumulation of a neurodegeneration associated protein comprising: (a) contacting a human induced neuron that has a genotype associated with the neurodegenerative disease with an agent that increases or reduces the level or activity of a gene product of a human homolog of a yeast gene that is a genetic modifier of toxicity associated with the neurodegeneration associated protein in yeast; (b) measuring the level of a phenotype in the neuron; and (c) determining that the level of the phenotype is altered as compared with the level of the phenotype in the absence of the agent, thereby identifying the agent as a modulator of the phenotype. In some embodiments the gene is a genetic enhancer of toxicity induced by the neurodegeneration associated protein. In some embodiments the gene is a genetic enhancer of toxicity induced by the neurodegeneration associated protein, and the agent reduces the level or activity of a gene product of the human homolog of the gene. In some embodiments the gene is a genetic suppressor of toxicity induced by the protein. In some embodiments the gene is a genetic suppressor of toxicity induced by the protein, and the agent increases the level or activity of a gene product of the human homolog. In some embodiments the neurodegeneration associated protein comprises an alpha-synuclein protein, TDP-43 protein, FUS protein, A-beta protein, or polyglutamine-expanded protein. In some embodiments the neurodegeneration associated protein comprises an alpha-synuclein protein, and the phenotype comprises nitrosative stress, mitochondrial dysfunction, defective endoplasmic reticulum-associated degradation (ERAD), or impaired ER-to-Golgi trafficking. In some embodiments the neurodegeneration associated protein comprises an Abeta protein and the phenotype comprises a defect in endocytosis. In some embodiments the neurodegeneration associated protein comprises a TDP-43 protein and the phenotype comprises an increase in stress granule formation or a defect in endocytosis. In some embodiments the induced neuron is derived from an iPS cell or ES cell. In some embodiments the neuron is derived from a subject who has a mutation in or at least one extra copy of a gene that encodes neurodegeneration associated protein. In some embodiments the neuron is derived from an iPS cell derived from a human subject who has the neurodegenerative disease. In some embodiments the neuron is derived from an iPS cell derived from a human subject who has a mutation in or at least one extra copy of a gene that encodes the neurodegeneration associated protein. In some embodiments the neuron is derived from an iPS cell or ES cell and is genetically engineered to have a mutation in or at least one extra copy of a gene that encodes the neurodegeneration associated protein. In some embodiments the neuron is a central nervous system neuron. In some embodiments the neuron is a cortical neuron. In some embodiments the neuron is a midbrain neuron. In some embodiments the neuron is a dopaminergic neuron. In some embodiments the neuron is an excitatory neuron. In some embodiments the neuron is a motor neuron. In some embodiments the agent is a small molecule. In some embodiments the method further comprises performing a screen to identify the agent.

In some aspects, described herein is a method of identifying a candidate therapeutic agent for a neurodegenerative disease characterized by abnormal accumulation of a neurodegeneration associated protein comprising: (a) contacting a neuron that has a genotype associated with the neurodegenerative disease with an agent that increases or reduces the level or activity of a gene product of a human homolog of a yeast gene that is a genetic modifier of toxicity associated with the neurodegeneration associated protein in yeast; (b) measuring the level of a phenotype in the neuron; and (c) determining that the level of the disease-associated phenotype is reduced as compared with the level of the phenotype in the absence of the agent, thereby identifying the agent as a candidate therapeutic agent for the neurodegenerative disease. In some embodiments the gene is a genetic enhancer of toxicity induced by the neurodegeneration associated protein and the agent reduces the level or activity of a gene product of the human homolog of the gene. In some embodiments the gene is a genetic suppressor of toxicity induced by the protein and the agent increases the level or activity of a gene product of the human homolog. In some embodiments the neurodegeneration associated protein comprises an alpha-synuclein protein, TDP-43 protein, FUS protein, A-beta protein, or polyglutamine-expanded protein. In some embodiments the neurodegeneration associated protein comprises an alpha-synuclein protein, and the phenotype comprises nitrosative stress, mitochondrial dysfunction, defective endoplasmic reticulum-associated degradation (ERAD), or impaired ER-to-Golgi trafficking. In some embodiments the neurodegeneration associated protein comprises an Abeta protein and the phenotype comprises a defect in endocytosis. In some embodiments the neurodegeneration associated protein comprises a TDP-43 protein and the phenotype comprises an increase in stress granule formation or a defect in endocytosis. In some embodiments the method further comprises performing a screen to identify one or more additional agents that modulate the level or activity of a gene product of the human homolog.

In some aspects, described herein is a method of identifying a candidate therapeutic agent for treating a human subject who has a neurodegenerative disease comprising: (a) contacting a neuron that has a genotype associated with a neurodegenerative disease with an agent that reduces toxicity of a neurodegeneration associated protein associated with the disease in a yeast cell that expresses the neurodegeneration associated protein; (b) measuring the level of a phenotype associated with the disease in the neuron; and (c) identifying the agent as a candidate therapeutic agent for treating the subject if the level of the phenotype is reduced as compared with the level of the phenotype in the absence of the agent. In some embodiments the neurodegeneration associated protein comprises an alpha-synuclein protein, TDP-43 protein, FUS protein, A-beta protein, or polyglutamine-expanded protein. In some embodiments the neurodegenerative disease is a synucleinopathy, TDP-43 proteinopathy, FUS-opathy, Alzheimer's disease, or Huntington's disease. In some embodiments the neuron is not engineered to have an extra copy of a gene encoding the neurodegeneration associated protein and has not been derived or cultured in the presence of an agent that enhances the phenotype. In some embodiments the phenotype is detectable in the yeast cell in the absence of the agent. In some embodiments the neurodegeneration associated protein comprises an alpha-synuclein protein and the phenotype comprises nitrosative stress, mitochondrial dysfunction, defective endoplasmic reticulum-associated degradation (ERAD), or impaired ER-to-Golgi trafficking. In some embodiments the neurodegeneration associated protein comprises an Abeta protein and the phenotype comprises a defect in endocytosis. In some embodiments the neurodegeneration associated protein comprises a TDP-43 protein and the phenotype comprises an increase in stress granule formation or a defect in endocytosis. In some embodiments the subject has a disease-associated mutation in at least one copy of the gene encoding the neurodegeneration associated protein or has at least one extra copy of the gene encoding the protein. In some embodiments the agent is a small molecule. In some embodiments step (b) comprises measuring the level of at least two phenotypes associated with the disease in the neuron and step (c) comprises determining that the agent inhibits at least two of the phenotypes. In some embodiments the method comprises identifying the agent by screening a small molecule library to identify a small molecule that reduces toxicity induced by the neurodegeneration associated protein in yeast cells. In some embodiments the method further comprises administering a candidate therapeutic agent identified in step (c) or an analog thereof to the subject. In some embodiments steps (a) and (b) are performed with at least two different agents; and step (c) comprises identifying an agent that has greater ability to reduce the level of the phenotype than at least half of the agents tested as a candidate therapeutic agent for treating the subject. In some embodiments the method further comprises administering a candidate therapeutic agent identified in step (c) or an analog thereof to the subject.

In some aspects, described herein is a human neuron that has (i) a neurodegenerative disease-associated mutation or variation in a gene that encodes a neurodegeneration associated protein or at least one extra copy of a gene that encodes a neurodegeneration associated protein and (ii) a genetic alteration that increases or decreases the functional activity of a human homolog of a yeast gene that is a genetic modifier of toxicity associated with the NAP in yeast. In some embodiments the yeast gene is a suppressor of toxicity associated with the neurodegeneration associated protein in yeast, and the genetic alteration decreases the functional activity of the human homolog. In some embodiments the yeast gene is an enhancer of toxicity associated with the neurodegeneration associated protein in yeast, and the genetic alteration increases the functional activity of the human homolog. In some embodiments the neuron is derived from a human subject who has the neurodegenerative disease. In some embodiments the neuron is derived from an iPS cell or ES cell. In some embodiments the neuron is derived from an iPS cell derived from a human subject who has the neurodegenerative disease. In some embodiments the neuron is engineered to have a mutation in or at least one extra copy of a gene that encodes the neurodegenerative disease associated protein, the human homolog, or both. In some embodiments the neuron is a central nervous system neuron. In some embodiments the neuron is a cortical neuron. In some embodiments the neuron is a midbrain neuron. In some embodiments the neuron is a dopaminergic neuron. In some embodiments the neuron is an excitatory neuron. In some embodiments the neuron is a motor neuron. In some embodiments the neurodegeneration associated protein comprises an alpha-synuclein protein, TDP-43 protein, FUS protein, A-beta protein, or polyglutamine-expanded protein.

In some aspects, described herein is a cell culture comprising any of the afore-mentioned neurons and a plurality of neurons that are isogenic thereto. In some aspects, described herein is a cell culture comprising any of the afore-mentioned neurons and a plurality of neurons and glial cells that are isogenic thereto.

In some aspects, described herein are compositions comprising a human neuron or cell culture described herein and a test agent. In some embodiments the test agent is a small molecule. In some embodiments the test agent is a small molecule that reduces toxicity of the neurodegeneration associated protein in yeast. In some aspects, described herein is a method of identifying a candidate therapeutic agent for treatment of a neurodegenerative disease comprising: (a) providing any of the afore-mentioned compositions; (b) measuring the level of a phenotype associated with the disease in the neuron; and (c) identifying the agent as a candidate therapeutic agent for treatment of the neurodegenerative disease if the level of the phenotype is reduced as compared with the level of the phenotype in the absence of the agent.

In some aspects, described herein is a method of identifying a phenotype associated with a neurodegenerative disease characterized by abnormal accumulation of a neurodegeneration associated protein comprising steps of: (a) providing a yeast cell that expresses the protein at a level sufficient to induce toxicity in the cell, wherein the yeast cell has a genetic background that corresponds to the genotype of a patient who has the disease with respect to at least one mutation or genetic variation; and (b) identifying an agent that inhibits toxicity of the protein in the yeast cell. In some embodiments the method further comprises (c) providing a human neuron that has a genotype associated with the disease in the patient; and (d) determining whether the agent inhibits a phenotype associated with the disease in the neuron, wherein the agent is identified as a candidate therapeutic agent for treating the subject if the agent inhibits the phenotype. In some embodiments the neuron is not exposed to a phenotype enhancer. In some embodiments the neurodegeneration associated protein comprises an alpha-synuclein protein, TDP-43 protein, FUS protein, A-beta protein, or polyglutamine-expanded protein. In some embodiments the subject has a synucleinopathy, Alzheimer's disease, a TDP-43 proteinopathy, a FUS-opathy, or a polyglutamine expansion disease. In some embodiments the method comprises determining the genotype of the patient with regard to one or more mutations or genetic variations associated with the disease and selecting or generating the yeast cell that corresponds to the genotype. In some embodiments determining the genotype comprises identifying one or more mutations or genetic variations present in the subject that increases the risk of developing the disease.

In some aspects, described herein are models for and methods applicable to a wide variety of neurodegenerative diseases. In some aspects, the neurodegenerative disease is associated with a gain or loss of function of a gene product, e.g., due to a mutation in the gene encoding the gene product. In some aspects, the neurodegenerative disease may (in at least some patients) be caused by a gain or loss of function of a gene product, e.g., due to a mutation in the gene encoding the gene product.

In some aspects, the disclosure provides a method of identifying a candidate therapeutic agent for treatment of a neurodegenerative disease comprising: (a) contacting an induced human neuron that has a genotype associated with the neurodegenerative disease with an agent that enhances viability or at least in part normalizes an abnormal phenotype of a yeast cell that serves as a model for the disease; (b) measuring the level of a phenotype associated with the disease in the neuron; and (c) identifying the agent as a candidate therapeutic agent for treatment of the neurodegenerative disease if the level of the phenotype in the neuron is reduced as compared with the level of the phenotype in the absence of the agent. In some aspects, the disclosure provides a method of selecting a candidate therapeutic agent for treatment of a neurodegenerative disease comprising: (a) contacting an induced human neuron that has a genotype associated with a neurodegenerative disease with an agent that enhances viability or at least in part normalizes an abnormal phenotype of a yeast cell that serves as a model for the disease; (b) measuring the level of a phenotype associated with the disease in the neuron; (c) determining that the level of the phenotype is altered as compared with the level of the phenotype in the absence of the agent; and (d) selecting the agent a candidate therapeutic agent for treatment of the neurodegenerative disease. In some aspects, the disclosure provides a method of identifying a phenotype associated with a neurodegenerative disease comprising steps of: (a) providing a yeast cell that is engineered to serve as a model of a neurodegenerative disease; (b) detecting a phenotype that is present in the engineered yeast cell as compared with a control yeast cell; (c) providing an induced human neuron that has a genotype associated with the disease; and (d) detecting the phenotype in the neuron, thereby identifying a phenotype associated with the neurodegenerative disease. In some aspects, the disclosure provides a method of identifying a candidate therapeutic agent for a neurodegenerative disease comprising: (a) contacting an induced human neuron that has a genotype associated with the neurodegenerative disease with an agent that increases or reduces the level or activity of a gene product of a human homolog of a yeast gene that is a genetic modifier of viability of a yeast cell engineered to serve as a model of a neurodegenerative disease; (b) measuring the level of a disease-associated phenotype in the neuron; and (c) determining that the level of the disease-associated phenotype is reduced as compared with the level of the phenotype in the absence of the agent, thereby identifying the agent as a candidate therapeutic agent for the neurodegenerative disease.

In some aspects, the disclosure provides a method of identifying a candidate therapeutic agent for treating a human subject who has a neurodegenerative disease comprising: (a) contacting an induced human neuron that has a genotype associated with the neurodegenerative disease with an agent that enhances viability or at least in part normalizes an abnormal phenotype of a yeast cell that serves as a model for the disease; (b) measuring the level of a phenotype associated with the disease in the neuron; and (c) identifying the agent as a candidate therapeutic agent for treating the subject if the level of the phenotype in the neuron is reduced as compared with the level of the phenotype in the absence of the agent.

In certain embodiments an induced human neuron overexpresses is capable of overexpressing or has a gain of function mutation in a neurodegeneration associated protein or neurodegeneration associated RNA. In certain embodiments an induced human neuron has a loss of function mutation in one or both copies of a neurodegenerative disease gene, wherein loss of function of the gene is associated with a neurodegenerative disease. In certain embodiments an induced human neuron is genetically engineered to have a genotype associated with the disease. In certain embodiments an induced human neuron is derived from a subject who has the disease. In certain embodiments the disease is a synucleinopathy, Alzheimer's disease, a TDP-43 proteopathy, a FUSopathy, a nucleotide expansion disorder, a tauopathy, a parkinsonism disorder, an ataxia, a motor neuron disorder, a peripheral neuropathy, or a white matter disorder.

In some aspects, the disclosure provides an induced human nervous system cell that harbors a neurodegenerative disease gene that contains a mutation or genetic variation or is overexpressed, wherein the neurodegenerative disease gene is associated with a neurodegenerative disease, and wherein the cell (i) has a mutation or genetic variation in a gene that is a genetic modifier of the neurodegenerative disease gene or overexpresses said gene, wherein said genetic modifier has a yeast homolog, or (ii) has a mutation or genetic variation in or overexpresses a human homolog of a yeast gene that modifies viability or disease-associated phenotype(s) of yeast that serve as a model of the neurodegenerative disease. In some embodiments the mutation or genetic variation in the neurodegenerative disease gene, genetic modifier, or human homolog increases or decreases the amount or activity of a gene product of the gene relative to a normal level. In some embodiments the mutation, genetic variation, or overexpression causes or increases the risk of developing the neurodegenerative disease.

In certain embodiments methods described herein may be practiced using induced human glial cells, e.g., oligodendrocytes, instead or in addition to induced human neurons. For example, glial cells may be of particular interest in diseases in which gain-of-function or loss-of-function mutations have a detrimental effect on glial cells and/or in which neurodegeneration-associated proteins accumulate in glial cells. Thus the disclosure contemplates embodiments involving induced human glial cells wherever mention is made of induced human nervous system cells or induced human neurons.

The practice of certain aspects of the present invention may employ conventional techniques of molecular biology, cell culture, recombinant nucleic acid (e.g., DNA) technology, immunology, transgenic biology, microbiology, nucleic acid and polypeptide synthesis, detection, manipulation, and quantification, that are within the ordinary skill of the art. See, e.g., Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of December 2012; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., *Antibodies—A Laboratory*

Manual, Cold Spring Harbor Laboratory Press, Cold Spring Harbor, 1988. Information regarding diagnosis and treatments of various diseases, including neurodegenerative diseases, is found in Longo, D., et al. (eds.), Harrison's Principles of Internal Medicine, 18th Edition; McGraw-Hill Professional, 2011. Information regarding various therapeutic agents and human diseases, including cancer, is found in Brunton, L., et al. (eds.) Goodman and Gilman's The Pharmacological Basis of Therapeutics, 12$^{th}$ Ed., McGraw Hill, 2010 and/or Katzung, B. (ed.) Basic and Clinical Pharmacology, McGraw-Hill/Appleton & Lange; 11th edition (July 2009). All patents, patent applications, books, articles, documents, databases, websites, publications, references, etc., mentioned herein are incorporated by reference in their entirety. In case of a conflict between the specification and any of the incorporated references, the specification (including any amendments thereof), shall control. Applicants reserve the right to amend the specification based, e.g., on any of the incorporated material and/or to correct obvious errors. None of the content of the incorporated material shall limit the invention. Standard art-accepted meanings of terms are used herein unless indicated otherwise. Standard abbreviations for various terms are used herein.

DETAILED DESCRIPTION OF CERTAIN EMBODIMENTS

I. Glossary

Figure 1A:
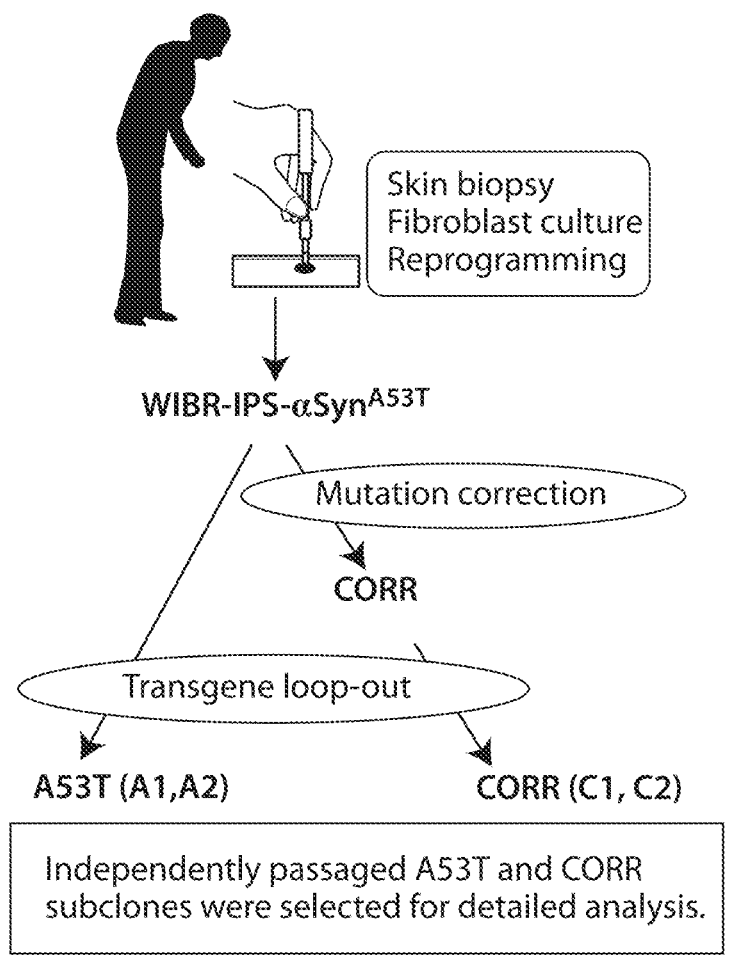
FIG. 1. iPS cell-derived cortical neurons were generated from a PD patient harboring the A53T αSyn mutation and isogenic mutation-corrected control lines. (A) Generation of A53T and A53T mutation-corrected (CORR) iPS cells. Fibroblasts were reprogrammed with Cre-recombinase-excisable lentiviral vectors. "Transgene loopout" refers to their excision. A zinc finger-mediated targeting strategy was used to correct the A53T mutation, and clones were identified with a drug-free selection strategy. Two subclones from each cell line were passaged up to 90 times and consistently differentiated into cortical neurons (B) Neuronal markers expressed during differentiation of A53T and CORR lines. Within 3 days of FGF2 withdrawal, cells elaborated processes expressing neuron-specific class III beta-tubulin (Tuj1). At 4 weeks the majority of cells were neurons, marked by microtubule-associated protein 2 (MAP2). Glutamatergic identity was confirmed by vesicular glutamate transporter-1 (VGLUT1). Neurons robustly expressed αSyn. Cell nuclei were labeled with Hoechst. (C) Neural progenitors were transduced with lentiviruses expressing eYFP under the neuron-specific promoter synapsin. Neurons marked by eYFP were predominantly TBR1-positive, indicating a deep cortical layer identity.

Descriptions and certain information relating to various terms used in the present disclosure are collected here for convenience.

"Agent" is used herein to refer to any substance, compound (e.g., molecule), supramolecular complex, material, or combination or mixture thereof. A compound may be any agent that can be represented by a chemical formula, chemical structure, or sequence. Example of agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counter-ion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (-)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e. hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

An "analog" of a first agent refers to a second agent that is structurally and/or functionally similar to the first agent. A "structural analog" of a first agent is an analog that is structurally similar to the first agent. A structural analog of an agent may have substantially similar physical, chemical, biological, and/or pharmacological propert(ies) as the agent or may differ in at least one physical, chemical, biological, or pharmacological property. In some embodiments at least one such property may be altered in a manner that renders the analog more suitable for a purpose of interest. In some embodiments a structural analog of an agent differs from the agent in that at least one atom, functional group, or substructure of the agent is replaced by a different atom, functional group, or substructure in the analog. In some embodiments, a structural analog of an agent differs from the agent in that at least one hydrogen or substituent present in the agent is replaced by a different moiety (e.g., a different substituent) in the analog. In some embodiments an analog may comprise a moiety that reacts with a target to form a covalent bond.

The terms "assessing", "determining", "evaluating", "assaying" are used interchangeably herein to refer to any form of detection or measurement, and include determining whether a substance, signal, disease, condition, etc., is present or not. The result of an assessment may be expressed in qualitative and/or quantitative terms. Assessing may be relative or absolute. "Assessing the presence of" includes determining the amount of something that is present or determining whether it is present or absent.

A "biological process", may be any set of operations or molecular events, with a defined beginning and end, pertinent to the functioning of integrated living units, e.g., cells, tissues, organs, and organisms. Typically it is a series of events accomplished by one or more ordered assemblies of molecular functions. A "biological pathway" may be any series of actions and/or interactions by and among molecules in a cell that leads to a certain product or a change in a cell. Typically a biological process encompasses or is carried out via one or more biological pathways. Biological pathways include, for example, pathways pertaining to metabolism, genetic information processing (e.g., transcription, translation, RNA transport, RNA degradation; protein folding, sorting, degradation, post-translational modification; DNA replication and repair), environmental information processing (e.g., membrane transport, signal transduction), and cellular processes (e.g., cell cycle, endocytosis, vesicle trafficking), etc. It will be appreciated that the various aforementioned biological processes encompass multiple specific pathways). In some embodiments a biological pathway or process is conserved in that the pathway or process is recognizably present in both yeast and mammalian cells).

Cellular marker" refers to a molecule (e.g., a protein, RNA, DNA, lipid, carbohydrate), complex, or portion thereof, the presence, absence, or level of which in or on a cell (e.g., at least partly exposed at the cell surface) characterizes, indicates, or identifies one or more cell type(s), cell lineage(s), or tissue type(s) or characterizes, indicates, or identifies a particular state (e.g., a diseased or physiological state such as apoptotic or non-apoptotic, a differentiation state, a stem cell state). In some embodiments a cellular marker comprises the presence, absence, or level of a particular modification of a molecule or complex, e.g., a co- or post-translational modification of a protein. A level may be reported in a variety of different ways, e.g., high/low; +/−; numerically, etc. The presence, absence, or level of certain cellular marker(s) may indicate a particular physiological or diseased state of a patient, organ, tissue, or cell. It will be understood that multiple cellular markers may be assessed to, e.g., identify or isolate a cell type of interest, diagnose a disease, etc. In some embodiments between 2 and 10 cellular markers may be assessed. A cellular marker present on or at the surface of cells may be referred to as a "cell surface marker" (CSM). It will be understood that a CSM may be only partially exposed at the cell surface. In some embodiments a CSM or portion thereof is accessible to a specific binding agent present in the environment in which such cell is located, so that the binding agent may be used to, e.g., identify, label, isolate, or target the cell. In some embodiments a CSM is a protein at least part of which is located outside the plasma membrane of a cell. Examples of CSMs include receptors with an extracellular domain, channels, and cell adhesion molecules. In some embodiments, a receptor is a growth factor receptor, hormone receptor, integrin receptor, folate receptor, or transferrin receptor. A cellular marker may be cell type specific. A cell type specific marker is generally expressed or present at a higher level in or on (at the surface of) a particular cell type or cell types than in or on many or most other cell types (e.g., other cell types in the body or in an artificial environment). In some cases a cell type specific marker is present at detectable levels only in or on a particular cell type of interest and not on other cell types. However, useful cell type specific markers may not be and often are not absolutely specific for the cell type of interest. A cellular marker, e.g., a cell type specific marker, may be present at levels at least 1.5-fold, at least 2-fold or at least 3-fold greater in or on the surface of a particular cell type than in a reference population of cells which may consist, for example, of a mixture containing cells from multiple (e.g., 5-10; 10-20, or more) of different tissues or organs in approximately equal amounts. In some embodiments a cellular marker, e.g., a cell type specific marker, may be present at levels at least 4-5 fold, between 5-10 fold, between 10-fold and 20-fold, between 20-fold and 50-fold, between 50-fold and 100-fold, or more than 100-fold greater than its average expression in a reference population. It will be understood that a cellular marker, e.g., a CSM, may be present in a cell fraction, organelle, cell fragment, or other material originating from a cell in which it is present and may be used to identify, detect, or isolate such material. In general, the level of a cellular marker may be determined using standard techniques such as Northern blotting, in situ hybridization, RT-PCR, sequencing, immunological methods such as immunoblotting, immunohistochemistry, fluorescence detection following staining with fluorescently labeled antibodies (e.g., flow cytometry, fluorescence microscopy), similar methods using non-antibody ligands that specifically bind to the marker, oligonucleotide or cDNA microarray, protein microarray analysis, mass spectrometry, etc. A CSM, e.g., a cell type specific CSM, may be used to detect or isolate cells or as a target in order to deliver an agent to cells. For example, the agent may be linked to a moiety that binds to a CSM. Suitable binding moieties include, e.g., antibodies or ligands, e.g., small molecules, aptamers, or polypeptides. Methods known in the art can be used to separate cells that express a cellular marker, e.g., a CSM, from cells that do not, if desired. In some embodiments a specific binding agent can be used to physically separate cells that express a CSM from cells that do not. In some embodiments, flow cytometry is used to quantify cells that express a cellular marker, e.g., a CSM, or to separate cells that express a cellular marker, e.g., a CSM, from cells that do not. For example, in some embodiments cells are contacted with a fluorescently labeled antibody that binds to the CSM. Fluorescence activated cell sorting (FACS) is then used to separate cells based on fluorescence.

A nucleotide or amino acid residue in a first nucleic acid or protein "corresponds to" a residue in a second nucleic acid or protein if the two residues perform one or more corresponding functions and/or are located at corresponding positions in the first and second nucleic acids or proteins. Corresponding functions are typically the same, equivalent, or substantially equivalent functions, taking into account differences in the environments of the two nucleic acids or proteins as appropriate. Residues at corresponding positions typically align with each other when the sequences of the two nucleic acids or proteins are aligned to maximize identity (allowing the introduction of gaps) using a sequence alignment algorithm or computer program such as those referred to below (see "Identity") and/or are located at positions such that when the 3-dimensional structures of the proteins is superimposed the residues overlap or occupy structurally equivalent positions and/or form the same, equivalent, or substantially equivalent intramolecular and/or intermolecular contacts or bonds (e.g., hydrogen bonds). The structures may be experimentally determined, e.g., by X-ray crystallography or NMR or predicted, e.g., using structure prediction or molecular modeling software. An alignment may be over the entire length of one or more of the aligned nucleic acid or polypeptide sequences or over at least one protein domain (or nucleotide sequence encoding a protein domain). A "domain" of a protein is a distinct functional and/or structural unit of a protein, e.g., an independently folding unit of a polypeptide chain. In some embodiments a domain is a portion of a protein sequence identified as a domain in the Conserved Domain Database of the NCBI (Marchler-Bauer A et al. (2013), "CDD: conserved domains and protein three-dimensional structure", Nucleic Acids Res. 41(D1):D384-52). In some embodiments corresponding amino acids are the same in two sequences (e.g., a lysine residue, a threonine residue) or would be considered conservative substitutions for each other. Examples of corresponding residues include (i) the catalytic residues of two homologous enzymes and (ii) sites for post-translational modification of a particular type (e.g., phosphorylation) within corresponding structural or functional domains that have similar effects on the structure or function of homologous proteins.

Computer-aided" as used herein encompasses methods in which a computer system is used to gather, process, manipulate, display, visualize, receive, transmit, store, or otherwise handle information (e.g., data, results, structures, sequences, etc.). A method may comprise causing the processor of a computer to execute instructions to gather, process, manipulate, display, receive, transmit, or store data or other information. The instructions may be embodied in a computer program product comprising a computer-readable medium.

"Detection reagent" refers to an agent that is useful to specifically detect a gene product or other analyte of interest, e.g., an agent that specifically binds to the gene product or other analyte. Examples of agents useful as detection reagents include, e.g., nucleic acid probes or primers that hybridize to RNA or DNA to be detected, antibodies, aptamers, or small molecule ligands that bind to polypeptides to be detected, and the like. In some embodiments a detection reagent comprises a label. In some embodiments a detection reagent is attached to a support. Such attachment may be covalent or noncovalent in various embodiments.

Methods suitable for attaching detection reagents or analytes to supports will be apparent to those of ordinary skill in the art. A support may be a substantially planar or flat support or may be a particulate support, e.g., an approximately spherical support such as a microparticle (also referred to as a "bead", "microsphere"), nanoparticle (or like terms), or population of microparticles. In some embodiments a support is a slide, chip, or filter. In some embodiments a support is at least a portion of an inner surface of a well or other vessel, channel, flow cell, or the like. A support may be rigid, flexible, solid, or semi-solid (e.g., gel). A support may be comprised of a variety of materials such as, for example, glass, quartz, plastic, metal, silicon, agarose, nylon, or paper. A support may be at least in part coated, e.g., with a polymer or substance comprising a reactive functional group suitable for attaching a detection reagent or analyte thereto.

"Druggable target" refers to a biological molecule, e.g., a protein or RNA, the level or activity of which is modulatable (capable of being modulated) by a small molecule. In certain embodiments a druggable target is a biological molecule for which at least one small molecule modulator has been identified. In certain embodiments such modulation is detectable in a cell-free assay, e.g., a protein activity assay. In certain embodiments such modulation is detectable in a cell-based assay using a cell that expresses the target. Any suitable assay may be used. One of ordinary skill in the art will be aware of many suitable assays for measuring protein activity and will be able to select an appropriate assay taking into account the known or predicted activit(ies) of the protein. The activity may, for example, be a binding activity, catalytic activity, transporter activity, or any other biological activity. In some embodiments modulation of a target may be detected by at least partial reversal of a phenotype induced by overexpression of the target or by deletion of the gene that encodes the target. In certain embodiments a druggable target is a biological molecule such as a protein or RNA that is known to or is predicted to bind with high affinity to at least one small molecule. In certain embodiments a protein is predicted to be "druggable" if it is a member of a protein family for which other members of the family are known to be modulated by or bind to one or more small molecules. In certain embodiments a protein is predicted to be "druggable" if it has an enzymatic activity that is amenable to the identification of modulators using a cell-free assay. In some embodiments the protein can be produced or purified in active form and has at least one known substrate that can be used to measure its activity An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments The term "expression" encompasses the processes by which nucleic acids (e.g., DNA) are transcribed to produce RNA, and (where applicable) RNA transcripts are processed and translated into polypeptides.

"Gain of function" generally refers to acquisition of a new, altered, and/or abnormal function or increased function as compared with a reference. The reference may be, e.g., a level or average level of function possessed by a normal gene product (e.g., a gene product whose sequence is the same as a reference sequence) or found in healthy cell(s) or subject(s). An average may be taken across any number of values. In certain embodiments the reference level may be the upper limit of a reference range. In certain embodiments the function may be increased by at least 10%, 20%, 30%, 40%, 50%, 60%, 70%, 80%, 90%, 95%, 99%, or 100% of the reference level. In certain embodiments the function may be increased by between 1 to 2-fold, 2 to 5-fold, 5 to 10-fold, 10 to 20-fold, 20 to 50-fold, 50 to 100-fold, or more, of the reference level. In certain embodiments the function may be increased to a level or within a range that has a statistically significant correlation with or demonstrated causative relationship with a neurodegenerative disease. A "gain of function" mutation in a gene results in a change in a gene product of the gene or increases the expression level of the gene product, such that it gains a new and abnormal function or an abnormally increased function as compared with a gene product of a normal gene. The function may be new in that it is distinct from the activit(ies) of the normal gene product or may result from an increase in or dysregulation of a normal activity of the gene product. The altered gene product encoded by a gene harboring a gain of function mutation may, for example, have one or more altered residues that causes the gene product to have the ability to interact with different cellular molecules or structures than does the normal gene product or causes the gene product to be mislocalized or dysregulated. For purposes hereof, gain of function mutations encompass dominant negative mutations. Dominant negative mutations result in an altered gene product that lacks a function of the normal gene product and acts antagonistically to the normal gene product by, for example, competing with the normal gene product in a context such as a binding partner, ligand, component of a multimolecular complex (e.g., an oligomer), or substrate but failing to fulfill the normal function of the gene product in that context. The altered gene product encoded by a gene harboring a dominant negative mutation may, for example, be a truncated or otherwise altered form of the normal gene product that retains sufficient structure to compete with the normal gene product. In some embodiments a phenotype or disease resulting from a gain of function mutation in a diploid cell or organism has an autosomal dominant inheritance pattern. A "function" may be any biological activity of a gene product. A biological activity may be, for example, catalyzing a particular reaction, binding to or transporting a particular molecule or complex, participating in or interfering with a biological process carried out by a cell or cells or within a subject, etc. The particular function(s) resulting from a gain of function mutation or lost due to a loss of function mutation may or may not be known.

The term "gene product" (also referred to herein as "gene expression product" or "expression product") encompasses products resulting from expression of a gene, such as RNA transcribed from a gene and polypeptides arising from translation of such RNA. It will be appreciated that certain gene products may undergo processing or modification, e.g., in a cell. For example, RNA transcripts may be spliced, polyadenylated, etc., prior to mRNA translation, and/or polypeptides may undergo co-translational or post-translational processing such as removal of secretion signal sequences, removal of organelle targeting sequences, or modifications such as phosphorylation, fatty acylation, etc. The term "gene product" encompasses such processed or modified forms. Genomic, mRNA, polypeptide sequences from a variety of species, including human, are known in the art and are available in publicly accessible databases such as those available at the National Center for Biotechnology Information (www.ncbi.nih.gov) or Universal Protein Resource (www.uniprot.org). Databases include, e.g., GenBank, RefSeq, Gene, UniProtKB/SwissProt, UniProtKB/Trembl, and the like. In general, sequences, e.g., mRNA and polypeptide sequences, in the NCBI Reference Sequence database may be used as gene product sequences for a gene of interest. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (dbSNP), available at the NCBI website at www.ncbi.nlm.nih.gov/projects/SNP/. (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). Multiple isoforms of certain proteins may exist, e.g., as a result of alternative RNA splicing or editing. In general, where aspects of this disclosure pertain to a gene or gene product, embodiments pertaining to allelic variants or isoforms are encompassed, if applicable, unless indicated otherwise. Certain embodiments may be directed to particular sequence(s), e.g., particular allele(s) or isoform(s).

"Genetic network" refers to a set of genes characterized in that each gene in the set has at least one interaction with at least one other gene in the set, along with the information indicating the interactions in which the genes are involved, i.e., indicating which pairs of genes interact. Two genes are considered to interact if they genetically interact and/or if they encode gene products (protein or RNA) that physically interact. A genetic network may be represented as a graph, in which genes that interact are connected by lines (edges). The lines may or may not encode information regarding the nature of the interaction and/or the nature of the interactants. Such information may, for example, be encoded in the form of arrows indicating the way in which one gene affects a gene with which it interacts (e.g., which gene is the effector), or by features of the lines such as colors, width, or pattern. A "node" is a gene that interacts with at least two other genes in a network. Each gene in the network represents a "node". Genetic interactions encompass any of the various ways in which a first gene or its encoded gene product(s) can affect a second gene or its encoded gene product(s). The effects of a gene are often accomplished by a gene product encoded by the gene, typically a protein, and such effects are exerted on one or more gene products of another gene or genes. Thus "expression or activity of a gene" should be understood as encompassing the expression or activity of a gene product encoded by the gene. Similarly an "effect on the expression or activity of a gene" typically refers to an effect on the expression or activity of gene product of the gene rather than on the gene itself. Thus, genetic interactions encompass any of the various ways in which the level of expression or activity of a gene product of a first gene can affect the level of expression or activity of a gene product of a second gene or can affect (e.g., suppress or enhance) the phenotypic manifestations of the gene product of the second gene. Examples include, e.g., enhancing or suppressing expression, enhancing or suppressing phenotypic effect, synthetic growth defect, synthetic rescue, synthetic lethality, etc.

"Identity" or "percent identity" is a measure of the extent to which the sequence of two or more nucleic acids or polypeptides is the same. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of $TG_A$ and $TG_B$ (here $TG_A$ and $TG_B$ are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., may be used to generate alignments and/or to obtain a percent identity. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm.nih.gov and/or McGinnis, S. and Madden, T L, W20-W25 Nucleic Acids Research, 2004, Vol. 32, Web server issue. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.) Percent identity may be evaluated over a window of evaluation. In some embodiments a window of evaluation may have a length of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more, e.g., 100%, of the length of the shortest of the sequences being compared. In some embodiments a window of evaluation is at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments no more than 20%, 10%, 5%, or 1% of positions in either sequence or in both sequences over a window of evaluation are occupied by a gap. In some embodiments no more than 20%, 10%, 5%, or 1% of positions in either sequence or in both sequences are occupied by a gap.

"Isolated" means 1) separated from at least some of the components with which it is usually associated in nature; 2) prepared or purified by a process that involves the hand of man; and/or 3) not occurring in nature, e.g., present in an artificial environment. In some embodiments an isolated cell is a cell that has been removed from a subject, generated in vitro, separated from at least some other cells in a cell population or sample, or that remains after at least some other cells in a cell population or sample have been removed or eliminated.

The term "label" (also referred to as "detectable label") refers to any moiety that facilitates detection and, optionally, quantification, of an entity that comprises it or to which it is attached. In general, a label may be detectable by, e.g., spectroscopic, photochemical, biochemical, immunochemical, electrical, optical, chemical or other means. In some embodiments a detectable label produces an optically detectable signal (e.g., emission and/or absorption of light), which can be detected e.g., visually or using suitable instrumentation such as a light microscope, a spectrophotometer, a fluorescence microscope, a fluorescent sample reader, a fluorescence activated cell sorter, a camera, or any device containing a photodetector. Labels that may be used in various embodiments include, e.g., organic materials (including organic small molecule fluorophores (sometimes termed "dyes"), quenchers (e.g., dark quenchers), polymers, fluorescent proteins); enzymes; inorganic materials such as metal chelates, metal particles, colloidal metal, metal and semiconductor nanocrystals (e.g., quantum dots); compounds that exhibit luminescensce upon enzyme-catalyzed oxidation such as naturally occurring or synthetic luciferins (e.g., firefly luciferin or coelenterazine and structurally related compounds); haptens (e.g., biotin, dinitrophenyl, digoxigenin); radioactive atoms (e.g., radioisotopes such as $^3H$, $^{14}C$, $^{32}P$, $^{33}P$, $^{35}S$, $^{125}I$), stable isotopes (e.g., $^{13}C$, $^2H$); magnetic or paramagnetic molecules or particles, etc. Fluorescent dyes include, e.g., acridine dyes; BODIPY, coumarins, cyanine dyes, napthalenes (e.g., dansyl chloride, dansyl amide), xanthene dyes (e.g., fluorescein, rhodamines), and derivatives of any of the foregoing. Examples of fluorescent dyes include Cy3, Cy3.5, Cy5, Cy5.5, Cy7, Alexa® Fluor dyes, DyLight® Fluor dyes, FITC, TAMRA, Oregon Green dyes, Texas Red, to name but a few. Fluorescent proteins include green fluorescent protein (GFP), blue, sapphire, yellow, red, orange, and cyan fluorescent proteins and fluorescent variants such as enhanced GFP (eGFP), mFruits such as mCherry, mTomato, mStrawberry; R-Phycoerythrin, etc. Enzymes useful as labels include, e.g., enzymes that act on a substrate to produce a colored, fluorescent, or luminescent substance. Examples include luciferases, beta-galactosidase, horseradish peroxidase, and alkaline phosphatase. Luciferases include those from various insects (e.g., fireflies, beetles) and marine organisms (e.g., cnidaria such as *Renilla* (e.g., *Renilla reniformis*, copepods such as *Gaussia* (e.g., *Gaussia princeps*) or *Metridia* (e.g., *Metridia longa, Metridia pacifica*), and modified versions of the naturally occurring proteins. A wide variety of systems for labeling and/or detecting labels or labeled entities are known in the art. Numerous detectable labels and methods for their use, detection, modification, and/or incorporation into or conjugation (e.g., covalent or noncovalent attachment) to biomolecules such as nucleic acids or proteins, etc., are described in Iain Johnson, I., and Spence, M. T. Z. (Eds.), *The Molecular Probes® Handbook—A Guide to Fluorescent Probes and Labeling Technologies*. 11th edition (Life Technologies/Invitrogen Corp.) available online on the Life Technologies website at http://www.invitrogen.com/site/us/en/home/References/Molecular-Probes-The-Handbook.html and Hermanson, G T., *Bioconjugate Techniques, $2^{nd}$* ed., Academic Press (2008). Many labels are available as derivatives that are attached to or incorporate a reactive functional group so that the label can be conveniently conjugated to a biomolecule or other entity of interest that comprises an appropriate second functional group (which second functional group may either occur naturally in the biomolecule or may be introduced during or after synthesis). For example, an active ester (e.g., a succinimidyl ester), carboxylate, isothiocyanate, or hydrazine group can be reacted with an amino group; a carbodiimide can be reacted with a carboxyl group; a maleimide, iodoacetamide, or alkyl bromide (e.g., methyl bromide) can be reacted with a thiol (sulfhydryl); an alkyne can be reacted with an azide (via a click chemistry reaction such as a copper-catalyzed or copper-free azide-alkyne cycloaddition). Thus, for example, an N-hydroxysuccinide (NHS)-functionalized derivative of a fluorophore or hapten (such as biotin) can be reacted with a primary amine such as that present in a lysine side chain in a protein or in an aminoallyl-modified nucleotide incorporated into a nucleic acid during synthesis. A label may be directly attached to an entity or may be attached to an entity via a spacer or linking group, e.g., an alkyl, alkylene, aminoallyl, aminoalkynyl, or oligoethylene glycol spacer or linking group, which may have a length of, e.g., between 1 and 4, 4-8, 8-12, 12-20 atoms, or more in various embodiments. A label or labeled entity may be directly detectable or indirectly detectable in various embodiments. A label or labeling moiety may be directly detectable (i.e., it does not require any further reaction or reagent to be detectable, e.g., a fluorophore is directly detectable) or it may be indirectly detectable (e.g., it is rendered detectable through reaction or binding with another entity that is detectable, e.g., a hapten is detectable by immunostaining after reaction with an appropriate antibody comprising a reporter such as a fluorophore or enzyme; an enzyme acts on a substrate to generate a directly detectable signal). A label may be used for a variety of purposes in addition to or instead of detecting a label or labeled entity. For example, a label can be used to isolate or purify a substance comprising the label or having the label attached thereto. The term "labeled" is used herein to indicate that an entity (e.g., a molecule, probe, cell, tissue, etc.) comprises or is physically associated with (e.g., via a covalent bond or noncovalent association) a label, such that the entity can be detected. In some embodiments a detectable label is selected such that it generates a signal that can be measured and whose intensity is related to (e.g., proportional to) the amount of the label. In some embodiments two or more different labels or labeled entities are used or present in a composition. In some embodiments the labels may be selected to be distinguishable from each other. For example, they may absorb or emit light of different wavelengths. In some embodiments the labels may be selected to interact with each other. For example, a first label may be a donor molecule that transfers energy to a second label, which serves as an acceptor molecule through nonradiative dipole—dipole coupling as in resonance energy transfer (RET), e.g., Förster resonance energy transfer (FRET, also commonly called fluorescence resonance energy transfer), "Loss of function" generally refers to reduction of function or absence of function as compared with a reference level. The reference level may be, e.g., a normal or average level of function possessed by a normal gene product or found in a healthy cell or subject. In certain embodiments the reference level may be the lower limit of a reference range. In certain embodiments the function may be reduced by at least 10%, 20%, 30%, 40%, 50%, 60%, 70%, 80%, 90%, 95%, 99%, or 100% of the reference level. A "loss of function" mutation in a gene refers to a mutation that causes loss (reduction or absence) of at least one function normally provided by a gene product of the gene. A loss of function mutation in a gene may result in a reduced total level of a gene product of the gene in a cell or subject that has the mutation (e.g., due to reduced expression of the gene, reduced stability of the gene product, or both), reduced activity per molecule of the gene product encoded by the mutant gene, or both. The reduction in expression, level, activity per molecule, or total function may be partial or complete. A mutation that confers a complete loss of function, or an allele harboring such a mutation, may be referred to as a null mutation or null allele, respectively. In some embodiments a loss of function mutation in a gene results in a reduction of at least 10%, 20%, 30%, 40%, 50%, 60%, 70%, 80%, 90%, 95%, 99%, or 100% in the level or activity of a gene product of the mutant gene, as compared with level or activity of a gene product encoded by a normal allele of the gene. A loss of function mutation may be an insertion, deletion, or point mutation. For example, a point mutation may introduce a premature stop codon, resulting in a truncated version of the normal gene product that lacks at least a portion of a domain that contributes to or is essential for activity, such as a catalytic domain or binding domain, or may alter an amino acid that contributes to or is essential for activity, such as a catalytic residue, site of post-translational modification, etc. In some embodiments a phenotype or disease resulting from a loss of function mutation in a diploid cell or organism has an autosomal recessive inheritance pattern.

"Modulate" as used herein means to decrease (e.g., inhibit, reduce, suppress) or increase (e.g., stimulate, activate, enhance) a level, response, property, activity, pathway, or process. A "modulator" is an agent capable of modulating a level, response, property, activity, pathway, or process. A modulator may be an inhibitor, antagonist, activator, or agonist. In some embodiments modulation may refer to an alteration, e.g., inhibition or increase, of the relevant level, response, property, activity, pathway, or process by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

"Misfolding" refers to a failure of a protein to attain or maintain its normal three-dimensional conformation, e.g., the tertiary structure in which it performs its normal biological function in a cell or organism. In some embodiments misfolding comprises formation of soluble oligomers comprising two, three, or more molecules of the protein (e.g., up to about 10-20 molecules of the protein), wherein the oligomers do not perform a normal function of the protein (e.g., oligomerization is not part of the normal assembly or activation pathway of the protein). In some embodiments misfolding comprises formation of larger protein aggregates, e.g., aggregates of a size sufficient to permit their detection using optical microscopy. In some embodiments an aggregate comprises an amyloid. As known in the art, an amyloid is a protein aggregate characterized by a cross-beta sheet structure. Amyloids are typically composed of ~5-10 nm wide cross-beta fibrils (also called "filaments"), in which the polypeptide chain is arranged in beta-sheets where the polypeptide is perpendicular to the fibril axis and hydrogen bonding is parallel. Amyloids may be identified using methods such as fluorescent dyes, polarimetry, circular dichroism, FTIR, conformation-specific antibodies, or X-ray diffraction. For example, an amyloid can typically be identified by detecting a change in the fluorescence intensity of planar aromatic dyes such as thioflavin T or Congo red upon binding to the amyloid. A "misfolded protein" is a protein that has failed to fold properly, has become unfolded, has folded into an abnormal conformation, and/or has formed a dysfunctional oligomer or larger protein aggregate or is in a conformation in which it is prone to form a dysfunctional oligomer or larger protein aggregate, e.g., an amyloid.

"Nucleic acid" is used interchangeably with "polynucleotide" and encompasses polymers of nucleotides. "Oligonucleotide" refers to a relatively short nucleic acid, e.g., typically between about 4 and about 100 nucleotides (nt) long, e.g., between 8-60 nt or between 10-40 nt long. Nucleotides include, e.g., ribonucleotides or deoxyribonucleotides. In some embodiments a nucleic acid comprises or consists of DNA or RNA. In some embodiments a nucleic acid comprises or includes only standard nucleobases (often referred to as "bases"). The standard bases are cytosine, guanine, adenine (which are found in DNA and RNA), thymine (which is found in DNA) and uracil (which is found in RNA), abbreviated as C, G, A, T, and U, respectively. In some embodiments a nucleic acid may comprise one or more non-standard nucleobases, which may be naturally occurring or non-naturally occurring (i.e., artificial; not found in nature) in various embodiments. In some embodiments a nucleic acid may comprise one or more chemically or biologically modified bases (e.g., alkylated (e.g., methylated) bases), modified sugars (e.g., 2'-O-alkyribose (e.g., 2'-O methylribose), 2'-fluororibose, arabinose, or hexose), modified phosphate groups or modified internucleoside linkages (i.e., a linkage other than a phosphodiester linkage between consecutive nucleosides, e.g., between the 3' carbon atom of one sugar molecule and the 5' carbon atom of another), such as phosphorothioates, 5'-N-phosphoramidites, alkylphosphonates, phosphorodithioates, phosphate esters, alkylphosphonothioates, phosphoramidates, carbamates, carbonates, phosphate triesters, acetamidates, carboxymethyl esters and peptide bonds). In some embodiments a modified base has a label (e.g., a small organic molecule such as a fluorophore dye) covalently attached thereto. In some embodiments the label or a functional group to which a label can be attached is incorporated or attached at a position that is not involved in Watson-Crick base pairing such that a modification at that position will not significantly interfere with hybridization. For example the C-5 position of UTP and dUTP is not involved in Watson-Crick base-pairing and is a useful site for modification or attachment of a label. In some embodiments a "modified nucleic acid" is a nucleic acid characterized in that (1) at least two of its nucleosides are covalently linked via a non-standard internucleoside linkage (i.e., a linkage other than a phosphodiester linkage between the 5' end of one nucleotide and the 3' end of another nucleotide); (2) it incorporates one or more modified nucleotides (which may comprise a modified base, sugar, or phosphate); and/or (3) a chemical group not normally associated with nucleic acids in nature has been covalently attached to the nucleic acid. Modified nucleic acids include, e.g., locked nucleic acids (in which one or more nucleotides is modified with an extra bridge connecting the 2' oxygen and 4' carbon i.e., at least one 2'-O,4'-C-methylene-β-D-ribofuranosyl nucleotide), morpholinos (nucleic acids in which at least some of the nucleobases are bound to morpholine rings instead of deoxyribose or ribose rings and linked through phosphorodiamidate groups instead of phosphates), and peptide nucleic acids (in which the backbone is composed of repeating N-(2-aminoethyl)-glycine units linked by peptide bonds and the nucleobases are linked to the backbone by methylene carbonyl bonds). Modifications may occur anywhere in a nucleic acid. A modified nucleic acid may be modified throughout part or all of its length, may contain alternating modified and unmodified nucleotides or internucleoside linkages, or may contain one or more segments of unmodified nucleic acid and one or more segments of modified nucleic acid. A modified nucleic acid may contain multiple different modifications, which may be of different types. A modified nucleic acid may have increased stability (e.g., decreased susceptibility to spontaneous or nuclease-catalyzed hydrolysis) or altered hybridization properties (e.g., increased affinity or specificity for a target, e.g., a complementary nucleic acid), relative to an unmodified counterpart having the same nucleobase sequence. In some embodiments a modified nucleic acid comprises a modified nucleobase having a label covalently attached thereto. Non-standard nucleotides and other nucleic acid modifications known in the art as being useful in the context of nucleic acid detection reagents, RNA interference (RNAi), aptamer, or antisense-based molecules for research or therapeutic purposes are contemplated for use in various embodiments of the instant invention. See, e.g., *The Molecular Probes® Handbook—A Guide to Fluorescent Probes and Labeling Technologies* (cited above), *Bioconjugate Techniques* (cited above), Crooke, S T (ed.) *Antisense drug technology: principles, strategies, and applications*, Boca Raton: CRC Press, 2008; Kurrcek. J. (ed.) *Therapeutic oligonucleotides*, RSC biomolecular sciences. Cambridge: Royal Society of Chemistry, 2008. A nucleic acid can be single-stranded, double-stranded, or partially double-stranded. An at least partially double-stranded nucleic acid can have one or more overhangs, e.g., 5' and/or 3' overhang(s). Where a nucleic acid sequence is disclosed herein, it should be understood that its complement and double-stranded form is also disclosed.

A "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. In some embodiments, a non-standard, naturally occurring amino acid is found in mammals. For example, ornithine, citrulline, and homocysteine are naturally occurring non-standard amino acids that have important roles in mammalian metabolism. Examples of non-standard amino acids include, e.g., singly or multiply halogenated (e.g., fluorinated) amino acids, D-amino acids, homo-amino acids, N-alkyl amino acids (other than proline), dehydroamino acids, aromatic amino acids (other than histidine, phenylalanine, tyrosine and tryptophan), and $\alpha,\alpha$ disubstituted amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, etc. Modifications may occur anywhere in a polypeptide, e.g., the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like. Modification may occur prior to or after an amino acid is incorporated into a polypeptide in various embodiments. Polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing.

As used herein, the term "toxic agent" refers to a substance that causes damage to cell function or structure or is metabolized or otherwise converted to such a substance when present in a cell or in the environment of a cell. Toxic agents include, e.g., oxidative stressors, nitrosative stressors, proteasome inhibitors, inhibitors of mitochondrial function, ionophores, inhibitors of vacuolar ATPases, inducers of endoplasmic reticulum (ER) stress, and inhibitors of endoplasmic reticulum associated degradation (ERAD). In some embodiments a toxic agent selectively causes damage to nervous system tissue. Toxic agents include agents that are directly toxic and agents that are metabolized to or give rise to substances that are directly toxic. It will be understood that the term "toxic agent" typically refers to agents that are not ordinarily present in a cell's normal environment at sufficient levels to exert detectable damaging effects. Typically they exert damaging effects when present at a relatively low concentration, e.g., at or below 1 mM, e.g., at or below 500 μM, e.g., at or below 100 μM. It will be understood that a toxic agent typically has a threshold concentration below which it does not exert detectable damaging effects. The particular threshold concentration will vary depending on the agent and, potentially, other factors such as cell type, other agents present in the environment, etc. Exemplary threshold concentrations may be in the range of 1 nM to 100 nM, 100 nM to 1 μm, 1 μm to 10 μm, or 10 μm to 100 μm. "Oxidative stressor" refers to an agent that causes an increase in the level of reactive oxygen species and/or a decrease in a biological system's ability to detoxify the reactive species or intermediates generated through their activity or to repair the resulting damage (e.g., damage to DNA or other biomolecules), resulting in impairment to the structure and/or function of the system. "Nitrosative stressor" refers to an agent that causes an increase in the level of reactive nitrogen species and/or a decrease in a biological system's ability to detoxify the reactive species or intermediates generated through their activity or to repair the resulting damage (e.g., damage to DNA or other biomolecules), resulting in impairment to the structure and/or function of the system. Proteasome inhibitors include, e.g., MG-132 (CAS number 133407-82-6) and bortezomib. Inhibitors of mitochondrial function include, e.g., inhibitors of mitochondrial oxidative phosphorylation such as compounds that inhibit any of mitochondrial complexes I-V, e.g., complex I inhibitors. Inhibitors of vacuolar ATPases include, e.g., bafilomycins and concanamycins. Inhibitors of ERAD include, e.g., eeyarestatin I or eeyarestatin II (Fiebiger, E., et al. (2004) Dissection of the dislocation pathway for type I membrane proteins with a new small molecule inhibitor, eeyarestatin. Mol. Biol. Cell 15, 1635-1646). Agents that selectively cause degeneration of dopaminergic neurons include, e.g., MPTP, MPP+, 6-hydroxydopamine, noralsolinol, and rotenone.

As used herein, the term "purified" refers to agents that have been separated from most of the components with which they are associated in nature or when originally generated or with which they were associated prior to purification. In general, such purification involves action of the hand of man. Purified agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate.

A "reference range" for a value, e.g., a reference range for a value associated with a gene product, biological activity, cell, or subject, refers to the range into which 95%, or in some embodiments 90%, of the values measured from normal or control gene products or healthy cells or subjects fall, or a range that encompasses only values that do not have a statistically significant correlation with neurodegenerative diseases in general or with a particular neurodegenerative disease of interest as compared to the average value in healthy cells or subjects. A reference range may be established from a representative sample of a population. In some embodiments a reference range may be established by performing measurements on gene products or healthy cells obtained from multiple subjects who are apparently healthy or at least free of a particular neurodegenerative disease of interest and not known to be at increased risk of developing the disease.

The term "sample" may be used to generally refer to an amount or portion of something. A sample may be a smaller quantity taken from a larger amount or entity; however, a complete specimen may also be referred to as a sample where appropriate. A sample is often intended to be similar to and representative of a larger amount of the entity of which it is a sample. In some embodiments a sample is a quantity of a substance that is or has been or is to be provided for assessment (e.g., testing, analysis, measurement) or use. A sample may be any biological specimen. In some embodiments a sample comprises a body fluid such as blood, cerebrospinal fluid, (CSF), sputum, lymph, mucus, saliva, a glandular secretion, or urine. In some embodiments a sample comprises cells, tissue, or cellular material (e.g., material derived from cells, such as a cell lysate or fraction thereof). A sample may be obtained from (i.e., originates from, was initially removed from) a subject. Methods of obtaining biological samples from subjects are known in the art and include, e.g., tissue biopsy, such as excisional biopsy, incisional biopsy, core biopsy; fine needle aspiration biopsy; surgical excision, brushings; lavage; or collecting body fluids that may contain cells, such as blood, sputum, lymph, mucus, saliva, or urine. A sample is often intended to be similar to and representative of a larger amount of the entity of which it is a sample. A sample of a cell line comprises a limited number of cells of that cell line. In some embodiments a sample may be obtained from an individual who has been diagnosed with or is suspected of having a neurodegenerative disease. In some embodiments a sample is obtained from skin or blood. In some embodiments a sample contains at least some intact cells. In some embodiments a sample retains at least some of the microarchitecture of a tissue from which it was removed. A sample may be subjected to one or more processing steps, e.g., after having been obtained from a subject, and/or may be split into one or more portions. The term sample encompasses processed samples, portions of samples, etc., and such samples are, where applicable, considered to have been obtained from the subject from whom the initial sample was removed. A sample may be procured directly from a subject, or indirectly, e.g., by receiving the sample from one or more persons who procured the sample directly from the subject, e.g., by performing a biopsy, surgery, or other procedure on the subject. In some embodiments a sample may be assigned an identifier (ID), which may be used to identify the sample as it is transported, processed, analyzed, and/or stored. In some embodiments the sample ID corresponds to the subject from whom the sample originated and allows the sample and/or results obtained by assessing the sample to be matched with the subject. In some embodiments the sample has an identifier affixed thereto.

A "small molecule" as used herein, is an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

"Specific binding" generally refers to a physical association between a target molecule (e.g., a polypeptide) or complex and a binding agent such as an antibody, aptamer or ligand. The association is typically dependent upon the presence of a particular structural feature of the target such as an antigenic determinant, epitope, binding pocket or cleft, recognized by the binding agent. For example, if an antibody is specific for epitope A, the presence of a polypeptide containing epitope A or the presence of free unlabeled A in a reaction containing both free labeled A and the binding agent that binds thereto, will typically reduce the amount of labeled A that binds to the binding agent. It is to be understood that specificity need not be absolute but generally refers to the context in which the binding occurs. For example, it is well known in the art that antibodies may in some instances cross-react with other epitopes in addition to those present in the target. Such cross-reactivity may be acceptable depending upon the application for which the antibody is to be used. One of ordinary skill in the art will be able to select binding agents, e.g., antibodies, aptamers, or ligands, having a sufficient degree of specificity to perform appropriately in any given application (e.g., for detection of a target molecule). It is also to be understood that specificity may be evaluated in the context of additional factors such as the affinity of the binding agent for the target versus the affinity of the binding agent for other targets, e.g., competitors. If a binding agent exhibits a high affinity for a target molecule that it is desired to detect and low affinity for nontarget molecules, the binding agent will likely be an acceptable reagent. Once the specificity of a binding agent is established in one or more contexts, it may be employed in other contexts, e.g., similar contexts such as similar assays or assay conditions, without necessarily re-evaluating its specificity. In some embodiments specificity of a binding agent can be tested by performing an appropriate assay on a sample expected to lack the target (e.g., a sample from cells in which the gene encoding the target has been disabled or effectively inhibited) and showing that the assay does not result in a signal significantly different to background. In some embodiments, a first entity (e.g., molecule, complex) is said to "specifically bind" to a second entity if it binds to the second entity with substantially greater affinity than to most or all other entities present in the environment where such binding takes place and/or if the two entities bind with an equilibrium dissociation constant, $K_d$, of $10^{-4}$ or less, e.g., $10^{-5}$ M or less, e.g., $10^{-6}$ M or less, $10^{-7}$ M or less, $10^{-8}$ M or less, $10^{-9}$ M or less, or $10^{-10}$ M or less. $K_d$ can be measured using any suitable method known in the art, e.g., surface plasmon resonance-based methods, isothermal titration calorimetry, differential scanning calorimetry, spectroscopy-based methods, etc. "Specific binding agent" refers to an entity that specifically binds to another entity, e.g., a molecule or molecular complex, which may be referred to as a "target". "Specific binding pair" refers to two entities (e.g., molecules or molecular complexes) that specifically bind to one another. Examples are biotin-avidin, antibody-antigen, complementary nucleic acids, receptor-ligand, etc.

A "subject" may be any vertebrate organism in various embodiments. A subject may be individual to whom an agent is administered, e.g., for experimental, diagnostic, and/or therapeutic purposes or from whom a sample is obtained or on whom a procedure is performed. In some embodiments a subject is a mammal, e.g. a human, non-human primate, or rodent (e.g., mouse, rat, rabbit). In some embodiments a human subject is at least 50, 60, 70, 80, or 90 years old.

"Treat", "treating" and similar terms as used herein in the context of treating a subject refer to providing medical and/or surgical management of a subject. Treatment may include, but is not limited to, administering an agent or composition (e.g., a pharmaceutical composition) to a subject. Treatment is typically undertaken in an effort to alter the course of a disease (which term is used to indicate any disease, disorder, syndrome or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease.

A "variant" of a particular polypeptide or polynucleotide has one or more additions, substitutions, and/or deletions with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polypeptide or polynucleotide comprises or consists of a polypeptide or polynucleotide that is at least 70%, 80%, 90%, 95%, 96%, 97%, 98%, 99%, or more identical in sequence to the original polypeptide or polynucleotide over at least 50%, 60%, 70%, 80%, 90%, 95%, 96%, 97%, 98%, 99%, or 100% of the original polypeptide or polynucleotide. In some embodiments the sequence of a variant polypeptide comprises or consists of a sequence that has N amino acid differences with respect to an original sequence, wherein N is any integer up to 1%, 2%, 5%, or 10% of the number of amino acids in the original polypeptide, where an "amino acid difference" refers to a substitution, insertion, or deletion of an amino acid. In some embodiments a substitution is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another in a conservative substitution. Certain conservative substitutions are substituting an amino acid in one row of the third column corresponding to a block in the second column with an amino acid from another row of the third column within the same block in the second column.

TABLE A

| | | |
|---|---|---|
| Aliphatic | Non-polar | G A P |
| | | I L V |
| | Polar - ucharged | C S T M |
| | | N Q |
| | Polar - charged | D E |
| | | K R |
| Aromatic | | H F W Y |

In some embodiments, proline (P), cysteine (C), or both are each considered to be in an individual group. Within a particular group, certain substitutions may be of particular interest in certain embodiments, e.g., replacements of leucine by isoleucine (or vice versa), serine by threonine (or vice versa), or alanine by glycine (or vice versa).

In some embodiments a variant is a biologically active variant, i.e., the variant at least in part retains at least one activity of the original polypeptide or polynucleotide. In some embodiments a variant at least in part retains more than one or substantially all known biologically significant activities of the original polypeptide or polynucleotide. An activity may be, e.g., a catalytic activity, binding activity, ability to perform or participate in a biological structure or process, etc. In some embodiments an activity of a variant may be at least 10%, 20%, 30%, 40%, 50%, 60%, 70%, 80%, 90%, 95%, or more, of the activity of the original polypeptide or polynucleotide, up to approximately 100%, approximately 125%, or approximately 150% of the activity of the original polypeptide or polynucleotide, in various embodiments. In some embodiments a variant, e.g., a biologically active variant, comprises or consists of a polypeptide at least 95%, 96%, 97%, 98%, 99%, 99.5% or 100% identical to an original polypeptide over at least 70%, 75%, 80%, 85%, 90%, 95%, 96%, 97%, 98%, or 99% or 100% of the original polypeptide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. Variants may be tested in one or more suitable assays to assess activity.

A "vector" may be any of a number of nucleic acid molecules or viruses or portions thereof that are capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses), vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA such as an shRNA or miRNA precursor). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EFlalpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase I promoter, e.g., a promoter for transcription of ribosomal RNA (other than 5S rRNA) or a functional variant thereof is used. In some embodiments, a promoter that ordinarily directs transcription by a eukaryotic RNA polymerase III (a "pol III promoter"), e.g., (a U6, H1, 7SK or tRNA promoter or a functional variant thereof) may be used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. Examples of virus vectors that may be used in mammalian cells include, e.g., adenoviruses, adeno-associated viruses, poxviruses such as vaccinia viruses and attenuated poxviruses, retroviruses (e.g., lentiviruses), Semliki Forest virus, Sindbis virus, etc. In some embodiments, regulatable (e.g., inducible or repressible) expression control element(s), e.g., a regulatable promoter, is/are used so that expression can be regulated, e.g., turned on or increased or turned off or decreased. For example, the tetracycline-regulatable gene expression system (Gossen & Bujard, Proc. Natl. Acad. Sci. 89:5547-5551, 1992) or variants thereof (see, e.g., Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390 for examples) can be employed to provide inducible or repressible expression. Other inducible/repressible systems may be used in various embodiments. For example, expression control elements that can be regulated by small molecules such as artificial or naturally occurring hormone receptor ligands (e.g., steroid receptor ligands such as naturally occurring or synthetic estrogen receptor or glucocorticoid receptor ligands), tetracycline or analogs thereof, metal-regulated systems (e.g., metallothionein promoter) may be used in certain embodiments. In some embodiments, tissue-specific or cell type specific regulatory element(s) may be used, e.g., in order to direct expression in one or more selected tissues or cell types. In some embodiments a vector capable of being stably maintained and inherited as an episome in mammalian cells (e.g., an Epstein-Ban virus-based episomal vector) may be used. In some embodiments a vector may comprise a polynucleotide sequence that encodes a polypeptide, wherein the polynucleotide sequence is positioned in frame with a nucleic acid inserted into the vector so that an N- or C-terminal fusion is created. In some embodiments the polypeptide encoded by the polynucleotide sequence may be a targeting peptide. A targeting peptide may comprise a signal sequence (which directs secretion of a protein) or a sequence that directs the expressed protein to a specific organelle or location in the cell such as the nucleus or mitochondria. In some embodiments the polypeptide comprises a tag. A tag may be useful to facilitate detection and/or purification of a protein that contains it. Examples of tags include polyhistidine-tag (e.g., 6x-His tag), glutathione-S-transferase, maltose binding protein, NUS tag, SNUT tag, Strep tag, epitope tags such as V5, HA, Myc, or FLAG. In some embodiments a protease cleavage site is located in the region between the protein encoded by the inserted nucleic acid and the polypeptide, allowing the polypeptide to be removed by exposure to the protease.

II. Cross-Species Platform for Neurodegenerative Disease Discovery

The present disclosure provides the insight that the use of yeast models for neurodegenerative diseases and neurodegeneration-associated clinical phenotypes in conjunction with human induced nervous system cells that serve as models for the disease or clinical phenotype represents a powerful cross-species platform for drug discovery and functional genomics. In some aspects, the present disclosure provides methods that use yeast and induced human nervous system cells in the identification of genes, genetic interactions, pathways, and/or pathological processes that play a role in neurodegenerative diseases. In some aspects, the present disclosure provides methods that use yeast and induced human nervous system cells in neurodegenerative disease-focused drug discovery.

Yeast, e.g., the baker's yeast *Saccharomyces cerevisiae*, has significant advantages as an experimental system. Yeast are straightforward to culture and maintain, have a short generation time, and are highly genetically tractable, meaning that they can be genetically modified, rapidly, predictably, and with high precision using well known and available techniques and reagents, and are amenable to high throughput chemical and genetic screens. Minimal genetic and epigenetic variation within strains contributes to screen reproducibility. Extensive genetic and protein interaction analysis in yeast means that considerable information regarding the yeast interactome, i.e., the set of physical interactions among molecules in a cell and interactions among genes, i.e., genetic interactions, in yeast cells is available. Molecular interactions can occur between molecules belonging to different biochemical families (proteins, nucleic acids, lipids, carbohydrates, etc.) and also within a given family (e.g., protein-protein interactions). While yeast cells lack the complexity of a multicellular organism with a nervous system, the highly conserved genome and eukaryotic cellular machinery that they share with human cells affords the possibility of understanding basic cell-autonomous mechanisms and physical and genetic interactions underlying complex disease processes.

As described further herein, a wide variety of neurodegenerative diseases can be modeled in yeast. For example, a number of neurodegenerative diseases are characterized by aggregation of particular proteins or gain-of-function mutations in certain genes. Yeast cells that are engineered to express an aggregation-prone protein or a protein that harbors a gain-of-function mutation associated with a neurodegenerative disease can exhibit phenotypes that are also observed in human neurons or glial cells derived from patients suffering from the disease and, when expressed at sufficient levels, such proteins are toxic to yeast. Such yeast cells serve as models for the neurodegenerative disease. A number of neurodegenerative diseases are characterized by loss-of-function mutations in certain genes, many of which have homologs in yeast. Yeast that are engineered to have a loss of function of the corresponding yeast homolog serve as models for the neurodegenerative disease. Certain yeast models have been used in chemical and genetic screens that have identified useful compounds and novel genetic interactions relevant to neurodegenerative diseases.

Induced nervous system cells are cells that have been derived in vitro, e.g., from a pluripotent cell such as an embryonic stem cell or induced pluripotent stem cell or by transdifferentiation from a non-neuronal cell, and that exhibit features characteristic of a nervous system cell, such as morphology and expression of cellular marker(s) characteristic of a nervous system cell. An induced nervous system cell may be, for example, an induced neuron, an induced glial cell, an induced neural progenitor cell, or an induced neural stem cell. The term "induced nervous system cell" includes cells that are descended from an induced nervous system cell so long as they exhibit features characteristic of a nervous system cell. Human induced nervous system cells have significant potential as cellular models for neurodegenerative diseases. However, the process of deriving mature, differentiated induced nervous system cells is time-consuming, labor-intensive, and expensive, and the resulting cell cultures may be heterogeneous. For example, the cell cultures obtained using the same differentiation protocol may contain cells with different cellular phenotypes in different proportions. These factors can hinder the use of induced nervous system cells in drug discovery and functional genomics. In some aspects, compositions and/or methods described herein provide for more effective utilization of human induced nervous system cells in neurodegenerative disease drug discovery. As described further herein, a wide variety of neurodegenerative diseases can be modeled in human induced nervous system cells.

In some aspects, methods described herein that make use of yeast models in conjunction with human induced nervous system cells provide for more effective utilization of yeast and/or human induced nervous system cells in neurodegenerative disease drug discovery. In some aspects, the invention provides methods that utilize yeast cells for the identification of disease-associated phenotypes that are conserved in human induced nervous system cells. In some aspects, the invention provides methods for the identification of druggable targets for neurodegenerative disease drug discovery and the matching of those targets with particular patient populations who are likely to benefit from compounds that modulate those targets. In some embodiments targets are identified in yeast-based genetic and/or chemical screens. In some embodiments targets are identified through analysis of genetic networks comprising yeast genes identified in yeast-based genetic and/or chemical screens, and/or human homologs of such genes. In some embodiments the relevance of the targets is confirmed by testing the effect of compounds, e.g., small molecules, identified in yeast on human induced nervous system cells that serve as models for a neurodegenerative disease and confirming that the compound reduces the level of a phenotype associated with the neurodegenerative disease. In some embodiments a biological pathway or process which is modulated by the compound is identified in yeast. In some embodiments a molecular target of a compound is identified in yeast, e.g., using genetic approaches, chemical genetic approaches, biochemical approaches, or a combination thereof. In some embodiments one or more analogs of the compound are synthesized. In some embodiments the compound or an analog of the compound serves as a candidate therapeutic agent.

In general, neurodegenerative diseases of interest herein can be classified into three major groups, as follows:

(1) Neurodegenerative diseases in which a known human protein or RNA aggregates and/or in which there is a known detrimental gain of function mutation in such a protein or RNA or in which there is increased expression of the protein or RNA (e.g., due to the patient having one or more extra copies of the gene). Examples of such proteins and neurodegenerative diseases in which they aggregate and/or are mutated or overexpressed include alpha-synuclein (Parkinson's disease and other disorders characterized by parkinsonism), A-beta (Alzheimer's disease), polyglutamine-expanded genes (Huntington's disease, ataxias). A yeast model for such disease can be generated by overexpression of the relevant wild type or mutant human protein in yeast. As discussed further herein, such proteins when overexpressed can exert toxic effects in yeast. The toxicity can be exploited to identify compounds that alleviate the toxic effects and genes that, when overexpressed or deleted, alleviate the toxic effects. A human nervous system cell model for such diseases can be produced by generating induced human nervous system cells from patients suffering from the disease or who have a genotype associated with the disease or by engineered inducible overexpression in human nervous system cells derived from pluripotent cells or derived by transdifferentiation from non-neuronal cells or derived from neural precursors.

(2) Neurodegenerative diseases in which there is a known loss of function of a protein (e.g., due to mutation) or and the protein has a yeast homolog. A yeast model for this group can be created by mutation or deletion of or otherwise disabling the yeast homolog. A human nervous system cell model for such diseases can be produced by generating induced human nervous system cells from patients suffering from the disease or who have a genotype associated with the disease or by engineering a gene targeted mutation or deletion in the gene or otherwise disabling the gene in human nervous system cells derived from pluripotent cells or derived by transdifferentiation from non-neuronal cells or derived from neural precursors.

(3) This group is a subcategory of the first group in which there is also a mutation or genetic variation in a human modifier gene (genetic modifier of the neurodegenerative disease) that has a yeast homolog. Patients having a disease in this group can be identified by various approaches such as sequencing known human modifier genes or any other type of genotyping method known in the art. Diseases in this group can be modeled in yeast by a combination of the appropriate yeast model of group (1) (i.e., the yeast model generated by overexpressing the protein) together with a mutation or deletion of or otherwise disabling the yeast homolog. Diseases in this group can be modeled in human nervous system cells either by generating an induced human neuron from a patient with the disease or by a combination of the appropriate engineered human nervous system cell model of group (1) together with engineering a gene targeted mutation or deletion in the human modifier gene or otherwise disabling the human modifier gene in human nervous system cells derived from pluripotent cells or derived by transdifferentiation from non-neuronal cells or derived from neural precursors.

It should be understood that the yeast models and human nervous system cell models can be generated using any of a wide variety of methods known in the art for genetically modifying yeast and human cells. Certain useful methods are described herein but it should be understood that the invention is not limited in this respect. Also, while the dual use of yeast models and corresponding human cellular models is described herein with particular reference to neurodegenerative diseases, it is contemplated that the approach may be applied to any mammalian diseases characterized by protein aggregation or gain-of-function mutations and any mammalian diseases characterized by loss-of-function mutations in human genes that have yeast homologs. The appropriate human cellular models may be generated by engineering of human pluripotent cells or precursor cells followed by differentiation into the relevant human cell types affected by the disease, or by directly engineering the appropriate cell types, as appropriate for the disease.

Certain aspects of the invention pertain to arranging genetic modifiers identified in yeast, sometimes together with human homologs of such yeast genes, into networks that convey useful information about cellular pathways that are implicated in neurodegenerative diseases. The networks may be represented as graphs, in which the genes (or, equivalently, the gene products encoded by the genes) are the nodes, and interactions are represented as lines connecting interacting nodes (genes). In some embodiments such genetic networks are augmented by including additional human genes such as known genetic modifiers of the neurodegenerative disease, human genes that interact with human homologs of yeast genetic modifiers, or both. In some embodiments such genetic networks facilitate the identification of disease-associated phenotypes that are present in human patient-derived neurons and facilitate identification of druggable targets for identification of compounds that can modulate neurodegenerative disease-associated phenotypes and serve as candidate therapeutic agents.}}

In some aspects, the present invention provides methods can identify genetic networks relevant to either gain-of-function or loss-of-function of neurodegeneration-associated genes. In certain embodiments the methods cross-compare existing human genetic datasets (e.g., datasets that identify human genes associated with neurodegenerative diseases) and dataset obtained from unbiased genetic screens in yeast to find novel connections between disparate genetic factors. "Unbiased" in this context means that the screens do not rely on pre-conceived notions (based on pathology or clinical phenotype) about the relationships between human genes that have been implicated in the disease. In certain embodiments the genetic networks identify biological pathways and processes that are implicated as being involved in neurodegenerative disease, e.g., biological pathways and processes the dysfunction of which contributes to or at least in part causes a neurodegenerative disease. In some embodiments such methods are used in coordination with small molecule screens and chemical genetic approaches to identify druggable nodes within these genetic networks. In certain embodiments genes identified as druggable nodes, and their gene products, are druggable targets for identification of compounds that modulate the biological pathways and processes in which they are involved. In certain embodiments the small molecule screens yield compounds that modulate one or more such genes or proteins that are druggable nodes in a genetic network identified as described herein. In certain embodiments the compounds may serve as hits or lead compounds for the development of analogs with one or more improved properties relative to an initial hit or lead. According to certain aspects of the invention such findings, e.g., druggable targets and compounds that modulate them, can be directly brought to bear on appropriate patient populations by, for example, demonstrating that genes or small molecules identified in yeast can reverse these phenotypes in patient neurons.

In some aspects, methods of the present invention are useful in identifying patients who would benefit from treatment with compounds that target particular biological pathways or processes identified as implicated in the disease at least in part through use of yeast models. For example, genetic or chemical screening in a yeast model of a neurodegenerative disease is used to identify a conserved biological pathway or process implicated in the disease or a conserved druggable target. Human patients who have mutations or genetic variations in a human gene that is either in the biological pathway or is involved in the biological process, or is connected to such a gene through a genetic network, are candidates for treatment with a compound that modulates the biological pathway or process or druggable target. In some instances, the biological pathway or process or druggable target is identified through use of a chemical screen in yeast, in which case compounds identified in the screen, or analogs thereof, are candidate compounds for treating the disease, e.g., in patients who have mutations or genetic variations in a human gene that is either in the biological pathway or is involved in the biological process, or is connected to such a gene through a genetic network.

Thus, certain aspects of the invention allow for dividing patients suffering from a neurodegenerative disease into different groups (stratifying) based on their having mutations or genetic variations in genes that are involved in or connected to a biological pathway or process identified in yeast as being implicated in the disease, and identifying compounds that are particularly appropriate for treating such patients, i.e., compounds that modulate the same biological pathway or process. The relevance of the biological pathway or process can be confirmed in human neurons derived from such patients by demonstrating that modulation of the biological pathway or process, e.g., through use of a compound identified in yeast, affects a disease-associated phenotype in such cells. The phenotype may be identified through the use of yeast, as described herein in the case of nitrosative stress and ERAD substrate accumulation, which were identified as phenotypes associated with alpha-synuclein expression in yeast and confirmed to be disease-associated phenotypes in neurons derived from a patient with a gain-of-function mutation in alpha synuclein. The compound identified in yeast may be a candidate therapeutic agent for treating patients having mutations or genetic variations in genes that are involved in or connected to a biological pathway or process or may be used as a starting point for the design of analogs suitable for treating such patients. Certain methods of the invention thus allow for dividing patients with neurodegenerative diseases into therapeutically relevant categories based on their genotype and/or based on particular phenotypes that are detectable in neurons derived from them. Certain methods of the invention allow for the identification of compounds that are particularly suited for treating patients in a particular genotypic or phenotypic category. It should be noted that the patients may not have been diagnosed as having a specific neurodegenerative disease based on clinical criteria. For example, the patient may have symptoms that could be consistent with any of a number of different diseases. The patient can be genotyped or "phenotyped" (i.e., human neurons derived from the patient can be examined to determine which biological pathways or processes are defective in the patient), and an appropriate compound can be selected accordingly. Genotyping can also allow more effective prophylactic treatment of patients before they become symptomatic or early in the disease. In some aspects, methods of the invention provide for more personalized treatment of neurodegenerative diseases. In some embodiments a yeast or induced nervous system model is generated for a particular patient, or an existing yeast or induced nervous system model that matches the patient's genotype is selected. Information obtained from the yeast and/or induced nervous system cell model, such as the identity of specific compounds that reduce disease-associated phenotypes in such models, is used to identify a therapeutic agent suitable for the patient. In some aspects, information regarding the genotypic and phenotypic categories may be stored on a non-transitory computer-readable medium, e.g., in a database. Information identifying patients and which category(ies) they fall into may be stored as well.

Abnormalities in the level or activity of particular proteins or RNAs in the nervous system cause or contribute to numerous neurodegenerative diseases and disease processes. In some aspects, described herein are compositions and methods useful for identifying, selecting, and/or characterizing agents that modulate, e.g., inhibit, cellular toxicity or cellular dysfunction caused at least in part by abnormal level or activity of a gene product encoded by a neurodegenerative disease gene. As used herein, a "neurodegenerative disease gene" is a gene that encodes a gene product whose abnormal level or activity in the nervous system (e.g., in neurons, glial cells, or both) is associated with a neurodegenerative disease. Such a gene is said to be associated with the neurodegenerative disease. The term "neurodegenerative disease gene" encompasses genes that encode neurodegeneration associated proteins or neurodegeneration associated RNAs and genes whose loss of function is associated with a neurodegenerative disease. In various embodiments abnormal level of activity of a gene product encoded by a neurodegenerative disease gene associated with a neurodegenerative disease may be a cause of the neurodegenerative disease (e.g., wherein the disease has an autosomal dominant or recessive inheritance pattern associated with mutations in the gene) and/or may increase the risk of developing the disease. In some embodiments the abnormal level or activity of the gene product may cause or contribute to damage to, dysfunction, or death of neurons, glial cells, or both. In some embodiments the neurodegenerative disease is an inherited single-gene disease, i.e., the disease can result from a mutation in a specific gene or, in some embodiments, from a mutation in any one of a variety of different genes, and has a dominant or recessive inheritance pattern. In some embodiments the disease has both a sporadic form that does not have a dominant or recessive inheritance pattern and an inherited (familial) form that has a dominant or recessive inheritance pattern.

In some aspects, described herein are compositions and methods useful for identifying, selecting, and/or characterizing agents that modulate, e.g., inhibit, cellular toxicity induced by a neurodegeneration associated gene product. In certain embodiments the gene product is a neurodegeneration associated protein. As used herein, the term "neurodegeneration associated protein" (NAP) refers to a protein that (i) accumulates in a misfolded form in at least a portion of the nervous system in individuals suffering from a neurodegenerative disease and is associated with damage to, dysfunction of, and/or death of neurons, glial cells, or both; (ii) is characterized in that a gain of function mutation in the gene that encodes the protein is associated with damage to, dysfunction of, and/or death of neurons, glial cells, or both, in individuals suffering from a neurodegenerative disease; or (iii) both (ii) and (ii). In some embodiments the gene product is a neurodegeneration associated RNA. As used herein, the term "neurodegeneration associated RNA" (NAR) refers to an RNA that (a) accumulates aberrantly in at least a portion of the nervous system in individuals suffering from a neurodegenerative disease and is associated with damage to, dysfunction of, and/or death of neurons, glial cells, or both, in individuals suffering from a neurodegenerative disease; (b) is characterized in that a known mutation in the gene that encodes the RNA is associated with damage to, dysfunction of, and/or death of neurons, glial cells, or both, in individuals suffering from a neurodegenerative disease; or (c) both (a) and (b).

In some embodiments the misfolded protein forms intracellular and/or extracellular aggregates that can be detected as intracellular or extracellular inclusions or deposits on histopathological examination of nervous system tissue using suitable techniques such as optical microscopy with appropriate stains and/or immunohistochemical detection using antibodies that bind to proteins present in the aggregates. For example, a spectrum of neurodegenerative diseases referred to as "synucleinopathies", including Parkinson's disease (PD), dementia with Lewy bodies (DLB), multiple system atrophy (MSA), the Lewy body variant of Alzheimer's disease, and pure autonomic failure are characterized by cytoplasmic aggregates containing alpha-synuclein, termed Lewy bodies. In some embodiments a synucleinopathy is Parkinsons's disease. In some embodiments a synucleinopathy may be neurodegeneration with brain iron accumulation (NBIA), e.g., NBIA2 (also called PLA2G6-associated neurodegeneration) or NBIA4 (associated with mutations in C19orf72). Aggregation of αSyn in cortical neurons is associated with the dementia that commonly accompanies PD, known as Parkinson disease dementia (PDD), and the closely related condition known as dementia with Lewy bodies (DLB).

Amyloid beta (Aβ or Abeta) peptides are the main component of amyloid plaques, which are found in the brains of patients with Alzheimer's disease (AD).

Abnormal cytoplasmic aggregates containing TDP-43 are found in neurons in a number of neurodegenerative diseases referred to as "TDP-43 proteinopathies", including subgroups of frontotemporal lobar degeneration (FTLD) and amyotrophic lateral sclerosis (ALS), which are sometimes referred to as FTLD-TDP and ALS-TDP. FUS has recently emerged as a significant disease-associated protein in subgroups of ALS and FTLD characterized by immunoreactivity of the neuronal inclusions for FUS and ubiquitin and may be negative for TDP-43, which are sometimes referred to as ALS-FUS and FTLD-FUS, respectively. Disease entities that are considered subtypes of FTLD-FUS include atypical frontotemporal lobar degeneration with ubiquitinated inclusions (aFTLD-U), neurofilament inclusion body disease (NIFID) and basophilic inclusion body disease (BIBD), which together with ALS-FUS comprise the FUS-opathies.

Tau is a microtubule (MT)-stabilizing protein encoded by the MAPT gene that is highly expressed in neurons. The MT-stabilizing function of Tau is important for axonal transport of proteins, neurotransmitters, and other cellular constituents. Tau misfolding and aggregation occurs in a variety of diseases ("tauopathies"). Insoluble proteinaceous deposits comprising hyperphosphorylated tau proteins, sometimes referred as neurofibrillary tangles (NFTs), are characteristic of these diseases. In neurodegenerative tauopathies, Tau misfolding and aggregation is associated with defects such as axonal transport deficits that appear to have deleterious consequences for the affected neurons, which can lead to synapse dysfunction and may ultimately lead to neuronal loss. Neurofibrillary tangles are a prominent pathological finding in the brains of patients with AD, along with β-amyloid aggregates. Prominent filamentous Tau inclusions and brain degeneration in the absence of β-amyloid aggregates are hallmarks of certain neurodegenerative tauopathies, often accompanied by dystrophic processes (axons, dendrites) termed neuropil threads. Such non-AD neurodegenerative tauopathies include sporadic corticobasal degeneration, progressive supranuclear palsy (PSP), corticobasal degeneration (CBD), and Pick's disease (PiD), as well as hereditary frontotemporal dementia and parkinsonism linked to chromosome 17 (FTDP-17). FTDP-17 is an autosomal dominant disorder characterized by behavioral and personality changes, cognitive impairment, and motor symptoms. FTDP-17 is caused by mutations in the MAPT gene.

It should be noted that aggregates in certain of the diseases characterized by protein aggregates may sometimes contain one or more additional proteins. Furthermore, multiple types of aggregates may occur in the same individual. For example, Tau and αSyn pathology often co-exist within the same individual, and haplotype variation at the Tau (MAPT) locus is a well-established genetic risk factor for late-onset parkinsonism, of which the great majority of cases likely represent PD. It should also be noted that damage to or dysfunction of glial cells can play a significant role in a number of neurodegenerative diseases. For example, cytoplasmic inclusions may be seen in glial cells in addition to neurons and in certain conditions glial cytoplasmic inclusions are prominent. For example, in multiple system atrophy, the main cell type presenting aggregates composed of α-synuclein are oligodendroglial cells.

Many of these neurodegenerative diseases exist in both a familial form, often characterized by a dominant or recessive inheritance pattern, and a sporadic form that does not have a clear inheritance pattern and often has a later onset than the familial forms. In some embodiments a neurodegeneration associated protein or neurodegeneration associated RNA is characterized in that particular sequence variant(s) of the gene that encodes the protein or RNA or particular mutation(s) in the gene that encodes the protein or RNA are associated with an altered risk, e.g., increased risk, of developing a neurodegenerative disease that is characterized by aggregation of the neurodegeneration associated protein or RNA. In some embodiments a neurodegeneration associated protein or neurodegeneration associated RNA is characterized in that an increased level the protein or RNA relative to a normal level is associated with an increased risk of developing a neurodegenerative disease that is characterized by aggregation of the neurodegeneration associated protein or RNA. An increased level of the neurodegeneration associated protein or RNA may result from, e.g., overexpression of the gene that encodes the RNA or protein, presence of one or more extra copies of the gene or a portion thereof that encodes the RNA or protein, increased production of the RNA or protein from a precursor thereof, or increased stability of the RNA or protein. Mutations in a variety of different genes have been identified as causes of neurodegenerative diseases, and in some instances such mutations are clearly associated with altered level and/or activity of the encoded gene product. For example, mutations giving rise to familial forms of neurodegenerative diseases have been identified in the genes encoding alpha-synuclein, TDP-43, and FUS, and certain of these mutations have been shown to induce misfolding and aggregation of the respective protein. Mutations giving rise to familial forms of Alzheimer's disease have been identified in the genes encoding amyloid precursor protein (APP) (the precursor to Aβ) and presenilins 1 and 2 (proteins that normally cleave APP). Most AD-associated mutations in the APP and presenilin genes increase the production of Aβ. Mutations in a number of other human genes are associated with neurodegenerative diseases that have an autosomal dominant inheritance pattern. (See Table B for examples). For example, certain mutations in LRRK2 are strongly associated with autosomal dominant PD or parkinsonism. In general, a finding that a mutation in a particular gene is strongly associated with a disease that has an autosomal dominant inheritance pattern indicates that the mutation results in a gain of function that plays a key role in the pathogenesis of the disease. In some embodiments the role of the relevant gene or mutation may be confirmed if non-human animals, e.g., mice, engineered to express a human gene having a mutation that is found in patients who have the disease or engineered to have a corresponding mutation in the animal's homologous gene exhibit neurodegeneration associated phenotypes, e.g., phenotypes resembling those observed in the disease. In some embodiments the role of the relevant gene or mutation may be confirmed if isolated neurons engineered to express a human gene having a mutation that is found in patients who have the disease exhibit neurodegeneration associated phenotypes, e.g., phenotypes resembling those observed in the disease. A neurodegenerative disease gene characterized in that gain of function of the gene causes a neurodegenerative disease or significantly increases the risk that a subject will develop a neurodegenerative disease may be referred to herein as a "gain of function (GOF) neurodegenerative disease gene". In accordance with certain embodiments of the disclosure, agents that inhibit cellular toxicity induced by a gain of function mutation of a GOF neurodegenerative disease gene are candidate therapeutic agents for treatment of neurodegenerative diseases that are associated with gain of function of the gene, e.g., due to a mutation in the gene. In some embodiments a GOF neurodegenerative disease gene has a homolog in yeast.

In certain embodiments the neurodegenerative disease is a polynucleotide expansion disorder. Polynucleotide expansion disorders are characterized by the presence of multiple consecutive repeats of a particular nucleotide sequence in a gene, exceeding the upper limit of a normal range of repeats typically present in the gene, i.e., "expanded". The normal range differs between different genes. The length of the repeat is typically between 3 and 6 nucleotides. In the non-affected population, repeat tracts are short and stable, showing no length changes. In affected individuals, the tracts are longer and unstable, with a strong tendency to add (expansion) repeat units. Trinucleotide repeats (TNRs), which include CAG, CTG, CGG and GAA triplets, are the most common unstable disease-associated DNA repeats, and disorders in which the repeat is a triplet are often referred to as trinucleotide expansion disorders. Neurodegenerative diseases that are polynucleotide expansion disorders include a number of disorders caused by a CAG repeat expansion in protein-coding portions of specific genes. The CAG repeat encodes a polyglutamine (polyQ) tract; hence these disorders are also referred to as polyglutamine expansion disorders. Polyglutamine expansion disorders are characterized by cellular synthesis and aggregation of neurodegeneration associated proteins that contain abnormally long polyglutamine tracts. These disorders include Huntington's disease, a number of spinocerebellar ataxias, and spino-bulbar muscular atrophy (see Table B). Particular genes and proteins that encode or contain expanded polyQ tracts in certain of these diseases are discussed further below. PolyQ expansion disorders typically exhibit an autosomal dominant mode of inheritance (except spino-bulbar muscular atrophy, which shows X-linked inheritance), midlife onset, and a progressive course. Typically the number of CAG repeats correlates with the severity of disease and correlates inversely with the age at onset (i.e., individuals with more repeats tend to have earlier onset.

Numerous lines of evidence indicate that neurodegeneration associated proteins play a key role in the pathogenesis of neurodegenerative diseases characterized by misfolding and aggregation of the protein. In some embodiments agents that inhibit cellular toxicity induced by such proteins are candidate therapeutic agents for treatment of neurodegenerative diseases that are associated with aggregation of the protein.

Many neurodegenerative diseases result at least in part from loss of function mutations in particular neurodegenerative disease genes. See Table B for examples. A neurodegenerative disease gene characterized in that loss of function of the gene causes a neurodegenerative disease or significantly increases the risk that a subject will develop a neurodegenerative disease may be referred to herein as a "loss of function (LOF) neurodegenerative disease gene". Reduced level or activity of a gene product of a LOF neurodegenerative disease gene may cause or contribute to damage to, dysfunction, or death of neurons, glial cells, or both. In some aspects, described herein are compositions and methods useful for identifying, selecting, and/or characterizing agents that modulate, e.g., inhibit, a detrimental effect of loss of function of a LOF neurodegenerative disease gene. In some embodiments a GOF or LOF neurodegenerative disease gene has a homolog in yeast. Such diseases include, among others, various types of ataxia, several subtypes of Charcot-Marie Tooth disease, and certain types of parkinsonism that are pathologically distinct from PD in that they are not synucleinopathies (see Table B). Parkinsonism disorders that are pathologically distinct from PD may be characterized by neurofibrillary tangles that contain various proteins, such as the microtubule-binding protein Tau, and typically substantially lack α-syn. Table C lists a number of genetic risk factors for parkinsonism ("parkinsonism genes"), including certain genes that are risk factors for PD and others that are risk factors for other forms of parkinsonism. Most of these are Mendelian single-gene mutation risk factors (indicated as having a dominant or recessive inheritance pattern). "Complex" inheritance pattern indicates genome wide association study (GWAS) risk factors for late-onset sporadic PD. ~60 loci are associated in the OMIM database with parkinsonism. In some embodiments a LOF neurodegenerative disease gene has a homolog in yeast. In some embodiments loss of function of the yeast homolog (e.g., due to disruption or deletion of the yeast gene) results in a detectable phenotype in yeast. In some embodiments the phenotype is decreased growth rate and/or decreased viability. In some embodiments expressing a normal form of the human LOF neurodegenerative disease gene in yeast at least partly complements a loss of function mutation of the yeast homolog, i.e., at least in part restores the phenotype to normal Certain aspects of the invention relate to model systems for neurodegenerative diseases that use yeast cells engineered in any of a variety of ways. The particular model may be selected based at least in part on characteristics of the disease and/or the identity of the genes and gene products involved. For example, Applicants have developed model systems for neurodegenerative diseases that use yeast cells that are engineered to express a neurodegeneration associated protein. As discussed further below, these systems are based at least in part on the discovery that a variety of different neurodegeneration associated proteins are toxic to yeast cells. Yeast cells that express a sufficient level of a neurodegeneration associated protein exhibit reduced growth and/or viability. Such cells can be used, among other things, to identify compounds and genes that modulate toxicity associated with the protein. For example, compounds that inhibit such toxicity can be identified by culturing yeast cells that express the neurodegeneration associated protein in the presence of an agent, measuring cell growth or viability in the presence of the agent, and comparing cell growth or viability measured in the presence of the agent to cell growth or viability in the absence of the agent. If cell growth or viability is increased in the presence of the agent as compared to cell growth or viability in the absence of the agent, the agent is identified as an agent that inhibits toxicity induced by the protein. In some embodiments, yeast cells engineered to express a neurodegeneration associated RNA may be used as models for neurodegenerative diseases characterized by expression of such an RNA.

In certain embodiments the neurodegenerative disease is a polynucleotide expansion disorder characterized by repeats located outside the protein-coding regions of the relevant genes, usually resulting in RNA transcripts that contain a polynucleotide expansion in a non-protein-coding region (e.g., in an intron or in the 5' or 3' untranslated region). This group of disorders includes myotonic dystrophy, Friedrich's ataxia, and several types of spinocerebellar ataxia (see Table B). Triplet repeats (CAG or other trinucleotides mentioned above) are found in most of these disorders, but certain disorders feature repeats of other lengths (e.g., 4, 5, or 6 nucleotides such as CCUG, AUUCU, UGGAA, or GGGGCC repeats). Polynucleotide expansions in non-protein-coding regions of a gene may lead to loss of expression of the gene, which in turn results in disease. However, various lines of evidence suggest that toxic mRNA species with expanded polynucleotide repeats (e.g., CUG repeats) contribute significantly to disease development in a number of these disorders. CUG RNA repeats lead to the sequestration and/or altered function of RNA-binding proteins, including proteins that affect splicing and/or translation of a variety of mRNAs that display abnormalities in splicing or translation in tissues of patients with DM1. In certain embodiments the polynucleotide expansion disorder is characterized by the formation of nuclear RNA aggregates, often termed "foci", comprising the abnormally expanded RNA transcript, in affected tissues. RNA foci are observed in DM1 and in a number of other neurodegenerative diseases characterized by non-coding repeat expansions. These foci have been shown to sequester various proteins and may contribute to toxicity. Nuclear aggregates containing mRNAs with expanded CAG repeats in protein-coding regions have been observed, suggesting that RNA toxicity may play a role in certain polyQ expansion disorders.

In some embodiments, yeast cells that overexpress a yeast homolog of a gene product of a neurodegenerative disease gene or harbor a gain of function mutation of a yeast homolog of a gene product of a neurodegenerative disease gene may be used as a model for such a disease. In some embodiments the neurodegenerative disease gene is characterized in that a gain of function of a gene product of the gene is associated with a neurodegenerative disease. A disease may be presumed to result from a gain of function of a gene product if overexpression of the gene product or expression of a particular mutant or variant of the gene product recapitulates one or more phenotypes characteristic of the disease in isolated cells or in an animals, if knocking out or reducing gene dosage or expression in isolated cells or in an animals does not recapitulate these phenotype(s), and/or if human disease can be caused by having one or more extra copies of the encoding gene.

In some embodiments, yeast cells that have reduced or absent expression of a yeast homolog of a gene product of a neurodegenerative disease gene or harbor a loss of function mutation of a yeast homolog of a gene product of a neurodegenerative disease gene may be used as a model for such a disease. In some embodiments the neurodegenerative disease gene is characterized in that a loss of function of a gene product of the gene is associated with a neurodegenerative disease. A disease may be presumed to result from a loss of function of a gene product if deleting, disrupting, or mutating the gene so as to reduce production of a functional gene product or reducing the copy number or expression of the gene recapitulates one or more phenotypes characteristic of the disease in isolated cells or in an animals, if overexpression of the gene product or expression of a particular mutant or variant of the gene product that is associated with the disease does not recapitulate these phenotype(s), and/or if human disease can be caused by mutations that reduce the level of the gene product without altering its sequence of the gene product or that result in production of a functionally inactive gene product that is too short or otherwise unsuitable to serve as a dominant negative version of the gene product.

In some embodiments yeast cells that (a) express a neurodegenerative disease gene product, (b) overexpress or have a gain of function of a yeast homolog of a gene product of a neurodegenerative disease gene (e.g., a neurodegenerative disease gene whose gain of function is associated with a neurodegenerative disease), or (c) lack expression or have a loss of function of a yeast homolog of a gene product of a neurodegenerative disease gene (e.g., a neurodegenerative disease gene whose loss of function is associated with a neurodegenerative disease), are engineered to contain one or more modifications that relate to genetic modifier(s) of the neurodegenerative disease. For example, in certain embodiments the yeast cells may be engineered to (i) have altered (e.g., increased or decreased) expression of a yeast homolog of a genetic modifier of the neurodegenerative disease; (ii) have an alteration in sequence (e.g., a gain of function mutation or a loss of function mutation) of a yeast homolog of a genetic modifier of the neurodegenerative disease; and/or (iii) express a gene product that is encoded by a genetic modifier of the neurodegenerative disease. In some embodiments a genetic modifier of a neurodegenerative disease is a gene characterized in that one or more variant(s) of the gene is associated with an increased risk of developing the disease as compared with one or more other alleles of the gene, e.g., as compared with an allele of the gene that has a standard sequence or that encodes a gene product that has a standard sequence. For example, alleles harboring particular mutations or genetic variations at a particular position (e.g., particular alleles of a single nucleotide polymorphism) may be associated with a higher risk of disease than the standard or most prevalent allele or than an allele that does not harbor such mutation or genetic variation. In some embodiments the particular modification(s) of the yeast cell that relate to genetic modifiers are selected to model an allele associated with an increased risk of the disease. For example, a genetic modifier whose loss of function is associated with a disease may be modeled by reducing the expression or activity of a yeast homolog of the genetic modifier, e.g., by deleting or disrupting the gene encoding the yeast homolog. A genetic modifier whose gain of function is associated with a disease may be modeled by increasing the expression or activity of a yeast homolog of the genetic modifier, e.g., by introducing an expression construct encoding the yeast homolog into the cell or by engineering an appropriate mutation in the endogenous yeast gene, or by ectopically expressing a gene product of the genetic modifier in the yeast cell. In some embodiments a genetic modifier has been identified in a genome wide association study as a gene that affects neurodegenerative disease risk. In some embodiments the increased risk has a complex inheritance pattern in that it does not follow a dominant or recessive inheritance pattern. In some embodiments the magnitude of the increased risk or odds ratio is between 1.1 and about 10. A genetic modifier may interact with or influence the phenotypic manifestation(s) of one or more other genes or gene products in a cell or subject. In some embodiments a genetic modifier of a neurodegenerative disease gene may increase the likelihood that a gene product of the gene will have pathological effects in a cell or subject. For example, a genetic modifier of α-Syn (or another neurodegenerative disease gene) may increase the likelihood that α-Syn will have pathological effects in a cell or subject.

In certain embodiments human nervous system cells used in any of the compositions or methods described herein are induced human nervous system cells.

The particular features and cellular markers exhibited by a nervous system cell, e.g., an induced nervous system cell, may depend on various factors such as its differentiation state, cell type or subtype, extracellular environment (e.g., components in the culture medium to which the cell or its precursor(s) have been exposed), etc. In the case of a neuron, e.g., an induced neuron, such features may include cellular processes characteristic of neurons (e.g., axons or dendrites), electrical excitability (e.g., ability to generate an action potential), and/or ability to form synapses. In general, an induced nervous system cell is a mammalian cell, e.g., a human, non-human primate, rodent (e.g., mouse or rat), bovine, canine, or feline cell. Unless otherwise stated or clearly evident from the context, for purposes of this disclosure, the term "induced nervous system cell" refers to a human induced nervous system cell. Similarly, "induced neuron" "induced neural stem cell", or "induced neural progenitor cell" refer to human cells, unless otherwise indicated or evident from the context. However, the disclosure also provides embodiments in which the induced nervous system cell is a non-human mammalian cell.

Pluripotent stem cells and induced neural stem cells are capable of prolonged or indefinite self-renewal and can be directed to differentiate to yield cells with features characteristic of mature neural or glial cells, including post-mitotic neurons. Thus, they can provide an ongoing source of differentiated nervous system cells comparable to the cell types that are affected by neurodegenerative diseases. Human induced nervous system cells derived from cells obtained from an individual suffering from a neurodegenerative disease typically carry all disease-relevant inherited genetic variations and mutations for that particular individual. Human induced nervous system cells derived from cells that do not naturally bear one or more particular inherited genetic variations or mutations of interest associated with the disease can be genetically engineered to bear one or more such genetic variations or mutations.

In some embodiments, information obtained through use of a yeast model for a neurodegenerative disease, such as yeast cells that express a neurodegeneration associated protein or neurodegeneration associated RNA, yeast cells that overexpress a yeast homolog of a human neurodegenerative disease gene whose gain of function is associated with a neurodegenerative disease, or yeast cells that have a loss of function of a yeast homolog of a human neurodegenerative disease gene whose loss of function is associated with a neurodegenerative disease is applied to human induced neurons that have a genotype associated with the disease.

The human induced neurons may be derived from a patient who has the neurodegenerative disease and/or may harbor one or more genetic variations or mutations associated with the disease. In some embodiments information obtained through use of yeast cells may comprise (i) identity of cellular phenotypes that occur as a consequence of gain of function or loss of function of a yeast homolog of a neurodegenerative disease gene, wherein gain or loss of function of the neurodegenerative disease gene is associated with a neurodegenerative disease, (ii) identity of compounds or genes that modulate (e.g., reduce) toxicity associated with a gain or loss of function of a neurodegenerative disease gene, and/or (iii) identity of compounds or genes that modulate cellular phenotypes associated with a gain or loss of function of a neurodegenerative disease gene. Information obtained through use of yeast cells may comprise, for example, identity of cellular phenotypes that occur as a consequence of expression of a neurodegeneration associated protein, identity of compounds or genes that modulate toxicity of a neurodegeneration associated protein, and/or identity of compounds or genes that modulate phenotypes associated with expression of a neurodegeneration associated protein by a cell. In some aspects, methods described herein may identify or characterize agents or genes that modulate toxicity of a neurodegeneration associated protein, that modulate (e.g., reduce) toxicity associated with a gain or loss of function of a neurodegenerative disease gene, and/or that modulate susceptibility to or manifestation of a neurodegenerative disease; and/or identify or characterize candidate therapeutic agents for treating a neurodegenerative disease.

In some embodiments a phenotype exhibited by yeast that serve as a model for a neurodegenerative disease or group of diseases is also detectable in an induced human neuron that has a genotype associated with one or more of the diseases. For example, in some embodiments a phenotype exhibited by yeast that express a neurodegeneration associated protein associated with a particular disease or group of diseases is also detectable in an induced human neuron that has a genotype associated with the disease. Applicants hypothesized that phenotypes that occur at relatively early time points after inducing expression of a NAP in yeast would be detectable in human induced neurons that have a genotype associated with the disease, e.g., neurons derived from patients suffering from the disease. Applicants confirmed this in the case of alpha-synuclein and Parkinson's disease. As described in the Examples, Applicants found that a number of phenotypes observed in yeast cells that express a toxicity-inducing level of alpha-synuclein were also detectable in human induced cortical neurons derived from patients with familial Parkinson's disease harboring a mutation in alpha-syn or a triplication of the gene encoding alpha-syn. Significantly, the phenotypes were detectable in human induced neurons that had not been exposed either during derivation in vitro or thereafter to agents that have been used by others in efforts to elicit detectable phenotypes in neurons derived from patients with PD, such as MG-132 (CAS number 133407-82-6), hydrogen peroxide, 6-hydroxydopamine, concanamycin A, and valinomycin. Without wishing to be bound by any theory, phenotypes detectable in yeast cells that serve as models for a neurodegenerative disease, e.g., yeast that express a protein associated with a neurodegenerative disease, may directly reflect early stages in the disease process and may be present in human neurons even before the disease becomes symptomatic.

In some aspects, agents capable of inhibiting phenotype(s) that are conserved between yeast that serve as a model for a neurodegenerative disease, e.g., yeast that express a neurodegeneration associated protein associated with a neurodegenerative disease, and induced human neurons that harbor one or more mutations associated with the disease are candidate therapeutic agents for treating the disease. In some aspects, genes that modulate such phenotypes are targets for identification of agents to treat the disease. For example, in some embodiments agents that enhance or inhibit the level or activity of a gene product of a human gene that is a homolog of a yeast gene whose overexpression or deletion enhances or suppresses toxicity of a neurodegeneration associated protein are candidate therapeutic agents for treating the disease. In some embodiments, agents that increase or decrease the level or activity of a gene product of a human gene that is a homolog of a yeast gene whose overexpression or deletion enhances or suppresses toxicity associated with gain or loss of function of a yeast homolog of a neurodegenerative disease gene are candidate therapeutic agents for treating a neurodegenerative disease associated with gain or loss of function of the neurodegenerative disease gene.

In some embodiments, yeast cells that serve as a model of a neurodegenerative disease and human neurons are used in the same method. For example, in some embodiments a method of identifying an agent that modulates a phenotype associated with a neurodegenerative disease in a human neuron comprises (i) identifying an agent that modulates toxicity induced by a neurodegeneration associated protein in yeast cells; and (ii) determining that the agent modulates a phenotype associated with the disease in an induced nervous system cell, e.g., a neuron, that has a genotype associated with the disease. In some embodiments a method of identifying an agent inhibits a phenotype associated with the disease in a human neuron comprises (i) identifying an agent that inhibits toxicity induced by a NAP in yeast; and (ii) determining that the agent inhibits a phenotype associated with the disease in an induced nervous system cell, e.g., a neuron, that has a genotype associated with the disease. In some embodiments a method of identifying a human gene that modulates a phenotype associated with a neurodegenerative disease in a human neuron comprises (i) identifying a yeast gene that modulates toxicity induced by a neurodegeneration associated protein in yeast; and (ii) determining that overexpression, deletion, or mutation of a human homolog of the yeast gene modulates a phenotype associated with the disease in an induced nervous system cell, e.g., a neuron, that has a genotype associated with the disease. In certain embodiments any of the foregoing methods may be applied with respect to a neurodegeneration associated RNA.

In some embodiments a method of identifying an agent that modulates a phenotype associated with a neurodegenerative disease comprises (i) identifying an agent that modulates toxicity induced by a gain or loss of function of a yeast homolog of a neurodegenerative disease gene in yeast cells, wherein the neurodegenerative disease gene is associated with the neurodegenerative disease; and (ii) determining that the agent modulates a phenotype associated with the disease in an induced nervous system cell, e.g., a neuron, that has a genotype associated with the disease. In some embodiments a method of identifying an agent that inhibits a phenotype associated with a neurodegenerative disease comprises (i) identifying an agent that inhibits toxicity induced by a gain or loss of function of a yeast homolog of a neurodegenerative disease gene in yeast; and (ii) determining that the agent inhibits a phenotype associated with the disease in an induced nervous system cell (e.g., an induced neuron) that has a genotype associated with the disease.

In some embodiments a method of identifying a human gene that modulates a phenotype associated with a neurodegenerative disease comprises (i) identifying a yeast gene that modulates toxicity induced by a gain or loss of function of a yeast homolog of a neurodegenerative disease gene in yeast; and (ii) determining that overexpression or loss of function of a human homolog of the yeast gene modulates a phenotype associated with the disease in an induced nervous system cell (e.g., an induced neuron) that has a genotype associated with the disease. In some embodiments human genes identified according to methods described herein are useful as targets for the development of candidate therapeutic agents. For example, in some embodiments an agent that inhibits expression or activity of a human gene product that exacerbates a neurodegenerative disease-associated phenotype when overexpressed is a candidate therapeutic agent for treating the disease. In some embodiments an agent that inhibits expression or activity of a human gene product the loss of function of which inhibits a neurodegenerative disease-associated phenotype is a candidate therapeutic agent for treating the disease.

In some embodiments of any of the methods, the phenotype is conserved between yeast that serve as a model for the neurodegenerative disease (e.g., yeast that express the neurodegeneration associated protein) and human induced neurons that have a genotype associated with the disease. In any embodiments, a cell, e.g., a neuron, is considered to have a genotype associated with the disease if the cell's genome comprises a gene harboring one or more mutations or genetic variations associated with the disease. A genetic variation associated with a disease may be any genetic variation that is associated with a statistically significant increased risk of developing the disease as compared with the risk in the general population. In other words, individuals who have at least one copy of a gene having the particular variation are, in general, more likely to develop the disease than members of the general population. In some embodiments the risk is increased by a factor of at least 1.1, 1.2, 1.5, 2, 2.5, 3, 3.5, 4, 4.5, 5, 6, 7, 8, 9, 10-fold, or more. In some embodiments a genetic variation or mutation is a difference in DNA sequence at one or more positions as compared with a standard sequence. In some embodiments a genetic variation or mutation is a difference in DNA sequence at one or more positions as compared with the sequence at that position that is found most commonly in the human population. A "position" may be a single nucleotide or a sequence of one or more nucleotides. In some embodiments a variation is a substitution, addition, or deletion. In some embodiments a variation is a particular allele of a single nucleotide polymorphism (SNP), e.g., a minor allele. In some embodiments a mutation is one that occurs in individuals who have a familiar form of a neurodegenerative disease. In some embodiments a genetic variation comprises having one or more extra copies of a gene (i.e., more than one copy on at least one chromosome) encoding a neurodegeneration associated protein, wherein having one or more extra copies of the gene is associated with the disease. A mutation associated with a disease may be any genetic variation that causes a form of a disease that has a dominant or recessive inheritance pattern and/or that has a frequency of less than 1% in a population.

In some aspects, use of both yeast and human induced neuron model systems for neurodegenerative diseases draws on strengths of both systems in a complementary manner. Yeast can provide genetically and epigenetically uniform populations of cells that allow for highly synchronous induction of protein expression and are amenable to high throughput screening. Yeast may be used to rapidly test large numbers (e.g., thousands to millions) of compounds. Compounds identified in such screens may be tested to determine their effect on disease-associated phenotype(s) in human induced neurons, which provide a highly disease-relevant cellular environment. In some embodiments, one or more agents or genetic modifiers identified as modulators of toxicity of a neurodegeneration associated protein or RNA using a yeast model or identified as modulators of toxicity resulting from a gain or loss of function of a yeast homolog of a neurodegenerative disease gene is characterized by measuring its effect on one or more disease-associated phenotypes in a human induced neuron. In some embodiments such a measurement may confirm that an agent or genetic modifier that inhibits toxicity of a neurodegeneration associated protein or RNA in yeast also inhibits a disease-associated phenotype in a human induced neuron or that an agent or genetic modifier that increases toxicity of a neurodegeneration associated protein or RNA in yeast also increases a disease-associated phenotype in a human induced neuron. In some embodiments such a measurement may confirm that an agent or genetic modifier that inhibits toxicity resulting from a gain or loss of function of a yeast homolog of a neurodegenerative disease gene in yeast also inhibits a disease-associated phenotype in a human induced neuron or that an agent or genetic modifier that increases toxicity resulting from a gain or loss of function of a yeast homolog of a neurodegenerative disease gene in yeast also increases a disease-associated phenotype in a human induced neuron.

In some embodiments a screen using yeast that serve as a model for a neurodegenerative disease is used to identify one or more candidate agents for treatment of the disease, and the ability of a candidate agent identified in the screen to inhibit a disease-associated phenotype in an induced neuron is measured. If the candidate agent inhibits the phenotype, the candidate agent is confirmed as a candidate therapeutic agent for treatment of the disease. In some embodiments a screen using yeast that express a neurodegeneration associated protein is used to identify one or more candidate agents for treatment of a neurodegenerative disease associated with the neurodegeneration associated protein, and the ability of a candidate agent identified in the screen to inhibit a disease-associated phenotype in a human induced neuron is measured. If the candidate agent inhibits the phenotype, the candidate agent is confirmed as a candidate therapeutic agent for treatment of the disease. In some embodiments multiple compounds identified in one or more yeast-based screens are tested for their effect on one or more disease-associated phenotype(s) in such neurons. A compound that exhibits higher potency and/or efficacy with respect to inhibiting one or more disease-associated phenotypes as compared with one or more other compounds tested may be selected for further development or for use to treat a patient who has the disease. In certain embodiments the foregoing methods may be applied with respect to a neurodegeneration associated RNA.

In some embodiments an induced neuron is generated from a human subject in need of treatment for a neurodegenerative disease (such a subject may sometimes be termed a "patient"). The neuron is contacted with a compound identified in a screen using yeast that serve as a model of the disease, and the effect of the compound on one or more disease-associated phenotype(s) in the neuron is determined.

A compound that inhibits at least one disease-associated phenotype may be selected for treatment of that particular patient. In some embodiments multiple compounds identified using yeast are tested for their effect on one or more disease-associated phenotype(s) in induced neurons derived from the patient. A compound that exhibits superior potency and/or efficacy with respect to inhibition of at least one disease-associated phenotype in neurons derived from the patient as compared with one or more other compounds tested may be selected for treatment of that particular patient.

In some embodiments, engineered induced human neurons serve as models of a neurodegenerative disease. For example, in some embodiments induced human neurons are engineered to have a genotype that is associated with the disease or are engineered to have altered expression or activity of a neurodegenerative disease gene associated with the disease. In some embodiments the induced neurons are derived from human embryonic stem cells. In some embodiments the induced neurons are derived from human somatic cells, which may be used to generate iPS cells. In some embodiments the cells are derived from subjects that are apparently free of a neurodegenerative disease (and, in some embodiments, without a family history of a neurodegenerative disease). The step(s) of genetic alteration may be performed on the ES cells, somatic cells, iPS cells, or at any stage during the course of deriving nervous system cells. In some embodiments induced human neurons are engineered to overexpress a neurodegeneration associated protein or neurodegeneration associated RNA. For example, induced neurons that overexpress alpha-synuclein, TDP-43, a polyQ repeat protein, Abeta, Tau, or FUS may be generated. In some embodiments induced human neurons are engineered to harbor a mutation in a gene that encodes a neurodegeneration associated protein or neurodegeneration associated RNA, wherein the mutation is associated with a neurodegenerative disease or has a substantially similar or greater effect on expression or activity of a gene product of the gene as does a mutation associated with a neurodegenerative disease. For example, if a neurodegenerative disease is associated with a gain of function mutation, an induced neuron that harbors a gain of function mutation may be generated. If a neurodegenerative disease is associated with a loss of function mutation in a neurodegenerative disease gene, an induced neuron that harbors a loss of function mutation in such gene may be generated. Table B lists a variety of neurodegenerative diseases with autosomal recessive inheritance patterns associated with mutations in particular human genes (listed in the left column) wherein an induced neuron model may be generated by deleting, disrupting, or otherwise disabling or inhibiting the expression of the gene or inhibiting activity of its gene product. In some embodiments an engineered mutation in an induced neuron is the same as a mutation identified in subjects with the disease and/or results in the same change in sequence of an encoded gene product as a mutation identified in subjects with the disease. In some embodiments an engineered mutation in an induced neuron is at the same position as a mutation identified in subjects with the disease and results in a change that has the same, greater than, or a substantially similar effect to that of a mutation identified in subjects with the disease. In some embodiments an engineered mutation in an induced neuron is at a different position to a mutation identified in subjects with the disease and results in a change that has the same, greater than, or a substantially similar effect to that of a mutation identified in subjects with the disease. An effect of first mutation is substantially similar to the effect of a second mutation if the magnitude of the two effects differs by no more than 5%, 10%, 15%, 20%, or 25% on an absolute basis or relative to a reference value, which is typically the value associated with a normal gene product, e.g., a gene product having a standard sequence. In many cases a number of different engineered mutations may produce the same, greater than, or a substantially similar effect to that of a mutation identified in subjects with the disease. For example, a naturally occurring loss of function mutation could be effectively mimicked by any of a variety of engineered mutations that substantially reduce expression of the gene or that alter or delete portions of the sequence that encode domains or amino acids important for activity of an encoded protein.

In some embodiments subjects having a particular mutation or variation of a neurodegenerative disease gene or a genetic modifier have a relative risk or odds ratio of developing the disease of at least 1.1, 1.2, 1.5, 2.0, 2.5, 3.0, 3.5, 4.0, 4.5, or 5.0 as compared with the overall population or compared with subjects who do not have that particular mutation or variation. The overall population may be represented by a sample, e.g., a randomly selected sample, which may be matched with regard to one or more demographic variables such as age.

In some aspects, the disclosure relates to yeast strains having a genetic background that corresponds to a patient with a neurodegenerative disease, methods of generating such strains, and/or methods of using such strains. For example, in some embodiments yeast cells express or are capable of expressing a NAP associated with the disease and have a genetic background that corresponds to the genotype of a patient with respect to one or more genetic modifiers of toxicity of the NAP. In some embodiments yeast cells express or are capable of expressing a NAP associated with the disease and have a genetic background that corresponds to the genotype of a patient with respect to one or more mutations or genetic variations associated with the neurodegenerative disease. In some embodiments a screen to identify inhibitors of toxicity of the NAP is performed using such yeast cells. In some embodiments a compound identified in such a screen may be tested in a neuron derived from the patient or having a genotype bearing one or more of the same mutations or genetic variations associated with the disease as does the patient. In some embodiments a yeast strain used in the screen may be constructed to correspond to the genotype of a patient with respect to one or more genetic modifiers of toxicity of the NAP or may be selected from a set of existing yeast strains. In some embodiments a yeast strain is engineered to overexpress or have reduced or absent expression of one or more yeast genes, e.g., one or more yeast genes that is a genetic modifier of toxicity of the NAP and/or that is a yeast homolog of a human gene that comprises a mutation or variation associated with the disease. In some embodiments the patient is genotyped to determine the presence or absence of one or more mutations or genetic variations known to be associated with the disease. A yeast strain having a genetic background that corresponds to that of a particular patient with regard to one or more mutations or genetic variations present in the patient may be generated or selected from pre-existing strains. Genotyping may be performed using any method known in the art. In some embodiments genotyping comprises sequencing and/or amplifying at least a portion of one or more human genes, e.g., one or more human genes characterized in that mutations or genetic variations in the gene are known to be associated with the disease. In some embodiments a mutation or genetic variation is one that has been identified in a genome wide association study (GWAS). In some embodiments genotyping comprises exome sequencing, RNA sequencing, or whole genome sequencing. In some embodiments genotyping comprises contacting genomic DNA from a biological sample obtained from the subject with a support, e.g., an array, comprising probes that bind specifically to nucleic acids, e.g., DNA, harboring specific alleles of single nucleotide polymorphisms, mutations, or other genetic variations. In some embodiments cDNA, RNA, mRNA derived from a biological sample obtained from the subject may be used. A probe or primer may comprise a suitable detection reagent and/or a suitable detection reagent may be incorporated during the course of DNA sequencing or amplification. In some embodiments a patient's genome or exome may have been at least partly sequenced and stored (e.g., in a database). The previously determined sequence may be accessed and analyzed to determine whether it harbors one or more genetic variations or mutations in a neurodegenerative disease gene or in a genetic modifier associated with a neurodegenerative disease. Once a human gene is determined to harbor a mutation or genetic variation associated with the disease in a particular patient, a yeast strain with a genotype matching that of the patent may be constructed by engineering a yeast strain to overexpress a yeast homolog of the human gene or to lack or have reduced expression or activity of a yeast homolog of the human gene or may be selected from existing strains. The yeast strain is engineered so that it is expresses or is capable of expressing a NAP associated with the disease (e.g., it harbors a nucleic acid that encodes the NAP under control of a regulatable, e.g., inducible, promoter, so that the cell expresses the NAP under appropriate conditions). In some embodiments, if the gene in the patient is present at increased copy number or harbors a mutation or variation that increases the level or activity of the human gene product, the yeast strain may be engineered to overexpress a yeast homolog of the human gene. In some embodiments, if the gene in the patient harbors a mutation or variation that reduces the activity or level of the human gene product, the yeast strain may be engineered to lack or have reduced expression or activity of a yeast homolog of the human gene. In some embodiments two or more yeast strains may be generated wherein a first yeast strain overexpresses a yeast homolog of the human gene, and a second yeast strain has reduced expression or activity of a yeast homolog of the human gene. The yeast strain that exhibits increased toxicity associated with the NAP as compared with a yeast strain that expresses the NAP at about the same level but is wild type with respect to the yeast homolog may be used in the screen. Yeast genes that modify (suppress or enhance) toxicity of various NAPs in yeast when overexpressed or deleted, and human homologs of certain of these genes, have been identified (see discussion below). Such genes may be overexpressed or disabled in yeast strains that correspond to the genotype of a human subject having a genotype associated with a neurodegenerative disease. Examples of various mutations and genetic variations associated with neurodegenerative disease are described herein and/or in references cited herein. A subject may be genotyped with respect to any mutations or genetic variations known in the art that is associated with a neurodegenerative disease. In some embodiments one or more human homologs of yeast genes that are genetic modifiers of toxicity of a NAP are at least partially sequenced (e.g., exons and/or regulatory regions may be sequenced) to identify one or more mutations or genetic variations in such genes. Yeast strains corresponding to patient genotypes are an aspect of the present disclosure.

In some embodiments a therapeutic agent for a subject in need of treatment for a neurodegenerative disease may be selected based on the subject's genotype, by selecting an agent that inhibits toxicity of a neurodegeneration associated protein that is associated with the disease in yeast cells that have a genetic background that corresponds to that of the patient. In some embodiments any of the foregoing methods described in this paragraph may be applied with regard to a neurodegenerative disease associated with a neurodegeneration associated RNA. In some embodiments any of the foregoing methods described in this paragraph may be applied with regard to a neurodegenerative disease associated with loss of function of a neurodegenerative disease gene. For example, yeast cells that have reduced or absent expression of a yeast homolog of a neurodegenerative disease gene whose loss of function is associated with the disease may be generated. In some embodiments such yeast cells may be used in a screen to identify agents that enhance viability or reduce a phenotype resulting from the reduced or absent expression of the yeast homolog. In some embodiments a compound identified in such a screen may be tested in a neuron derived from a patient who has a loss of function of the neurodegenerative disease gene or in a neuron engineered to have a loss of function mutation or reduced expression of the gene.

In some embodiments, a yeast strain has a genetic background that corresponds to the genotype of a patient with a neurodegenerative disease with respect to one or more genetic modifiers of a neurodegenerative disease that is associated with a gain of function of a neurodegenerative disease gene. For example, in some embodiments yeast cells that express a neurodegenerative disease gene associated with the disease or that overexpress a yeast homolog of the neurodegenerative disease gene are, in addition, engineered to have a genetic background that corresponds to the genotype of a patient with respect to one or more genetic modifiers of the neurodegenerative disease. For example, in certain embodiments the yeast cells may, in addition to expressing a neurodegenerative disease gene associated with the disease or overexpressing a yeast homolog of the neurodegenerative disease gene, be engineered to (i) have altered (e.g., increased or decreased) expression of a yeast homolog of a genetic modifier of the neurodegenerative disease or (ii) have an alteration in sequence (e.g., a gain of function mutation or a loss of function mutation) of a yeast homolog of a genetic modifier of the neurodegenerative disease; wherein the altered expression and/or alteration in sequence of the yeast homolog is selected to correspond in effect and/or sequence to the genetic modifier as present in the patient. For example, if the genetic modifier in the patient is believed to result in a loss of function of the gene product, the yeast may be engineered to have loss of function of the yeast homolog (e.g., by at least partly deleting or disrupting the yeast homolog). In some embodiments in which the allele of the genetic modifier present in the patient has a gain of function relative to alleles that are not associated with the disease, the yeast may be engineered to express a gene product that is encoded by the genetic modifier present, e.g., to express the form of the gene product that is associated with disease as present in the patient.

In some embodiments, a yeast strain has a genetic background that corresponds to the genotype of a patient with respect to one or more genetic modifiers of a neurodegenerative disease that is associated with a loss of function of a neurodegenerative disease gene. For example, in some embodiments yeast cells that lack expression or have a loss of function of a yeast homolog of a gene product of a neurodegenerative disease gene whose loss of function is associated with a neurodegenerative disease are, in addition, engineered to have a genetic background that corresponds to the genotype of a patient with respect to one or more genetic modifiers of the neurodegenerative disease. For example, in certain embodiments the yeast cells may, in addition to lacking expression or having a loss of function of a yeast homolog of a gene product of a neurodegenerative disease gene, be engineered to (i) have altered (e.g., increased or decreased) expression of a yeast homolog of a genetic modifier of the neurodegenerative disease or (ii) have an alteration in sequence (e.g., a gain of function mutation or a loss of function mutation) of a yeast homolog of a genetic modifier of the neurodegenerative disease; wherein the altered expression and/or alteration in sequence of the yeast homolog is selected to correspond in effect and/or sequence to the genetic modifier as present in the patient.

In some embodiments an induced neuron used in a method or composition described herein has one or more features and/or expresses one or more cellular markers characteristic of a neuron type that is affected by a neurodegenerative disease in at least some humans suffering from the disease. For example, in some embodiments, if the disease is PD, dementia with Lewy bodies, Alzheimer's disease, FTLD, ALS, or another neurodegenerative disease that is a cause of dementia and/or is associated with degeneration of cortical neurons, the induced neuron has features and/or expresses one or more cellular markers characteristic of a cortical neuron. In some embodiments, if the disease is PD or another neurodegenerative disease that is a cause of the motor symptoms typically associated with PD (tremor, hypokinesia, rigidity, and postural instability, i.e., parkinsonism), the induced neuron is a dopaminergic neuron. In some embodiments, if the disease is ALS or another neurodegenerative disease that is a cause of degeneration of motor neurons, the induced neuron has features and/or expresses one or more cellular markers characteristic of a motor neuron.

In some embodiments induced neurons may be generated or engineered to have a genetic background that corresponds to a patient with a neurodegenerative disease. As described herein, induced neurons that have a genetic background that corresponds to a patient with a neurodegenerative disease may be created without requiring genetic engineering by generating induced neurons from iPS cells derived from cells obtained from that patient or derived from other cell types obtained from the patient (such as fibroblasts) without going through a pluripotent stage. Induced neurons that have a genetic background that corresponds to a patient with a neurodegenerative disease may be created using genetic engineering. Cells may be engineered to overexpress a neurodegenerative disease gene that encodes a neurodegeneration associated protein or neurodegeneration associated RNA in the cells, to express a mutant form of a neurodegeneration associated protein or RNA wherein the mutant form has a gain of function associated with the neurodegenerative disease, or to harbor a gain of function or loss of function mutation in an endogenous neurodegenerative disease gene whose gain or loss of function, respectively, is associated with a neurodegenerative disease.

Certain compositions and methods are exemplified herein with regard to induced neurons derived from patients with Parkinson's disease and yeast that express an alpha-synuclein protein. For example, as described herein, phenotypes observed in yeast cells engineered to express alpha-synuclein led to the identification of Parkinsons's disease-associated phenotypes in induced neurons derived from PD patients. Small molecules identified by screening for compounds that inhibit alpha-synuclein toxicity in yeast inhibited these phenotypes both in yeast and in PD patient derived induced neurons. These results confirmed the ability of the compounds to beneficially affect human neurons affected by a synucleinopathy. However, methods described herein may be used in the context of other neurodegenerative diseases and/or other neurodegeneration associated proteins, neurodegeneration associated RNA, neurodegenerative disease genes, and genetic modifiers, and the disclosure encompasses such embodiments directed to such methods and related compositions. For example, certain embodiments may be directed to any of the genes and/or diseases listed in Table B, C, and/or D.

In certain aspects, compositions and/or methods described herein relate to diseases that may be classified into any of the following three general categories, and which may be modeled in human induced nervous system cells and/or yeast as described herein. (1) Diseases in which a known protein (e.g., alpha-synuclein, Abeta, TDP-43, FUS, polyglutamine-containing protein) aggregates, is encoded by a gene that contains a toxic gain of function mutation, or is overexpressed and such overexpression is toxic. Yeast models of diseases in this class may be generated by expressing at least a portion of the wild type or mutant human protein in yeast. Alternately or additionally, if the gene has a yeast homolog, a yeast model may be generated by overexpressing the yeast homolog or introducing a mutation into the yeast homolog that mimics the human disease-causing mutation. The mutation may be introduced into the endogenous gene or a mutated version of the gene may be integrated elsewhere in the genome or introduced on a non-integrating plasmid. Human induced neuron models of such diseases may be produced by generating induced neurons from patients who have the disease (or are at high risk of developing the disease based on their genotype) or by inducible expression of at least a portion of the wild type or mutant human protein in induced neurons derived from human ES cells, iPS cells, or neural progenitor cells. In some embodiments an induced neuron model is produced by generating induced neurons from a particular patient who has the disease. In some embodiments such a model may be of particular use to identify or validate candidate therapeutic agents for that patient. A yeast model for such diseases may be generated by expression of the wild-type or mutant human protein in yeast. (2) Diseases in which there is known or presumed loss of function of a neurodegenerative disease protein and such protein has a yeast homolog. These diseases include numerous forms of parkinsonism and ataxia that have an autosomal recessive inheritance pattern, i.e., both copies of the gene that encodes the neurodegenerative disease protein harbor mutations or polymorphisms resulting in loss of function of the protein. Yeast models of diseases of this class may be generated by mutation (e.g., disruption or at least partial deletion) of the gene that encodes the yeast homolog so as to reduce the expression or activity of the protein. Human induced neuron models of such diseases may be produced by generating induced neurons from patients who have the disease (or are at high risk of developing the disease based on their genotype) or by gene targeted mutation in hES, iPS, or neural progenitor cells, from which neurons are subsequently generated. In some embodiments a mutation engineered in human iPS or ES cells may create a conditional allele that retains normal activity until the cells are exposed to inducing conditions. (3) Diseases in which a patient has a disease associated with a neurodegeneration associated protein or RNA (diseases of type (1) above and also has a mutation or polymorphism in a modifier gene (genetic modifier) that has a yeast homolog. Yeast models of diseases in this class may be generated by expressing at least a portion of the wild type or mutant human neurodegeneration associated protein or RNA in yeast in combination with mutation or overexpression of the yeast homolog of the modifier gene. If the mutation or polymorphism in the human modifier gene results in a loss of function, then the yeast homolog may be mutated so as reduce the expression or activity of the protein. If the mutation or polymorphism in the human modifier gene results in a gain of function, then the yeast homolog may be overexpressed or mutated so as to mimic the gain of function mutation or polymorphism in the modifier gene. In certain embodiments the human NAP or NAR may be expressed at a level that results in no or limited toxicity by itself, but the toxicity of which is increased in the presence of mutation or overexpression of the yeast homolog of the modifier gene. In certain embodiments screens or compound characterization performed using yeast models in which toxicity of a NAP or NAR is exacerbated by mutation or overexpression of a homolog of a particular modifier gene may result in identification or validation of candidate therapeutic agents that are particularly effective or appropriate for use in treating patients who harbor mutations or polymorphisms of the modifier gene that have similar effects on its activity. Human induced neuron models of such diseases may be produced by (i) generating induced neurons from a particular patient who has the disease and has the mutation or polymorphism; (ii) introducing the mutation or polymorphism in the modifier gene into an ES, iPS, or neural progenitor cell line that harbors an engineered or naturally occurring disease-causing mutation in the gene that encodes the neurodegeneration associated protein or RNA or harbors an extra copy of the gene that encodes the neurodegeneration associated protein or RNA and generating neurons from the cell line; (iii) introducing the mutation or polymorphism in the modifier gene into a human ES, iPS, or neural progenitor cell line engineered to overexpress the NAP or NAR or engineered to harbor a disease-causing mutation in the NAP or NAR.

The disease categories described above may overlap in certain embodiments. For example, mutations in certain genes can cause neurodegenerative diseases with an autosomal recessive inheritance pattern (as in category (2) above) and may in at least some patients also be associated with aggregation of a neurodegeneration associated protein (as in category (3) above). Certain of the genes whose loss of function results in diseases with an autosomal recessive inheritance pattern (as in category (2) above) may also be modifier genes for diseases associated with a neurodegeneration associated protein. For example, when both copies of the gene that encodes the neurodegenerative disease protein harbor mutations or polymorphisms resulting in loss of function of the protein, the patient may develop an autosomal recessive form of disease, whereas when only one copy harbors such a mutation or polymorphism, the patient may be at increased risk of developing a sporadic form of the disease. In certain embodiments a yeast model of a disease that falls into both categories (2) and (3) may be generated as described under either (2) or (3), or both types of yeast models may be used. In certain embodiments compounds identified as useful in both types of yeast models and/or identified as useful in both types of induced neuron models may be tested in induced neurons that are derived from a particular patient or that incorporate a particular mutation or variant of a polymorphism found in the patient, and a compound showing greater efficacy in alleviating disease-associated phenotype(s) in the induced neurons may be selected for treatment of the patient.

TABLE B

Selected neurodegenerative disease genes with yeast (Saccharomyces cerevisiae) homologs

| Human | Yeast | Disease | Human protein product | Inheritance/comments |
|---|---|---|---|---|
| Ataxia | | | | |
| FRDA (also known as FXN)* | YFH1 | FA | Frataxin, a nuclear-encoded mitochondrial protein involved in iron-sulphur cluster enzyme biogenesis | Autosomal recessive, generally caused by expansion of an unstable GAA repeat in the first intron; FA is the most common inherited ataxia[24] |
| ATXN2 | PBP1 | SCA2 | Ataxin 2, which has a putative role in RNA metabolism | Autosomal dominant, caused by an expanded polyglutamine tract |
| CACNA1A | CCH1 | SCA6 | Ataxin 6, α1A transmembrane subunit of the P/Q-type voltage-gated calcium channel | Autosomal dominant, caused by an expanded polyglutamine tract |
| ATXN7 | SGF73 | SCA7 | Ataxin 7, a subunit of histone acetyltransferase complexes | Autosomal dominant, caused by an expanded polyglutamine tract |
| ATXN10 | ATXN10 | SCA10 | Ataxin 10 | Autosomal dominant, caused by a pentanucleotide (ATTCT) repeat expansion |
| TBP | SPT15 | SCA17 | TATA-box-binding protein | Autosomal dominant SCA caused by an expanded polyglutamine tract |
| TDP1 | TDP1 | SCAN1 | TDP1, a DNA-repair protein | Autosomal recessive |
| ATM | TEL1 | AT | ATM, a key regulator of the DNA-damage response | Autosomal recessive |

TABLE B-continued

Selected neurodegenerative disease genes with yeast (*Saccharomyces cerevisiae*) homologs

| Human | Yeast | Disease | Human protein product | Inheritance/comments |
|---|---|---|---|---|
| SETX | SEN1 | Ataxia with oculomotor apraxia | Senataxin | Autosomal recessive |
| MT-ATP6 | ATP6 | Ataxia with retinitis pigmentosa | ATP synthase F0 subunit 6 | Mitochondrial |
| CABC1 | ABC1/COQ8 | Ataxia, epilepsy | Coenzyme Q synthesis pathway protein | Autosomal recessive |
| COQ2 | COQ2 | Multiple system atrophy (MSA) | Coenzyme Q synthesis pathway protein | Autosomal recessive |
| Dementia | | | | |
| SORL1 (also known as LR11) | PEP1, VTH1, VTH2, YNR065C | AD | Sortilin 1, a neuronal sorting receptor of the LDL receptor family | Genetically associated with late-onset AD |
| CHMP2B | DID4 | FTD | CHMP2B, an ESCRTIII subunit important in endosomal-lysosomal trafficking | Autosomal dominant |
| VCP | CDC48 | FTD | VCP/p97 (valosin-containing protein) ATPase involved in ER-associated degradation and mitophagy, among other processes. | Autosomal dominant fronto-temporal dementia and inclusion body myopathy (some families present with parkinsonism) |
| Lysosomal storage disease | | | | |
| CTSD | PEP4 | NCL | Cathepsin D, a lysosomal protease | Autosomal recessive congenital NCL |
| CLN3* | YHC3 (also known as BTN1) | NCL (BD) | CLN3, a lysosomal transmembrane protein | Autosomal recessive juvenile NCL (also known as BD)[78] |
| SMPD1 | PPN1 | NP type A | Sphingomyelin phosphodiesterase, a lysosomal enzyme | Autosomal recessive |
| NPC1* | NCR1 | NP type C | NPC1, a late endosomal protein involved in cholesterol trafficking | Autosomal recessive, associated with intraneuronal accumulation of unesterified cholesterol[79] |
| Upper/lower motor neuron disease | | | | |
| SOD1 | SOD1 | ALS | Superoxide dismutase, a major antioxidant enzyme | Autosomal dominant |
| VAPB | SCS2, SCS22 | SMA, ALS, FTD-ALS | VAPB, a membrane protein involved in vesicle trafficking | Autosomal dominant |
| DCN1* | NIP100 | ALS | p150 subunit of dynactin, a protein involved in axonal transport | Autosomal dominant (probably a dominant negative mutation)[80] |
| Upper motor neuron disease | | | | |
| REEP1 | YOP1 | HSP | REEP1, a mitochondrial protein | Autosomal dominant |
| SPG7* | AFG3, RCA1 | HSP | Paraplegin, a mitochondrial AAA protease | Autosomal recessive, leads to axonal degeneration of corticospinal tracts and dorsal columns[81] |
| HSPD1 | HSP60 | HSP | HSP60/Chaperonin (mitochondrial) | Autosomal dominant cause of HSP (but recessive mutants also exist that lead to another disease (MitCHAP-60). |
| Movement disorder | | | | |
| ATP13A2 (also known as PARK9) | ATP13A2 | PD | ATPase, involved in metal ion homeostasis | Autosomal recessive parkinsonism |
| DJ1 (also known as PARK7) | HSP31 | PD | DJ1, a redox-activated chaperone | Autosomal recessive parkinsonism |
| EIF4G1 (also known as PARK18) | TIF4631/2 | PD | EIF4G1 is a translation initiation factor. | Autosomal dominant parkinsonism and dementia (synucleinopathy). |

TABLE B-continued

Selected neurodegenerative disease genes with yeast (*Saccharomyces cerevisiae*) homologs

| Human | Yeast | Disease | Human protein product | Inheritance/comments |
|---|---|---|---|---|
| PANK2 | CAB1 | PKAN | Pantothenate kinase 2, involved in CoA biosynthesis | Autosomal recessive parkinsonism and brain iron accumulation |
| RAB7L1 (also known as PARK16) | YPT7 | RAB7 | RAB7 and RAB7L proteins involved in endocytosis. | Sporadic PD risk factor locus. |
| UCHL1 | YUH1 | PD | UCHL1, a protein of unclear function | Controversial susceptibility gene for familial PD; modulates toxicity in an AD mouse model |
| VPS13A | VPS13 | NA | Chorein, which has putative involvement in membrane protein trafficking | Autosomal recessive movement disorder associated with acanthocytes in the blood and degeneration of the basal ganglia |
| VPS35 (also known as PARK17) | VPS35 | PD | VPS35, a key component for retromer | Autosomal recessive parkinsonism (synucleinopathy) |
| Peripheral neuropathy | | | | |
| GARS | GRS1, GRS2 | CMT2D, distal SMA type V | Glycyl-tRNA synthetase | Autosomal dominant degeneration of peripheral sensory and motor neurons (CMT2D) or just motor neurons (distal SMA type V) |
| GDAP1 | GTT2 | CMT4A | GDAP1 | Autosomal recessive degenerative disease of peripheral motor and sensory neurons |
| MTMR2, SBF2 | YMR1 | CMT4B1, CMT4B2 | MTMR2 and MTMR13 are myotubularin-related proteins linked with vesicular trafficking | Autosomal recessive |
| FIG. 4 | FIG. 4 | CMT4J | FIG. 4, a phosphatase in the vacuolar membrane associated with endosome-lysosome trafficking | Autosomal recessive |
| YARS | TYS1 | DICMT-C | Tyrosyl-tRNA synthetase | Autosomal dominant degeneration of peripheral sensory and motor neurons |
| SPTLC1 | LCB1 | HSN | Serine palmitoyltransferase 1, which is involved in sphingolipid synthesis | Autosomal dominant degeneration of peripheral sensory neurons |
| White matter disease | | | | |
| ABCD1* | PXA1, PXA2 | X-linked ALD | ABCD1, a peroxisomal protein involved in very-long-chain fatty acid transport | X-linked ALD degenerative white matter disease[82] |
| PEX1, PEX5, PEX10, PEX13 PEX14, PEX19, | PEX1, PEX5, PEX10, PEX13 PEX14, PEX19 | Zellweger syndrome | Peroxisome biogenesis proteins | Autosomal recessive degenerative white matter disease |
| XPC, ERCC2, DDB1, DDB2, RAD1, RAD30 | RAD4, RAD3, RSE1 (SF3B3), CMR1, ERCC4, POLH | XP type C, XP type D, XP type E, XP type F, XP variant | Multiple DNA-repair proteins | Autosomal recessive; neurologic manifestations, when present, generally include one or more of dementia, ataxia, peripheral neuropathy and deafness |

*Genes that have been used to create yeast models (see indicated references in Khurana, K. and Lindquist, S., Nature Reviews Neuroscience 11, 436-449 (2010)).

Abbreviations:
ABCD1, ATP-binding cassette, subfamily D, member 1; AD, Alzheimer's disease; ALD, adrenoleukodystrophy; ALS, amyotrophic lateral sclerosis; AT, ataxia telangiectasia; ATM, ataxia telangiectasia mutated; BD, Batten disease; CACNA1A, calcium channel, voltage-dependent, P/Q type, α1 A subunit; CHMP2B, chromatin-modifying protein 2B; CLN3, ceroid-lipofuscinosis, neuronal 3; CMT, Charcot-Marie—Tooth disease; DDB, damage-specific DNA binding; DICMT, dominant intermediate CMT; ERCC2, excision repair cross-complementing rodent repair deficiency, complementation group 2; ESCRTIII, endosomal sorting complex required for transport III; FA, Friedreich's ataxia; FTD, frontotemporal dementia; GDAP1, ganglioside-induced differentiation-associated protein 1; HSN, hereditary sensory neuropathy; HSP, hereditary spastic paraplegia; HSP31, heat-shock protein 31; NA, neuroacanthocytosis; NCL, neuronal ceroid lipofuscinosis; NP, Niemann—Pick disease; PD, Parkinson's disease; PEP, peptidase; PKAN, pantothenate kinase-associated neurodegeneration; REEP1, receptor expression-enhancing protein 1; SBF2, SET-binding factor-2 (also known as MTMR13); SCA, spinocerebellar ataxia; SCAN, spinocerebellar ataxia with axonal neuropathy; SMA, spinal muscular atrophy; SPG7, spastic paraplegia 7; SPTLC1, serine palmitoyltransferase, long chain base subunit 1; TDP1, tyrosyl-DNA phosphodiesterase 1; UCHL1, ubiquitin carboxyl-terminal esterase L1; VAPB, vesicle-associated membrane protein B; VPS, vacuolar protein sorting; XP, xeroderma pigmentosum.

TABLE C

Selected genetic risk factors for parkinsonism

| PARK locus | Gene | Map position | Inheritance | Clinical phenotype | Pathology |
|---|---|---|---|---|---|
| PARK1/4 | SNCA | 4q21 | Dominant or Complex | Parkinsonism with common dementia | Lewy bodies |
| PARK2 | parkin | 6q25-q27 | Recessive | Early-onset, slowly progressing parkinsonism | Lewy bodies (variable) |
| PARK6 | PINK1 | 1p35-p36 | Recessive | Early-onset, slowly progressing parkinsonism | One case exhibiting Lewy bodies |
| PARK7 | DJ-1 | 1p36 | Recessive | Early-onset parkinsonism | Unknown |
| PARK8 | LRRK2 | 12q12 | Dominant or Complex | Late-onset parkinsonism | Lewy bodies (usually) |
| PARK9 | ATP13A2 | 1p36 | Recessive | Early-onset parkinsonism with Kufor-Rakeb syndrome | Unknown |
| PARK16 | RAB7L1 | 1q32 | Complex | Late-onset parkinsonism | Unknown |
| PARK17 | VPS35 | 16q12 | Recessive | Late-onset parkinsonism | Unknown |
| PARK18 | EIF4G1 | 3q27 | Dominant | Late-onset parkinsonism, dementia | Lewy bodies |
| na | PANK2 | 20p13 | Recessive | Early-onset parkinsonism, chorea, dementia, dystonia | Iron accumulation; no Lewy bodies |
| na | MAPT | 17q21 | Dominant | Dementia, sometimes parkinsonism | Tau pathology |
| na | Ataxin 2 | 12q24 | Dominant | Usually ataxia, sometimes parkinsonism | Ataxin-2 aggregates; no Lewy bodies |
| na | Ataxin-3 | 14q21 | Dominant | Usually ataxia, sometimes parkinsonism | Ataxin-3 aggregates; no Lewy bodies |
| na | Ataxin-7 | 3p21 | Dominant | Usually ataxia, sometimes parkinsonism | Ataxin-7 aggregates; no Lewy bodies |
| na | GBA | 1q21 | Dominant | Late-onset parkinsonism | Lewy bodies |
| na | VCP | 9p13 | Dominant | Dementia, sometimes parkinsonism | TDP-43 inclusions |

TABLE D

Selected parkinsonism genes with yeast homologs

| Human gene name | Yeast gene name | BLAST E-value |
|---|---|---|
| VCP | CDC48 | 0 |
| ATP13A2 | YPK9 | E-150 |
| PPP2R2B | CDC55 | E-118 |
| POLG | MIP1 | E-115 |
| ATP1A3 | PMR1 | E-106 |
| MT-CYB | COB | 7.00E-98 |
| ADH1C | SFA1 | 2.00E-92 |
| VPS35 | VPS35 | 5.00E-83 |
| PRKCG | PKC1 | 7.00E-78 |
| TAF1 | TAF1 | 1.00E-58 |
| SLC30A10 | ZRC1 | 2.00E-54 |
| SLC20A2 | PHO89 | 3.00E-39 |
| PANK2 | CAB1 | 2.00E-37 |
| GLUD2 | GDH3 | 3.00E-34 |
| EIF4G1 | TIF4631 | 2.00E-29 |
| EIF4G1 | TIF4632 | 1.00E-28 |
| LRRK2 | SPS1 | 2.00E-22 |
| PDE8B | PDE2 | 3.00E-20 |
| CSF1R | BCK1 | 9.00E-20 |
| SPR | IRC24 | 1.00E-15 |
| UCHL1 | YUH1 | 3.00E-15 |
| PINK1 | MEK1 | 1.00E-14 |
| HTRA2 | NMA111 | 1.00E-13 |
| PLA2G6 | NAS6 | 4.00E-13 |
| ATXN2 | PBP1 | 5.00E-12 |
| PARK2 | HEL1 | 1.00E-11 |
| FUS | CUS2 | 2.00E-10 |
| ATXN7 | SGF73 | 6.00E-10 |
| GIGYF2 | SYH1 | 6.00E-09 |

III. Neurodegenerative Diseases, Neurodegenerative Disease Genes and Gene Products, Neurodegeneration Associated Proteins and Nucleic Acids, and Genetic Modifiers Sequences of the neurodegenerative disease gene products of interest herein often comprise or consist of sequences encoded by human neurodegenerative disease genes, although sequences of non-human mammalian homologs may be used certain embodiments. In general, the sequence of a neurodegeneration associated protein or neurodegeneration associated RNA of interest herein often comprises or consists of a sequence of a human neurodegeneration associated protein or RNA, e.g., human alpha-synuclein, although a non-human mammalian homolog of a human NAP may be used in certain embodiments. In some embodiments the sequence of a gene product of a neurodegenerative disease gene, e.g., a NAP, comprises or consists of a naturally occurring sequence. It will be appreciated that a genetic locus may have more than one sequence or allele in a population of individuals. In some embodiments a naturally occurring sequence is a standard sequence. Unless otherwise indicated, a sequence listed in the Reference Sequence (RefSeq) Database as a reference sequence for a protein that is referred to herein by a particular name, abbreviation, or symbol, is considered to be a "standard sequence". If a sequence has been updated subsequent to the time of the present disclosure a version current at the time of the present disclosure or an updated version thereof may be used in certain embodiments. It will be appreciated that a genetic locus may have more than one sequence or allele in a population of individuals. In some embodiments a naturally occurring sequence differs from a standard sequence at one or more amino acid positions. A naturally occurring polynucleotide or polypeptide whose sequence differs from a standard sequence, that performs the normal function(s) of the polynucleotide or polypeptide, and is not associated with a greater risk of developing a neurodegenerative disease than the standard sequence may be referred to as having a "normal sequence". In some embodiments a naturally occurring sequence differs from a standard sequence and is associated with a greater risk of developing a neurodegenerative disease than the standard sequence. For example, in some embodiments a NAP or NAR contains a mutation that is associated with a dominantly or recessively inherited form of a neurodegenerative disease.

In some embodiments a neurodegeneration associated protein or RNA may comprise a biologically active variant of a naturally occurring NAP or NAR. In the context of a yeast cell or method involving a yeast cell, a "biologically active" variant of a naturally occurring NAP or NAR at least in part retains the ability of a naturally occurring NAP or NAR to induce a decrease cell growth or viability and/or form cytoplasmic inclusions in a yeast cell in which the biologically active variant is expressed. In the context of a mammalian nervous system cell (e.g., an induced human nervous system cell) or a method involving a mammalian nervous system cell, a "biologically active" variant of a naturally occurring NAP or NAR that induces a phenotype in such cell at least in part retains the ability to cause a phenotype caused by the naturally occurring NAP or NAR.

In some embodiments a neurodegeneration associated protein comprises an alpha-synuclein protein, e.g., a human alpha-synuclein protein. In humans, alpha-synuclein is encoded by the SNCA gene (chromosomal location 4q21.3-q22), which has been assigned NCBI Gene ID 6622. In certain embodiments the sequence of an alpha-synuclein protein used in the compositions and methods described herein comprises the sequence of a naturally occurring alpha-synuclein protein or a biologically active variant thereof. A biologically active variant of an alpha-synuclein protein may contain one or more additions, substitutions, and/or deletions relative to the sequence of a naturally occurring alpha-synuclein protein. In some embodiments the sequence of an alpha-synuclein protein comprises a standard alpha-synuclein sequence. Human alpha-synuclein is normally 140 amino acids in length and has the following standard amino acid sequence (GenBank and NCBI Reference Sequence Accession Number NP_000336):

(SEQ ID NO: 1)
MDVFMKGLSKAKEGVVAAAEKTKQGVAEAAGKTKEGVLYVGSKTKEGVV
HGVATVAEKTKEQVTNVGGAVVTGVTAVAQKTVEGAGSIAAATGFVKKD
QLGKNEEGAPQEGILEDMPVDPDNEAYEMPSEEGYQDYEPEA

In some embodiments an alpha-synuclein protein is a mutant alpha-synuclein protein, e.g., the sequence of the protein comprises the sequence of a naturally occurring mutant form of alpha-synuclein. In some embodiments an alpha-synuclein harbors a mutation or genetic variation that causes a dominantly inherited form of PD or is associated with a significantly increased risk of developing PD. A mutation may be in a coding sequence or regulatory region. Certain point mutations in alpha-synuclein (A30P, E46K, A53T) are known to cause a dominantly inherited form of PD. HSOQ, G51D, A18T, and A29S point mutations in alpha-synuclein have also been associated with PD. In some embodiments an alpha synuclein protein comprises a A53T mutation. In some embodiments an alpha synuclein protein comprises a A30P mutation. In some embodiments an alpha synuclein protein comprises a E46K mutation. In some embodiments an alpha-synuclein protein comprises a G51D mutation. In some embodiments an alpha-synuclein protein comprises a HSOQ mutation. In some embodiments an alpha synuclein protein comprises a G51D mutation. In some embodiments an alpha-synuclein protein comprises a A18T mutation. In some embodiments an alpha synuclein protein comprises a A29S mutation. In certain embodiments a human subject harbors an A30P, E46K, or A53T mutation in at least one allele of the gene encoding alpha-synuclein. In certain embodiments a human subject harbors an HSOQ, G51D, A18T, or A29S mutation in at least one allele of the gene encoding alpha-synuclein. In certain embodiments a human neuron or glial cell harbors an A30P, E46K, or A53T mutation in at least one allele of the gene encoding alpha-synuclein. In certain embodiments a human neuron or glial cell harbors a HSOQ, G51D, A18T, or A29S mutation in at least one allele of the gene encoding alpha-synuclein. It is reasonable to expect that additional mutations in alpha-synuclein will be discovered, e.g., in amino acids 29-30 or in amino acids 46-53 or in the 1-3 amino acids flanking these regions. In certain embodiments an alpha-synuclein protein has a mutation in amino acids 29-30 or amino acids 46-53 or in the 1-3 amino acids flanking these regions. In certain embodiments a biologically active alpha-synuclein protein comprises a fragment of a naturally occurring alpha-synuclein protein that lacks up to about 45 amino acids from the C-terminus. In some embodiments a biologicallly active alpha-synuclein protein has one or more mutations in the region consisting of residues 61-95, a region that has been implicated in driving fibril formation. In some embodiments the mutation is a nonconservative substitution. In some embodiments the mutation is an insertion of one or more amino acids that reduces the helical content of the region. In some embodiments the mutation is a proline substitution or insertion. In some embodiments an alpha-synuclein protein may lacks an internal exon as compared with transcripts encoding NP_000336. For example, the protein may comprise NACP112 (RefSeq Accession Number NP_009292).

In some embodiments a neurodegeneration associated protein comprises a leucine-rich repeat kinase 2 (LRRK2) protein, e.g., a human LRRK2 protein. Human LRRK2 has the following standard amino acid sequence (GenBank and NCBI Reference Sequence Accession Number NP_940980.3):

(SEQ ID NO: 6)
MASGSCQGCEEDEETLKKLIVRLNNVQEGKQIETLVQILEDLLVFTYSE

HASKLFQGKNIHVPLLIVLDSYMRVASVQQVGWSLLCKLIEVCPGTMQS

LMGPQDVGNDWEVLGVHQLILKMLTVHNASVNLSVIGLKTLDLLLTSGK

ITLLILDEESDIFMLIFDAMHSFPANDEVQKLGCKALHVLFERVSEEQL

TEFVENKDYMILLSALTNFKDEEEIVLHVLHCLHSLAIPCNNVEVLMSG

NVRCYNIVVEAMKAFPMSERIQEVSCCLLHRLTLGNFFNILVLNEVHEF

VVKAVQQYPENAALQISALSCLALLTETIFLNQDLEEKNENQENDDEGE

EDKLFWLEACYKALTWHRKNKHVQEAACWALNNLLMYQNSLHEKIGDED

GHFPAHREVMLSMLMHSSSKEVFQASANALSTLLEQNVNFRKILLSKGI

HLNVLELMQKHIHSPEVAESGCKMLNHLFEGSNTSLDIMAAVVPKILTV

MKRHETSLPVQLEALRAILHFIVPGMPEESREDTEFHHKLNMVKKQCFK

NDIHKLVLAALNRFIGNPGIQKCGLKVISSIVHFPDALEMLSLEGAMDS

VLHTLQMYPDDQEIQCLGLSLIGYLITKKNVFIGTGHLLAKILVSSLYR

FKDVAEIQTKGFQTILAILKLSASFSKLLVHHSFDLVIFHQMSSNEVIE

QKDQQFLNLCCKCFAKVAMDDYLKNVMLERACDQNNSIMVECLLLLGAD

ANQAKEGSSLICQVCEKESSPKLVELLLNSGSREQDVRKALTISIGKGD

SQIISLLLRRLALDVANNSICLGGFCIGKVEPSWLGPLFPDKTSNLRKQ

TNIASTLARMVIRYQMKSAVEEGTASGSDGNFSEDVLSKFDEWTFIPDS

SMDSVFAQSDDLDSEGSEGSFLVKKKSNSISVGEFYRDAVLQRCSPNLQ

RHSNSLGPIFDHEDLLKRKRKILSSDDSLRSSKLQSHMRHSDSISSLAS

EREYITSLDLSANELRDIDALSQKCCISVHLEHLEKLELHQNALTSFPQ

QLCETLKSLTHLDLHSNKFTSFPSYLLKMSCIANLDVSRNDIGPSVVLD

```
PTVKCPTLKQFNLSYNQLSFVPENLTDVVEKLEQLILEGNKISGICSPL

RLKELKILNLSKNHISSLSENFLEACPKVESFSARMNFLAAMPFLPPSM

TILKLSQNKFSCIPEAILNLPHLRSLDMSSNDIQYLPGPAHWKSLNLRE

LLFSHNQISILDLSEKAYLWSRVEKLHLSHNKLKEIPPEIGCLENLTSL

DVSYNLELRSFPNEMGKLSKIVVDLPLDELHLNFDFKHIGCKAKDIIRF

LQQRLKKAVPYNRMKLMIVGNTGSGKTTLLQQLMKTKKSDLGMQSATVG

IDVKDWPIQIRDKRKRDLVLNVWDFAGREEFYSTHPHFMTQRALYLAVY

DLSKGQAEVDAMKPWLFNIKARASSSPVILVGTHLDVSDEKQRKACMSK

ITKELLNKRGFPAIRDYHFVNATEESDALAKLRKTIINESLNFKIRDQL

VVGQLIPDCYVELEKIILSERKNVPIEFPVIDRKRLLQLVRENQLQLDE

NELPHAVHFLNESGVLLHFQDPALQLSDLYFVEPKWLCKEVIAQILTVK

VEGCPKHPKGIISRRDVEKFLSKKRKFPKNYMSQYFKLLEKFQIALPIG

EEYLLVPSSLSDHRPVIELPHCENSEIIIRLYEMPYFPMGFWSRLINRL

LEISPYMLSGRERALRPNRMYWRQGIYLNWSPEAYCLVGSEVLDNHPES

FLKITVPSCRKGCILLGQVVDHIDSLMEEWFPGLLEIDICGEGETLLKK

WALYSFNDGEEHQKILLDDLMKKAEEGDLLVNPDQPRLTIPISQIAPDL

ILADLPRNIMLNNDELEFEQAPEFLLGDGSFGSVYRAAYEGEEVAVKIF

NKHTSLRLLRQELVVLCHLHHPSLISLLAAGIRPRMLVMELASKGSLDR

LLQQDKASLTRTLQHRIALHVADGLRYLHSAMIIYRDLKPHNVLLFTLY

PNAAIIAKIADYGIAQYCCRMGIKTSEGTPGFRAPEVARGNVIYNQQAD

VYSFGLLLYDILTTGGRIVEGLKFPNEFDELEIQGKLPDPVKEYGCAPW

PMVEKLIKQCLKENPQERPTSAQVFDILNSAELVCLTRRILLPKNVIVE

CMVATHHNSRNASIVVLGCGHTDRGQLSFLDLNTEGYTSEEVADSRILC

LALVHLPVEKESWIVSGTQSGTLLVINTEDGKKRHTLEKMTDSVTCLYC

NSFSKQSKQKNFLLVGTADGKLAIFEDKTVKLKGAAPLKILNIGNVSTP

LMCLSESTNSTERNVMWGGCGTKIFSFSNDFTIQKLIETRTSQLFSYAA

FSDSNIITVVVDTALYIAKQNSPVVEVWDKKTEKLCGLIDCVHFLREVM

VKENKESKHKMSYSGRVKTLCLQKNTALWIGTGGGHILLLDLSTRRLIR

VIYNFCNSVRVMMTAQLGSLKNVMLVLGYNRKNTEGTQKQKEIQSCLTV

WDINLPHEVQNLEKHIEVRKELAEKMRRTSVE
```

In some embodiments the LRRK2 protein comprises a mutation associated with autosomal dominant PD or parkinsonism. In some embodiments the mutation is between amino acids 1400 and 2100, e.g., between amino acids 1420 and 1450 or between amino acids 2000 and 2030. In some embodiments the mutation is at position 2019, 1699, 1441, 2020, or 1437. In some embodiments the mutation is a G2019S, Y1699C, R1441C, R1441G, R1441H, I2012T, I2020T, or N1437H mutation. In certain embodiments a human neuron, e.g., an induced human neuron, harbors a mutation associated with autosomal dominant PD or parkinsonism in at least one allele of the gene encoding LRRK2, e.g., a mutation resulting in a G2019S, Y1699C, R1441C, R1441G, R1441H, I2012T, I2020T, or N1437H mutation in the encoded protein.

In some embodiments a neurodegeneration associated protein comprises a vacuolar protein sorting 35 (VPS35), e.g., a human VPS35 protein. VPS35 encodes a subunit of the retromer, a complex involved in endosome-to trans golgi transport in mammalian cells or endosome-to-vacuole transport in yeast. Mutation in VPS35 is associated with various neurodegenerative diseases. See, e.g., Zimprich, A. et al. A Mutation in VPS35, Encoding a Subunit of the Retromer Complex, Causes Late-Onset Parkinson Disease. Am J Hum Genet 89, 168-175 (2011); Vilariño-Güell C, et al., VPS35 mutations in Parkinson disease Am J Hum Genet. (2011) 89(1):162-7. Human VPS35 is encoded by the VPS35 gene (chromosomal location 16q12), which has been assigned NCBI Gene ID: 55737. Human VPS35 is normally 796 amino acids in length and has the following standard amino acid sequence (NCBI Reference Sequence Accession Number NP_060676.2):

(SEQ ID NO: 7)
```
MPTTQQSPQDEQEKLLDEAIQAVKVQSFQMKRCLDKNKLMDALKHASNM

LGELRTSMLSPKSYYELYMAISDELHYLEVYLTDEFAKGRKVADLYELV

QYAGNIIPRLYLLITVGVVYVKSFPQSRKDILKDLVEMCRGVQHPLRGL

FLRNYLLQCTRNILPDEGEPTDEETTGDISDSMDFVLLNFAEMNKLWVR

MQHQGHSRDREKRERERQELRILVGTNLVRLSQLEGVNVERYKQIVLTG

ILEQVVNCRDALAQEYLMECIIQVFPDEFHLQTLNPFLRACAELHQNVN

VKNIIIALIDRLALFAHREDGPGIPADIKLFDIFSQQVATVIQSRQDMP

SEDVVSLQVSLINLAMKCYPDRVDYVDKVLETTVEIFNKLNLEHIATSS

AVSKELTRLLKIPVDTYNNILTVLKLKHFHPLFEYFDYESRKSMSCYVL

SNVLDYNTEIVSQDQVDSIMNLVSTLIQDQPDQPVEDPDPEDFADEQSL

VGRFIHLLRSEDPDQQYLILNTARKHFGAGGNQRIRFTLPPLVFAAYQL

AFRYKENSKVDDKWEKKCQKIFSFAHQTISALIKAELAELPLRLFLQGA

LAAGEIGFENHETVAYEFMSQAFSLYEDEISDSKAQLAAITLIIGTFER

MKCFSEENHEPLRTQCALAASKLLKKPDQGRAVSTCAHLFWSGRNTDKN

GEELHGGKRVMECLKKALKIANQCMDPSLQVQLFIEILNRYIYFYEKEN

DAVTIQVLNQLIQKIREDLPNLESSEETEQINKHFHNTLEHLRLRRESP

ESEGPIYEGLIL
```

In some embodiments the VPS35 protein comprises a mutation associated with autosomal dominant PD, parkinsonism, and/or NBIA. In some embodiments the mutation is between positions 610 and 630 or between positions 310 and 330. In some embodiments the mutation is at position 620 or 316. In some embodiments the mutation is a D620N or P316S mutation. In certain embodiments a human neuron, e.g., an induced human neuron, harbors a mutation associated with autosomal dominant PD, parkinsonism, or NBIA in at least one allele of the gene encoding VPS35, e.g., a mutation resulting in a D620N or P316S mutation in the encoded protein. In some embodiments a phenotype associated with loss-of-function of VPS35 is defective endocytosis. As described further herein (see Example 11), VPS35 was identified as a genetic modifier of alpha-synuclein toxicity in yeast, in that deletion of yeast VPS35 enhances αSyn toxicity. As vps35 mutants have defective endocytosis, this finding highlights a disease-associated phenotype conserved between yeast and human neurons. Patients deficient in VPS35 have neurons deficient in this process. In addition, perturbed endocytosis is also a phenotype in neurons from patients with Parkinson's disease (sporadic disease involving synuclein aggregation and also patients with synuclein SNPs and synuclein point mutations) who do not have VPS35 mutations. While only a small fraction of patients with parkinsonism have mutations in VPS35, the identification in yeast of the connection between alpha-synuclein and VPS 35 deficiency implicates the much broader role of VPS35 and the biological processes in which it is involved in synucleinopathies.

In some embodiments a neurodegeneration associated protein comprises a eukaryotic translation initiation factor 4-gamma 1 (EIF4G1), e.g., a human EIF4G1 protein. Human EIF4G1 is encoded by the EIF4G1 gene (chromosomal location 3q27.1), which has been assigned NCBI Gene ID:1981. In some embodiments the EIF4G1 protein comprises a mutation associated with autosomal dominant PD or parkinsonism. In some embodiments the mutation is between positions 1240 and 1260. In some embodiments the mutation is at position 1250. In some embodiments the mutation is a R1250H mutation. In certain embodiments a human neuron, e.g., an induced human neuron, harbors a mutation associated with autosomal dominant PD or parkinsonism in at least one allele of the gene encoding EIF4G1, e.g., a mutation resulting in a R1250H mutation in the encoded protein.

In some embodiments a neurodegeneration associated protein comprises a β-glucocerebrosidase (GBA) protein, also referred to as GCase. β-glucocerebrosidase is the lysosomal enzyme that is deficient in Gaucher disease (GD). In humans, GBA is encoded by the GBA gene (chromosomal location 1q21), which has been assigned NCBI Gene ID 2629. Human GBA is normally 536 amino acids in length and has the following standard amino acid sequence (NCBI Reference Sequence Accession Numbers NP_001005741.1; NP_001005741.1; and NP_001005742.1).

(SEQ ID NO: 8)
MEFSSPSREECPKPLSRVSEVIAGSLTGLLLLQAVSWASGARPCIPKSF

GYSSVVCVCNATYCDSFDPPTFPALGTFSRYESTRSGRRMELSMGPIQA

NHTGTGLLLTLQPEQKFQKVKGFGGAMTDAAALNILALSPPAQNLLLKS

YFSEEGIGYNIIRVPMASCDFSIRTYTYADTPDDFQLHNFSLPEEDTKL

KIPLIHRALQLAQRPVSLLASPWTSPTWLKTNGAVNGKGSLKGQPGDIY

HQTWARYFVKFLDAYAEHKLQFWAVTAENEPSAGLLSGYPFQCLGFTPE

HQRDFIARDLGPTLANSTHHNVRLLMLDDQRLLLPHWAKVVLTDPEAAK

YVHGIAVHWYLDFLAPAKATLGETHRLFPNTMLFASEACVGSKFWEQSV

RLGSWDRGMQYSHSIITNLLYHVVGWTDWNLALNPEGGPNWVRNFVDSP

IIVDITKDTFYKQPMFYHLGHFSKFIPEGSQRVGLVASQKNDLDAVALM

HPDGSAVVVVLNRSSKDVPLTIKDPAVGFLETISPGYSIHTYLWRRQ

It will be understood that the sequence above is a precursor polypeptide. In human cells, the enzyme contains either a 39 amino acid (amino acids 1-39) or 19 amino acid (amino acids 1-19) signal peptide that directs the nascent polypeptide to transit the endoplasmic reticulum (ER) membrane before being cleaved in the ER lumen. The enzyme is then glycosylated and shuttled through the trans-golgi network into maturing lysosomes. For purposes of describing positions within the GBA protein, e.g., positions of mutations, it is assumed that the 40$^{th}$ amino acid in SEQ ID NO: 8 (underlined and bold A) is position 1. For example, an R120W mutation refers to a substitution of W in place of R at position 159 in the sequence above or at the corresponding position in a variant or fragment of SEQ ID NO: 8, e.g., a position that aligns with position 159 when the variant or fragment is aligned with SEQ ID NO: 8.

Clinical, genetic and pathological studies have shown that mutations in the gene that encodes GBA are risk factors for PD and various other synucleinopathies such as Lewy body dementia. Some patients with GD and some carriers of mutations that give rise to GD develop parkinsonism, and subjects with PD have an increased frequency of GBA mutations as compared to healthy subjects. GBA mutation carriers with PD typically exhibit glucocerebrosidase-positive Lewy bodies. In some embodiments a gene encoding a GBA protein comprises a mutation that gives rise to GD when the mutation is present in both alleles of the GBA gene in a subject (homozygous) or when the mutation is present in one allele of the GBA gene and the other allele contains a different mutation (compound heterozygous). In some embodiments the mutation gives rise to GD type I (OMIM #230800, sometimes referred to as the non-neuropathic form of GD). In some embodiments the mutation gives rise to GD type II (OMIM #230900, sometimes referred to as the acute neuropathic form of GD) or GD type III (OMIM #2301000, sometimes referred to as the chronic neuropathic form of GD). In some embodiments the mutation is 84GG (chr1 155210452-0155210453insG), IVS2+1 (chr1 155210420G>A/155210420G>T), R120W, L174P, K198T, E326K, R329C, T369M, N370S, V394L, D409H, L444P, R496H, Q497R, RecTL (naturally occurring form of which arises from a genetic recombination between the glucocerebrosidase gene and pseudogene that introduces a deletion of 55 bp and mutation D409H in exon 9, as well as mutations L444P, A456P, and V460V in exon 10), D406H, N370S, or a RecNcil (chr1 155205043T>C/15599045G>C/155204994G>C) mutation. In some embodiments the mutation results in an altered protein sequence relative to a normal sequence, e.g., a reference sequence. In some embodiments the mutation is between positions 120 and 500, e.g., between positions 320 and 330 or between positions 365 and 375 or between positions 490 and 500. In some embodiments the mutation is at position 120, 174, 198, 326, 329, 369, 370, 394, 409, 444, 496, or 497. In some embodiments the mutation in the protein is R120W, L174P, K198T, E326K, R329C, T369M, N370S, V394L, D409H, L444P, R496H, or Q497R. In some embodiments the gene or protein comprises multiple mutations. In certain embodiments a human neuron, e.g., an induced human neuron, harbors one or more mutations associated with GD, e.g., a 84GG, IVS2+1, R120W, L174P, K198T, E326K, R329C, T369M, N370S, V394L, D409H, L444P, R496H, Q497R, RecTL or a RecNcil mutation.

In some embodiments a neurodegeneration associated protein comprises a TDP-43 protein, e.g., a human TDP-43 protein. In humans, TDP-43 is encoded by the TARDBP gene (chromosomal location 1p36.2), which has been assigned NCBI Gene ID 23435. TDP-43 comprises two highly conserved RRMs (RNA-recognition motifs; RRM1 and RRM2) and a glycine-rich C-terminal region. In certain embodiments the sequence of a TDP-43 protein used in the compositions and methods described herein comprises the sequence of a naturally occurring TDP-43 protein or a biologically active variant thereof. In some embodiments the sequence of a TDP-43 protein comprises a standard TDP-43 sequence. Human TDP-43 is normally 414 amino acids in length and has the following standard amino acid sequence (NCBI Reference Sequence Accession Number NP_031401):

(SEQ ID NO: 2)
MSEYIRVTEDENDEPIEIPSEDDGTVLLSTVTAQFPGACGLRYRNPVSQ

CMRGVRLVEGILHAPDAGWGNLVYVVNYPKDNKRKMDETDASSAVKVKR

AVQKTSDLIVLGLPWKTTEQDLKEYFSTFGEVLMVQVKKDLKTGHSKGF

GFVRFTEYETQVKVMSQRHMIDGRWCDCKLPNSKQSQDEPLRSRKVFVG

RCTEDMTEDELREFFSQYGDVMDVFIPKPFRAFAFVTFADDQIAQSLCG

EDLIIKGISVHISNAEPKHNSNRQLERSGRFGGNPGGFGNQGGFGNSRG

GGAGLGNNQGSNMGGGMNFGAFSINPAMMAAAQAALQSSWGMMGMLASQ

QNQSGPSGNNQNQGNMQREPNQAFGSGNNSYSGSNSGAAIGWGSASNAG

SGSGFNGGFGSSMDSKSSGWGM.

C-terminal fragments of human TDP-43 have been recovered from the central nervous system of patients with frontotemporal lobar degeneration with ubiquitin-positive inclusions and amyotrophic lateral sclerosis (Neumann et al. Science, 314(5796):130-3. 2006). Certain disease associated C-terminal fragments of TDP-43 correspond to approximately amino acid residues 252-414 of SEQ ID NO: 2. In some embodiments, a biologically active variant TDP-43 protein (i) contains one or more amino acid substitutions relative to SEQ ID NO: 2, and (ii) is at least 70%, 80%, 85%, 90%, 95%, 98% or 99% identical to SEQ ID NO: 2 (or 70%, 80%, 85%, 90%, 95%, 98% or 99% identical to amino acids 252-414 of SEQ ID NO: 2). A biologically active variant TDP-43 polypeptide differing in sequence from SEQ ID NO: 2 (or differing in sequence from amino acids 252-414 of SEQ ID NO: 2) may include one or more amino acid substitutions (conservative or non-conservative), one or more deletions, and/or one or more insertions. In certain embodiments a biologically active TDP-43 fragment comprises or consists of amino acid residues 252-414 of SEQ ID NO: 2.

Mutations in TDP-43 have been found in patients with sporadic and familial FTLD and/or ALS. In certain embodiments a mutant TDP-43 protein has a mutation in the portion of the protein encoded by exon 6 of the TARDBP gene.

Nucleic acids encoding variant TDP-43 proteins can be used to identify those variants that exhibit toxicity in yeast cells, e.g., equivalent or enhanced toxicity in yeast cells relative to that exhibited by the human TDP-43 protein of SEQ ID NO: 2. Such variants, e.g., enhanced toxicity variants, may be used in screening and other methods described herein. Human TDP-43 is encoded by the nucleotide sequence set forth in NCBI Reference Sequence Accession Number NM_007375 (coding sequence is from positions 135-1379), although of course other nucleic acid sequences encoding the protein may be used.

In some embodiments a NAP comprises a fused in sarcoma (FUS) polypeptide, e.g., a human FUS polypeptide. In humans, FUS is encoded by the FUS gene (chromosomal location 16p11.2), which has been assigned NCBI Gene ID 2521. Human FUS has the following standard amino acid sequence (NCBI Reference Sequence Accession Number NP_004951):

(SEQ ID NO: 3)
MASNDYTQQATQSYGAYPTQPGQGYSQQSSQPYGQQSYSGYSQSTDTSGY

GQSSYSSYGQSQNTGYGTQSTPQGYGSTGGYGSSQSSQSSYGQQSSYPGY

GQQPAPSSTSGSYGSSSQSSSYGQPQSGSYSQQPSYGGQQQSYGQQQSYN

PPQGYGQQNQYNSSSGGGGGGGGGNYGQDQSSMSSGGGSGGGYGNQDQS

GGGGSGGYGQQDRGGRGRGGSGGGGGGGGGGYNRSSGGYEPRGRGGGRGG

RGGMGGSDRGGFNKFGGPRDQGSRHDSEQDNSDNNTIFVQGLGENVTIES

VADYFKQIGIIKTNKKTGQPMINLYTDRETGKLKGEATVSFDDPPSAKAA

IDWFDGKEFSGNPIKVSFATRRADFNRGGGNGRGGRGRGGPMGRGGYGGG

GSGGGGRGGFPSGGGGGGGQQRAGDWKCPNPTCENMNFSWRNECNQCKAP

KPDGPGGGPGGSHMGGNYGDDRRGGRGGYDRGGYRGRGGDRGGFRGGRGG

GDRGGFGPGKMDSRGEHRQDRRERPY

One of ordinary skill in the art will appreciate that slightly shorter isoforms with sequences available at NCBI Reference Sequence Accession Numbers NP_001164105.1 and NP_001164408.1 (isoform 3) also exist. FUS protein is characterized by an N-terminal QGSY-rich region, a highly conserved RNA recognition motif (RRM), multiple RGG repeats, which are extensively dimethylated at arginine residues, and a C-terminal zinc finger motif. It is an RNA binding protein that was initially identified as a fusion protein arising as a result of a chromosomal translocation in certain human cancers.

In some embodiments a neurodegeneration associated protein comprises an amyloid beta protein, e.g., human amyloid beta protein. In some embodiments, a polypeptide used in the compositions and methods described herein, e.g., a polypeptide expressed in a yeast model of amyloid beta toxicity, comprises a fusion protein that comprises a signal sequence and a human amyloid beta protein. As used herein, the term "human amyloid beta protein" refers to a sequence identical to a naturally occurring 38-43 amino acid amyloid beta peptide that is derived via proteolytic processing of the human amyloid precursor protein (APP) and is associated with amyloid pathologies. The term includes naturally occurring wild type amyloid beta peptides as well as naturally occurring mutant amyloid beta peptides. Wild type amyloid beta peptides include amyloid beta 1-38, amyloid beta 1-39, amyloid beta 1-40, amyloid beta 1-41, amyloid beta 1-42, and amyloid beta 1-43. Amyloid beta mutations include A2T, H6R, D7N, A21G, E22G (Arctic), E22Q (Dutch), E22K (Italian), D23N (Iowa), A42T, and A42V (wherein the numbering is relative to the amyloid beta peptide of SEQ ID NO: 3). These mutations may optionally be present in any of the amyloid beta peptides 1-38, 1-39, 1-40, 1-41, 1-42, and 1-43.

Amino acids 1-43 of human amyloid beta, which amino acids are used as the backbone of certain amyloid beta peptides described herein, are as follows:

(SEQ ID NO: 4)
DAEFRHDSGYEVHHQKLVFFAEDVGSNKGAIIGLMVGGVVIAT.

As used herein, the term "signal sequence" refers to a peptide sequence that is present within a polypeptide and causes the polypeptide to be targeted to the endoplasmic reticulum within a cell. An exemplary signal sequence is the yeast Kar2p signal sequence. However, a wide variety of signal sequences are known and can be used to cause endoplasmic reticulum targeting of polypeptides that contain them. Signal sequences are reviewed in e.g., Wilkinson et al. (1997) J Membr Biol. 155(3):189-97, Haguenauer-Tsapis (1992) Mol Microbiol. 6(5):573-9, and Pool (2005) Mol Membr Biol. 22(1-2):3-15. In various embodiments a signal sequence may be present at the N-terminus or C-terminus of a polypeptide or as an internal sequence.

In some embodiments the fusion polypeptide comprises the yeast Kar2p signal sequence at the amino terminus and the human amyloid beta 1-42 peptide at the carboxy terminus. In certain embodiments amino acid sequence of the fusion polypeptide comprises or consists of:

```
                                            (SEQ ID NO: 5)
MFFNRLSAGKLLVPLSVVLYALFVVILPLQNSFHSSNVLVRGDAEFRH
DSGYEVHHQKLVFFAEDVGSNKGAIIGLMVGGVVIA.
```

The yeast Kar2p signal sequence corresponds to amino acids 1-42 of SEQ ID NO: 1 and the human amyloid beta 1-42 peptide corresponds to amino acids 43-84 of SEQ ID NO: 4.

In some embodiments a polypeptide containing a signal sequence and a human amyloid beta protein may optionally be fused with a second domain. The second domain of the fusion protein can optionally be an immunoglobulin element, a dimerizing domain, a targeting domain, a stabilizing domain, or a purification domain. In some embodiments an amyloid beta protein, e.g., a human amyloid beta protein, can be fused with a heterologous molecule such as a detection protein. Exemplary detection proteins include: a fluorescent protein such as green fluorescent protein (GFP), cyan fluorescent protein (CFP) or yellow fluorescent protein (YFP); an enzyme such as β-galactosidase or alkaline phosphatase (AP); an epitope such as glutathione-S-transferase (GST) or hemagglutinin (HA). For example, an amyloid beta protein can be fused to GFP at the N- or C-terminus or other parts of the amyloid beta protein. These fusion proteins provide methods for rapid and easy detection and identification of the amyloid beta protein, e.g., in a recombinant yeast cell or mammalian cell, e.g., human cell, engineered to express the protein.

In some embodiments a NAP comprises a polyglutamine (polyQ) repeat protein. As used herein, a "polyglutamine repeat protein" is a polypeptide comprising at least 6 consecutive glutamine residues. In certain embodiments a NAP comprises an expanded polyQ region. An expanded polyQ region is a region that contains more glutamine residues than in a normal wild type protein. A polyQ expanded protein is a protein containing an expanded polyQ region. polyQ expansion disorders are characterized by the presence of intracellular aggregates containing a polyQ expanded protein in at least some affected neurons. The polyQ expansion disorder Huntington's disease is an autosomal dominantly inherited neurodegenerative disease caused by a polyQ-expansion in the Huntingtin (Htt) protein. The spinocerebellar ataxias type 1 (SCA1), 2 (SCA2), 3 (SCA3), 6 (SCA6), 7 (SCA7), and 17 (SCA17) and DRPLA (dentatorubropallidoluysian atrophy) are autosomal dominantly inherited progressive cerebellar ataxias caused by polyQ expansions in the proteins encoded by SCA1, SCA2, SCA3, SCA6, SCA7, SCA17, ATN1, (i.e. ataxin-1, ataxin-2, ataxin-3, α-1A subunit of the P/Q type voltage-dependent calcium channel, ataxin-7, TATA-binding protein (TBP), and atrophin-1, respectively). In some embodiments a polyQ repeat protein comprises a polyQ expanded huntingtin polypeptide. In some embodiments a NAP comprises a polypeptide encoded by exon one of the human huntingtin gene. The polyQ region typically is 6-35 glutamine residues in length in a wild-type huntingtin polypeptide and may be expanded in a mutant huntingtin polypeptide. In certain embodiments a mutant huntingtin polypeptide has at least 36, at least 37, at least 40, at least 45, at least 70, or at least 100 glutamine residues in a polyQ region. In certain embodiments a huntingtin polypeptide having an expanded polyQ region comprises the first 17 amino acids of exon 1 followed by at least 72 glutamine residues, e.g., 72-250 glutamine residues. In some embodiments the glutamine residues are encoded by CAG (in DNA) or CUG (in RNA). Lengths of expanded polyQ regions associated with spinocerebellar ataxias are known in the art. In certain embodiments the number of consecutive glutamines in a polyglutamine repeat protein is at least 1.0, 1.25, 1.5, 2, 2.5, 3, 3.5, 4.5, 5, or 10 times the lower limit of the range characteristic of the disease. In certain embodiments the number of consecutive glutamines in a polyglutamine repeat protein is up to 1.0, 1.25, 1.5, 2, 2.5, 3, 3.5, 4.5, 5 and 10 times the upper limit of a range characteristic of the disease. In some embodiments the number of consecutive glutamines in a polyglutamine repeat protein is between 50 and 100, 100 and 150, 150 and 200, 200 and 350, 350 and 500, 500 and 750, or 750 and 1,000.

In certain embodiments a gene that encodes a neurodegeneration associated RNA comprises multiple consecutive repeats of a particular nucleotide sequence. Typically a repeated nucleotide sequence (sometimes termed a "repeat unit" herein) in a neurodegeneration associated RNA or gene encoding such an RNA is between 2 and 6 nucleotides long, e.g., a trinucleotide. In certain embodiments the repeat unit in the gene is a CAG triplet, which results in a CUG triplet in the RNA. In certain embodiments the number of consecutive repeat units, e.g., CAG triplets, in a neurodegenerative disease gene that causes a polynucleotide expansion disorder is at least 0.5, 1.0, 1.25, 1.5, 2, 2.5, 3, 3.5, 4.5, 5, or 10 times the lower limit of a range characteristic of the disease. In certain embodiments the number of consecutive repeat units, e.g., CAG triplets, in a neurodegenerative disease gene that causes a polynucleotide expansion disorder is up to 1.0, 1.25, 1.5, 2, 2.5, 3, 3.5, 4.5, 5 and 10 times the upper limit of a range characteristic of the disease. In some embodiments the number of consecutive nucleotide repeats, e.g., CAG triplets, in a neurodegenerative disease gene that causes a polynucleotide expansion disorder is between 50 and 100, 100 and 150, 150 and 200, 200 and 350, 350 and 500, 500 and 750, or 750 and 1,000.

In some embodiments a NAP comprises a fusion protein comprising a NAP joined at its N-terminus or C-terminus to a second polypeptide or joined to second and third polypeptides at its N- and C-terminus. The second (and/or third) polypeptide can be, for example, an epitope, a selectable protein, an enzyme, or a detection protein. For example, the second polypeptide can be beta-galactosidase, green fluorescent protein (GFP), FLAG, Myc, or the like. For example, in certain embodiments a fusion protein comprising an alpha-synuclein protein, a TDP-43 protein, an amyloid beta peptide, or a polyQ polypeptide, and a second polypeptide, optionally further comprising a third polypeptide, may be used. It should be understood that the polypeptide components of a fusion protein may be directly joined to each other or may be joined via a linker peptide. In general, a linker peptide may comprise any amino acid sequence and may be of any length, e.g., between 1 and 100 amino acids in length, e.g., between about 10 and about 25 amino acids in length. Suitable linkers may comprise multiple Gly and/or Ser residues.

In some embodiments a mammalian nucleic acid sequence, e.g., a human nucleic acid sequence, e.g., a human cDNA sequence encoding a NAP, may be codon optimized for increased expression in a yeast cell.

In some embodiments a neurodegenerative disease gene is a loss of function (LOF) neurodegenerative disease gene. In some embodiments the disease has an autosomal recessive inheritance pattern. In some embodiments the LOF gene is associated with a synucleinopathy. In some embodiments the LOF gene is associated with parkinsonism, e.g., PD or non-PD parkinsonism. In some embodiments the LOF gene is associated with NBIA.

In some embodiments the LOF neurodegenerative disease gene is ATP13A2. The human ATP13A2 gene encodes an 1180 amino acid protein of ~130 kDa belonging to the P5 subfamily of P-type transport ATPases that are predicted to contain ten transmembrane-spanning domains. Mutations in the ATP13A2 gene (PARK9) cause autosomal recessive, juvenile-onset Kufor-Rakeb syndrome (KRS), a neurodegenerative disease characterized by parkinsonism. Mutations identified to date as causing KRS include 3057delC, 1632_1653 dup22, 1306+5G→>A, and a frame-shift mutation in exon 22 of ATP13A2 (c.2473C>AA, p.Leu825AsnfsX32). They produce truncated forms of ATP13A2 with impaired protein stability and/or impaired activity, resulting in a loss of function. A variety of homozygous (e.g., F182L, G504R, G877R, L3292, and L6025) and heterozygous (e.g., T12M, G533R and A746T) missense mutations in ATP13A2 have been identified in subjects with early-onset parkinsonism. In some embodiments the LOF neurodegenerative disease gene is a gene listed in Table C, wherein mutations in the gene cause parkinsonism with a recessive inheritance pattern. In some embodiments the LOF neurodegenerative disease gene is a parkinsonism gene that has a yeast homolog, e.g., the gene is a gene listed in Table D.

IV. Human Induced Nervous System Cells

As noted above, an "induced nervous system cell", as used herein, refers to a cell that has been derived in vitro from a pluripotent cell, e.g., a pluripotent stem cell, or from a non-neuronal somatic cell and that exhibits features characteristic of a nervous system cell. A pluripotent cell is an undifferentiated cell that is capable of giving rise to cells of the three germ layers: endoderm, mesoderm, and ectoderm, and typically has the ability to self-renew for a prolonged or indefinite period. In general, pluripotent cells are positive for at least one master pluripotency transcription factor such as OCT4 (also known as POU5F1), SOX2, and/or NANOG, e.g., all three of these factors. Pluripotent human stem cells typically express one or more cell surface pluripotency-associated markers, e.g., SSEA4, SSEA3, TRA1-60, and/or TRA-1-81. Additional features characteristic of a pluripotent cell are the ability to form a teratoma when introduced into an immunocompromised mouse (e.g., a SCID mouse) and form embryoid bodies that can differentiate in vitro under appropriate conditions to give rise to cells of the three germ layers. In some embodiments a pluripotent stem cell has undergone or is capable of undergoing at least 50, 60, 70, 80, 90, or 100 population doublings and/or at least 50, 60, 70, 80, 90, or 100 passages in culture without significant loss of pluripotency.

In some embodiments a pluripotent stem cell is an embryonic stem cell (ES cell). ES cells are pluripotent stem cells derived from an early stage embryo, e.g., a blastocyst, or from a blastomere isolated from an early stage embryo. As used herein the term "early stage embryo" encompasses pre-implantation embryos from the first cell division up to and including the blastocyst stage e.g., 4-cell embryos, 8-cell embryos, morulas, or blastocysts. An ES cell is typically derived in vitro from an early stage embryo that has been created using in vitro fertilization or from a blastomere isolated from such an embryo. Any of a variety of methods known in the art may be used to derive, identify, and/or characterize an ES cell. See, e.g., Turksen, K. (ed.) Human Embryonic Stem Cell Protocols, Methods in Molecular Biology, Vol. 331 Humana Press, Inc. Totowa, N H, 2006, Turksen, K. (ed.), *Human Embryonic Stem Cell Handbook*, Methods in Molecular Biology, Vol. 873 Humana Press (a brand of Springer), 2012 (e.g., Ch. 1-6 in particular for methods of deriving human ES cells). See also U.S. Pat. Nos. 5,843,780; 6,200,806; 7,029,913; U.S. Pat. Pub. No. 20090186407; PCT/US2011/000850 (WO/2011/142832). ES cells and ES cell colonies are readily recognized by those skilled in the art. For example, primate ES colonies exhibit a compact morphology (tightly packed cells) and sharp colony boundaries and contain cells with high nucleus to cytoplasm ratios and prominent nucleoli. Areas of differentiated cells can appear at the edges of ES cell colonies, especially if the cells become crowded. Such cells are often larger and flatter. If desired, such cells can be substantially removed during mechanical passaging. Numerous human ES cell lines are available. Hundreds of human ES cell lines are listed on the US National Institutes of Health Human Embryonic Stem Cell Registry (http://grants.nih.gov/stem_cells/registry/current.htm) and/or the European Human Embryonic Stem Cell Registry (www.hescreg.eu). In some embodiments an ES cell may be generated using somatic cell nuclear transfer. In this approach the nucleus of a non-pluripotent cell is introduced into an enucleated oocyte of the same species, which is subsequently allowed to begin developing to an early stage embryo, e.g., a blastocyst, from which an ES cell may be derived.

In some embodiments a pluripotent cell is an induced pluripotent stem cell. As used herein, an induced pluripotent stem (iPS) cell is a cell that is derived from a somatic cell by reprogramming the cell to a pluripotent state. iPS cells possess certain key features of ES cells including cell morphology, colony morphology, long-term self-renewal, expression of pluripotency-associated markers, similar genome-wide expression profile, ability to form teratomas in immunocompromised mice, and ability to give rise to cells of multiple cell lineages in vitro under appropriate conditions. It will be understood that the term "iPS cell" includes the original derived pluripotent cell and its descendants that retain pluripotent stem cell properties. "Reprogramming", as used herein, refers to altering the differentiation state or identity of a cell (e.g., its cell type) or a process by which this occurs. In general, reprogramming a first cell generates a second cell with a differentiation state or identity distinct from that which would result from a differentiation program that the first cell or a corresponding cell would normally follow in vivo and results in cells of one or more types distinct from those that the first cell or a corresponding cell would give rise to in vivo. A "corresponding cell" is a cell of the same type or having sufficiently similar features that a person of ordinary skill in the art would reasonably consider it to be of the same or substantially the same cell type. Cell type may refer to a category of cell such as "neuron" or "glial cell" or a subtype within a broader category. A subtype may be defined on the basis of characteristic features, characteristic cellular markers (e.g., neurotransmitters produced by the cell or that stimulate the cell) characteristic location where cells of that subtype may be found in the body, functional properties, etc. For example, a neuron may be cortical neuron, dopaminergic neuron, glutamaterigic neuron, or "motor neuron, to name but a few. In some embodiments cell type is defined based on expression level of a particular set of one or more cellular markers. One of ordinary skill in the art will be able to select an appropriate set of cellular markers by which to assign or define the cell type or state of a cell. Examples of suitable sets of markers are described herein but the invention is not limited to those markers as others may be used. In some embodiments reprogramming causes a cell to assume a less differentiated state. In some embodiments reprogramming confers on a cell the potential to develop into one or more cell types into which it would not otherwise be capable of developing. In some embodiments reprogramming generates a pluripotent cell from a somatic cell. In some embodiments a somatic cell is a mature, differentiated cell. In some embodiments reprogramming alters a cell to one of a cell lineage different to that which a corresponding cell would develop into or give rise to in vivo under normal conditions. In some embodiments reprogramming generates somatic cells of a second cell lineage or second cell type from somatic cells of a first cell lineage or first cell type that is different to the second cell lineage or first cell type. In some embodiments this transformation may occur without generating a detectable pluripotent cell as an intermediate, in which case it may be referred to as "trans-differentiation". Reprogramming a cell to a particular cell type, cell lineage, or cell state may occur over the course of one or more cell cycles. For example, it may take multiple rounds of cell division to generate a pluripotent stem cell from a somatic cell or to generate a differentiated cell of a first cell type from a differentiated cell of a different cell type.

In general, reprogramming may be performed by a method comprising contacting at least one somatic cell with one or more reprogramming agents under suitable conditions and for a suitable time for the cell to be reprogrammed. In some embodiments reprogramming is performed by a method comprising introducing a reprogramming factor or a nucleic acid encoding a reprogramming factor into a cell or inducing expression in a cell of a reprogramming factor encoded by an exogenous nucleic acid. The term "reprogramming factor" encompasses proteins that are capable of causing or contributing to reprogramming a cell. Many useful reprogramming factors are transcription factors that are naturally expressed by or present in mammalian cells of the type or state to be generated. These proteins may normally contribute to inducing or maintaining cell identity or state by affecting gene expression. The term "reprogramming agent" encompasses reprogramming factors and also agents that are capable of (i) substituting for a reprogramming factor in a method of reprogramming, (ii) inhibiting expression of an endogenous RNA or protein that may otherwise inhibit reprogramming, and/or (iii) detectably increasing reprogramming efficiency or speed as compared with the efficiency or speed that would be achieved in the absence of the reprogramming agent. In some embodiments a reprogramming agent may stimulate a signaling pathway that leads to expression or activation of an endogenous reprogramming factor, inhibit a signaling pathway that leads to expression or activation of an endogenous inhibitor of reprogramming, or activate or inhibit an enzyme that modifies chromatin structure, such as a DNA or histone acetylase, deacetylase, methylase, or demethylase.

In some embodiments a method of reprogramming comprises performing one or more manipulations on cells such as introducing nucleic acid(s), e.g., vector(s), that encode particular proteins or RNAs into cells and/or culturing them in medium containing particular compounds, which may enter the cells or act on cell surface receptors to induce reprogramming and/or increase its efficiency or speed. The particular manipulations and/or protocol used may be selected as appropriate depending, e.g., on the desired cell type or state, the type or state of the cells to be reprogrammed, etc. In some embodiments a reprogramming method is performed in vitro. In some aspects a reprogramming method does not require and typically does not include nuclear or cytoplasmic transfer or cell fusion, e.g., with oocytes, embryos, germ cells, or pluripotent cells. Any aspect or embodiment may expressly exclude nuclear or cytoplasmic transfer or cell fusion, e.g., fusion of a somatic cell with an oocyte, embryo, germ cell, or pluripotent cell or transfer of a somatic cell nucleus to an oocyte, embryo, germ cell, or pluripotent cell.

Reprogramming often comprises exposing a plurality of cells to a reprogramming agent or combination thereof in culture and identifying or selecting one or more cells or cell colonies having features of a desired cell type or state. The one or more cells or at least a portion of the cell colony may be isolated and expanded in culture and may be propagated as a distinct cell line under conditions appropriate to maintain its new cell identity or state. In some embodiments such conditions are typical culture conditions for a cell of that type. In some embodiments continued exposure to at least one, some, or all of the exogenous reprogramming agents is not necessary in order to maintain the identity or state of the reprogrammed cells, e.g., the identity or state of the reprogrammed cells is stable in the absence of such agents.

In some embodiments reprogrammed cells may be induced to differentiate to yield cells of one or more different cell lineages or cell types. For example, pluripotent cells generated through reprogramming may be allowed or induced to differentiate into multipotent progenitor cells, e.g., neural progenitor cells, which may be allowed or induced to further differentiate to give rise to mature, differentiated cells of various types. Differentiation to one or more desired cell lineages or cell types may be induced by subjecting a cell to an appropriate set of one or more manipulations or placing the cell under conditions that are permissive for differentiation. It will be understood that differentiation may occur over the course of one or multiple cell cycles. The particular manipulations and/or protocol to be used to cause differentiation may be selected as appropriate depending, e.g., on the desired cell type(s) and/or the starting cell type.

Somatic cells may be reprogrammed to iPS cells by a variety of methods. In some embodiments iPS cells are generated by a method comprising introducing one or more reprogramming factors or nucleic acids encoding such factor(s) into a somatic cell and/or inducing expression in the cell of one or more exogenous nucleic acid(s) encoding such factors. In some embodiments the reprogramming factors include at least one, two, or all of OCT4, SOX2, and KLF4 (OSK factors), and, optionally, c-MYC (OSKM factors). Other reprogramming factors, such as NANOG and LIN28 are also of use. For example, the combination of OCT4, SOX2, NANOG, and LIN28 (OSNL factors) can induce pluripotency. Many variations or alternative combinations are possible. For example, different KLF and/or MYC family members may be used instead of or in addition to KLF4 and/or c-MYC. For example, KLF2 or KLF5 can substitute for KLF4; N-MYC or L-Myc for c-MYC. In some embodiments 1, 2, 3, 4, 5, or more reprogramming factors are used. In some embodiments the reprogramming factors include at least OCT4. In some embodiments SAL4, NANOG, ESRRB, and LIN28 (SNEL factors) or SAL4, LIN28, ESRRB, and DPPA2 (SLED factors) may be used. In some embodiments reprogramming may be enhanced (e.g., its efficiency or speed may be increased) by use of one or more additional reprogramming factors in combination with one or more of the OSKM, OSNL, or other factors. For example, the Gli-like transcription factor Glis1 (Glis family zinc finger 1) was shown to markedly enhance the generation of iPS cells from fibroblasts when expressed together with OSK factors (Maekawa M, et al., Nature. (2011) 474(7350):225). SV40 large T (LT) is another example of a factor capable of enhancing reprogramming. In some embodiments an appropriate set of reprogramming factors introduced or expressed for a sufficient time at an appropriate level under suitable culture conditions causes activation of the endogenous pluripotency genes OCT4, SOX2, and NANOG, which may result in a self-sustaining pluripotent state in some of the cells. In some embodiments exogenous DNA (e.g., DNA encoding reprogramming factors) introduced into cells is naturally silenced and/or at least in part removed or lost after induction of pluripotency, e.g., after a self-sustaining pluripotent state is reached, or after a pluripotent cell, induced neural stem cell or induced neural progenitor cell has been differentiated to a desired cell type. Inserted DNA may comprise target sites for a recombinase so that removal of the region between these sites may be performed by recombinase-mediated excision. Such excision may leave only a short residual sequence comprising portions of the recombinase target site. Episomal plasmids used to reprogram cells may thereafter be lost. iPS cells and/or induced nervous system cells free of introduced genetic material or essentially free of exogenous genetic material (e.g., containing only a residual recombinase target site or portions thereof) can be produced by such methods.

In some embodiments, one or more reprogramming factors are introduced into cells by introducing one or more nucleic acid sequences encoding the factor(s). In some embodiments, the one or more nucleic acid sequences comprise DNA. In some embodiments, the one or more nucleic acid sequences comprise RNA. In some embodiments, the one or more nucleic acid sequences comprise a nucleic acid construct. In some embodiments, the one or more nucleic acid sequences comprise a vector for delivery of the reprogramming factors into a target cell (e.g., a mammalian somatic cell, e.g., a human fibroblast, keratinocyte, or blood cell). For example, iPS cells can be generated by introducing genes encoding a suitable set of reprogramming factors into somatic cells by infection with retroviruses, e.g., lentiviruses. Any suitable vector may be used. Examples of suitable vectors are described by Stadtfeld and Hochedlinger (Genes Dev. 24:2239-2263, 2010, incorporated herein by reference). Other suitable vectors are apparent to those skilled in the art. In some embodiments two, three, four, or more factors are encoded in a nucleic acid single cassette. For example, reprogramming factors may be delivered in a single virus using 2A "self-cleaving" peptides, which support efficient polycistronic expression from a single promoter. It will be understood that biologically active variants of reprogramming factors or other reprogramming agents may be used in certain embodiments.

A variety of techniques can be employed in the generation of iPS cells instead of or in addition to inserting genes encoding one or more of the factors into the genome. Such methods may involve use of small molecules, transient transfection, infection using non-integrating viruses (e.g., adenovirus, Sendai virus) or plasmids (e.g., comprising elements of the Epstein-Barr virus such as the EBNA1 gene and the OriP DNA) able to replicate extra-chromosomally as a circular episome, protein transduction, introduction of translatable mRNA encoding one or more reprogramming factors, and/or RNA interference to inhibit expression of selected genes (e.g., p53-p21 pathway genes). Molecules that act on signaling pathways involved in ES cell self-renewal and pluripotency, such as TGFβ and/or MEK pathways, may be used. Non-limiting examples of reprogramming agents that may be used in place of a reprogramming factor and/or in combination with one or more reprogramming factors to enhance reprogramming include kinase inhibitors, e.g., Aurura A kinase inhibitors (Li Z, Rana T M Nat Commun. 2012; 3:1085), TGF-beta pathway inhibitors such as TGF-13/Activin/Nodal receptor inhibitors (e.g., A-83-01), MEK inhibitors (e.g., PD0325901), GSK3β inhibitors (e.g., CHIR99021), ROCK inhibitors (e.g., HA-100), compounds that activate Oct-4 such as Oct4 activating compound 1 and structural analogs thereof (Li, T, et al, Proc Natl Acad Sci USA. 2012; 109(51):20853-8), retinoic acid receptor agonists, among others, may be used in certain embodiments. Histone deacetylase (HDAC) inhibitors (e.g., valproic acid, suberoylanilide hydroxamic acid, sodium butyrate, trichostatin A), histone methyltransferase inhibitors (e.g., BIX-01294), and other modulators of endogenous chromatin modifying enzymes can improve reprogramming efficiency. These compounds may act by reducing the epigenetic barriers to reprogramming. Further discussion and description of reprogramming, certain reprogramming methods, methods of characterizing reprogrammed cells, and/or methods of generating differentiated cells from iPS cells that may be used in certain embodiments may be found in, e.g., US Pat. Pub. Nos. 20110076678; 20110088107; 20100310525; Lyssiotis, C A, et al, Proc Natl Acad Sci USA., 106(22):8912-7, 2009; Carey B W, Proc Natl Acad Sci USA; 106(1): 157-62, 2009, Hockemeyer D, et al., Cell Stem Cell. 2008; 3(3):346-53; and/or Lakshmipathy, U. and Vemuri, M C (eds.), Pluripotent Stem Cells—Methods and Protocols, Methods in Molecular Biology, Vol. 873 Humana Press (a brand of Springer), and references cited in any of the foregoing.

In some embodiments reprogramming may be performed at least in part by introducing mRNA into a cell wherein the introduced mRNA encodes at least one reprogramming factor. The mRNA may be in vitro transcribed mRNA. Non-limiting examples of producing in vitro transcribed mRNA are described by Warren et al. (Cell Stem Cell 7(5):618-30, 2010, Mandal P K, Rossi D J. Nat Protoc. 2013 8(3):568-82, and/or PCT/US2011/032679 (WO/2011/130624) the teachings of each of which are incorporated herein by reference). The protocols described may be adapted to produce one or more mRNAs of interest herein. In some embodiments, mRNA, e.g., in vitro transcribed mRNA, comprises one or more modifications (e.g., modified ribonucleotides) that increase stability or translatability of said mRNA. In some embodiments the modification comprises substitution of 5-methylcytidine (5mC) for cytidine, substitution of pseudouridine (psi) for uridine, or both. In some embodiments at least 50%, 60%, 70%, 80%, 90%, 95%, or all of the cytidines, uridines, or both, are substituted by 5mC or psi, respectively. In some embodiments the mRNA is subjected to phosphatase treatment. In some embodiments the modification attenuates interferon signaling. In some embodiments media is supplemented with an inhibitor of interferon signaling. In some embodiments the inhibitor binds to an interferon. In some embodiments the inhibitor comprises a decoy receptor, such as B18R protein, a vaccinia virus decoy receptor for type I interferons.

In some embodiments, mRNA, e.g., in vitro transcribed mRNA comprises a 5' cap. The cap may be wild-type or modified. Examples of suitable caps and methods of synthesizing mRNA containing such caps are apparent to those skilled in the art. In some embodiments, mRNA, e.g., in vitro transcribed mRNA, comprises an open reading frame flanked by a 5' untranslated region and a 3' untranslated region that enhance translation of said open reading frame, e.g., a 5' untranslated region that comprises a strong Kozak translation initiation signal, and/or a 3' untranslated region comprises an alpha-globin 3' untranslated region. In some embodiments, mRNA, e.g., in vitro transcribed mRNA, comprises a polyA tail. Methods of adding a polyA tail to mRNA are known in the art, e.g., enzymatic addition via polyA polymerase or ligation with a suitable ligase. In some embodiments, mRNA is introduced into a somatic cell in an amount and for a period of time sufficient to maintain expression of a reprogramming factor or other reprogramming agent encoded by said mRNA until cellular reprogramming of said somatic cell occurs. The sufficient period of time may vary depending, e.g., on the type of somatic cell and the reprogramming factors employed. One of ordinary skill in the art can readily determine the appropriate period of time by routine experimentation. In some embodiments, mRNA is introduced into somatic cells at various intervals during the course of reprogramming.

In some embodiments reprogrammed pluripotent human cells are naïve pluripotent cells that exhibit hallmarks of naive pluripotency such as driving Oct4 transcription by its distal enhancer, retaining a pre-inactivation X chromosome state, and global reduction in DNA methylation and in H3K27me3 repressive chromatin mark deposition on developmental regulatory gene promoters. Naïve human pluripotent cells may be derived as described in Gafni, O., et al., Nature. 2013 Dec. 12; 504(7479):282-6. In some embodiments such cells are genetically unmodified.

The present disclosure contemplates any suitable method for introducing nucleic acids, e.g., DNA or RNA, into cells, e.g., to carry out reprogramming and/or genetic modification. In some embodiments, a nucleic acid is introduced into a somatic cell via electroporation. In some embodiments, a nucleic acid is introduced into a somatic cell via transfection. A suitable transfection reagent may be used, of which many are known in the art. In some embodiments, a nucleic acid may be complexed with a vehicle, e.g., a cationic vehicle, e.g., a cationic liposome or a nanoparticle. In some embodiments the vehicle facilitates uptake of nucleic acids via endocytosis and/or facilitates release of the nucleic acid from an endosome. In some embodiments the nucleic acid may be incorporated into or carried by a vector.

In some embodiments, reprogramming mammalian somatic cells may comprise a recently emerging method comprising stressing the cells by, e.g., transient exposure to chemical or physical stimuli such as low-pH conditions (e.g., about pH 5.7). The cells may thereby be stimulated to undergo stimulus-triggered acquisition of pluripotency (STAP), and cell lines comprising pluripotent cells may be derived under appropriate conditions (see, e.g., Obokata, H., et al., Stimulus-triggered fate conversion of somatic cells into pluripotency. Nature, 2014; 505 (7485): 641-647; and Obokata, H., et al., Bidirectional developmental potential in reprogrammed cells with acquired pluripotency. Nature, 2014; 505 (7485): 676-680).

In general, human iPS cells may be generated from somatic cells of any type. In some embodiments human iPS cells are generated from fibroblasts, keratinocytes, adipose tissue cells, mesenchymal stem cells (which may be obtained from adipose tissue), peripheral blood mononuclear cells (PMNCs), or epithelial cells recovered from urine. These cell types may be particularly convenient for deriving human iPS cells as they may be readily obtained from living human subjects noninvasively or with minimal or low invasiveness. In some embodiments human iPS cells are derived from purified human $CD34^+$ cells, which may be isolated from peripheral blood.

In some embodiments an ES cell, iPS cell, or induced nervous system cell is derived and/or maintained under physiological oxygen conditions. Physiological $O_2$ conditions encompass use of media having $PO_2$ values corresponding to an $O_2$ concentration between 2.0% and 7.0%, e.g., between 4.0% and 6.0%, e.g., between 4.5% and 5.5%. For example, the $PO_2$ can be about 20-50 mm Hg, e.g., about 30-40 mm Hg, e.g., about 36 mm Hg, which can be achieved through use of incubators and culture chambers containing a gas mixture having an $O_2$ concentration in the appropriate range or otherwise controlling the $O_2$ concentration of the media. In some embodiments, derivation and/or subsequent culturing is performed at least in part under conditions that protect cells from oxidative stress by, e.g., including one or more anti-oxidants or activators of endogenous anti-oxidant systems in the culture medium. See, e.g., Lengner C J, et al., Derivation of pre-X inactivation human embryonic stem cells under physiological oxygen concentrations, Cell. 2010; 141(5):872-83 and/or PCT/US2011/000850. In some embodiments a female ES cell or female iPS cell derived and maintained under physiological $O_2$ and/or conditions that protect the cell from oxidative stress has two active X chromosomes.

In some embodiments induced neural stem cells are derived from pluripotent human cells. The term "induced neural stem cell" refers to an induced nervous system cell that exhibits features characteristic of neural stem cells, such as multipotency, self-renewal, neurosphere forming ability, and expression of cellular markers characteristic of neural stem cells. Neural stem cells are multipotent and have the capacity to give rise to mature neurons, astrocytes, and oligodendrocytes. In some embodiments induced neural progenitor cells are derived from pluripotent human cells. The term "induced neural progenitor cell" refers to an induced nervous system cell that is more differentiated or specified towards a particular cell fate than a neural stem cells, is less differentiated than a mature neuron, and is capable of giving rise to cells with characteristics of mature neurons. In some embodiments an induced neural progenitor cell is capable of giving rise both to neurons and glial cells (e.g., astrocytes and/or oligodendrocytes).

Induced neural stem cells and induced neural progenitor cells may be differentiated in culture to give rise to mature neurons and, in some embodiments, glial cells. In some embodiments mature neurons are post-mitotic. Methods for inducing such differentiation are known in the art. In general, such methods comprise culturing induced neural stem cells or induced neural progenitor cells in suitable culture medium for an appropriate time to generate the desired cell type(s). The culture medium may comprise one or more agents that promotes neural differentiation and/or may lack one or more agents that may inhibit neural differentiation or promote differentiation along a non-neural cell lineage pathway. Methods for generating neurons in culture from human pluripotent stem cells (PSCs) such as iPS or ES cells neural stem cells and neural progenitor cells are known in the art. Non-limiting examples are described in detail in the Examples, but other methods maybe used. The particular methods, culture media, may be selected as appropriate to generate cells of desired cell types or subtypes. In some embodiments a cell culture comprising both neurons and glial cells may be generated. In some embodiments neural cells are generated with the need for EB- or stromal-feeder based protocols. In some embodiments neural cells may be generated from iPS cells as described in U.S. Pat. Pub. No.

20100021437. In some embodiments neurons may be generated from pluripotent stem cells or from non-neural somatic cells such as fibroblasts by expressing Brn2, Asc11, MytL1, optionally in combination with co-expression of and NeuroD1 and/or one or more microRNAs. In some embodiments neurons may be generated from pluripotent stem cells (PSCs), which may be iPS cells or ES cells, by expressing neurogenin-2 (Ngn2) or NeuroD1 in the cells (e.g., as described in Zhang, Y., et al, (2013) Neuron 78, 785-798). In some embodiments midbrain floor-plate precursors may be derived from pluripotent stem cells (PSCs) by using a modified dual-SMAD inhibition protocol (Fasano, C. A., et al., Cell Stem Cell 6, 336-347 (2010); Chambers, S. M. et al. Nature Biotechnol. 27, 275-280 (2009). In some embodiments dual SMAD inhibition may be achieved by exposure to an ALK inhibitor and a BMP inhibitor. In some embodiments a BMP inhibitor comprises Noggin or a biologically active variant thereof. In some embodiments an ALK inhibitor, e.g., the small molecule SB431542, blocks phosphorylation of ALK4, ALK5, ALK7 receptors. In some embodiments dual SMAD inhibition may be achieved by exposure to small molecules LDN193189 and SB431542, 'LSB'). In some embodiments activating or enhancing of sonic hedgehog (SHH) and canonical WNT signaling, e.g., by exposure to small molecule activators of sonic hedgehog (SHH), canonical WNT signaling, and FGF8 is used to generate midbrain dopaminergic (DA) neurons from such cells. Such neurons can be maintained in vitro for several months are engraftable into mammalian species such as rodents and non-human primates (see Kriks, S., et al., (2011), Nature, Vol. 480, pp. 547-553, doi:10.1038/nature10648, where a combination of agents suitable to generate DA midbrain precursors is referred to as LSB/S/F8/CHIR, and wherein conditions useful for producing dorsal forebrain fated precursors (LSB) or (2) ventral/hypothalamic fated precursors (LSB/S/F8). In some embodiments an activator of canonical WNT signaling is an agent that inhibits GSKI3 (e.g., a small molecule such as CHIR99021). In some embodiments activation of SHH signaling is achieved using purmorphamine, a small molecule agonist, alone or in combination with recombinant SHH. One of ordinary skill in the art will be aware of other agents that may be used to (i) inhibit SMAD signaling and/or (ii) activate canonical WNT signaling, SHH signaling, or FGF8 signaling. Methods are available for generating glial progenitor cells from pluripotent human cells. The glial progenitor cells can be differentiated to oligodendrocytic and astrocytic cells. Both astrocytes and oligodendrocytes are efficiently derived from human iPSC-derived human oligodendrocyte precursor cells (OPCs) (Wang., S., et al. Cell Stem Cell 12, 252-264).

In some embodiments, induced human nervous system cells may be generated by transdifferentiation, e.g., in vitro. As used herein, "transdifferentiation" refers to the process of deriving a non-pluripotent somatic cell of a first cell type from a non-pluripotent cell of a second cell type in vitro without generating a pluripotent cell as an intermediate step. In some embodiments induced neural stem cells, induced neural progenitor cells, or induced neurons are generated by transdifferentiation from somatic cells, e.g., fibroblasts or keratinocytes. Methods for generating induced neural stem cells, induced neural progenitor cells, or induced neurons by transdifferentiation are known in the art (see, e.g., Ring, K L, et al., (2012) Cell Stem Cell 11, 100-109; Pang, Z P, et al., (2012), Nature, 476: 220-224).

In some embodiments an induced neural progenitor cell may have characteristics and/or express cellular markers indicative of cells that are fated to develop into neurons and/or glial cells having cell bodies located in the central nervous system or a component thereof. For purposes hereof, the central nervous system includes the brain, spinal cord, cranial nerves, and retina. In some embodiments an induced neural progenitor cell may lack characteristics and/or may not express cellular markers indicative of cells that are fated to develop into neurons and/or glial cells having cell bodies located in the peripheral nervous system. In some embodiments an induced neural progenitor cell may have characteristics and/or express cellular markers indicative of cells that are fated to develop into neurons and/or glial cells located in the brain or a particular region or subregion of the brain, such as the forebrain, midbrain, cortex, hippocampus, striatum, or a particular nucleus of the brain, e.g., a region, subregion, or nucleus that is frequently affected in a neurodegenerative disease. One of ordinary skill in the art will be aware of appropriate markers for identifying nervous system cells of interest. Suitable markers may be, for example, transcription factors, enzymes involved in the synthesis of neurotransmitters or uptake of molecules that serve as neurotransmitter precursors, receptors for neurotransmitters, intermediate filament proteins, ion channel subunits, cell adhesion molecules, etc. Pax6, Nestin, Forse-1 and Otx-2 are examples of markers whose expression is characteristic of a neural progenitor cell that is anterior/forebrain-fated. Tbr1, is a transcription factor characteristic of developing deep cortical layers. TUJ1 (neuron-specific class III β-tubulin) is a characteristic marker of immature and mature neurons. MAP2 is a characteristic marker of mature neurons. Characteristic astrocyte markers include, e.g., glial fibrillary acidic protein (GFAP). Characteristic oligodendrocyte markers include, e.g., 04 and OLIG2. VGLUT1 (vesicular glutamate transporter-1) is a marker of glutamatergic neurons and is widely expressed by hippocampal and cortical neurons. Tyrosine hydroxylase is a characteristic cellular marker for dopaminergic neurons. In some embodiments lack of expression or barely detectable expression of a marker may be characteristic of a cell type of interest. For example, in some embodiments, an induced central nervous system cell is characterized in that expression of the peripheral nervous system marker peripherin is not detectable or is negligibly detectable, e.g., barely detectable above background. It will be appreciated that these markers are merely exemplary. Other suitable markers are known in the art, some of which are described in references cited herein.

A number of disease-specific iPS cell lines have been established from patients with neurodegenerative diseases, e.g., from patients with Parkinson's disease (Soldner F, et al., Cell; 136(5):964-77, 2009), amyotrophic lateral sclerosis (Dimos et al., Science. 2008; 321(5893):1218-21), and Alzheimer's disease (Israel et al., Nature. 2012; 482:216-20). These lines or lines derived using the same methods or other methods, e.g., from other subjects, may be used in various embodiments.

In some embodiments a human induced nervous system cell derived from an individual suffering from a neurodegenerative disease or having at least one disease-relevant inherited genetic variation or mutation is genetically corrected. As used herein, a "genetically corrected cell" is a cell that is derived from a cell or individual that harbors an inherited disease-associated genetic variation or mutation at a location in its genome, wherein the genetically corrected cell is genetically engineered so as to alter the sequence of its genome at that location to a sequence that is not associated with the disease, e.g., a standard sequence. A cell and its genetically corrected counterparts are isogenic except at the particular location(s) that have been corrected. It will be understood that different cells derived from the same cell or individual may not be genetically identical at each and every position in the genome. For example, cells may acquire mutations in culture and thus the genomic sequence of two cells derived from a single cell or individual may differ at one or more positions. However, the level of such mutations is sufficiently low so that a cell and its genetically corrected counterpart are considered isogenic herein except at the particular location(s) that have been corrected. In some embodiments, a genetically corrected cell or cell line serves as a control for a cell or cell line derived from the same individual that has not been genetically corrected.

In some embodiments a human induced nervous system cell is genetically engineered to have a genotype associated with a neurodegenerative disease. In some embodiments the cell is engineered to have a mutation in a neurodegenerative disease gene. In some embodiments the human induced nervous system cell is derived from a cell, e.g., an iPS cell or ES cell, that is not known to have a genotype associated with a neurodegenerative disease. In some embodiments the cell originates from a subject who does not have a neurodegenerative disease. In some embodiments the subject does not have a family history of a familial form of a neurodegenerative disease. In some embodiments the subject does not have a family history of a sporadic form of a neurodegenerative disease. The cell may be genetically engineered to harbour a mutation known to cause the neurodegenerative disease. In some embodiments the mutation is in a gene that encodes a neurodegeneration associated protein, e.g., alpha-synuclein, TDP-43, FUS, Tau, a protein comprising a polyQ expansion, or APP or a neurodegeneration associated RNA. For example, an iPS cell or ES cell or neural stem cell or neural progenitor cell may be genetically engineered to harbor one or more particular mutations or variations of interest. The cell may be differentiated to give rise to mature neurons. It will be understood that a genetically engineered cell may be any cell that inherits the alteration. Thus a genetically engineered cell may be a descendant of the original cell that was subjected to genetic engineering.

In some embodiments the cell is genetically engineered to overexpress a gene whose overexpression causes a neurodegenerative disease. In some embodiments the gene is SNCA. In some embodiments the cell is genetically engineered to have a gain of function mutation in a gene whose gain of function causes a neurodegenerative disease. In some embodiments the cell is genetically engineered to have a gain of function mutation in a gene whose gain of function causes a neurodegenerative disease. In some embodiments the cell is genetically engineered to have a loss of function mutation in a gene whose loss of function causes a neurodegenerative disease. Mutations may be introduced into one or both copies of the gene in various embodiments. In some embodiments, e.g., if the disease has an autosomal dominant inheritance pattern, a gain of function mutation is introduced into one copy of the gene. In some embodiments, e.g., if the disease has an autosomal recessive inheritance pattern, loss of function mutations are introduced into both copies of the gene.

In some embodiments a cell that has a mutation in a neurodegenerative disease gene associated with a particular disease or has an extra copy of such gene is engineered to have a mutation or variation in one or both copies of at least one additional neurodegenerative disease gene or genetic modifier that is associated with the disease. For example, a cell with a mutation in SNCA or an extra copy of a gene encoding a-Syn may be engineered to also have a mutation in ATP13A2, LRRK2, VPS35, GBA or other genes listed in Table B or C. In some embodiments the gene has a yeast homolog.

Figure 10:
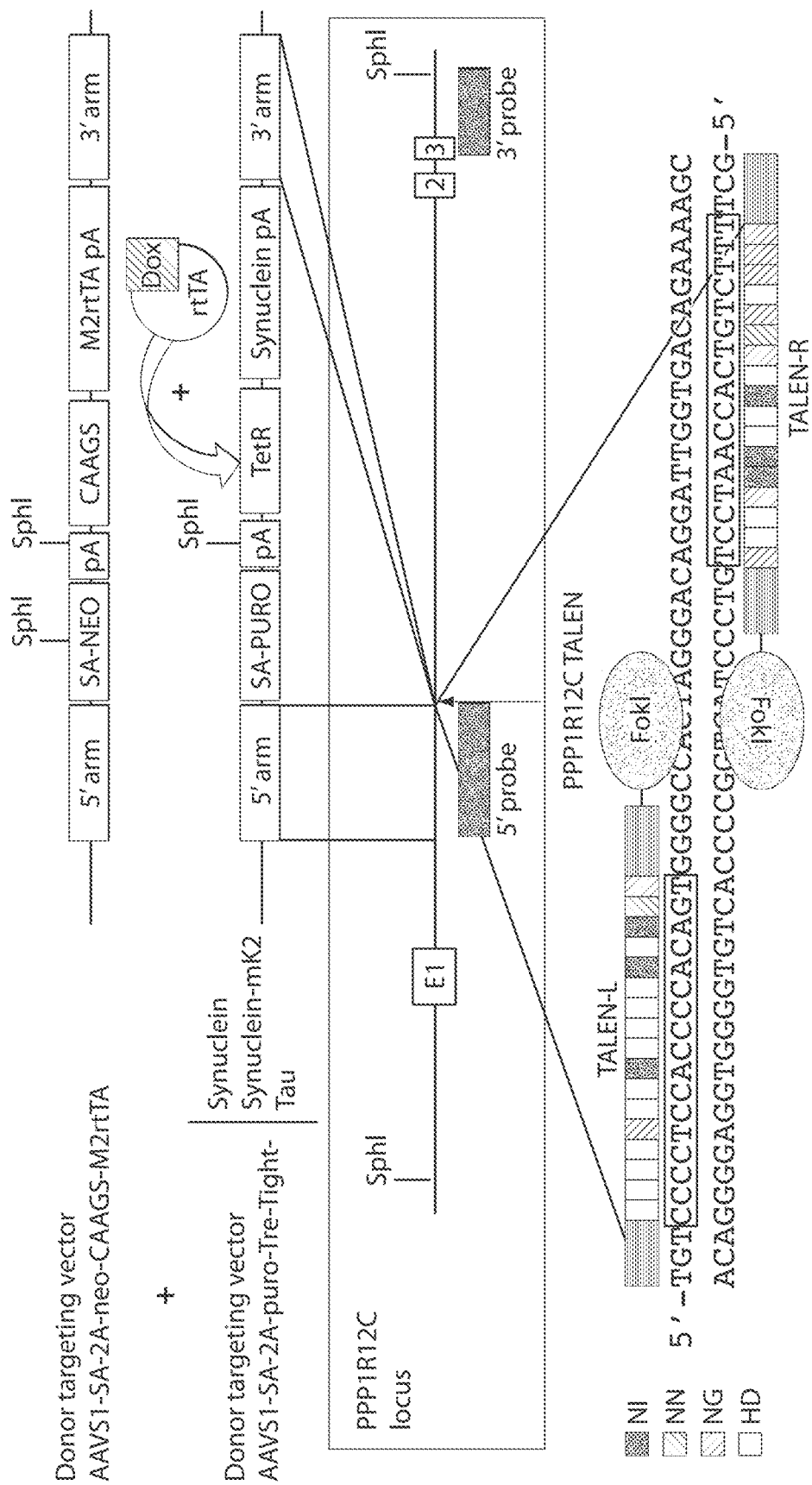
FIG. 10. Double-targeting strategy to generate doxycycline-inducible transgenic αSyn-overexpressing hESC lines.

In some embodiments a human induced nervous system cell comprises a nucleic acid sequence encoding a NAP or NAR under control of a regulatable, e.g., inducible, promoter. Expression of the NAP or NAR can be induced in such cells when desired (e.g., by culturing them in the presence of an inducing agent or in the absence of a repressing agent, depending on the particular regulation system employed). Cells of the same cell line, cultured under conditions in which the NAP or NAR is not expressed, may be used as control cells. In some embodiments, different amounts of an inducing or repressing agent may permit different levels of expression. FIG. 10 depicts an exemplary strategy that uses TALENs to generate doxycycline-inducible transgenic αSyn-overexpressing hESC lines (or lines expressing an αSyn-mK2 fusion protein, Tau, or other protein or RNA of interest), which can be differentiated to induced human neurons. The nucleic acid construct is targeted to the AAVS1 locus. In certain embodiments two constructs may be used, a first construct that encodes a NAP or NAR (which may be operably linked to a promoter and, in some embodiments, a sequence that permits transcriptional regulation of the promoter, e.g., transcriptional activation or repression) and a second construct that encodes a protein that acts as an activator or repressor of transcription. In some embodiments a tetracycline transactivator or repressor system may be used. In some embodiments the two constructs may be targeted to the same location of homologous chromosomes (e.g., the AAVS1 locus of each chromosome 19). A variety of other systems may be used to achieve regulatable induction of expression or activity. In some embodiments, a loss of function mutation may be regulatable. For example, an endogenous neurodegenerative disease gene may be mutated to reduce or eliminate its expression or the activity of its gene product. The cell may be engineered to comprise a regulatable transgene encoding the same gene product (which may be targeted to a safe harbor locus) to replace the function of the endogenous gene. Expression of the transgene may be repressed to replicate the effect of a loss of function mutation. In some embodiments expression of a second transgene comprising a mutated version of the gene may be induced, to replicate the effect of a mutation associated with a neurodegenerative disease. In some embodiments at least a portion of a gene may be placed between recognition sites for a recombinase. DNA located between such sites can be removed by introducing or inducing expression of the recombinase in the cell. Such systems may be used, for example, to produce deletions, which may reduce expression of a gene or result in a gene product with altered (e.g., reduced) function or may bring a coding sequence under control of a promoter and thereby induce expression, etc. Suitable systems are known in the art. For example, the Cre/Lox recombinase system may be used. A target gene may be modified by the insertion of two loxP sites that allow the excision of the flanked (floxed) gene segment through Cre-mediated recombination. In some embodiments, expression of Cre may be under control of a regulatable promoter or Cre activity may be regulated by a small molecule. For example, Cre may be fused to a steroid hormone ligand binding domain so that its activity is regulated by receptor ligands. Cre-ER(T) or Cre-ER(T2) recombinases may be used, which comprise a fusion protein between a mutated ligand binding domain of the human estrogen receptor (ER) and the Cre recombinase, the activity of which can be induced by, e.g., 4-hydroxytamoxifen. Other methods of generating inducible genetic alterations, e.g., knockouts, known in the art may be used. For example, different recombinases (e.g., Dre or the Flp/Frt system) may be used, and/or other means of rendering recombinase activity regulatable may be used.

A variety of methods may be used to introduce genetic alterations into the genome of human cells, e.g., to introduce or correct mutations or genetic variations. In certain embodiments such methods may be used to introduce a mutation or variation into a cell that lacks such mutation or variation or to correct a mutation or variation in a cell that has such mutation or variation. In some embodiments genetic engineering may be performed using methods that make use of homologous recombination. In some embodiments insertions, deletions, and/or substitutions may be generated by introducing one or more double-strand breaks (DSBs) or single-strand nicks into the genome of a cell at a selected target site, which are then repaired by the cell, e.g., using endogenous DNA repair mechanisms such as non-homologous end joining (NHEJ) or homology-directed repair (HDR) pathways. Repair may alter the sequence that was present prior to introduction of the DSB or nick, allowing, for example, the introduction of deletions, insertions, or replacement of specific nucleotides at the target site (e.g., to create or correct point mutations or single nucleotide variations). In some embodiments one or more transgenes may be integrated into an endogenous locus, optionally in combination with at least partially deleting or disrupting the endogenous sequence. In some embodiments at least a portion of an endogenous gene encoding a NAP is replaced with a modified sequence that contains a mutation or genetic variation absent in the endogenous gene or does not contain a mutation or genetic variation present in the endogenous gene. In some embodiments a sequence encoding a NAP operably linked to a promoter is inserted at a location in the genome distinct from the location of the endogenous gene that encodes the NAP in order to create a cell with one or more extra copies of the gene as compared to a normal cell. The location may be a specifically selected location or may be random. In some embodiments, for example, the NAP comprises an alpha-synuclein. An iPS or ES cell having two copies of the gene encoding alpha-syn may be modified to comprise three, four, or more copies, as found in certain patients with familial PD.

In some embodiments integration of exogenous DNA in the genome of a mammalian cell, e.g., a human cell, occurs at a "safe harbor" locus. A "safe harbor" locus is an intragenic or extragenic region of the human genome that is able to accommodate the predictable expression of newly integrated DNA without adverse effects on the host cell. In some embodiments the safe harbour locus is the AAVSV1 (the natural integration site for the wild-type AAV on chromosome 19), ROSA26, or CCR5 locus. The locations of these loci are well known in the art. The AAVS1 site is in chromosome 19 (position 19q13.42) and integration in the AAVS1 locus may disrupt the gene phosphatase 1 regulatory subunit 12C (PPP1R12C). The human ROSA26 locus is in chromosome 3 (position 3p25.3). The human CCR5 gene is located on chromosome 3 (position 3p21.31).

In some embodiments, a cell may be genetically modified using a nuclease that is targeted to one or more selected DNA sequences. Such methods may be used to induce precise cleavage at selected sites in endogenous genomic loci. In some embodiments a mutation is engineered in a pluripotent stem cell, neural stem cell, or neural progenitor cell, so that the mutation is inherited by descendants of the cell, e.g., mature neurons derived from the cell. Genetic engineering in which DNA is inserted, replaced, or removed from a genome, e.g., at a defined location of interest, using targetable nucleases, may be referred to as "genome editing". Examples of such nucleases include zinc-finger nucleases (ZFNs), TALENs, engineered meganuclease homing endonucleases, and RNA directed nucleases such as CRISPR (clustered regularly interspaced short palindromic repeats)-associated (Cas) nucleases, e.g., derived from type II bacterial CRISPR/Cas systems (e.g., Cas9). In some embodiments the nuclease comprises a DNA cleavage domain and a DNA binding domain (DBD) that targets the nuclease to a selected DNA sequence. The DNA cleavage domain may create a DSB or nick at or near the site to which it is targeted. The DBD converts the nuclease into a site-specific nuclease. As known in the art, ZFNs comprise DBDs selected or designed based on DBDs of zinc finger (ZF) proteins. DBDs of ZF proteins bind DNA in a sequence-specific manner through one or more zinc fingers, which are regions of amino acid sequence whose structure is stabilized through coordination of a zinc ion. TALENs comprise DBDs selected or designed based on DBDs of transcription activator-like (TAL) effectors (TALEs) of *Xanthomonas* spp. ZFN or TALEN dimers induce targeted DNA DSBs that stimulate DNA damage response pathways. The binding specificity of the designed zinc-finger domain directs the ZFN to a specific genomic site. TALEs contain multiple 33-35-amino-acid repeat domains, each of which recognizes a single base pair Like ZFNs, TALENs induce targeted DSBs that activate DNA damage response pathways and enable custom alterations. The DNA cleavage domain of an engineered site-specific nuclease may comprise a catalytic domain from a naturally occurring endonuclease such as the Fok1 endonuclease or a variant thereof. In some embodiments FokI cleavage domain variants with mutations designed to improve cleavage specificity and/or cleavage activity may be used (see, e.g., Guo, J., et al. (2010) Journal of Molecular Biology 400 (1): 96-107; Doyon, Y., et al., (2011) Nature Methods 8: 74-79. RNA directed nucleases such as CRISPR/Cas systems may be used in some embodiments. In such systems a Cas nuclease, such as Cas9 (e.g., *Streptococcus pyogenes* Cas9), is guided to a particular DNA sequence of interest by an engineered guide RNA complementary to the sequence of interest (sometimes termed a single guide RNA).

In general, use of nuclease-based systems for genetic engineering, e.g., genome editing, entails introducing a nuclease or a nucleic acid encoding a nuclease into cells (and also introducing a guide RNA or construct encoding a guide RNA in the case of CRISP/Cas systems) and maintaining the cells under conditions and for a time appropriate for the nuclease to cleave the cell's DNA. In some embodiments a nuclease that cleaves only one strand of dsDNA (a nickase) may be used to stimulate HDR without activating the NHEJ repair pathway. Nickases may be created by inactivating the catalytic activity of one nuclease monomer in the ZFN or TALEN dimer required for double stranded cleavage or inactivating a catalytic domain of a Cas protein. For example, mutations of one of the catalytic residues (D10 in the RuvC nuclease domain and H840 in the HNH nuclease domain), e.g., to alanines (D10A, H840A) convert Cas9 into DNA nickases. A nucleic acid encoding a nuclease operably linked to a promoter capable of directing expression in the cell may be introduced into the cell in a plasmid or other vector. In some embodiments mRNA encoding the nuclease may be introduced. In some embodiments the nuclease itself may be introduced. sgRNA may be introduced directly (by methods such as transfection) or by expressing it from a nucleic acid construct such as an expression vector. In some embodiments a sgRNA and Cas protein are expressed from a single expression vector that has been introduced into the cell or, in some embodiments, from different expression vectors. In some embodiments multiple sgRNAs comprising sequences complementary to different genes, e.g. 2, 3, 4, 5, or more genes, are introduced into the same cell individually sequentially or together or as part of a single nucleic acid or expressed from one or more nucleic acid constructs. In some embodiments alterations in multiple genes may thereby be generated in the same step. In some embodiments a nucleic acid (e.g., a plasmid or linear DNA) comprising a sequence to be inserted into the genome at the location of cleavage is also introduced into a cell containing the nuclease. In some embodiments two or more cleavages are produced, and a nucleic acid of interest is inserted between the cleavage locations, optionally at least in part replacing an endogenous gene by a version that incorporates a mutation, genetic variation, or genetic correction. In some embodiments the nucleic acid comprises regions of homology to the regions flanking the cleavage site, so that homology-directed repair is stimulated. In some embodiments a nucleic acid comprising a sequence that is homologous to either side of the target site and contains a desired alteration as compared to a sequence present in the cell's genome is introduced in addition to the polypeptide, e.g., resulting in homology directed repair. A nucleic acid comprising a sequence to be at least in part introduced into the genome, e.g., a nucleic acid sequence comprising homologous sequence(s) and a desired alteration may be referred to as a "donor sequence". The donor sequence may become at least in part physically integrated the genome at the site of a break or may be used as a template for repair of the break via homologous recombination, resulting in the introduction of all or part of the nucleotide sequence present in the donor into the genome of the cell. Thus, a sequence in a cell's genome can be altered and, in certain embodiments, can be converted into a sequence present in a donor nucleic acid. It will be understood that terms such as "insert", "replace", etc., represent insertion of a nucleic acid sequence or replacement of one nucleotide sequence by another, (i.e., insertion or replacement of a sequence in the informational sense), and do not necessarily require physical or chemical incorporation of an introduced nucleic acid into the genome, e.g., repair may entail producing a copy of at least a portion of the donor sequence. In some embodiments the donor sequence may be contained in a circular DNA (e.g. a plasmid), a linear double-stranded DNA (e.g., a linearized plasmid or a PCR product), or single-stranded DNA, e.g., a single-stranded oligonucleotide. In some embodiments the donor sequence has between about 10-25 bp and about 50-100 bp of homology to either side or each side of the target site in the genome. In some embodiments a longer homologous sequence may be used, e.g., between about 100-500 bp up to about 1-2 kB, or more. In some embodiments an alteration is introduced into one allele of a gene. In some embodiments a first alteration is introduced into one allele of a gene, and a different alteration is introduced into the other allele. In some embodiments the same alteration is introduced into both alleles. For example, both copies of a gene may be corrected in a cell harboring a homozygous mutation or variation. In some embodiments different alterations that have functionally equivalent effects may be introduced into two alleles. In some embodiments two or more distinct alterations are introduced into one allele, or into both alleles. In some embodiments two alleles or target sites (or more) may be genetically modified in a single step. In some embodiments two alleles or target sites (or more) may be genetically modified in separate steps.

In some embodiments cells that have a desired genetically engineered alteration may be identified or selected. For example, in some embodiments the donor sequence or vector used to deliver the donor sequence may comprise a selectable marker, which may be used to select cells that have incorporated at least a portion of the donor sequence comprising the selectable marker into their genome. In some embodiments selection is not used. In some embodiments cells may be screened, e.g., by Southern blot to identify those cells or clones that have a desired genetic alteration.

Methods of designing, generating and using ZFNs and/or TALENs are described in, e.g., WO2011097036; Urnov, F D, et al., Nature Reviews Genetics (2010), 11: 636-646; Miller J C, et al., Nat Biotechnol. (2011) 29(2):143-8; Cermak, T., et al. Nucleic Acids Research (2011) 39 (12): e82, Sanjana, N. E. et al. A transcription activator-like effector toolbox for genome engineering. Nat Protoc 7, 171-192 (2012) and references in any of the foregoing. ZFN, TALEN, and CRISPR/Cas-based methods for genome engineering are reviewed in Gaj, T., et al., Trends Biotechnol. 2013 July; 31(7):397-405. Epub 2013 May 9. Use of CRISPR/Cas systems in genome engineering is described in, e.g., Cong L, et al. Multiplex genome engineering using CRISPR/Cas systems. Science. 2013; Wang, H. et al. One-step generation of mice carrying mutations in multiple genes by CRISPR/Cas-mediated genome engineering. Cell 153, 910-918 (2013); Ran, F. A. et al. Double Nicking by RNA-Guided CRISPR Cas9 for Enhanced Genome Editing Specificity. Cell 154, 1380-1389 (2013). In some embodiments CRISPR/Cas systems may be of particular use for generating multiple genetic alterations in a cell. Use of ZFNs to perform genetic engineering of human pluripotent cells is described in Hockemeyer, D. et al. (2009) Nat Biotechnol 27: 851-857 and/or in US Pat. Pub. No. 20110027235. Use of TALENs to perform genome engineering in human embryonic stem cell (ESC) and induced pluripotent stem cell (iPSC) cells is described in Hockemeyer, D., et al. (2011) Nature Biotechnology 29 (8): 731-4. Generation of isogenic pluripotent stem cells differing exclusively at two early onset Parkinson point mutations using ZFNs is described in Soldner F, et al. (2011) Cell 146(2):318-31 and/or in US Pat. Pub. No. 20120192301, which also describes use of TALENs for this purpose.

In some embodiments, transcription of a neurodegenerative disease gene may be upregulated or inhibited using a protein comprising (a) a DNA-binding TALE or catalytically inactive Cas protein (e.g., Cas9) guided to an appropriate region of the gene (e.g., a promoter region); and (b) an effector domain comprising a transcriptional activation domain or transcriptional repression domain that is active in mammalian cells. The protein is guided to an appropriate region of the gene (e.g., a promoter region) either by its DBD (in the case of TALE) or by a sgRNA (in the case of Cas). See, e.g., Zhang, F., et al. (2011) Efficient construction of sequence-specific TAL effectors for modulating mammalian transcription. Nat. Biotechnol. 29, 149-153; Cong, L., et al. (2012) Comprehensive interrogation of natural TALE DNA-binding modules and transcriptional repressor domains. Nat. Commun., DOI: 10.1038/ncomms1962; Maeder M L, et al. Robust, synergistic regulation of human gene expression using TALE activators. Nat Methods 2013; 10:243-245. Cheng, A. W. et al. (2013) Multiplexed activation of endogenous genes by CRISPR-on, an RNA-guided transcriptional activator system. Cell Res. 23, 1163-1171. Catalytically inactive Cas9 may be generated by mutating both of the catalytic residues (D10 and H840 in Cas9), e.g., to alanine. Exemplary transcriptional repressor domains include, e.g., the mSin interaction domain (SID), Tbx3 repression domain, and KRAB repression domain. Exemplary transcriptional activation domains include, e.g., VP16 minimal activation domain and multimers thereof comprising, e.g., between 3 and 15, e.g., 4-10 copies of the VP16 minimal activation domain. In some embodiments about 3-5 sgRNAs targeted to the proximal promoter region are used. In some embodiments expression of a neurodegenerative disease gene or genetic modifier is inhibited using an RNAi agent. In some embodiments delivery of a nucleic acid construct encoding a ZFN, TALE, sgRNA, Cas protein, or RNAi agent (e.g., a shRNA) is achieved using a lentiviral or AAV viral vector.

Human cells that have one or more desired genetic alterations may be expanded in culture and, if desired, differentiated in vitro, introduced into non-human animals to be used as disease models, used to identify or confirm disease associated phenotypes, used to identify or confirm candidate therapeutic agents, and/or for other purposes. As described herein, induced human neurons having one or more genetic alterations may serve as models for neurodegenerative diseases. In some aspects, such neurons are used in conjunction with yeast that are engineered to serve as a model of the same disease.

In some embodiments a cell, cell line, or cell population may be assessed for one or more characteristics of interest and/or a cell, cell line, or cell population may be selected for use in a method described herein based on exhibiting one or more such characteristics. For example, cells may be assessed to determine or confirm their pluripotency, cell type, or genotype, or to compare two or more cells, cell populations, or cell lines. Techniques for assessing cell characteristics of interest are known in the art. Such techniques include, e.g., visual inspection (e.g., using an optical microscope), flow cytometry, immunofluorescence, quantitative real-time reverse-transcriptase PCR, G-banding, DNA and/or RNA fluorescence in situ hybridization (FISH), immunocytochemistry, enzyme assays, microarray analysis, DNA sequencing (optionally using high throughput sequencing methods such as massively parallel sequencing, e.g., using the Illumina platform (Illumina, San Diego, Calif.)), bisulfite sequencing, chromatin immunoprecipitation and microarray analysis (ChIP-Chip), chromatin immunoprecipitation and sequencing (ChIP-Seq), allele-specific expression analysis, differentiation assays (e.g., embryoid body (EB) formation assay, teratoma formation assay), electrophysiologic techniques (e.g., patch clamp recording), use of suitable detetion reagents, e.g., molecular indicators (e.g., indicators for detection of ions (e.g., calcium), metabolites or substrates (e.g., ATP), cellular biomolecules (e.g., DNA), particular organelles, etc.). One or more such techniques may be used. In some embodiments expression of one or more molecular markers, e.g., cell surface markers may be used. In some embodiments genome-wide expression profiling may be used. In some embodiments "genome-wide" refers to methods in which at least 80%, 90%, 95%, or more of the predicted protein-coding genes are assessed. In some embodiments "genome-wide" refers to methods in which at least 80%, 90%, 95%, or more of the predicted protein-coding and functional RNA-coding genes are assessed. The genes may be assessed with respect to expression level (e.g., mRNA expression level), association with a disease, or other attributes.

Whether or not a cell line or cell population is considered to exhibit a particular characteristic may be determined by assessing a representative sample of cells from the cell line or cell population. The number of cells assessed may depend on factors such as the characteristic being assessed, the assessment technique. Certain characteristics may be assessed at the level of individual cells (e.g., by examining individual cells), while other characteristics are typically assessed based on part or all of the cells in the sample (e.g., analyses performed on RNA or DNA extracted from multiple cells). It will be appreciated that a cell line or cell population may be considered to exhibit a characteristic even if the characteristic is not present or detected in all cells of a sample. For example, depending on factors such as the particular characteristic and method of assessment, at least 40%, 50%, 60%, 70%, 75%, 80%, 85%, 90%, 95%, 99%, or more of the cells may exhibit the characteristic in various embodiments.

In some embodiments a characteristic of a cell line or cell population remains stable for at least 5 weeks in culture, e.g., at least 10, 20, 30, 40, 50, 60, 70, 80, 90, 100 weeks, or more (during which time the cells are passaged as appropriate) under appropriate culture conditions. In some embodiments of the invention, a characteristic of a cell line or cell population remains stable for at least 10 passages or population doublinges, e.g., at least 20, 30, 40, 50, 60, 70, 80, 90, 100 passages or population doublings, or more. A characteristic is considered "stable" if the cell line or cell population continues to exhibit the characteristic without substantial change, e.g., the characteristic is essentially unchanged over a time period of interest under appropriate culture conditions. For example, a cell line or cell population that is "positive" for expressing a particular marker remains positive. It will be understood that the proportion of cells in a sample that exhibit a particular characteristic may differ somewhat among different samples and/or when assessed multiple times. In some embodiments, if a characteristic is stable, such characteristic does not exhibit a trend towards a substantial change when assessed at different time points. In some embodiments, a substantial change is a change (increase or decrease) of more than 20%) relative to an initial value. In some embodiments a substantial change is a change of more than 50%) relative to an initial value. In some embodiments a substantial change is a change of more than 1.5-fold relative to an initial value.

In some embodiments, a cell, cell line, or cell population has a normal karyotype. In general, a cell has a normal karyotype if the cell has the normal complement of chromosomes for a diploid cell of that species and there are no evident chromosomal abnormalities such as translocations, inversions, or deletions. Karyotype can be assessed using, e.g., G-banding or FISH. In certain embodiments, greater than 75%, 80%, 85%, 90%, 95%, or more than 95% of cells examined in a sample of cells from a cell line or cell population display a normal karyotype. In some embodiments at least 20, 50, or 100 cells are examined.

In some embodiments, a cell, cell line, or cell population may be identified as being of a particular cell type or particular cell lineage (e.g., a neural lineage) based at least in part on expression of a reporter protein whose expression is under control of a promoter that functions selectively in cells of that particular cell type or cell lineage, i.e., the promoter selectively directs transcription of an operably linked nucleic acid in cells of that particular cell type or cell lineage and not in many or most other cell types or cell lineages. For example, a pan-neuronal promoter such as the synapsin promoter may be used to identify neurons; a GFAP promoter may be used to identify glial cells. In some embodiments the reporter protein is a fluorescent protein or an enzyme that is capable of acting on a substrate to produce an optically detectable product, e.g., a fluorescent or colored product. In some embodiments the fraction or proportion of cells that are of one or more particular cell types or cell lineages in a cell population or cell sample is determined. For example, it may be of interest to use a cell population or cell sample containing at least a specified percentage of neural cells or neural cells of a particular subtype of interest.

V. Yeast Models for Neurodegenerative Diseases

In some embodiments, yeast that express a neurodegeneration associated protein or neurodegeneration associated RNA are used as yeast models of neurodegenerative diseases associated with aggregation and/or inappropriate accumulation of such neurodegeneration associated protein or neurodegeneration associated RNA. Such yeast models may be created by introducing an expression construct encoding the neurodegeneration associated protein or neurodegeneration associated RNA into yeast. For example, as discussed above, model systems ("models") in which yeast cells are engineered to express a protein that accumulates in a misfolded form in the nervous system in subjects with a neurodegenerative disease have been developed (see, e.g., U.S. Pat. No. 7,045,290). For example, yeast cells are engineered to express an alpha synuclein polypeptide in the case of synucleinopathies, an amyloid beta protein in the case of a disease involving amyloidosis, a TDP-43 protein in the case of TDP-43 proteopathies, or a huntingtin protein in the case of Huntington's disorder. In certain embodiments the yeast cell has a reduced growth rate or no growth as a result of expressing the protein. In certain embodiments the yeast cell has reduced viability as compared with a yeast cell that does not express the protein. A decrease or inhibition of growth or viability indicates toxicity of the protein in the yeast cell. Toxicity of the protein in yeast correlates with human and/or other mammalian neurodegenerative state associated with misfolding or abnormal accumulation, e.g., aggregation, of the protein. If such a yeast cell is exposed to an agent or condition, one can test the ability of the agent or condition to modulate, e.g., inhibit, toxicity in the cell by measuring growth or viability of the cell and comparing the growth or viability with the growth or viability of a yeast cell cultured in the absence of the agent. For example, a screen may be performed that comprises culturing yeast cells that express a neurodegeneration associated protein in the presence of an agent, measuring cell growth or viability in the presence of the agent, and comparing cell growth or viability measured in the presence of the agent to cell growth or viability in the absence of the agent. If cell growth or viability is increased or decreased in the presence of the agent as compared to cell growth or viability in the absence of the agent, the agent is identified as an agent that modulates toxicity induced by the protein. In some embodiments a method of screening for an agent that decreases toxicity associated with a neurodegenerative disease protein comprises: contacting a yeast cell that expresses a neurodegenerative disease protein with an agent; and evaluating the yeast cell for viability, wherein an increase in viability of the yeast cell as compared to viability of the yeast cell in the absence of the agent indicates that the agent decreases toxicity associated with a neurodegenerative disease protein. In some embodiments, agent that inhibit toxicity associated with the protein are candidate therapeutic agents for treating a neurodegenerative disease characterized by accumulation of the protein. In certain embodiments the protein forms detectable aggregates in the yeast cell. Compounds can be tested for their ability to modulate, e.g., inhibit, formation or persistence of aggregates.

A yeast model for neurodegenerative diseases characterized by abnormal accumulation of alpha-synuclein (synucleinopathies) was developed based at least in part on the discovery that expression of a human alpha-synuclein protein in yeast cells is toxic and results in the formation of alpha-synuclein-containing cytoplasmic aggregates (see, e.g., U.S. Pat. No. 7,045,290. In some embodiments a method of screening for a compound that decreases alpha synuclein associated toxicity comprises: contacting a yeast cell engineered to express a polypeptide comprising alpha synuclein with a candidate compound; and evaluating the yeast cell for viability, wherein an increase in viability of the yeast cell as compared to viability of the yeast cell in the absence of the candidate compound indicates that the candidate compound decreases alpha synuclein associated toxicity.

A yeast model for neurodegenerative diseases characterized by abnormal accumulation of TDP-43, such as frontotemporal dementia (FTD) and amyotrophic lateral sclerosis (ALS) was developed based at least in part on the discovery that expression of a human TDP-43 protein in yeast cells is toxic and results in the formation of multiple cytoplasmic aggregates in yeast cells (US Pat. Pub. No. 20110053857). This model permits, among other things, the carrying out of screens using TDP-43-expressing yeast cells to identify compounds or genetic factors that modulate TDP-43-induced toxicity or TDP-43-induced inclusion formation. Compounds identified by such screens that inhibit TDP-43-induced toxicity or TDP-43-induced inclusion formation can be used for the treatment or prevention of TDP-43 proteinopathies such as frontotemporal lobar degeneration or amyotrophic lateral sclerosis.

A yeast model for neurodegenerative diseases characterized by abnormal accumulation of amyloid beta, such as Alzheimer's disease, was developed based at least in part on the discovery that a fusion polypeptide containing a signal sequence and a human amyloid beta protein is toxic when expressed in a yeast cell (US Pat. Pub. Nos. 20130022988 and 20130045483). This model permits, among other things, the carrying out of screening assays using amyloid beta-expressing yeast cells to identify compounds or genetic factors that modulate amyloid beta-induced toxicity. Compounds identified by such screens that inhibit amyloid beta-induced toxicity can be used for the treatment or prevention of neurodegenerative diseases characterized by accumulation of amyloid beta (Abeta), such as Alzheimer's disease. In some aspects, a yeast model for neurodegenerative diseases characterized by accumulation of amyloid beta (Abeta), such as Alzheimer's disease, features yeast that express a polypeptide comprising an Abeta peptide fused to a signal sequence.

A yeast model for neurodegenerative diseases characterized by abnormal accumulation of proteins comprising polyQ repeats was developed based at least in part on the discovery that a huntingtin polypeptide comprising abnormally large number of polyQ repeats is toxic when expressed in a yeast cell (U.S. Pat. No. 7,045,290).

Yet another yeast model involves yeast that express a FUS protein. The model is based at least in part on the discovery that FUS is toxic when expressed in a yeast cell (Ju S, et al. (2011) A Yeast Model of FUS/TLS-Dependent Cytotoxicity. PLoS Biol 9(4): e1001052. doi:10.1371/journal.pbio.1001052). A FUS yeast model permits, among other things, the carrying out of screening assays using FUS-expressing yeast cells to identify compounds or genetic factors that modulate FUS-induced toxicity. In some aspects, compounds identified by such screens that inhibit FUS-induced toxicity are candidate therapeutic agents for the treatment or prevention of FUS-opathies such as FTLD-FUS.

In some embodiments, yeast that express a neurodegeneration associated protein or neurodegeneration associated RNA are used as models of neurodegenerative diseases associated with a gain of function mutation of the gene that encodes the neurodegeneration associated protein or neurodegeneration associated RNA. Such yeast models may be created by introducing an expression construct encoding the neurodegeneration associated protein or neurodegeneration associated RNA into yeast. In some embodiments the expression construct encodes a mutant form of the neurodegeneration associated protein or neurodegeneration associated RNA, wherein the mutant form harbors a gain of function mutation associated with the disease. In some embodiments the neurodegeneration associated protein or neurodegeneration associated RNA aggregates or accumulates aberrantly in the nervous system of subjects with the disease. In some embodiments the neurodegeneration associated protein or neurodegeneration associated RNA does not typically accumulate aberrantly in the nervous system of subjects with the disease. In some embodiments the neurodegeneration associated protein or neurodegeneration associated RNA is not typically present in detectable aggregates in the nervous system of subjects with the disease.

In some embodiments, yeast that express a neurodegeneration associated protein or neurodegeneration associated RNA are used as models of neurodegenerative diseases associated with a gain of function mutation of the gene that encodes the neurodegeneration associated protein or neurodegeneration associated RNA. In some embodiments, yeast models of neurodegenerative diseases associated with aggregation and/or aberant accumulation of a neurodegeneration associated protein or associated with aggregation and/or aberrant accumulation of a neurodegeneration associated RNA or associated with a gain of function mutation of a neurodegenerative disease gene are created by generating yeast that express the neurodegeneration associated protein or neurodegeneration associated RNA.

In some embodiments, neurodegenerative diseases associated with a gain of function of a neurodegenerative disease gene that has a yeast homolog are modeled using yeast that have a gain of function of the yeast homolog. A mutation imparting a gain of function may be engineered in the endogenous yeast gene, or an expression construct encoding a mutant yeast homolog may be introduced into the yeast. The particular mutation may correspond to mutation(s) that are associated with the disease or may mimic the effect of such mutation(s) on activity of the gene product. In some embodiments yeast that are engineered to overexpress the yeast homolog serve as a model of the disease.

In some embodiments, neurodegenerative diseases associated with a loss of function of a neurodegenerative disease gene that has a yeast homolog are modeled using yeast that have a loss of function of the yeast homolog. In some embodiments, yeast models of neurodegenerative diseases associated with a loss of function of a neurodegenerative disease gene that has a yeast homolog are created by generating yeast that have a deletion or disruption in the endogenous yeast homolog. In some embodiments such yeast may be obtained or selected from existing collections of yeast strains harboring disruptions or deletions. In some embodiments a nucleic acid sequence encoding the gene product of the yeast homolog is placed under control of a regulatable expression control element, e.g., a regulatable promoter such as the GAL promoter. The yeast may express the gene product at normal levels under certain conditions, and the disease may be modeled by culturing the yeast under conditions in which expression is reduced or absent as compared with a normal expression level. Table B lists a number of neurodegenerative diseases associated with loss of function of a neurodegenerative disease gene and indicates the corresponding yeast homologs. Fitness and loss-of-function phenotypes for yeast are systematically catalogued at the Saccharomyces Genome Database (yeastgenome.org). In some embodiments of the present invention, phenotypes associated with loss of function of a yeast homolog listed in Table B may be identified in human neurons.

In some embodiments, any of the yeast models may have a mutation in or may overexpress one or more genes that is a yeast homolog of a human gene that is a genetic modifier of the neurodegenerative disease or is a yeast homolog of a second neurodegenerative disease gene capable of causing the disease. Certain parkinsonism genes with yeast homologs are listed in Table D. In some embodiments a yeast model for a synucleinopathy, e.g., PD, expresses alpha-synuclein and also expresses a gene product of a gene characterized in that mutations in the gene are associated with PD with a dominant or complex inheritance pattern and/or wherein gain of function mutations in or extra copies of the gene are associated with PD, e.g., LRRK2, RAB7L1, GBA, or EIF4G1, or overexpresses or has a gain of function mutation in a yeast homolog of said gene. In some embodiments the yeast expresses a mutant form of the human gene, wherein the mutant form is associated with the disease. The yeast homologs of LRRK2 and EIF4G1are listed in Table D. In some embodiments a yeast model for a synucleinopathy, e.g., PD, expresses alpha-synuclein and has reduced or absent expression or activity of a gene product of a yeast gene characterized in that mutations in the human homolog of the yeast gene are associated with PD with a recessive or complex inheritance pattern and/or wherein loss of function mutations in the human homolog of the yeast gene are associated with PD. In some embodiments the human gene is ATP13A2, VPS35, or PINK1. The yeast homologs of these genes are listed in Table D.

Figure 13:
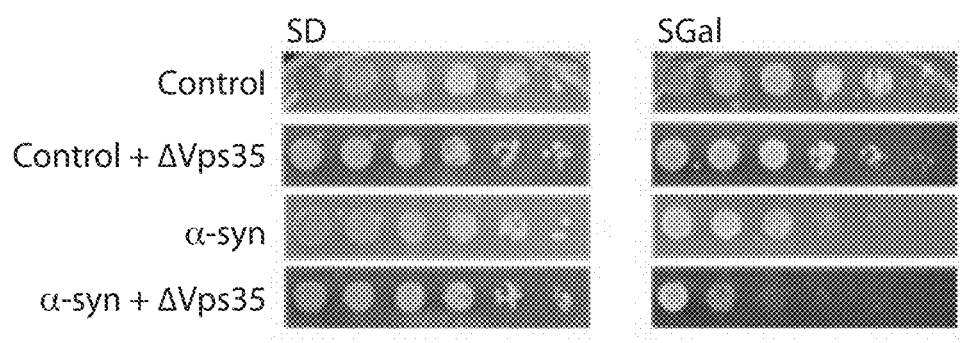
FIG. 13. Yeast model of αSyn cytotoxicity in combination with deletion of Vps35. Left panel (labeled (A): Deletion of Vps35 enhances toxicity of αSyn. Right panel (no label): Mutant human Vps35 does not restore viability as a gene encoding WT human Vps35 does.
Figure 13:
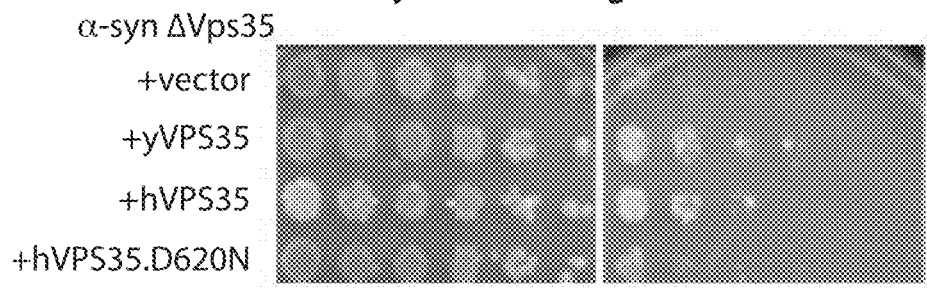
Figure 14A:
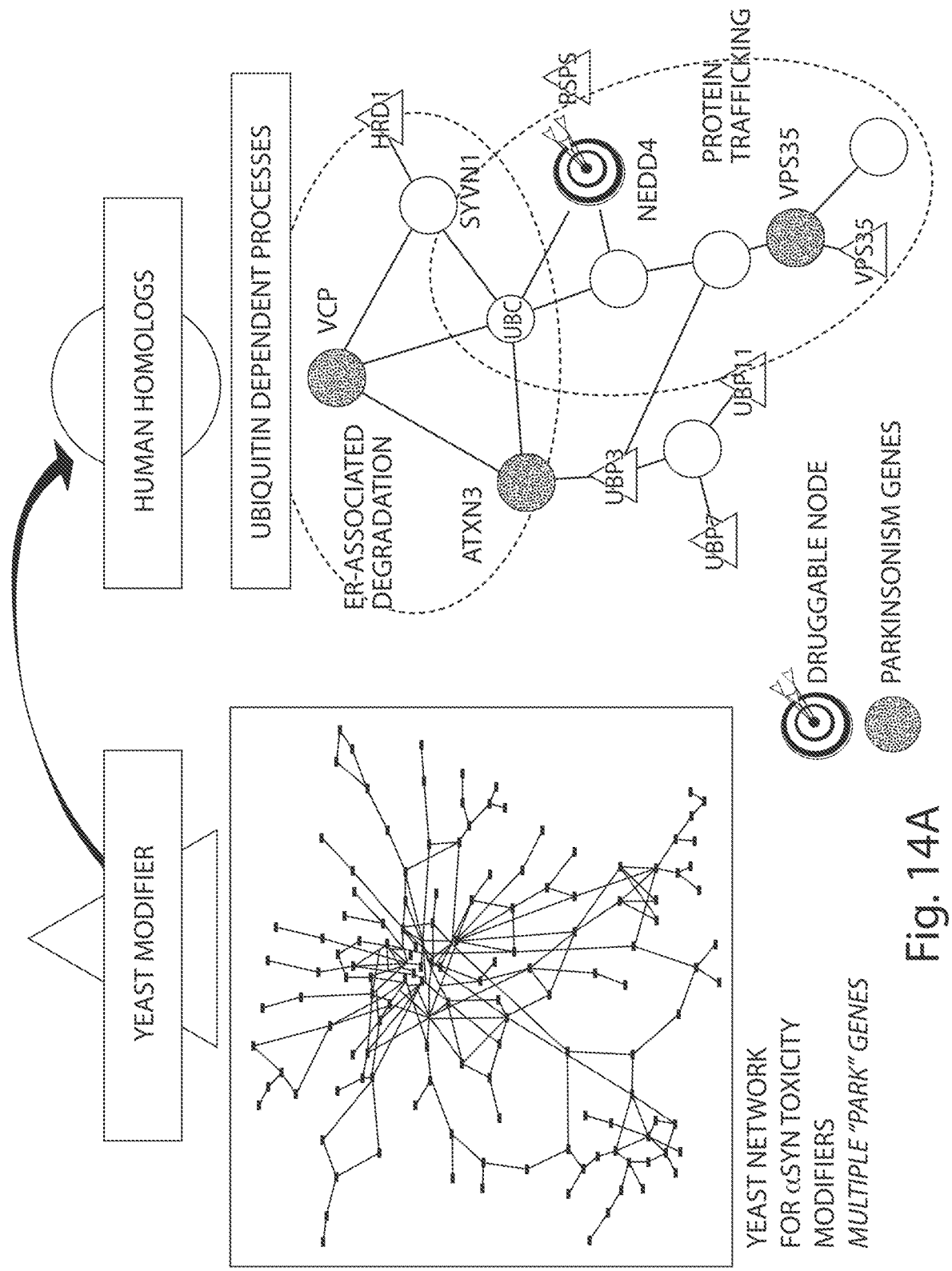
FIG. 14. (A) An alpha synuclein interaction map is "humanized" by finding human homologs of yeast nodes and using computational methods (Steiner forest) to augment the yeast interactome (left portion of panel). Triangles represent yeast genes; Circles represent human genes. The right portion of the panel shows a magnified view of part of the network centered around ubiquitin. The network structure reveals ubiquitin related processes associated with ER-associated degradation and protein trafficking and identifies NEDD4 as a druggable node. The map links numerous parkinsonism genes (blue circles) to alpha synuclein, including 4 PARK genes—PARK 2, PARK9, PARK17, PARK18. (B) Same as right portion of (A) but showing names of genes.
Figure 14B:
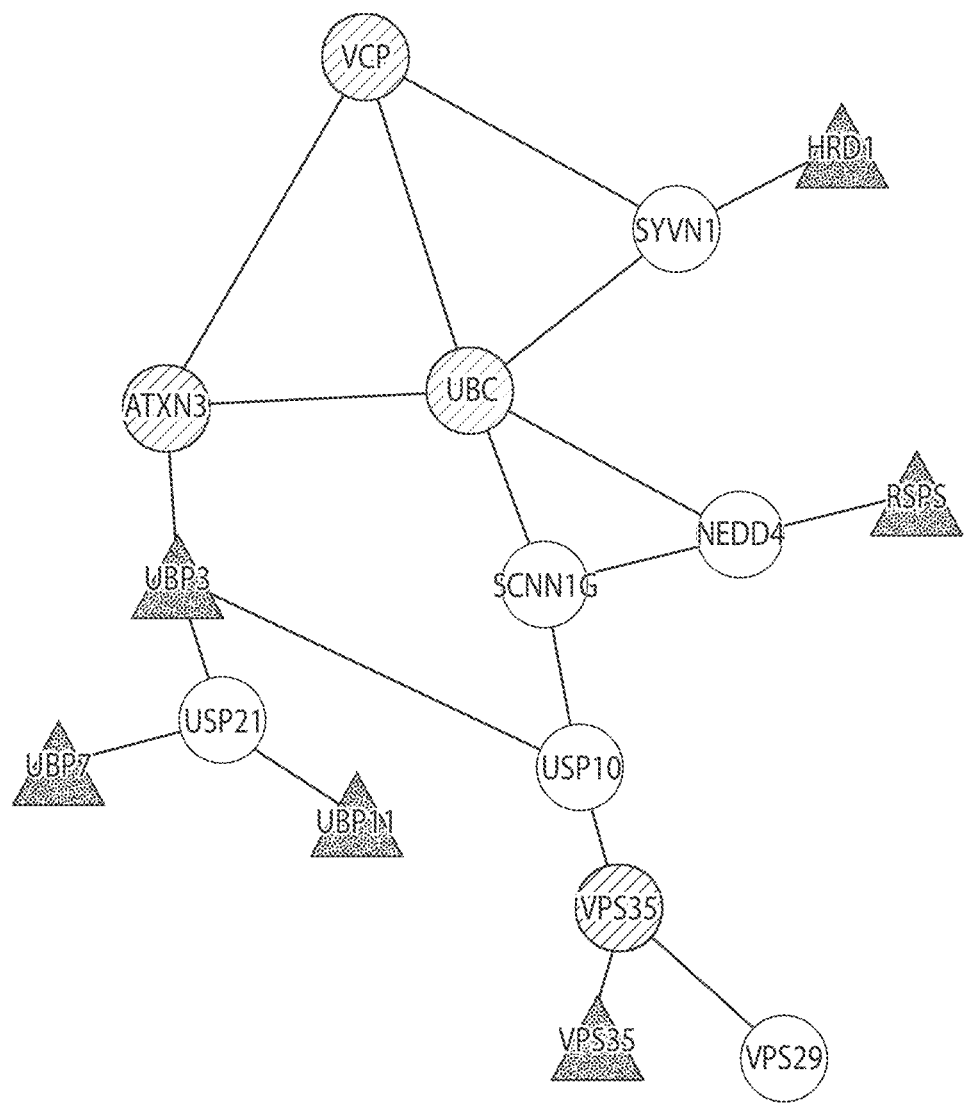
Figure 15:
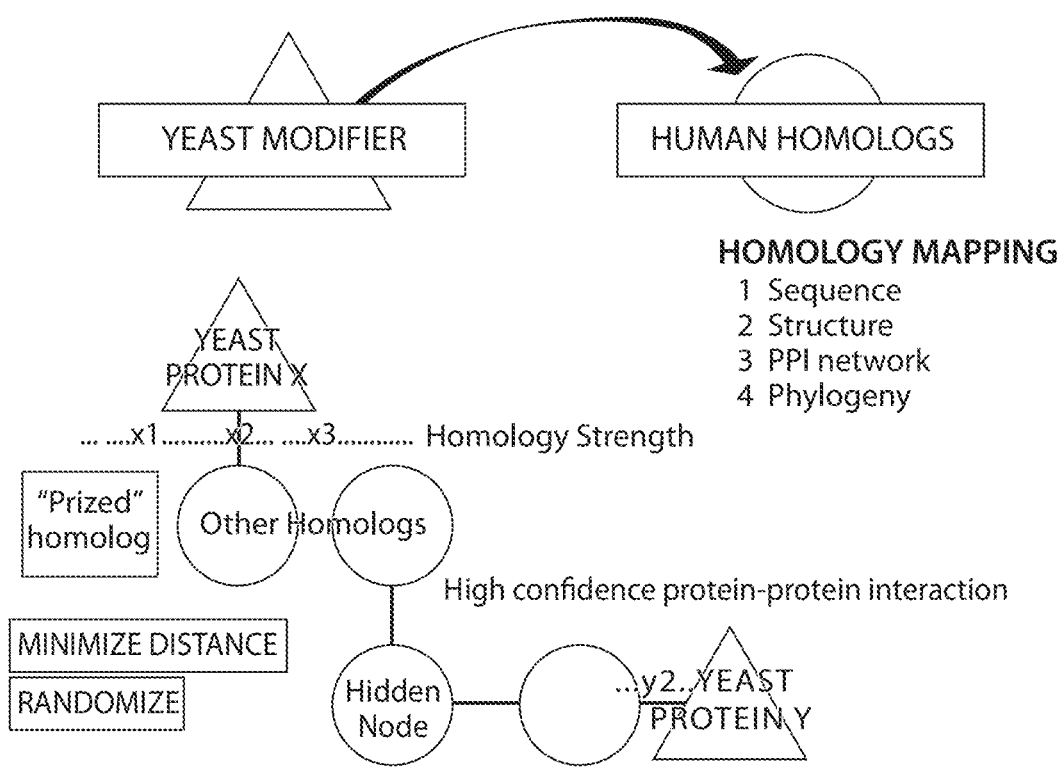
FIG. 15. Schematic diagram of network construction showing process of connecting yeast protein X and yeast protein Y, both encoded by genetic modifiers identified in yeast screen.
Figure 16:
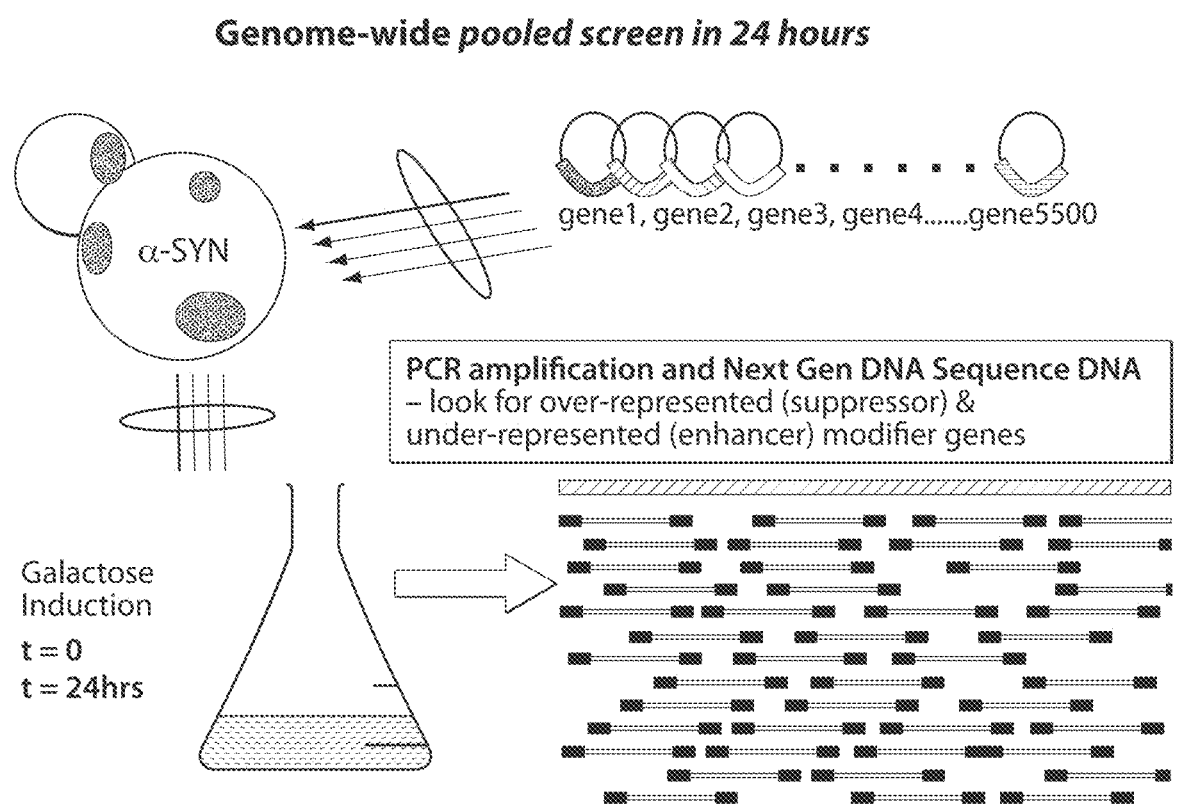
FIG. 16. Schematic diagram of genome-wide pooled screen to identify genetic modifiers in yeast.

In some embodiments, any of the yeast models, e.g., a yeast model that expresses a neurodegeneration associated protein or RNA or that lacks expression of a yeast homolog of a neurodegenerative disease gene, may also overexpress or have reduced or absent expression or activity one or more yeast genes, that when overexpressed or deleted, respectively, enhances toxicity in the yeast model but has little or no effect on a control strain. In some embodiments the yeast gene that, when overexpressed or deleted, enhances toxicity in the yeast model, is a yeast homolog of a genetic modifier of the neurodegenerative disease in humans. In some embodiments the yeast gene is identified in a screen for yeast genes whose overexpression or deletion (or disruption) enhances or suppresses toxicity in a yeast model. In some embodiments the yeast serves as a model for patients with the disease who have a mutation or genetic variation associated with the disease in the genetic modifier. For example, deletion of VPS35 enhances αSyn toxicity but has no effect in the control strain (FIG. 13). In some embodiments, such a strain may serve as a model of particular relevance for patients with mutations in the human VPS35 gene or mutations in other genes encoding gene products involved in the same pathways, processes, or complex.

Yeast Cells

Yeast strains that can be used in the compositions and methods described herein include, but are not limited to,

*Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*. Although certain compositions and methods are exemplified herein in regard to *Saccharomyces cerevisiae* this is merely for illustrative purposes. In certain embodiments other yeast strains can be substituted for *S. cerevisiae*.

Certain aspects of the disclosure relate to methods for identifying or characterizing agents, e.g., small molecules, using yeast. Methods described herein can optionally be carried out in yeast strains bearing mutations in one or more genes that affect a membrane efflux pump and/or that affect permeability for small molecules. For example, a yeast strain may have a mutation in the ERG6 gene, the PDR1 gene, the PDR3 gene, the PDR5 gene, the SNQ2 gene, and/or any other gene which affects membrane efflux pumps and/or affects permeability for small molecules, wherein the effect of the mutation is to inhibit efflux of a small molecule or to increase entry of a small molecule into yeast cells. In some embodiments the yeast strain bears mutations in 2, 3, 4, 5, or more such genes. In some embodiments the yeast strain bears a mutation in at least one PDR gene, e.g., PDR1 and/or PDR3. In some embodiments the yeast strain bears a mutation in at least one gene that encodes an ATP-binding cassette (ABC) transporter, e.g., PDR5. In some embodiments the yeast strains bears mutations in PDR1, PDR3, and ERG6. In some embodiments the mutation is in a gene that enhances or is required for expression or activity of a membrane efflux pump, e.g., a transcription factor that directs transcription of the gene encoding the pump.

A nucleic acid encoding a polypeptide described herein, e.g., a polypeptide comprising a NAP, may be transfected into a yeast cell using nucleic acid vectors that include, but are not limited to, plasmids, linear nucleic acid molecules, artificial chromosomes, and episomal vectors. Three well known systems used for recombinant plasmid expression and replication in yeast cells include integrative plasmids, low-copy-number ARS-CEN plasmids, and high-copy-number 2μ plasmids. See Sikorski, "Extrachromosomal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994.

An example of the integrative plasmids is YIp, which is maintained at one copy per haploid genome, and is inherited in Mendelian fashion. Such a plasmid, containing a gene of interest, a bacterial origin of replication and a selectable gene (typically an auxotrophic marker), is typically produced in bacteria. The purified vector is linearized within the selectable gene and used to transform competent yeast cells. Yeast perform homologous recombination such that the cut, selectable marker recombines with the mutated (usually a point mutation or a small deletion) host gene to restore function. Of course integration may be targeted to any region of the yeast genome that is homologous to a sequence within the vector. For example, if the integrative plasmid contains a second yeast gene in addition to the selectable gene, linearizing the plasmid within the second yeast gene will greatly increase the frequency of integration in the immediate vicinity of the homologous sequence in the genome. Subsequent excision by homologous recombination between the introduced sequence and the endogenous sequence may result in replacement of at least a portion of the endogenous sequence by the introduced sequence.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2μ plasmids is YEp, which contains a sequence approximately 1 kb in length (named the 2μ sequence). The 2μ sequence acts as a yeast replicon giving rise to higher plasmid copy number. However, these plasmids are unstable and require selection for maintenance. Copy number is increased by having on the plasmid a selection gene operatively linked to a crippled promoter.

A wide variety of plasmids can be used in the compositions and methods described herein. In some embodiments the plasmid is an integrative plasmid (e.g., pRS303, pRS304, pRS305, pRS306, or a derivative thereof). See, e.g., Alberti et al. (2007) "A suite of Gateway cloning vectors for high-throughput genetic analysis in *Saccharomyces cerevisiae*" Yeast 24(10):913-19. In some embodiments the plasmid is an episomal plasmid (e.g., p426GPD, p416GPD, p426TEF, p423GPD, p425GPD, p424GPD or p426GAL).

Regardless of the type of plasmid used, yeast cells are typically transformed by chemical methods (e.g., as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/μg of DNA. Transformed cells are then isolated on selective media. Of course, any suitable means of introducing nucleic acids into yeast cells can be used.

The yeast vectors (plasmids) described herein typically contain a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerol-phosphate dehydratase or IGP dehydratase); or 5) LYS2 (α-aminoadipate-semialdehyde dehydrogenase).

The yeast vectors (plasmids) described herein may also contain promoter sequences. A "promoter" is a region of a nucleic acid sequence at which initiation of transcription is controlled. It may contain genetic elements at which regulatory proteins and molecules may bind, such as RNA polymerase and other transcription factors, to initiate the specific transcription a nucleic acid sequence. The phrases "operatively linked" and "operatively positioned" mean that a promoter is in a correct functional location and/or orientation in relation to a nucleic acid sequence to control transcriptional initiation and/or expression of that sequence.

A promoter may be one that is naturally associated with a nucleic acid sequence whose transcription it controls, e.g., as may be obtained by isolating the 5' non-coding sequences located upstream of the coding segment of a gene. Such a promoter can be referred to as the "endogenous" or "native" promoter of the gene or open reading frame. Alternatively, a promoter associated with a nucleic acid sequence may be a recombinant or heterologous promoter, which refers to a promoter that is not normally associated with the nucleic acid sequence in its natural environment. Such promoters may include promoters of other genes and promoters not "naturally occurring."

A promoter may be constitutive or regulatable, e.g., inducible or repressible. For example, various promoters may be employed to regulate expression in yeast cells. Examples of inducible yeast promoters include GAL1-10, GAL1, GALL, and GALS. Examples of repressible yeast promoters include Met25. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. Yeast expression vectors containing promoters inducible by glucocorticoids have also been described (Picard et al., Gene. 1990; 86(2):257-61). For example, the presence of multiple glucocorticoid response elements renders a linked promoter inducible by glucocorticoids in yeast that express a mammalian glucocorticoid receptor. Similar approaches may be used to generate yeast vectors that are regulatable by other steroids. Naturally occurring or synthetic ligands of a steroid hormone receptor may be used. In some embodiments regulatable expression may be achieved using a tetracycline-regulatable promoter, which may be regulated using a tetracycline antibiotic, e.g., tetracycline, doxycycline, or an analog thereof, in a yeast strain that expresses tTA or rtTA. The promoter may comprise one or more copies of the Tet operator (TetO), e.g., 7 copies (though a lower or higher number of copies may be used). tTA activity is downregulated in the presence of tetracycline antibiotics, whereas rtTA is activated by such antibiotics, thereby permitting control of promoter activity. See, e.g., Gari E, et al., Yeast. (1997) 13(9):837-48 and/or Belli G, et al., Nucleic Acids Res. (1998) 26(4):942-7 for further details. Examples of useful yeast vectors and regulatory elements, e.g., promoters, are described in Mumberg D, et al. Gene. 1995; 156(1):119-22; Ronicke V, et al., Methods Enzymol. 1997; 283:313-22, Funk M, et al., Methods Enzymol. 2002; 350: 248-57, all incorporated herein by reference. In some embodiments yeast vectors containing constitutive or inducible promoters such as alpha factor, alcohol oxidase, and PGH may be used.

In some embodiments, a yeast strain is used that allows for expression, e.g., inducible expression, from GAL promoters on carbon sources other than galactose. In some embodiments, the strain carries an integrated or episomal (e.g., plasmid-borne) gene encoding a fusion protein, wherein the Gal4 DNA binding domain is fused to a transcriptional activation domain and a regulatory domain. The fusion protein is characterized in that its ability to activate transcription is regulated by binding of a small molecule to the regulatory domain. For example, in some embodiments, the fusion protein does not activate transcription in the absence of the small molecule, whereas in the presence of the small molecule, the fusion protein activates transcription. Exemplary small molecules include, e.g., steroid hormones, wherein the corresponding regulatory domain comprises at least a portion of a receptor for the small molecule. For example, the small molecule may be an estrogen (e.g., estradiol), or analog thereof (e.g., tamoxifen), and the corresponding regulatory domain comprises at least a portion of the estrogen receptor (ER). Exemplary activation domains include, e.g., viral protein activation domains such as the herpes simplex virus protein VP16 activation domain. In some embodiments, the strain carries an integrated or episomal (e.g., plasmid-borne) gene encoding a Gal4-ER-VP16 fusion protein. Presence of an estrogen receptor ligand, e.g., estradiol, in the medium, allows for expression from GAL promoters on carbon sources other than galactose. One of skill in the art will appreciate that numerous ways exist to render expression of a molecule of interest, e.g., a NAP, conditional, e.g., on culture media containing galactose or other carbon sources.

Certain methods described herein may comprise disrupting an endogenous gene in a yeast cell or may make use of a yeast cell in which an endogenous gene is disrupted. Gene disruption may comprise any of a variety of ways of disabling a gene, e.g., inserting a sequence into the gene, deleting at least a portion of the gene, or both. An insertion may, for example, introduce a stop codon, shift the reading frame, or otherwise prevent production of a functional protein. Certain methods described herein may comprise mutating one or more genes in a yeast cell. In some embodiments a mutation comprises making a desired alteration to the sequence of the gene. Methods suitable for performing such manipulations are well known in the art. Collections of gene disruption mutants of various yeast such as S. cerevisiae are known in the art (see, e.g., Giaever, et al., Nature. 2002; 418(6896): 387-91). In some embodiments a collection of deletion strains includes strains with deletions in at least 70%, 80%, 85%. 90%, 95%, or more of the open reading frames in the genome. In some embodiments DNA sequences sometimes termed "molecular bar codes" uniquely identify each strain in a collection, enabling their growth to be analyzed in parallel, e.g., in a co-culture, and the fitness contribution of each gene to be quantitatively assessed by, e.g., hybridization to high-density oligonucleotide arrays, or other means of assessing the abundance of the gene. A set of yeast strains in which the nearly 20% of yeast genes required for viability are under control of Tet-regulatable promoters has been constructed (Mnaimneh, S., et al. 2004. Cell 118:31-44; collection is available under the name Yeast Tet-promoters Hughes Collection (yTHC) from ThermoFisher Scientific, Pittsburgh, Pa.). The endogenous promoter has been replaced with a Tet-titratable promoter in the genome in these strains. This allows the expression of the gene to be switched off by the addition of a tetracycline antibiotic to the yeast growth medium. In some embodiments such strains may be used to identify essential genes that enhance or suppress toxicity of a NAP.

In some embodiments synthetic genetic array (SGA) analysis may be used. In some embodiments SGA analysis involves a series of replica-pinning procedures, in which mating and meiotic recombination are used to convert an input array of single mutants into an output array of double mutants (see, e.g., Tong, A. H. Y. et al. (2001) Science 294: 2364-2368). A yeast strain engineered to express or be capable of expressing a NAP may be used as a "query strain" in an SGA screen to identify genes whose deletion confers increased toxicity, e.g., lethality or reduced growth rate.

Screening Assays in Yeast Cells

Certain aspects of the present disclosure comprise screening for a candidate agent or a genetic factor that modulates, e.g., inhibits, toxicity induced by a NAP in yeast and/or utilizing agents or information obtained from such a screen in conjunction with human neurons. Certain aspects of the present disclosure comprise screening for a candidate agent or a genetic factor that modulates, e.g., inhibits, toxicity induced by a NAR in yeast and/or utilizing agents or information obtained from such a screen in conjunction with human neurons. Certain aspects of the present disclosure comprise screening for a candidate agent or a genetic factor that modulates, e.g., enhances, viability in yeast models that have reduced or absent expression of a yeast homolog of a LOF neurodegenerative disease gene or inhibits a phenotype resulting from reduced or absent expression of the yeast homolog. In certain embodiments, screening methods use yeast cells that are engineered to express a NAP, e.g., an alpha-synuclein, amyloid beta, TDP-43, FUS, or polyglutamine expanded protein. In certain embodiments, screening methods use yeast cells that are engineered at least in part by deleting or disrupting a yeast homolog of a LOF neurodegenerative disease gene. Various types of candidate drugs may be screened, including nucleic acids, polypeptides, small molecule compounds, and peptidomimetics. In some embodiments genetic agents can be screened by contacting the yeast cell with a nucleic acid construct coding for a gene. For example, one may screen cDNA libraries expressing a variety of genes, to identify genes that modulate toxicity of a NAP.

For chemical screens, e.g., screening small molecules, yeast strains bearing suitable mutations designed to inhibit membrane efflux pumps and/or increase permeability for drugs may be used. For example, a yeast strain bearing mutations in the ERG6 gene, the PDR1 gene, the PDR3 gene, and/or the PDR5 gene may be used. A large number of compounds can be screened under a variety of growth conditions and/or in yeast with a variety of genetic backgrounds. A toxicity screen may, for example, identify compounds that interact with the NAP or that interact with or alter expression or activity of one or more proteins that interact with the NAP or are involved in processes or pathways affected by the presence of the NAP or involved in one or more mechanisms by which it induces toxicity.

In certain embodiments, candidate agents can be screened from large libraries of synthetic or natural compounds. An agent to be tested may be referred to as a test agent. Any agent may be used as a test agent in various embodiments. In some embodiments a library of FDA approved compounds that can be used by humans may be used. Compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd.(Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China). Combinatorial libraries are available and can be prepared. Libraries of natural compounds in the form of bacterial, fungal, plant and animal extracts are commercially available or can be readily prepared by methods well known in the art. Compounds isolated from natural sources, such as animals, bacteria, fungi, plant sources, and marine samples may be tested for the presence of potentially useful pharmaceutical agents. It will be understood that the agents to be screened could also be derived or synthesized from chemical compositions or man-made compounds. In some embodiments a library comprises at least 10,000 compounds, at least 50,000 compounds, at least 100,000 compounds, at least 250,000 compounds, or more.

In some embodiments, a screen may be a high throughput screen (HTS). High throughput screens often involve testing large numbers of compounds with high efficiency, e.g., in parallel. For example, tens or hundreds of thousands of compounds can be routinely screened in short periods of time, e.g., hours to days. Often such screening is performed in multiwell plates containing, e.g., e.g., 96, 384, 1536, 3456, or more wells (sometimes referred to as microwell or microtiter plates or dishes) or other vessels in which multiple physically separated cavities or depressions or areas are present in or on a substrate. High throughput screens can involve use of automation, e.g., for liquid handling, imaging, data acquisition and processing, etc. Certain general principles and techniques that may be applied in embodiments of a HTS are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Useful methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser.

Certain embodiments relate to genetic screens. For example, genomic libraries and disruption libraries can be screened to find genetic suppressors or enhancers of NAP-induced toxicity in yeast. Because the yeast genome is small, 10,000 transformants of each type should be sufficient for good coverage although lower or higher numbers may of course be used. Libraries of plasmids each comprising a yeast open reading frame operably linked to a yeast promoter are available. For example, the yeast FLEXGene overexpression library includes plasmids representing more than 5,000 yeast open reading frames, including essential genes (Kelley, S. et al., Genome Res. 17 (2007) 536-543.). In certain embodiments yeast strains that exhibit increased NAP-associated toxicity due to increased expression or activity of a genetic enhancer of such toxicity or due to decreased expression or activity of a gene that when overexpressed reduces such toxicity are used in screens described herein.

Certain embodiments contemplate screening assays using fluorescent resonance energy transfer (FRET). FRET occurs when a donor fluorophore is in close proximity (10-60 A) to an acceptor fluorophore, and when the emission wavelength of the first overlaps the excitation wavelength of the second (Kenworthy A K et al., 2001. Methods. 24:289-96). FRET should occur when cyan fluorescent protein (CFP) and yellow fluorescent protein (YFP) fusion proteins are actually part of the same complex.

For example, a NAP can be fused to CFP and to YFP respectively, and integrated into the yeast genome under the regulation of a GAL1-10 promoter. Cells are grown in galactose to induce expression. Upon induction, cells produce the fusion proteins, which aggregate and bring the CFP and YFP close together. Because proteins in the aggregates are tightly packed, the distance between the CFP and YFP is less than the critical value of 100 Angstroms that is necessary for FRET to occur. In this case, the energy released by the emission of CFP will excite the YFP, which in turn will emit at its characteristic wavelength. FRET based screening can be used to identify candidate compounds including, drugs, genes or other factors that can disrupt the interaction of CFP and YFP by maintaining the proteins in a state that does not allow aggregation to occur.

An embodiment contemplates screening assays using fluorescence activated cell sorting (FACS) analysis. FACS provides the means of scanning individual cells for the presence of fluorescently labeled/tagged moiety, which allows for a rapid, reliable, quantitative, and multiparameter analysis on either living or fixed cells. For example, a NAP can be suitably labeled, and provide a useful tool for the analysis and quantitation of protein aggregation as a result of other genetic or growth conditions of individual yeast cells.

Screens (e.g., for compounds and/or for genetic suppressors or enhancers) can be carried out under a variety of different conditions. For example, a variety of different culture media can be used. Culture media can contain different carbon sources, e.g., different sugars such as glucose, glycerol, galactose, raffinose, etc. In some embodiments, multiple screens may be performed using two, three, or more different culture conditions (e.g., culture media containing different carbon sources), and compounds or genes identified as "hits" under at least two different culture conditions are identified. In some embodiments, screens are performed under two or more different culture conditions (e.g., using culture media containing different carbon sources), wherein the different culture conditions (e.g., different carbon sources) result in different levels of mitochondrial respiration. For example, growth using culture media containing glucose, glycerol, or galactose result in different levels of mitochondrial respiration. In glucose, yeast cells ferment and respiration remains low until all glucose is converted to ethanol. In galactose respiration is moderately active. In glycerol, yeast cells are completely dependent on respiration for growth. In some embodiments, a screen is performed in parallel using media containing glucose, galactose, or glycerol as a carbon source.

In some embodiments an agent that modulates, e.g., inhibits, toxicity associated with a NAP in yeast does not significantly affect the level of expression of the NAP. For example, in some embodiments the agent does not significantly inhibit expression from the particular promoter used to direct expression of the NAP, e.g., the GAL promoter. For example, in certain embodiments the level of expression of the NAP and/or the level of expression directed by the promoter may be reduced by no more than 1%, 2%, or 5% when yeast cells are cultured in the presence of the agent as compared to in its absence. In certain embodiments the level of expression of the NAP and/or the level of expression directed by the promoter may be reduced by no more than 10% when yeast cells are cultured in the presence of the agent as compared to in its absence.

In some embodiments an agent or gene that selectively modulates toxicity associated with a NAP may be identified or used. In some embodiments an agent may have at least a 2, 5, 10, 25, 50, or 100-fold greater ability to modulate, e.g., inhibit, toxicity associated with a particular NAP than toxicity associated with 1, 2, 3, or more other NAPs when used at its most effective concentration for the particular NAP in question. In some embodiments a method may comprise determining that an agent has at least a 2, 5, 10, 25, 50, or 100-fold greater ability to modulate, e.g., inhibit, toxicity associated with a particular NAP than toxicity associated with 1, 2, 3, or more other NAPs. For example, a method may comprise determining that an agent has at least a 2, 5, 10, 25, 50, or 100-fold greater ability to modulate, e.g., inhibit, toxicity associated with an alpha-synuclein protein than toxicity associated with Abeta, TDP-43, FUS, and/or polyglutamine expanded Htt. In some embodiments, overexpression or deletion of a gene may have at least a 2, 5, 10, 25, 50, or 100-fold greater ability to modulate, e.g., inhibit, toxicity associated with a particular NAP than toxicity associated with 1, 2, 3, or more other NAPs. In some embodiments a method may comprise determining that overexpression or deletion of a gene has at least a 2, 5, 10, 25, 50, or 100-fold greater ability to modulate, e.g., inhibit, toxicity associated with a particular NAP than toxicity associated with 1, 2, 3, or more other NAPs.

Figure 9A:
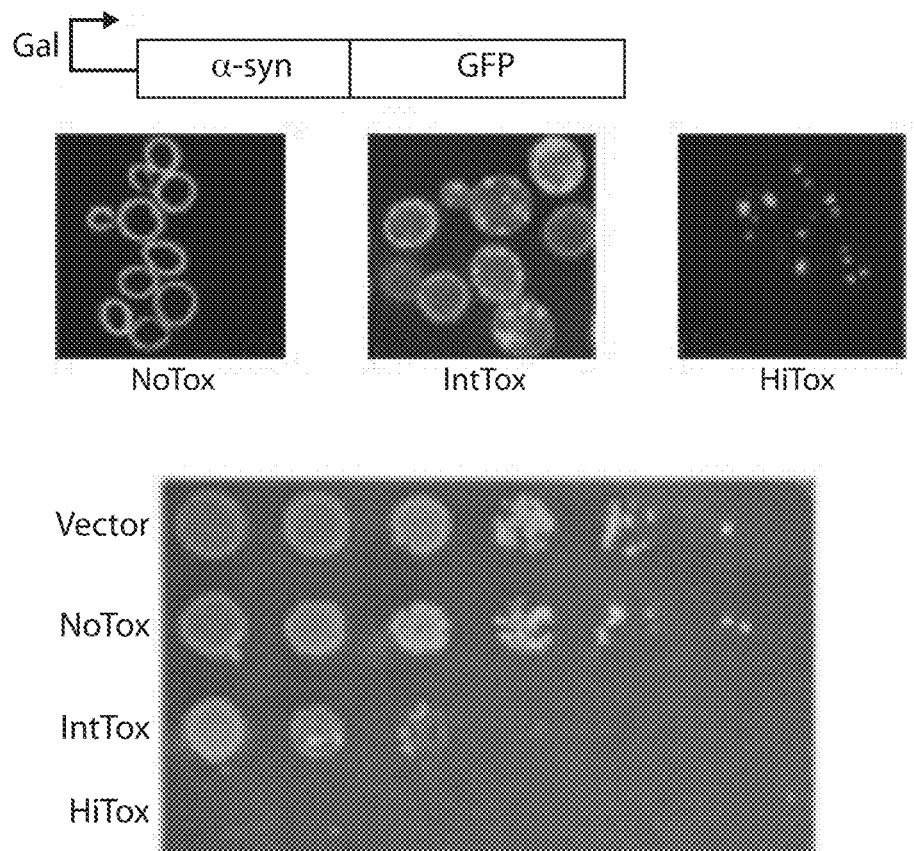
FIG. 9. Yeast model of αSyn cytotoxicity demonstrating different levels of toxicity associated with different levels of αSyn expression. (A) αSyn-green fluorescent protein (GFP) is expressed under a regulatable (galactose [Gal]-inducible) promoter at increasing copy number. Abnormal focal accumulation of αSyn and reduced growth are dose sensitive, ranging from no toxicity (1 copy; NoTox), to intermediate toxicity (2-3 copies; IntTox) to high toxicity (4 copies; HiTox). Left panel is immunofluorescence. Right panel is a spot assay in which there is fivefold serial dilution starting with equal numbers of cells. (B) Data from another experiment showing relative growth in liquid culture of NoTox, IntTox, and HiTox yeast strains.
Figure 9B:
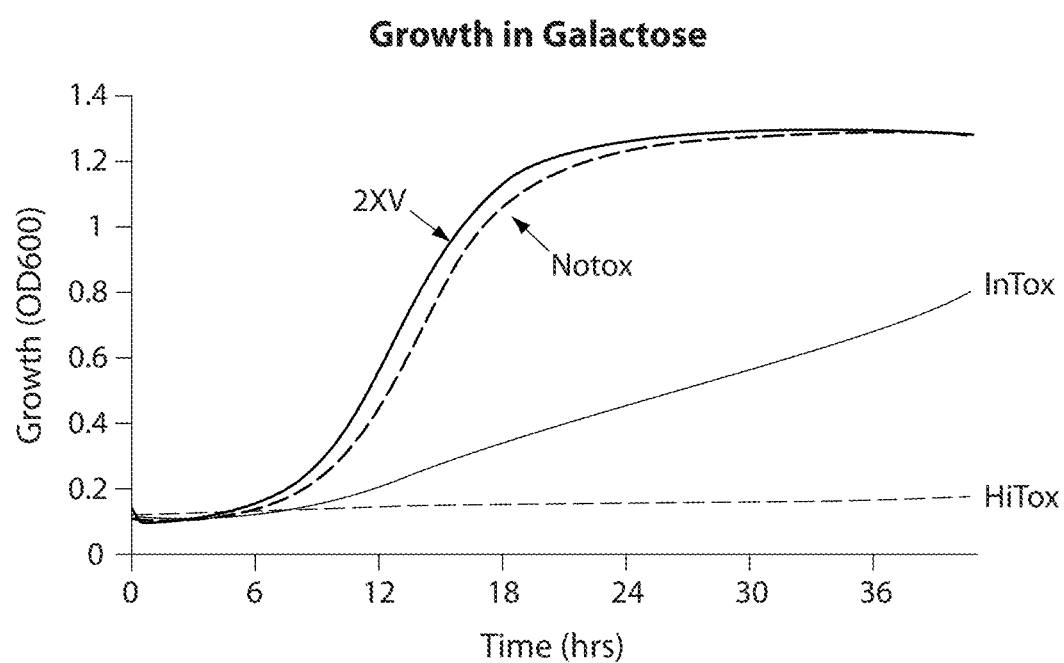

In some aspects, yeast cells that express different levels of a NAP and/or that exhibit different levels of toxicity may be of use. In some embodiments, at least 2 or 3 distinct levels of toxicity may be achieved, e.g., by expressing different amounts of a NAP or NAR or by making multiple genetic alterations (e.g., expressing a NAP in combination with an enhancer of toxicity or in combination with deleting a suppressor of toxicity). Different levels of toxicity may include, e.g., non-toxic, low toxicity, intermediate toxicity, or high toxicity. In some embodiments a low level of toxicity refers to a slight inhibition of growth, detectable reduction in growth but less than the toxicity induced by three copies of alpha-synuclein under control of a GAL promoter. In some embodiments an intermediate level of toxicity refers to about the level of toxicity induced by three copies of alpha-synuclein under control of a GAL promoter. In some embodiments a high level of toxicity refers to about the level of toxicity induced by four or five (or more) copies of alpha-synuclein under control of a GAL promoter. See FIGS. 9(A) and 9(B) for examples of different levels of toxicity. Growth rate or toxicity may be assessed on solid media or in liquid culture in various embodiments. In some embodiments, a strain with a high level of toxicity (HiTox strain) exhibits little or no increase in cell number or mass after induction of expression of a NAP. For example, by about 6 hours after induction most or essentially all cells are dead or have lost the capacity to divide. In some embodiments, a strain with an intermediate level of toxicity (IntTox strain) has a growth rate of between about 15%-20% and about 30%, 40%, and 50% of that of a control strain over the course of time during which the control strain is in a logarithmic growth phase. In some embodiments, a strain with a low level of toxicity (LoTox strain) has a growth rate of between about 50% and about 60%, 70%, 80% or 90% of a control strain. In some embodiments an IntTox strain or LoTox strain has an approximately linear growth curve (e.g., in liquid culture) during at least the time period when a control strain is in a logarithmic growth phase after being inoculated into fresh medium under conditions in which the NAP is produced. In some embodiments a NoTox strain has a growth rate at least 90%-95% or more of that of a control strain. A control strain may be a strain that lacks expression of the NAP but is otherwise isogenic or essentially isogenic to the strain that expresses the NAP. In some embodiments a control strain may have one or more copies of the same or an equivalent vector as used to introduce a sequence encoding the NAP but lacking a sequence encoding a NAP (an "empty vector"). Strains with similar or different levels of toxicity may be generated for other yeast models described herein. It will be understood that the levels of toxicity are exemplary. Different levels of toxicity may be defined as appropriate for a particular screen or method.

The particular yeast strain and/or level of toxicity used in a given composition or method may be selected as appropriate or desirable depending, e.g., on the purpose for which it is used. In some embodiments yeast cells that express a NAP at a nontoxic or low toxicity level may facilitate identification of genes whose deletion (or other disablement) or overexpression enhances toxicity. In some embodiments an intermediate level of toxicity may facilitate identification of agents capable of enhancing or inhibiting toxicity and/or identification of genetic suppressors and enhancers of toxicity. In some embodiments a strain that exhibits a high level of toxicity may facilitate identifying agents capable of inhibiting toxicity and/or identification of genetic suppressors of toxicity. In some embodiments a strain exhibiting a high level of toxicity may be useful for comparing or testing the strengths of agents or genetic modulators.

In general, a desired level of expression may be achieved in a variety of ways. For example, the vector copy number, number of copies of the open reading frame encoding the NAP, the strength of the promoter used, the level of inducing agent (in the case of an inducible promoter), genetic background, culture conditions, etc., may be selected to achieve a desired expression level and/or level of toxicity. In some embodiments an intermediate or high level of toxicity is achieved by integrating into the yeast genome at least 2, 3, 4, or more copies of an open reading frame encoding the NAP, operably linked to a promoter. In some embodiments toxicity imparted by a given level of expression of a NAP may be reduced or enhanced by culturing the yeast in the presence of a small molecule or other agent or culture condition that inhibits or enhances such toxicity. In some embodiments a yeast strain with a genetic background that enhances or inhibits toxicity associated with a NAP may be used. For example, yeast strains that have a deletion of a yeast gene that inhibits toxicity, or that overexpress a yeast gene that enhances toxicity, may be used to increase the level of toxicity imparted by a given level of expression.

In some aspects, methods described herein may be used or adapted for use with yeast that express a NAR or that have reduced expression or activity of a yeast homolog of a LOF neurodegenerative disease gene.

A variety of screens have been performed using yeast models for neurodegenerative diseases. Screening of compound libraries has resulted in the identification of small molecules able to inhibit toxicity induced by the relevant NAP. For example, yeast screens that identified certain compounds that inhibit alpha-synuclein toxicity are described in U.S. Pat. No., U.S. Pat. Pub. Nos. 20080261953 and 20100273776). Yeast screens that identified certain compounds that inhibit amyloid beta toxicity are described in U.S. Pat. Pub. No. 20130022988.

Genetic screens have been performed resulted in the identification of enhancers and suppressors of toxicity induced by the relevant NAP. For example, yeast genes whose underexpression (e.g., deletion) in yeast resulted in altered alpha-synuclein toxicity have been identified (US Pat. Pub. No. 20050255450). Yeast genes whose overexpression in yeast resulted in altered alpha-synuclein toxicity have been identified (US Pat. Pub. No. 20090099069; US Pat. Pub. No. 20090304664; US Pat. Pub. No. 20110064722). Human homologs of a number of these genes have been identified as risk modulators in PD and/or other synucleinopathies. Yeast genes whose underexpression (e.g., deletion) in yeast resulted in altered Htt toxicity have been identified. See, e.g., US Pat. Pub. No. 20050255450. Yeast genes whose overexpression in yeast resulted in increased or decreased A-beta toxicity have been identified (US Pat. Pub. No. 20130045483). Human homologs of a number of these genes have been identified as risk modulators in Alzheimer's disease. Yeast genes whose overexpression in yeast resulted in altered TDP-43 toxicity have been identified (see, e.g., US Pat. Pub. No. 20120237499).

Yeast genes whose overexpression or underexpression (e.g., deletion) in yeast resulted in increased or decreased FUS toxicity have been identified (see, e.g., cited above).

In some embodiments agents that increase viability, e.g., reduce toxicity, in a yeast model may be may be tested in animal models of a neurodegenerative disease. In some embodiments agents that inhibit toxicity of a NAP in yeast, e.g., candidate therapeutic agents, may be tested in animal models of a neurodegenerative disease. Animal models that may be used are known in the art. Such models include, e.g., animals exposed to toxic agents (e.g., rotenone, MPTP, for synucleinopathies), animals that harbor transgenes encoding a NAP (optionally comprising a mutation associated with the disease), etc. In some embodiments the ability of an agent to improve memory, locomotion, movement, or any aspect of behavior or cognition may be assessed. In some embodiments the ability of an agent to reduce disease-associated pathology (e.g., evidence of neurodegeneration detectable using histopathology) may be assessed.

In some embodiments a pooled screen is performed in yeast cells that serve as a model of the neurodegenerative disease. In some embodiments the yeast cells have a phenotype, e.g., altered, e.g., reduced, viability or growth, as compared with control yeast. The screen may be used identify genetic modifiers that, when overexpressed, increase or decrease the viability or survival of the model yeast strain. In some embodiments a pooled library containing inducible (e.g., Gal-inducible) open reading frames of at least 50%, 60%, 70%, 80%, 90%, 95%, 99%, or all genes in the yeast genome may be transformed en masse into a yeast model strain, e.g., a yeast strain that expresses a neurodegeneration-associated protein or lacks expression of a yeast homolog of a loss-of-function neurodegenerative disease gene. Expression of the ORF is then induced (e.g., with galactose) for an appropriate period of time, e.g., 24 hrs. The appropriate period of time can be selected so as to provide sufficient time for the induced ORFs to be expressed and have an effect on the phenotype. Plasmid DNA is extracted and sequenced at t=0 and t=24 hrs. The DNA may be amplified (e.g., using PCR) prior to sequencing. In some embodiments high-throughput sequencing (often referred to as "next-generation" sequencing) may be used. As known in the art, next generation sequencing encompasses a variety of technologies that parallelize the sequencing process, producing thousands or millions of sequences (often relatively short "reads") concurrently. Fragmented sequence reads can then be assembled on the basis of their overlapping regions. Genes over-represented at t=24 hrs versus t=0 are putative suppressors; under-represented genes are putative enhancers. In some embodiments, pooled transformants are divided into two aliquots and one set is cultured using medium containing glucose (to keep the Gal-inducible ORFs turned off) and one set is cultured using medium containing galactose to turn on the neurodegeneration-associated protein (in the case of yeast models that include a neurodegeneration-associated protein) and all the transformed overexpressed yeast genes. DNA is isolated from the cultures at an appropriate time point (e.g., 24 hours) and compared to identify over-represented and under-represented genes. It will be understood that any system for inducible expression in yeast may be used.

In some embodiments a pooled screen may be performed using a library of yeast deletion mutants wherein the different mutants are uniquely identified by molecular bar codes, thus allowing quantification of the relative number of yeast cells having different deletions. Description of such a library may be found in Chu A M and Davis R W. Methods Mol Biol. 2008; 416:205-20. Expression of an inducible human neurodegeneration associated protein may be induced in a pool of such yeast cells, and the culture maintained for an appropriate period of time, e.g., 24 hours. DNA is extracted and sequenced at t=0 and t=24 hrs. Bar codes over-represented at t=24 hrs versus t=0 identify genes that are putative enhancers of toxicity (i.e., their loss reduces toxicity); underrepresented bar codes identify genes that are putative suppressors of toxicity (their loss enhances toxicity).

Once a compound is identified, its molecular target may if desired be identified using a variety of different approaches. A variety of genetic, chemical, and biochemical approaches can be used to identify the molecular target of a small molecule, and the invention is not limited in this respect. In some embodiments the compound may cause a phenotype in yeast distinct from its ability to inhibit toxicity or otherwise reverse a neurodegeneration associated phenotype. For example, the compound may itself be toxic to yeast at sufficiently high concentrations. Yeast screens can reveal the target space for small molecules that suppress growth by identifying genetic alterations that restore it. In some embodiments, yeast cells are selected for genetic alterations that allow growth at high concentrations of the small molecule. This may be done by any of a variety of approaches. For example, the compound may be contacted with (1) a library of over-expression yeast strains covering most genes in the yeast genome (5,800 genes), (2) a library of yeast containing at least 100,000 random transposon-insertions, e.g., ~300,000 random transposon-insertions (e.g., as described in Kumar, A., et al., Multipurpose transposon insertion libraries for large-scale analysis of gene function in yeast Methods Mol Biol 416, 117 (2008)), (3) a library of yeast harboring spontaneous genomic point mutations arising from at least $10^5$, $10^6$, $2 \times 10^6$ cells or more, or (4) a library of yeast containing deletions of non-essential genes in the yeast genome. Yeast that exhibit increased ability to survive in the presence of toxic concentrations of the compound are identified and the genes that are overexpressed or mutated in such yeast are determined. The genes identified in such screens are candidate targets of the small molecule. The effects of altering gene dosage of a candidate target may indicate it is the central node or target: e.g., increased dosage increases sensitivity to the compound and decreased gene dosage decreases sensitivity to the compound indicates it is the central node and target of the compound. A "central node", or "hub", is a node in a network that is connected to more other nodes than the average node in the network. In some embodiments a central hub is connected to at least 2, 3, 5, or more times as many nodes as the average node in a network. These hubs, by virtue of their function (if known) and/or the biological pathway(s) and process(es) in which they are involved can pinpoint critical biological processes and pathways that link genetic modifiers. Knowledge of these processes and pathways can in turn be used to identify phenotypes in relevant neuronal models. In some embodiments a biochemical approach is used such as purifying the molecular target using the compound as an affinity reagent or crosslinking the compound to the target, etc.

In some embodiments computational approaches may be used to predict one or more physico-chemical, pharmacokinetic and/or pharmacodynamic properties of compounds identified in screens or such properties may be evaluated in vitro or in animal models. For example, absorption, distribution, metabolism, and excretion (ADME) parameters can be predicted or determined. Such information can be used, e.g., to select hits for further testing or modification. For example, small molecules having characteristics typical of "drug-like" molecules can be selected and/or small molecules having one or more undesired characteristics can be avoided. Additional compounds can be identified or designed based on initial compounds identified in a screen such as those described herein. In some embodiments, structures of hit compounds are examined to identify a pharmacophore, which can be used to design additional compounds, e.g., analogs of a hit identified in a screen. An additional compound, e.g., an analog, may, for example, have one or more improved (i.e., more desirable) pharmacokinetic and/or pharmacodynamic properties as compared with an initial hit or may simply have a different structure. For example, a compound may have higher affinity for the molecular target of interest, lower affinity for a non-target molecule, greater solubility (e.g., increased aqueous solubility), increased stability, increased half-life, increased bioavailability, increased oral absorption, and/or reduced side effect(s), etc. Optimization can be accomplished through empirical modification of the hit structure (e.g., synthesizing compounds with related structures and testing them in cell-free or cell-based assays or in non-human animals) and/or using computational approaches.

VI. Neurogenerative Disease-Associated Phenotypes in Neurons Having a Neurodegeneration-Associated Genotype To facilitate use of neurons, e.g., induced human neurons, as models for a neurodegenerative disease it is useful to establish neurodegenerative disease-associated phenotypes, i.e., cellular phenotypes that are associated with the disease, that are detectable in such neurons. A cellular phenotype may be any detectable characteristic or property of a cell. In the context of the present disclosure, a cellular "phenotype" associated with a disease may be any detectable deviation from a characteristic or property displayed by a cell that distinguishes the cell from a normal cell or cell derived from a subject who does not have the disease and is not at increased risk of developing the disease relative to the general population. Phenotypes inherent to naturally occurring disease-associated genetic mutations or variations are of particular interest. In some aspects, the disclosure provides methods of identifying neurodegenerative disease-associated phenotypes that are detectable in human neurons having a genotype associated with a neurodegenerative disease, e.g., induced neurons derived from patient iPS cells or engineered to harbor a disease-associated genotype. In some embodiments the methods may be used to identify a neurodegenerative disease-associated phenotype that is detectable in induced neurons that are not derived or cultured in the presence of a phenotype enhancer at a level sufficient to enhance the phenotype and/or are not genetically engineered to have more than two copies of a gene that encodes a neurodegeneration associated protein associated with the disease. While exemplified herein with regard to neurons, the invention encompasses similar methods applied to identify neurodegenerative disease-associated phenotypes in glial cells, e.g., oligodendrocytes. As used herein a "phenotype enhancer" is an agent or condition that induces a phenotype and/or increases the strength of a phenotype. A phenotype enhancer may cause a cell to exhibit a phenotype that it would not otherwise ordinarily exhibit over its typical lifespan, may accelerate development of a phenotype that would otherwise take longer to become detectable, and/or may cause a phenotype to be more intense. A "level sufficient to enhance a phenotype" is a level sufficient to induce a phenotype and/or increase the strength of a phenotype. A phenotype enhancer may be a toxic agent, or any agent that imposes stress on a cell, e.g., any agent that disrupts cellular homeostasis, e.g., by burdening or inhibiting a molecule or pathway that cells normally use to protect against or counteract environmental insults such as elevated temperature, presence of toxic agents, mechanical damage, etc. A phenotype enhancer may be an agent that induces a cellular stress response such as the heat shock response or unfolded protein response.

In some embodiments a neurodegenerative disease-associated phenotype that is detectable in a human neuron, e.g., an induced neuron, may be identified based at least in part on observing the phenotype in a yeast model of the disease. In some embodiments a method of identifying a phenotype associated with a neurodegenerative disease associated with a neurodegeneration associated protein comprises: (a) providing a yeast cell that expresses the protein at a level sufficient to induce toxicity in the cell; (b) detecting a phenotype in the yeast cell, wherein the phenotype is associated with expression of the protein; (c) providing an induced neuron derived from a human subject who has the disease or engineered to have a genotype associated with the disease; and (d) detecting the phenotype in the neuron, thereby identifying a phenotype associated with the neurodegenerative disease. In some embodiments the yeast cell expresses the protein at a level sufficient to reduce growth and/or viability of the cell. In some embodiments expression of the protein in the yeast cell is inducible. For example, in some embodiments expression of the gene that encodes the protein is under control of an inducible promoter. Expression of the protein is induced, and the cell is examined to detect a phenotype. In some embodiments the cell is examined within 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 60 hours, 72 hours, 84 hours, or 96 hours, after inducing expression of the protein. In an embodiments the cell is examined about 2-8 hours, e.g., about 6 hours after induction of the protein. In certain embodiments the cell is examined before significant reduction in growth rate or viability cell death has occurred. In some embodiments the growth rate is within about 10%, or within about 25% of the rate in an isogenic yeast strain that does not express the protein.

Disease-associated phenotypes detectable in induced neurons have a number of uses. In some embodiments a phenotype detectable in patient-derived neurons is used to assess the potential effect of an agent or condition on a neurodegenerative disease. In some embodiments an agent is contacted with a patient-derived neuron, and the effect of the agent on the phenotype is measured. In some embodiments an agent that inhibits the phenotype is identified as a candidate agent for treating the disease. In some embodiments, a method of identifying a phenotype useful for assessing the effect of an agent or condition on a neurodegenerative disease associated with misfolding or abnormal accumulation of a protein comprising steps of: (a) providing a yeast cell that expresses the protein at a level sufficient to induce toxicity in the cell; (b) detecting a phenotype in the yeast cell associated with expression of the protein; (c) providing a neuron derived from a human subject who has the disease or engineered to have a genotype associated with the disease; and (d) detecting the phenotype in the neuron, thereby identifying a phenotype useful for assessing the effect of an agent or condition on the neurodegenerative disease. In some embodiments the neurons have not been derived or cultured in the presence of a phenotype enhancer and are not genetically engineered to have one or more additional copies of a gene encoding the protein. In some embodiments the subject has a dominant mutation associated with the disease. In some embodiments the neuron harbors a dominant mutation associated with the disease. In some embodiments the mutation is in a gene that encodes the protein. In some embodiments the methods further comprise providing an isogenic neuron in which the disease-associated mutation has been corrected; examining the mutation-corrected neuron; and determining that the phenotype is substantially reduced or substantially not detectable in the mutation-corrected neuron as compared to the non-mutation corrected neuron, thereby confirming that the phenotype is specifically associated with the mutation. In some embodiments the neuron and the isogenic mutation-corrected neuron are derived from the same pluripotent stem cell line, e.g., the same iPS cell line.

In general, the phenotype is detected in a human induced neuron using an assay that is suitable for detecting the phenotype in mammalian neurons. In some embodiments the assay may differ from that used to detect the phenotype in the yeast cells. In some embodiments non-human mammalian neurons, e.g., rodent neurons, engineered to express a NAP may be used to develop assays suitable for detecting disease-associated phenotypes in human neurons. In some embodiments, primary non-human mammalian brain-derived cultures may be used for such purposes. For example, primary rat cortical cultures that are virally transduced to express a NAP provide highly consistent and temporally synchronized neuronal/glial cultures useful for assay development. Assays for proteotoxicity-associated phenotypes identified in yeast cells engineered to express a neurodegenerative disease protein may be adapted for use in mammalian neurons using such genetically engineered non-human mammalian neurons.

In some aspects, the present disclosure provides phenotypes that are detectable in human neurons having a genotype associated with a neurodegenerative disease. In some embodiments the neurodegenerative disease is a synucleinopathy. In some aspects, the present disclosure provides phenotypes that are associated with a synucleinopath. Applicants found that phenotypes that precede cell death in yeast that express a toxicity-inducing level of alpha-synuclein are conserved and detectable in cortical neurons derived from iPS cells derived from PD patients (PD patient iPS cell-derived cortical neurons). For example, defective endoplasmic reticulum-associated degradation (ERAD) and impaired ER-to-Golgi trafficking were observed in yeast cells engineered to express a toxicity-inducing level of $\alpha$-Syn and were subsequently detected in neurons differentiated from iPS cells derived from PD patients harboring a A53T mutation in $\alpha$-Syn. The phenotypes were detected in such neurons in the absence of phenotype enhancers and without genetically engineered overexpression of a-Syn. By comparing the patient iPS cell-derived neurons with mutation-corrected control cells derived from the same iPS cell line, Applicants established that these phenotypes were associated with the defect in $\alpha$-Syn, thus confirming their relevance to human synucleinopathies. Among other things, the work described herein identifies ERAD substrate accumulation as an early and progressive pathologic phenotype in synucleinopathy patient-derived neurons. In some embodiments the ERAD substrate is glucocerebrosidase (GC, also referred to as GCase, encoded by the gene GBA) or neuroserpin (see, e.g., Examples). Identifying a perturbed process in yeast expressing $\alpha$-Syn (defective ERAD), thus led to the identification of GCase accumulation as a characteristic phenotype in human PD patient derived neurons. Notably, these results provided a mechanistic link between two parkinsonism genes, $\alpha$-Syn and GBA, despite the absence of a known homolog of GBA in yeast. Among other things, these findings underscore the capacity of combined use of yeast and human induced neuron model systems to facilitate identification of disease-relevant phenotypes, genes, and genetic interactions.

Applicants also discovered that nitrosative stress occurs in the vicinity of α-Syn in yeast expressing α-Syn. This discovery led to identification of α-Syn-interacting proteins that were nitrosylated in the human iPSC-derived neurons harboring dominant mutations in the gene encoding α-Syn but not in isogenic, mutation-corrected control neurons. Corroborating and mutually reinforcing data linked nitrosative stress to ER stress, and linked both pathologic processes directly to α-Syn. In some aspects, a phenotype associated with a synucleinopathy comprises increased nitric oxide, increased nitrosylation, and/or increased nitration of one or more proteins in the vicinity of α-Syn, in the vicinity of ER/Golgi vesicles, and/or in the vicinity of mitochondria. In some embodiments "in the vicinity" refers to a distance of up to 50 nm, up to 100 nm, up to 150 nm, or up to 200 nm. In some embodiments a phenotype associated with a synucleinopathy comprises increased nitration or nitrosylation of one or more proteins in neurons. In some embodiments the protein is protein is a synaptic protein (for example SNAP-25, synaptobrevin). In some embodiments the protein is a cytoplasmic protein (for example, VCP, clathrin, hsc70).

In some embodiments a phenotype detectable in neurons that have a genotype associated with a synucleinopathy comprises a defect in endocytosis (e.g., reduced endocytosis). In some embodiments a phenotype associated with a synucleinopathy comprises a defect in endocytosis. Endocytosis may be measured using any suitable endocytosis assay. In some embodiment endocytosis may be assessed, for example, by measuring uptake of a styryl due, such as FM1-43 or FM4-64 or similar compounds in neurons. Methods for performing such assays are well known in the art (Allaire, P D, et al., The Journal of Neuroscience (2006), 26(51):13202-13212). In some embodiments FM4-64 is used. In some embodiments endocytosis may be measured by labeling cell surface proteins, e.g., with biotin, allowing endocytosis to take place, removing or quenching free label and label remaining on uninternalized proteins, detecting internalized labeled protein. In some embodiments internalized labeled proteins may be isolated, e.g., using a reagent that binds to the label. In some embodiments such proteins may be visualized, e.g., on a gel. In some embodiments specific proteins may be detected by immunoblotting or immunofluorescence using appropriate antibodies, for example. An exemplary method is described in Wong, S E, et al., Endocrinology. 2009 October; 150(10):4713-23. doi: 10.1210/en.2009-0427. In some embodiments synaptic vesicle endocytosis may be assessed. In some embodiments endocytosis of a specific synaptic vesicle protein may be assessed. In some embodiments neurons may be subjected to a stimulus, e.g., one that causes depolarization.

In some embodiments a phenotype detectable in neurons that have a genotype associated with a synucleinopathy comprises a defect in protein translation, e.g., reduced protein translation. In some embodiments a phenotype associated with a synucleinopathy comprises a defect in protein translation. Methods for assessing protein translation include, e.g., ribosomal footprinting and S35-methionine incorporation. Standard assays known in the art may be used.

In some embodiments a phenotype detectable in neurons that have a genotype associated with a synucleinopathy comprises a defect in mitochondrial structure and/or function. In some embodiments a phenotype associated with a synucleinopathy comprises a defect in mitochondrial structure and/or function. Assays for mitochondrial function and/or structure may be used, e.g., electron microscopy or assays for increased levels of reactive oxygen species (see, e.g., Su, J., et al., Dis Model Mech. 2010 March-April; 3(3-4):194-208. doi: 10.1242/dmm.004267. Epub 2009 Dec. 28).

In some embodiments a phenotype detectable in neurons that have a genotype associated with a synucleinopathy comprises a defect in calcium flux, uptake, release, or signaling. In some embodiments a phenotype associated with a synucleinopathy comprises a defect in calcium flux, uptake, release, or signaling. A defect in calcium flux, uptake, release, or signaling may be assessed using, e.g., calcium imaging or staining for the transcription factor NFAT (the human homolog of yeast Crzl), e.g., staining for NFAT localization. A variety of molecules that may be used as cellular calcium sensors are known in the art. In some embodiments a fluorescent calcium sensor may be used. In some embodiments the calcium sensor is a small molecule (e.g., Oregon Green BAPTA-1-AM) or protein, which may be genetically encoded. For example, GCaMP6 proteins or other GCaMP family members may be used (Chen, T-S, et al., Nature (2013), Vol 499, pp. 235-302), or red single-wavelength "RCaMPs" engineered from circular permutation of the thermostable red fluorescent protein mRuby (Akerboom, J., et al., Front Mol Neurosci. 2013; 6:2. doi: 10.3389/fnmo1.2013.00002. Epub 2013 Mar. 4). Staining for NFAT may be performed using antibodies that bind to NFAT.

In some embodiments a phenotype detectable in neurons that have a genotype associated with a synucleinopathy comprises a defect in vesicle trafficking, e.g., a defect in ER to Golgi trafficking. In some embodiments a phenotype associated with a synucleinopathy comprises a defect in vesicle trafficking, e.g., a defect in ER to Golgi trafficking. In certain embodiments the defect is impaired vesicle trafficking, e.g., impaired ER to Golgi trafficking. ER to Golgi trafficking may be monitored by, e.g., monitoring the trafficking of a protein which normally moves from the ER through the Golgi. In some embodiments the protein is nicastrin. In some embodiments modification (e.g., glycosylation) is monitored as an indicator of trafficking. In some embodiments trafficking of a protein comprising a detectable label, e.g., comprising a fluorescent protein, may be monitored.

In some embodiments a phenotype detectable in neurons that have a genotype associated with Alzheimer's disease or other Abeta-related neurodegenerative disease comprises a defect in endocytosis. In some embodiments a phenotype associated with Alzheimer's disease or other Abeta-related neurodegenerative disease comprises a defect in endocytosis.

In some embodiments a phenotype detectable in neurons that have a genotype associated with a TDP-43 proteinopathy comprises a defect in protein translation. In some embodiments a phenotype associated with a TDP-43 proteinopathy comprises a defect in protein translation. In some embodiments a phenotype detectable in neurons that have a genotype associated with a TDP-43 proteinopathy comprises a defect in endocytosis. In some embodiments a phenotype associated with a TDP-43 proteinopathy comprises a defect in endocytosis. In some embodiments phenotype detectable in neurons that have a genotype associated with a TDP-43 proteinopathy comprises an increase in stress granule formation, e.g., resulting in increased level of stress granules. In some embodiments a phenotype associated with a TDP-43 proteinopathy comprises an increase in stress granule formation, e.g., resulting in increased level of stress granules. Stress granules are small dense cytoplasmic domains (e.g., about 0.75 to 5 µm$^2$) that contain translationally arrested mRNAs and various proteins. Stress granules may be assessed with immunofluorescence, e.g., for one or more proteins that localize to stress granules such as TIA-1.

In some aspects, methods described herein facilitate the identification of genes and gene products whose modulation can inhibit pathologic phenotypes that occur in a neurodegenerative disease associated with protein misfolding and/or aggregation. Such genes and gene products may, among other things, be particularly promising targets for development of therapeutic agents for such diseases. For example, a key E3 ubiquitin ligase that facilitates ERAD, Hrd1, was identified as a suppressor of α-Syn toxicity in a genome-wide yeast screen previously performed by Applicants' group (U.S. Pat. Pub. No. 20110064722 and reference 13) (confirmed herein). As described in the Examples, expression of the human Hrd1 homolog, Synoviolin, rescued rat cortical neurons from α-Syn-induced toxicity. In addition, expression of Synoviolin inhibited phenotypes such as abnormal ERAD substrate accumulation in cortical neurons derived from a PD patient with an A53T mutation in α-Syn. Thus, corroborating data from these three model systems underscore the potential of Synoviolin modulation as a therapeutic approach for treating synucleinopathies.

Figure 6A:
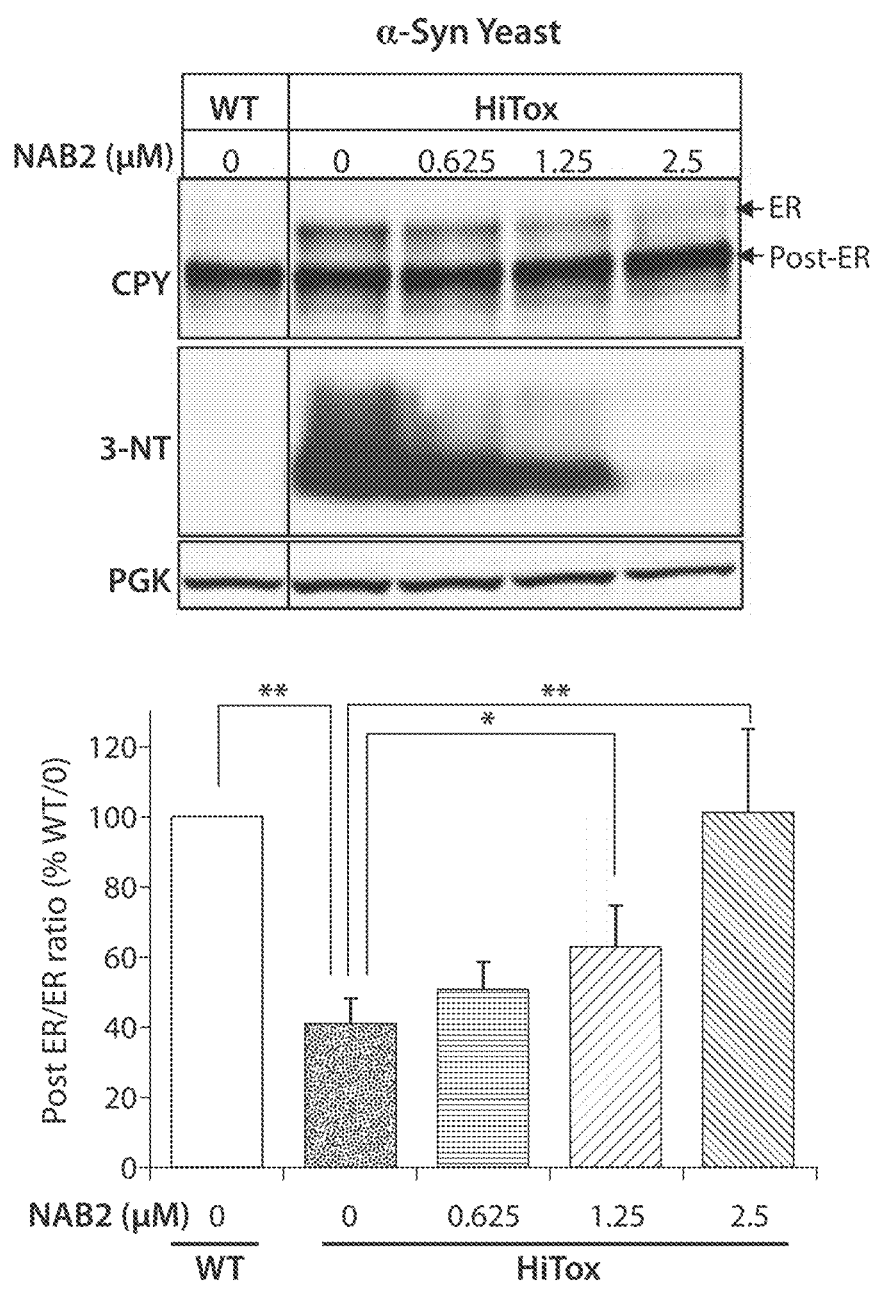
FIG. 6. A small molecule modifier identified in an unbiased yeast screen corrects analogous defects in yeast and patient synucleinopathy models. (A) NAB2 ameliorates the αSyn-induced ER accumulation of CPY and nitrosative stress in the yeast model. The ratio of ER to post-ER (vacuole) form is a steady-state measurement that reflects ERAD as well as forward trafficking from the ER (n=3). Nitrosative stress was monitored by protein nitration levels using the 3-NT antibody. (B) NAB2 increases the post-ER form of and ameliorates the ER accumulation of GCase and Nicastrin in αSyn$^{A53T}$ iPS neurons. Cells were treated with 20 μM NAB2 for 7-10 days between 8-12 weeks of neuronal differentiation. The baseline PD level was made equivalent to % control established in FIG. 4C-D to more faithfully depict the biological significance of the change (n=3). (C) NAB2 decreases nitrosative stress in αSyn$^{A53T}$ iPS neurons. A53T or mutation-corrected neural progenitors were transduced with lentivirus encoding RFP under the synapsin promoter. Upon differentiation, neurons were labeled with RFP. At 8-12 weeks of differentiation, neurons were treated with 5 μM NAB2 for 7-10 days, loaded with the NO sensor FL2 and imaged live (C; a representative experiment showing quantitation from 18-54 neurons for each condition; the same result was obtained in another independent experiment). All data represented as mean±SEM (*; $p<0.05$, ; $p<0.01$, *; $p<0.001$, two tail t-test compared to control condition). (D) Overexpressing Nedd4 phenocopies effects of NAB2, increasing mature forms of GCase and nicastrin. Neural cultures at 8-12 week differentiation were transduced with lentivirus expressing Nedd4 at MOI of 1, 2, or 5. Biochemical analysis was performed 10 days after viral transduction. The same trend was observed in three independent experiments. Baseline PD levels were equated to the percentage of control established as described above.
Figure 6B:
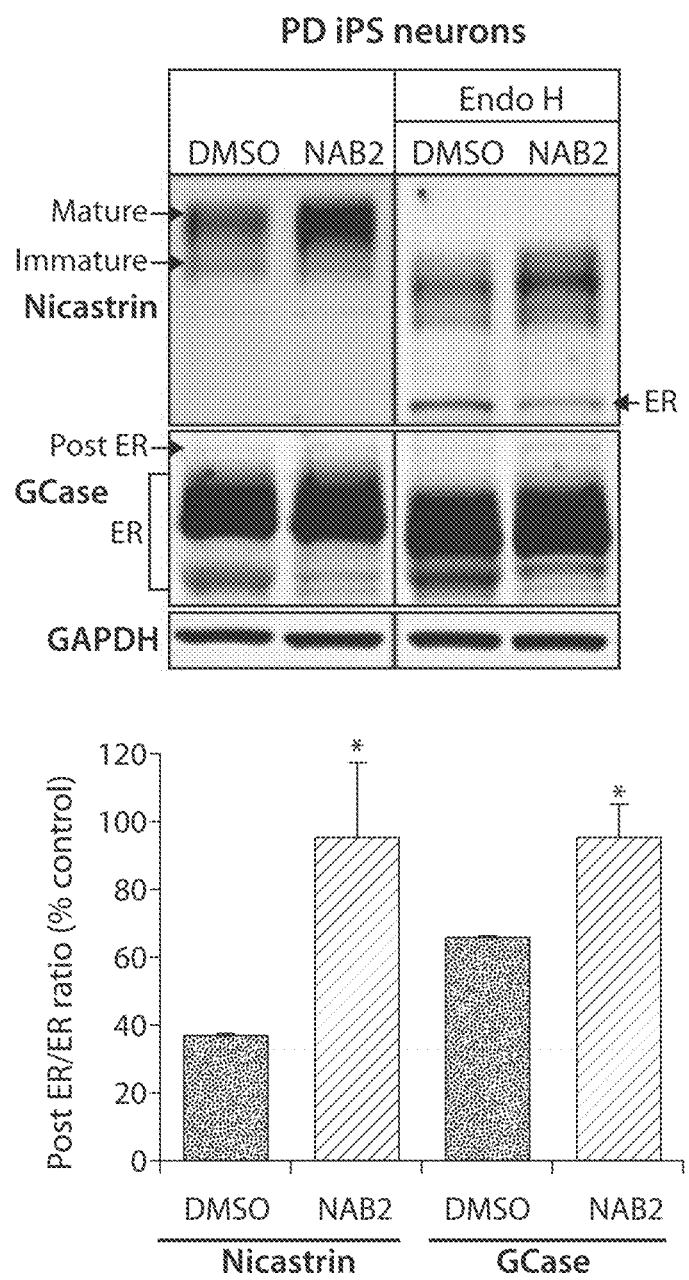
Figure 6C:
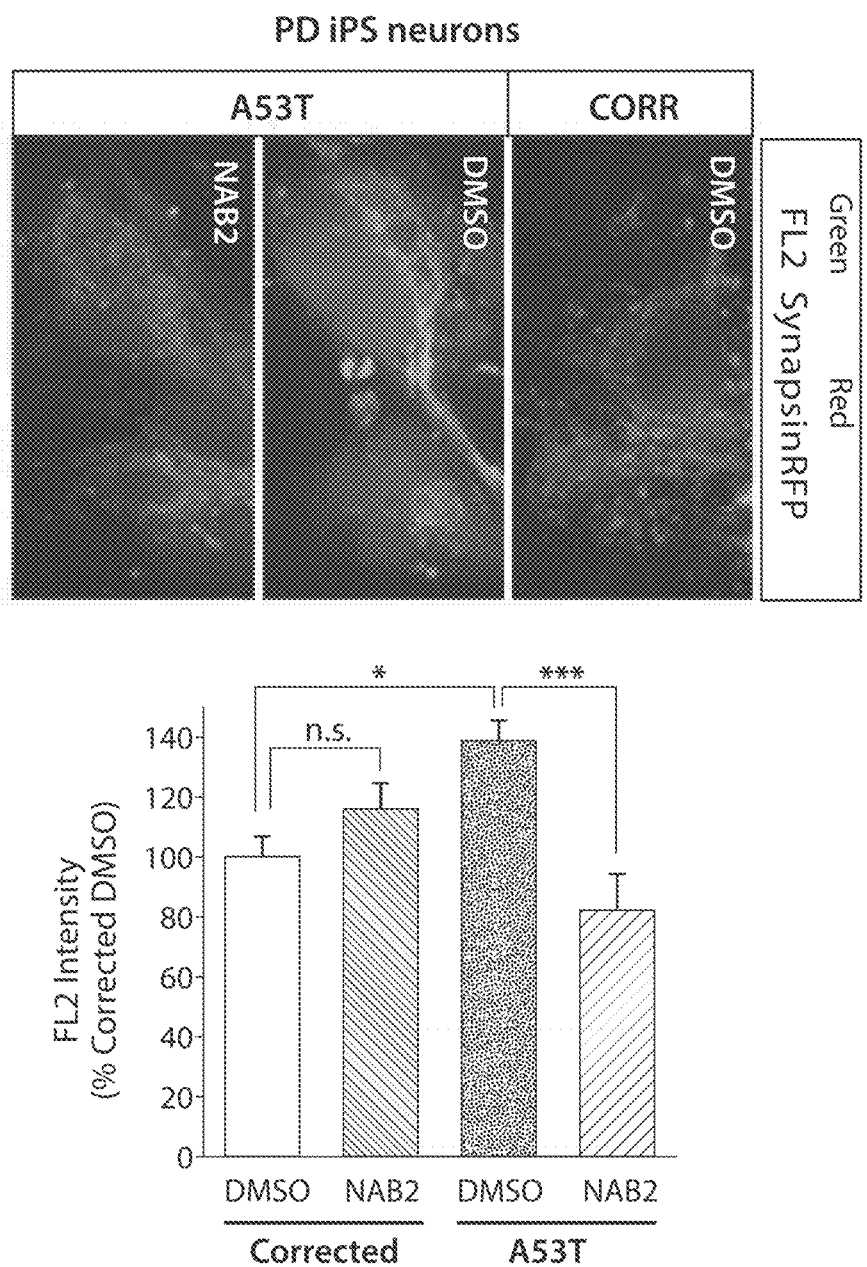
Figure 6D:
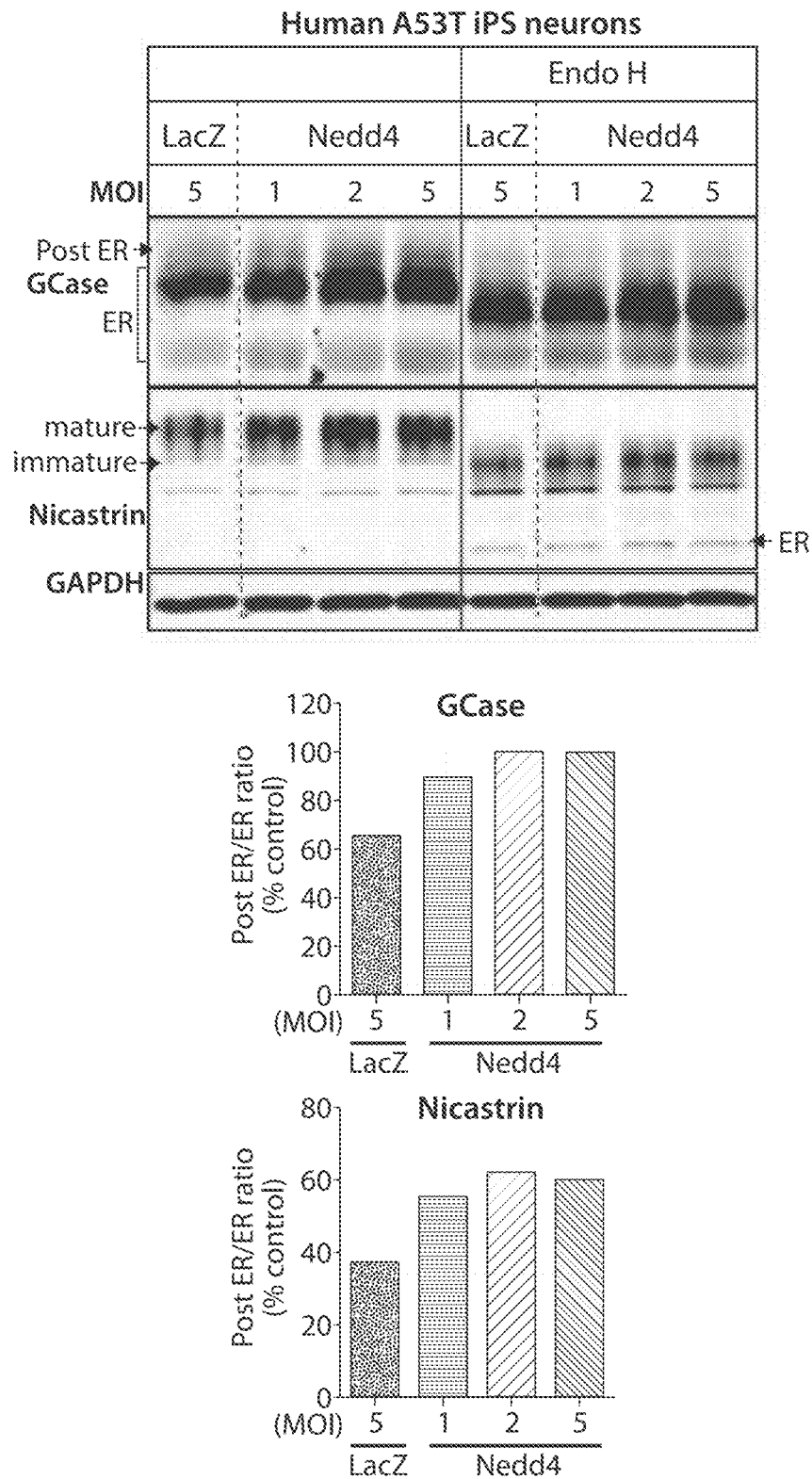
Figure 23A:
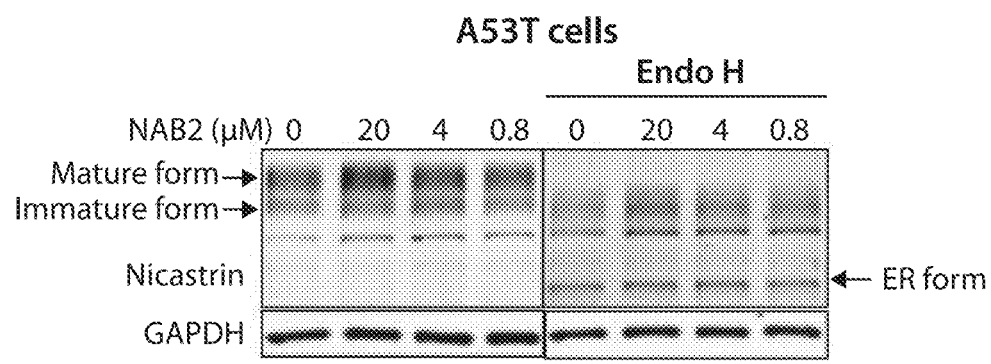
FIG. 23 NAB2 improves forward protein trafficking through the ER in Parkinson patient cortical neurons. Cells were treated with NAB2 (0~20 µM or 20 µM only for αSyn$^{triplication}$/S3 line) for 7-10 days between 8-12 weeks of neuronal differentiation. Trafficking from ER was assessed by probing for nicastrin with or without Endo H treatment. Quantitation from these samples was combined with that of the samples shown in FIG. 6 to generate the graphs in FIG. 6.
Figure 23B:
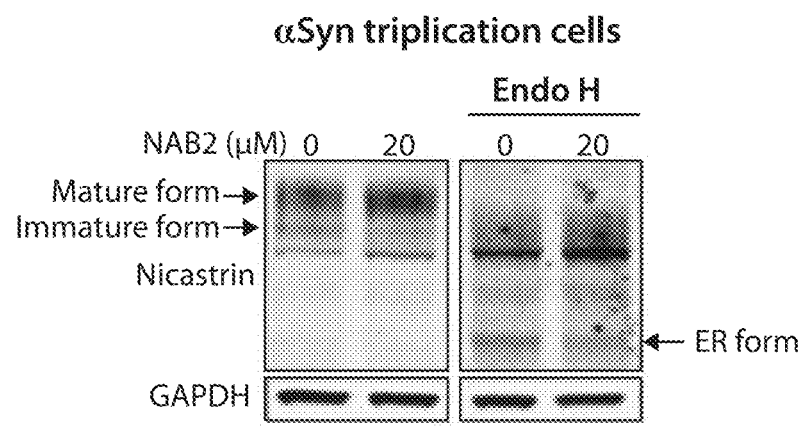

In some aspects, methods described herein facilitate the identification of agents, e.g., small molecules, whose modulation can inhibit pathologic phenotypes that occur in a neurodegenerative disease associated with protein misfolding and/or aggregation. In some aspects, such agents may be used as therapeutic agents for treating neurodegenerative diseases associated with the proteins that misfold in such diseases. For example, as described in patent application U.S. Ser. No. 61/794,870, a compound termed NAB2 (See Examples and FIG. 7) was identified in a high throughput screen as an inhibitor of αSyn toxicity in yeast. The compound was effective in worm and rodent neuronal synucleinopathy models. Chemical genetic analysis in yeast identified the ubiquitin ligase Rsp5/Nedd4 as an integral component of NAB2's target space (U.S. Ser. No. 61/794, 870 and ref 41). Rsp5 and its human homolog NEDD4 have been implicated in protein trafficking and ERAD in both yeast and neurons. NAB2 was found to reduce the accumulation of CPY in the yeast ER in a dose-dependent manner and to reduce specific αSyn-induced increase in protein nitration in yeast. Furthermore, in a dose-dependent manner NAB2 increased the post-ER and decreased the immature forms of Nicastrin and GCase in patient neurons from both the Contursi and Iowa kindreds (FIG. 6B and FIG. 23). Finally, as measured by the sensor FL2, NAB2 strongly decreased NO levels in A53T patient neurons without affecting its levels in mutation-corrected controls (FIG. 6C), and overexpression of Nedd4 in patient neurons phenocopied the effects of NAB2 (FIG. 6D).

VII. Yeast-Human Genetic Networks and Uses Thereof

In some aspects, the invention provides methods of identifying biological pathways, processes implicated in neurodegenerative diseases and druggable targets within such pathways and processes. The methods may be applied to any neurodegenerative disease described herein, e.g., a synucleinopathy, Alzheimer's disease, a TDP-43 proteopathy, a FUSopathy, a nucleotide expansion disorder, a tauopathy, a parkinsonism disorder, an ataxia, a motor neuron disorder, a peripheral neuropathy, or a white matter disorder. In some embodiments the disorder is associated with a gain of function mutation. In some embodiments the disorder is associated with a loss of function mutation. In some embodiments the methods involve analysis of sets of genetic modifiers identified in yeast screens, which may be augmented with human homologs of such genes, with known, human neurodegenerative disease genes and modifiers, and with hidden interactors that may be discovered using suitable algorithms. In some embodiments the methods are computer-aided.

In some aspects, the invention provides a method of identifying a target for neurodegenerative disease drug discovery comprising: (a) identifying a set of genes that are genetic modifiers of a phenotype displayed by yeast cells that serve as a model for a neurodegenerative disease or that are genetic modifiers of the effect of a compound that suppresses a phenotype displayed by yeast cells that serve as a model for a neurodegenerative disease; (b) analyzing the set of genes to identify a biological pathway or process implicated as being involved in the neurodegenerative disease; and (c) determining that modulating the implicated biological pathway or process in human neurons that serve as a model for the neurodegenerative disease reduces the level of a phenotype associated with the neurodegenerative disease in the human neurons, thereby identifying the biological pathway or process as a target for neurodegenerative disease drug discovery, optionally wherein the human neurons are induced human neurons, further optionally wherein the method further comprises (d) identifying a druggable target in the biological pathway or process, thereby identifying a druggable target for neurodegenerative disease drug discovery. The genetic modifiers may be identified using yeast models as described herein (e.g., by identifying yeast genes that, when overexpressed or deleted, modulate a phenotype displayed by the yeast model). The genetic modifiers may be analyzed using a variety of approaches to identify a biological pathway or process implicated in the disease and/or to identify a druggable target. For example, they may be analyzed to identify significantly enriched gene ontology (GO) terms among their gene annotations in the Gene Ontology database or other databases, thus identifying pathways and processes whose components (genes, proteins) are enriched (over-represented) among the genetic modifiers. In some embodiments the genetic modifiers are analyzed by generating a network comprising at least some of the genetic modifiers, wherein the genes that interact are connected by edges in the network. The interactions may be genetic and/or physical interactions. Molecular interaction data, e.g., protein-protein interaction data may be obtained using a variety of technologies such as affinity capture-luminescence, affinity capture-MS, affinity capture-RNA, affinity capture-western, biochemical, co-fractionation co-localisation, co-purification, far western, FRET, protein complementation assay, reconstituted complex, and yeast two-hybrid or three-hybrid approaches. Extensive data obtained from such assays and others are publicly available and stored in various databases such as the Biological General Repository for Interaction Datasets (BioGRID (http://thebiogrid.org/; Stark, C. et al. The biogrid interaction database: 2011 update. Nucleic Acids Res. 39, D698-D704 (2011)). IntAct (http://www.ebi.ac.uk/intactI; Hermjakob, H. et al. Intact: an open source molecular interaction database.Nucleic Acids Res. 32, D452-D455 (2004).), Molecular INTeraction database (MINT; http://mint.bio.uniroma2.it/mint/; Chatr-aryamontri, A, et al., Mint: a molecular interaction database. Nucleic Acids Res.

2007 January; 35(Database issue):D572-4), *Saccharomyces* Genome Database (http://yeastgenome.org), Human Protein Reference Database (HPRD; http://www.hprd.org/; Keshava Prasad, T. S. et al. Human protein reference database 2009 update. Nucleic Acids Res. 37, D767-D772 (2009).), Biomolecular Interaction Network Database (BIND; Bader, G. D., et al. Bind: the biomolecular interaction network database. Nucleic Acids Res. 31, 248-250 (2003) and the Database of Interacting Proteins (DIP; http://dip.doe-mbi.ucla.edu/dip/Main.cgi Xenarios, I. et al. Dip: the database of interacting proteins. Nucleic Acids Res. 28,289-291 (2000)). Databases such as Search Tool for the Retrieval of Interacting Genes/Proteins (STRING; http://string-db.org/; Szklarczyk, D. et al. The string database in 2011: functional interaction networks of proteins, globally integrated and scored. Nucleic Acids Res. 39, D561-D568 (2011); Szklarczyk, D. et al. The string database in 2011: functional interaction networks of proteins, globally integrated and scored. Nucleic Acids Res. 39, D561-D568 (2011)), Interologous Interaction Database (I2D; http://ophid.utoronto.ca/ophidv2.204/Brown, K. R. & Jurisica, I. Online predicted human interaction database. Bioinformatics 21, 2076-2082 (2005)), and iRefIndex (http://irefindex.org/wiki/index.php?title=iRefIndex Razick, S., Magklaras, G. & Donaldson, I. M. irefindex: a consolidated protein interaction database with provenance. BMC Bioinformatics 9, 405 (2008)) combine large portions of the above-mentioned sources into single datasets. For example, STRING is a database of known and predicted protein interactions, including direct (physical) and indirect (functional) associations.

Networks may be created and/or visualized using any of a variety of software tools and algorithms. One of ordinary skill in the art will appreciate that there are numerous ways to generate and/or visualize networks, any of which may be employed in embodiments of the present invention. For example, in some embodiments networks are created using a technique based on the Steiner tree problem, that uses previously reported interactions (e.g., protein-protein interactions) to determine how a set of genes are organized into functionally coherent pathways, revealing many components of the cellular response. The method uses constrained optimization to identify a subset of hits (in this case genetic modifiers identified in yeast screens and human homologs thereof, sometimes also including human genes that have been identified as genetic modifiers of the relevant neurodegenerative disease) that are connected directly or indirectly by high probability interactions. This is achieved by searching for the solution to the prize-collecting Steiner tree (PCST) problem (Huang, S C and Fraenkel, E., Sci. Signal., Vol. 2, Issue 81, p. ra40, and references therein). In this approach, the detected proteins/genes in experiments are defined as 'terminal nodes' and they are connected to each other either directly or through other undetected proteins (Steiner nodes) using protein-protein and protein-gene interactions. An important feature of the algorithm is that it is not required to connect all the terminal nodes. Rather, a network composed of high-confidence edges that ultimately link a subset of the termini is sought. To identify this network, costs are assigned to each interaction reflecting confidence that the interaction is real. In addition, penalties may be assigned to terminal nodes based on confidence in the relevant data for that node. The PCST algorithm identifies a relevant subnetwork by simultaneously minimizing the cost of edges included in the tree and the penalties of terminals that are excluded. A publicly available webserver, SteinerNet, which may be used to generate networks using the PCST approach is accessible at http://fraenkel.mit.edu/steinernet (Tuncbag, N., et al., *Nucl. Acids Res*. (2012) 40 (W1): W505-W509). In some embodiments, known human neurodegenerative disease genes and/or genetic modifiers may be "prized nodes" in a PCST-generated network. As noted above, other algorithmic approaches to the problem of constructing a network may be employed, and the invention is not limited in this respect. For example, flow optimization-based methods may be used (Lan, A., et al., Nucleic Acids Res. 2011; 39:W424-W429 and references therein). Other approaches include linear programming, Bayesian networks and maximum-likelihood-based approaches (see references cited in Tuncbag, N., et al.) In some embodiments a network may be visualized using any of a variety of software tools. For example, a network may be visualized using Cytoscape (http://www.cytoscape.org/; Cline, M S, et al., Nature Protocols 2, 2366-2382 (2007); Shannon, P., et al., Genome Research 2003 November; 13(11):2498-504).

In some embodiments of either approach (enrichment analysis, network analysis) the set of genetic modifiers may be augmented by including one or more human homologs of at least one of the genetic modifiers, one or more known human genetic modifiers of the neurodegenerative disease (e.g., genes identified as risk factors in human genetic studies such as kindred studies, GWAS studies, and the like, or identified using other approaches), and/or one or more human genes that are known to interact with one or more of the human homologs or known human genetic modifiers. Human homologs of yeast genes and proteins may be identified using a variety of approaches, such as sequence homology, structural homology (e.g., using structure predictions or experimentally determined structures), functional information, protein-protein interaction information), phylogeny, or combinations thereof. It will be understood that sequence or structure homology comparisons may involve only portions of the proteins, e.g., functional domains. In some embodiments a combination of methods may be used. For example, if yeast protein X and human protein X1 are identified as homologs based on sequence, then if proteins X and Y interact in yeast and proteins X1 and Y1 interact in human cells, it can be inferred that yeast protein Y and human protein Y1 are homologs.

Central nodes, which may represent druggable targets, may be identified visually or computationally in a computer-aided manner or by a combination thereof. In some embodiments, factors such as degree of confidence in the interaction, degree of homology, potential connectedness to a known human genetic modifier or yeast homolog thereof, may be used to generate a network. In some embodiments edges in a network are weighted equally, e.g., for purposes of identifying central nodes. In some embodiments edges in a network may be weighted based on confidence in the interaction (high confidence interactions may be assigned more weight), degree of homology (high degrees of homology may be assigned more weight, whether a node connects to a known human genetic modifier or yeast homolog thereof (which may increase the weight) or other factors. The weight of the edges can be taken into account when determining whether a node is a central node. For example, nodes can be ranked using a ranking system that takes into account both the number of nodes and the strength of the interactions in which the node participates.

In some embodiments a compound that modulates a druggable node is identified, e.g., in a screen in a yeast model of a neurodegenerative disease. In some embodiments the compound is contacted with human nervous system cells that serve as model for the disease to confirm that modulating the druggable node in the human nervous system cells reduces at least one disease-associated phenotype. In some embodiments a yeast-human genetic network is used in identifying the biological pathway, process, or molecular target of a compound identified in a screen in yeast.

In some embodiments, results of performing a gene set enrichment analysis or constructing a network may be stored on a non-transitory computer-readable medium. In some embodiments druggable nodes identified using the methods, and optionally compounds that modulate such druggable nodes, may be stored on a non-transitory computer-readable medium.

VIII. Pharmaceutical Compositions

In some aspects, candidate therapeutic agents for treating a neurodegenerative disease are identified as described herein. Suitable preparations, e.g., substantially pure preparations, of an active agent, e.g., an active agent identified as described herein, may be combined with one or more pharmaceutically acceptable carriers or excipients, etc., to produce an appropriate pharmaceutical composition. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds is well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types).

A pharmaceutical composition is typically formulated to be compatible with its intended route of administration. For example, preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution, Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate. fixed oils, polyethylene glycols, glycerine, propylene glycol or other synthetic solvents; preservatives, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic. Pharmaceutical compositions and agents for use in such compositions may be manufactured under conditions that meet standards or criteria prescribed by a regulatory agency such as the US FDA (or similar agency in another jurisdiction) having authority over the manufacturing, sale, and/or use of therapeutic agents. For example, such compositions and agents may be manufactured according to Good Manufacturing Practices (GMP) and/or subjected to quality control procedures appropriate for pharmaceutical agents to be administered to humans.

For oral administration, agents can be formulated by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art.

Formulations for oral delivery may incorporate agents to improve stability in the gastrointestinal tract and/or to enhance absorption.

For administration by inhalation, pharmaceutical compositions may be delivered in the form of an aerosol spray from a pressured container or dispenser which contains a suitable propellant, e.g., a gas such as carbon dioxide, a fluorocarbon, or a nebulizer. Liquid or dry aerosol (e.g., dry powders, large porous particles, etc.) can be used. The disclosure contemplates delivery of compositions using a nasal spray or other forms of nasal administration. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Compounds administered nasally may be transported into the brain.

For topical applications, pharmaceutical compositions may be formulated in a suitable ointment, lotion, gel, or cream containing the active components suspended or dissolved in one or more pharmaceutically acceptable carriers suitable for use in such composition.

For local delivery to the eye, pharmaceutical compositions may be formulated as solutions or micronized suspensions in isotonic, pH adjusted sterile saline, e.g., for use in eye drops, or in an ointment. In some embodiments intraocular administration is used. Routes of intraocular administration include, e.g., intravitreal injection, retrobulbar injection, peribulbar injection, subretinal, sub-Tenon injection, and subconjunctival injection. Compounds administered to the eye may be transported into the brain.

Pharmaceutical compositions may be formulated for transmucosal or transdermal delivery. For transmucosal or transdermal administration, penetrants appropriate to the barrier to be permeated may be used in the formulation. Such penetrants are generally known in the art. Pharmaceutical compositions may be formulated as suppositories (e.g., with conventional suppository bases such as cocoa butter and other glycerides) or as retention enemas for rectal delivery.

In some embodiments, a pharmaceutical composition includes one or more agents intended to protect the active agent(s) against rapid elimination from the body, such as a controlled release formulation, implants (e.g., macroscopic implants such as discs, wafers, etc.), microencapsulated delivery system, etc. Compounds may be encapsulated or incorporated into particles, e.g., microparticles or nanoparticles. Biocompatible polymers, e.g., biodegradable biocompatible polymers, can be used, e.g., in the controlled release formulations, implants, or particles. A polymer may be a naturally occurring or artificial polymer. Depending on the particular polymer, it may be synthesized or obtained from naturally occurring sources. An agent may be released from a polymer by diffusion, degradation or erosion of the polymer matrix, or combinations thereof. A polymer or combination of polymers, or delivery format (e.g., particles, macroscopic implant) may be selected based at least in part on the time period over which release of an agent is desired. A time period may range, e.g., from a few hours (e.g., 3-6 hours) to a year or more. In some embodiments a time period ranges from 1-2 weeks up to 3-6 months, or between 6-12 months. After such time period release of the agent may be undetectable or may be below therapeutically useful or desired levels. A polymer may be a homopolymer, copolymer (including block copolymers), straight, branched-chain, or cross-linked. Various polymers of use in drug delivery are described in Jones, D., Pharmaceutical Applications of Polymers for Drug Delivery, ISBN 1-85957-479-3, ChemTec Publishing, 2004. Useful polymers include, but are not limited to, poly-lactic acid (PLA), poly-glycolic acid (PGA), poly-lactide-co-glycolide (PLGA), poly(phosphazine), poly (phosphate ester), polycaprolactones, polyanhydrides, ethylene vinyl acetate, polyorthoesters, polyethers, and poly (beta amino esters). Other polymers useful in various embodiments include polyamides, polyalkylenes, polyalkylene glycols, polyalkylene oxides, polyalkylene terephtalates, polyvinyl alcohols, polyvinyl ethers, polyvinyl esters, poly-vinyl halides, polyvinylpyrrolidone, polyglycolides, polysiloxanes, polyurethanes and co-polymers thereof, poly (methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene, polyvinylpyrrolidone, poly(butyric acid), poly(valeric acid), and poly(lactide-cocaprolactone). Peptides, polypeptides, proteins such as collagen or albumin, polysaccharides such as sucrose, chitosan, dextran, alginate, hyaluronic acid (or derivatives of any of these) and dendrimers are of use in certain embodiments. Methods for preparation of such will be apparent to those skilled in the art. Additional polymers include cellulose derivatives such as, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxymethylcellulose, carboxyethyl cellulose, cellulose triacetate, cellulose sulphate sodium salt, polycarbamates or polyureas, cross-linked poly(vinyl acetate) and the like, ethylene-vinyl ester copolymers such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof. Chemical derivatives of the afore-mentioned polymers, e.g., substitutions, additions of chemical groups, for example, alkyl, alkylene, hydroxylations, oxidations, and other modifications routinely made by those skilled in the art can be used. A particle, implant, or formulation may be composed of a single polymer or multiple polymers. A particle or implant may be homogeneous or non-homogeneous in composition. In some embodiments a particle comprises a core and at least one shell or coating layer, wherein, in some embodiments, the composition of the core differs from that of the shell or coating layer. A therapeutic agent or label may be physically associated with a particle, formulation, or implant in a variety of different ways. For example, agents may be encapsulated, attached to a surface, dispersed homogeneously or nonhomogeneously in a matrix, etc. Methods for preparation of such formulations, implants, or particles will be apparent to those skilled in the art. Liposomes or other lipid-containing particles can be used as pharmaceutically acceptable carriers in certain embodiments. In some embodiments a controlled release formulation, implant, or particles may be introduced or positioned within a tumor, near a tumor or its blood supply, in or near a region from which a tumor was removed, at or near a site of known or potential metastasis (e.g., a site to which a tumor is prone to metastasize), etc. Microparticles and nanoparticles can have a range of dimensions. In some embodiments a microparticle has a diameter between 100 nm and 100 µm. In some embodiments a microparticle has a diameter between 100 nm and 1 µm, between 1 µm and 20 µm, or between 1 µm and 10 µm. In some embodiments a microparticle has a diameter between 100 nm and 250 nm, between 250 nm and 500 nm, between 500 nm and 750 nm, or between 750 nm and 1 µm. In some embodiments a nanoparticle has a diameter between 10 nm and 100 nm, e.g., between 10 nm and 20 nm, between 20 nm and 50 nm, or between 50 nm and 100 nm. In some embodiments particles are substantially uniform in size or shape. In some embodiments particles are substantially spherical. In some embodiments a particle population has an average diameter falling within any of the afore-mentioned size ranges. In some embodiments a particle population consists of between about 20% and about 100% particles falling within any of the aforementioned size ranges or a subrange thereof, e.g. about 40%, 40%, 50%, 60%, 70%, 80%, 90%, 95%, etc. In the case of non-spherical particles, the longest straight dimension between two points on the surface of the particle rather than the diameter may be used as a measure of particle size. Such dimension may have any of the length ranges mentioned above. In some embodiments a particle comprises a detectable label or detection reagent or has a detectable label or detection reagent attached thereto. In some embodiments a particle is magnetic, e.g., to facilitate removal or separation of the particle from a composition that comprises the particle and one or more additional components.

Forms of polymeric matrix that may contain and/or be used to deliver an agent include films, coatings, gels (e.g., hydrogels), which may be implanted or applied to an implant or indwelling device such as a stent or catheter.

In general, the size, shape, and/or composition of a polymeric material, matrix, or formulation may be appropriately selected to result in release in therapeutically useful amounts over a useful time period, in the tissue into the polymeric material, matrix, or formulation is implanted or administered.

In some embodiments, a pharmaceutically acceptable salt, ester, salt of such ester, active metabolite, prodrug, or any adduct or derivative of a compound or an analog thereof which upon administration to a subject in need thereof is capable of providing the compound, directly or indirectly, may be used. The term "pharmaceutically acceptable salt" refers to those salts which are, within the scope of sound medical judgment, suitable for use in contact with the tissues of humans and/or lower animals without undue toxicity, irritation, allergic response and the like, and which are commensurate with a reasonable benefit/risk ratio. A wide variety of appropriate pharmaceutically acceptable salts are well known in the art.

A therapeutically effective dose of an active agent in a pharmaceutical composition may be within a range of about 1 µg/kg to about 500 mg/kg body weight, about 0.001 mg/kg to about 100 mg/kg, about 0.001 mg/kg to about 10 mg/kg, about 0.01 mg/kg to about 25 mg/kg, about 0.1 mg/kg to about 20 mg/kg body weight, about 1 mg/kg to about 10 mg/kg, about 1 mg/kg to about 3 mg/kg, about 3 mg/kg to about 5 mg/kg, about 5 mg/kg to about 10 mg/kg. In some embodiments doses of agents may range, e.g., from about 10 µg to about 10,000 mg, e.g., from about 100 µg to about 5,000 mg, e.g., from about 0.1 mg to about 1000 mg once or more per day, week, month, or other time interval, in various embodiments. In some embodiments a single dose is administered while in other embodiments multiple doses are administered. Those of ordinary skill in the art will appreciate that appropriate doses in any particular circumstance depend upon the potency of the agent(s) utilized, and may optionally be tailored to the particular recipient. The specific dose level for a subject may depend upon a variety of factors including the activity of the specific agent(s) employed, severity of the disease or disorder, the age, body weight, general health of the subject, etc.

In certain embodiments an agent may be used at the maximum tolerated dose or a sub-therapeutic dose or any dose there between, e.g., the lowest dose effective to achieve a therapeutic effect. Maximum tolerated dose (MTD) refers to the highest dose of a pharmacological or radiological treatment that can be administered without unacceptable toxicity, that is, the highest dose that has an acceptable risk/benefit ratio, according to sound medical judgment. In general, the ordinarily skilled practitioner can select a dose that has a reasonable risk/benefit ratio according to sound medical judgment. A MTD may, for example, be established in a population of subjects in a clinical trial. In certain embodiments an agent is administered in an amount that is lower than the MTD, e.g., the agent is administered in an amount that is about 10%, 20%, 30%, 40%, 50%, 60%, 70%, 80%, or 90% of the MTD.

It may be desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with an appropriate pharmaceutically acceptable carrier.

It will be understood that a therapeutic regimen may include administration of multiple unit dosage forms over a period of time. In some embodiments, a subject is treated for between 1-7 days. In some embodiments a subject is treated for between 7-14 days. In some embodiments a subject is treated for between 14-28 days. In other embodiments, a longer course of therapy is administered, e.g., over between about 4 and about 10 weeks. In some embodiments multiple courses of therapy are administered. In some embodiments, treatment may be continued indefinitely. For example, a subject suffering from a neurodegenerative disease may continue to be treated indefinitely; a subject at risk of developing a neurodegenerative disease may be treated for any period during which such risk exists, e.g., indefinitely. A subject may receive one or more doses a day, or may receive doses every other day or less frequently, within a treatment period. Treatment courses may be intermittent.

In some embodiments, an agent is provided in a pharmaceutical pack or kit comprising one or more containers (e.g., vials, ampoules, bottles) containing the active agent and, optionally, one or more other pharmaceutically acceptable ingredients. Optionally associated with such container(s) can be a notice in the form prescribed by a governmental agency regulating the manufacture, use or sale of pharmaceutical products, which notice reflects approval by the agency of manufacture, use or sale for human administration. The notice may describe, e.g., doses, routes and/or methods of administration, approved indications (e.g., cancers that the agent or pharmaceutical composition has been approved for use in treating), mechanism of action, or other information of use to a medical practitioner and/or patient. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

One of ordinary skill in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure provides embodiments in which exactly one member of the group is present in, employed in, or otherwise relevant to a given product or process. The present disclosure also provides embodiments in which more than one, or all of the group members are present in, employed in, or otherwise relevant to a given product or process. Furthermore, it is to be understood that the present disclosure provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. For example, any dependent claim may depend on any preceding claim dependent on the same base claim unless otherwise indicated or unless it would be evident to one of ordinary skill in the art that a contradiction or inconsistency would arise. It is contemplated that all embodiments described herein are applicable to all different aspects described herein where appropriate. It is also contemplated that any of the embodiments or aspects or teachings can be freely combined with one or more other such embodiments or aspects whenever appropriate and regardless of where such embodiment(s), aspect(s), or teaching(s) appear in the present disclosure. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments may not have in every case been specifically set forth in so many words herein. It should also be understood that any embodiment or aspect can be explicitly excluded from the claims, regardless of whether the specific exclusion is recited in the specification. For example, any one or more agents, disorders, genes, NAPs, subjects, or combinations thereof, can be excluded.

Where the claims or description relate to a product (e.g., a composition of matter), it should be understood that methods of making or using the product according to any of the methods disclosed herein, and methods of using the product for any one or more of the purposes disclosed herein, are encompassed by the present disclosure, where applicable, unless otherwise indicated or unless it would be evident to one of ordinary skill in the art that a contradiction or inconsistency would arise. Where the claims or description relate to a method, it should be understood that product(s), e.g., compositions of matter, device(s), or system(s), useful for performing one or more steps of the method are encompassed by the present disclosure, where applicable, unless otherwise indicated or unless it would be evident to one of ordinary skill in the art that a contradiction or inconsistency would arise.

Where ranges are given herein, embodiments are provided in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments an upper or lower limit differs by a factor of 2, 3, 5, or 10, from a particular value. Numerical values, as used herein, include values expressed as percentages. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided. "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. Individuals or entities performing different step(s) may or may not interact.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

EXAMPLES

Materials and Methods

Human Pluripotent Stem Cell Culture

Skin biopsy, human dermal fibroblast culture, iPS cell generation and mutation correction for the patient harboring the A53T mutation (WIBR-IPS-αSyn$^{A53T}$) have been described previously[2]. In that previous publication the A53T iPS line was referred to as WIBR-IPS-SNCA$^{A53T}$. To generate WIBR-IPS-αsyn$^{TRPL}$, fibroblasts from a male patient of the Iowa kindred harboring a triplication at the oSyn locus[5] were obtained from The Parkinson's Institute (Sunnyvale, Calif.). The relevant Institutional Review Boards and Stem Cell Research Oversight Committees previously approved all protocols. Fibroblasts were reprogrammed to iPS cells using a doxycycline-inducible Cre-excisable polycistronic lentivirus encoding the four human reprogramming factors (SOX2, KLF4, OCT4 and c-MYC) and a Cre-excisable constitutive active M2rtTA transactivator lentivirus. All lentiviruses were excised after reprogramming procedure as described in detail in a prior publication[52]. The male human embryonic stem cell line BG01 (NIH Code: BG01; BresaGen, Inc., Athens) has also been described previously[5,34].

Our pluripotent stem cell lines were initially maintained (5%$O_2$, 3% $CO_2$) on mitomycin C inactivated mouse embryonic fibroblast (MEF) feeder layers in hES medium [DMEM/F12 (Invitrogen) supplemented with 15% fetal bovine serum (FBS) (Hyclone), 5% KnockOut Serum Replacement (Invitrogen), 1 mM glutamine (Invitrogen), 1% nonessential amino acids (Invitrogen), 0.1 mM 13-mercaptoethanol (Sigma) and 4 ng/ml FGF2 (R&D systems)]. Cultures were passaged every 5 to 7 days either manually or enzymatically with collagenase type IV (Invitrogen; 1.5 mg/ml). Between 10 and 50 passages prior to differentiation, lines were passaged to plates pre-coated with growth factor-reduced matrigel (BD Biosciences; 1:30 in DMEM:F12) and cultured (21% $O_2$, 5% $CO_2$) in mTESR-1 medium (Stem Cell Technologies), thereafter being passaged every 5 to 7 days enzymatically with dispase (Invitrogen; 1 mg/mL) until differentiation (at passage 40-90). For karyotyping, standard G-banding chromosomal analysis of cell lines was performed every 10-20 passages (Cell Line Genetics, Inc). We confirmed mycoplasma-negative status of our cultures every 2-4 weeks (MycoAlert, Lonza).

Human Neural Induction by Embryoid Body (EB) Formation

A previously published protocol was adapted[53]. To initiate differentiation, on day 0 human ES or iPS cell colonies were pretreated for 30-60 min with 5 μM Y-27632/ROCK inhibitor (Calbiochem), single cell-dissociated after 5-10 min exposure to accutase (StemPro Accutase; Life Technologies) and then re-suspended in neural base (NB) medium, which is DMEM/F12 (Gibco/Life Technologies) supplemented with N2 and B27. N2 and B27 supplements from Life Technologies and used at ½-1% and 1-2%, respectively. Alternative products from Gemini Bio (N2 Neuroplex; Gem21) gave equivalent results. B27/Gem21 with or without vitamin A achieved similar differentiation for our cell lines. Cells were plated in AggreWell 800 microwells (StemCell Technologies; priming and plating per manufacturer's protocol; 2.4×10$^6$ cells were well) in NB medium supplemented with dual SMAD inhibitors[13] recombinant human Noggin (R&D Systems) at 200 ng/mL and 10 μM SB431542 (Tocris Bioscience), as well as 5 μM Y-27632. Noggin and SB431542 remained in the medium at these concentrations throughout the neural differentiation protocol.

On day 1 medium was ½-changed. By day 2, well-formed neuralized EBs (NEBs) were typically observed in the AggreWells and transferred to Petri dishes (4 AggreWell wells/Petri dish) overnight, in NB medium. On day 4, NEBs were transferred to a dish coated with growth factor-reduced Matrigel (1:30 in DMEM:F12; BD Biosciences) for attachment. Y-27632 was omitted from this day onward. From day 5 to day 10, attached NEBs were additionally exposed to 20 ng/mL FGF2 (R&D Systems) and recombinant human Dkk1 at 200 ng/mL (R&D Systems). On day 10, neural rosettes were dissected (P20 pipette tip), incubated in accutase supplemented with Dnase1 (Sigma Aldrich) for 10 min at 37° C. and gently dissociated to small cellular clumps and single cells. After washing, the rosettes were re-plated on plastic dishes pre-coated with poly-L-ornithine and laminin (BD Biocoat) at high density (200,000/cm$^2$) in neural progenitor cell (NPC) medium, which is NB medium supplemented with 20 ng/mL FGF2. (Life Technologies), supplemented overnight with 10 μm Y-27632. Typically, one Aggrewell 800 well provided enough NPCs for at least 1-2 6-wells at passage 0.

Thereafter, the surviving NPCs proliferated. Medium change was daily. They could be passaged up to 10 times before neural differentiation, and could successfully be freeze/thawed at early passage (p1 to p5) without compromising differentiation potential. Freezing medium was NPC medium with 10% FBS (Hyclone).

Human Neural Induction Directly from Single Cells

An alternative protocol was used for one experiment (FIG. S10B) to ensure phenotypes were independent of neural induction protocol. For this experiment NPCs were generated with dual SMAD inhibition but without recourse to embryoid body formation or exposure to Dkk1, closely following previously described protocols[13,52,54].

Human Cortical Neural Differentiation

To begin neural differentiation, NPCs were dissociated with accutase and re-plated on matrigel-coated T75 flasks (CytoOne). The next, day medium was fully changed to Neural Differentiation (ND) medium, which is NB medium supplemented with recombinant human BDNF and GNDF (both at 10 ng/mL; R&D Systems) and dibutyryl cyclic AMP (Sigma; 500 μM), and without FGF-2. Thereafter, media was ½-changed every other day. On day 7-9, differentiating neurons were gently dissociated to single cell, resuspended in pre-chilled Hank's balanced salt solution (HBSS; Gibco/Life Technologies) supplemented with 0.1% bovine serum albumin (Gibco/Life Technologies). After a wash step, cell were plated on 6- or 24-well plastic plates pre-coated with poly-ornithine and laminin (BD Biocoat) for biochemical assays; poly-D-lysine-(2 mg/mL, Sigma) and mouse laminin (1 mg/mL, BD Biosciences)-coated 8-well chambered coverglass (Lab-Tek; 70378-81) for cell-based imaging assays, or poly-D-lysine and laminin-coated 12 mm glass coverslips for electrophysiology. For maximum survival, we used 5 μm Y-27632 in the initial plating medium and we plated at high density (500,000 to 1×10$^6$ cells/cm$^2$). Medium was ½-changed every 3 days for up to 12 weeks.

PCR Mutation Analysis of Genomic αSyn in Human Cells

To confirm identity of IPS cell lines, neural progenitors and neurons, PCR mutation analysis was performed. This has been described previously[2]. Briefly, genomic DNA was amplified with αSyn/SNCA locus-directed primers (SNCA-genomic-1F: 50-GCTAATCAGCAATTTAAGGCTAG-30; SNCA-genomic-2R: 50-GATATGTTCTTA GAATGCTCAG-30). PCR products were purified (Qiagen), subjected to restriction digestion with Tsp45I (New England Biolabs) and separated on a 3% agarose gel. The A53T (G209A) mutation results in a novel Tsp45I site, and two additional fragments of 131 and 88 bp can accordingly be visualized.

Flow Cytometry of Human Neural Progenitors

After single cell dissociation of NPCs with Accutase (StemPro, Life Technologies), samples were prepared and stained for intracellular antigens with commercially available fixation, buffer and block reagents, according to manufacturer's protocol (Intracyte Intracellular FACS Kit; Neuromics). For antibody dilutions, refer to table entitled "Commercial Antibodies". Analysis was carried out using a BD LSRII flow cytometer, and processed in BD CellQuest Pro software.

Calcium Imaging of Human Neurons

Neurons in 8-well chambered coverglass (see above) were incubated in Tyrode's solution (in mM: 129 NaCl, 5 KCl, 2 CaCl$_2$, 1 MgCl$_2$, 25 HEPES, 30 Glucose, pH 7.4) containing 5 μM Fluo4-AM (Invitrogen, diluted in Tyrode's from 4.55 mM fresh stock in DMSO/20% F-127) for 45 minutes in the dark on the stage of a Nikon TE-2000S inverted microscope inside an environmental chamber (In Vivo Scientific) at room temperature and 5% $CO_2$. The solution was changed and the cells were incubated for an additional 45 minutes in Tyrode's at room temperature for dye de-esterification. Imaging was conducted inside the environmental chamber at room temperature and a 5% $CO_2$ atmosphere. With a standard FITC excitation filter, time-series images were captured using a Photometrics CoolSnap EZ camera controlled by the NIS-Elements AR software package. Time series experiments consisted of 600 512×512 frames with an interval of 1 second. After a baseline interval of approximately 250 frames, high-KCl Tyrode's solution was added to the well for a final KCl concentration of 30 mM. Image stacks were exported to ImageJ (NIH), fluorescence intensities were measured, and data were exported to and analyzed in Excel (Microsoft). Measurements shown represent $\Delta F = F/F_o$ (increase in fluorescence over baseline following background subtraction). Each trace represents the normalized fluorescence intensity change of one cell over time. Cells were assigned blindly to either RFP- or GFP-expressing populations, based upon still images taken prior to dye loading. Representative traces are shown.

Electrophysiologic Recordings from Human Neurons

Whole-cell patch-clamp recordings were performed on fluorescently labeled A53T (n=36) and mutation-corrected (n=22) neurons co-cultured or individually plated on glass coverslips. The recording micropipettes (resistance 3-6 MS2) were filled with solution containing (mM) 130 K-gluconate, 20 KCl, 10 HEPES buffer, 0.2 EGTA, 4 MgATP, 0.3 Na$_2$GTP and 10 disodium phosphocreatine. The bath solution was composed (mM) of 140 NaCl, 4 KCl, 10 HEPES, 2 CaCl$_2$, 10 glucose and 2 MgCl$_2$ (pH 7.4). Recordings were made using an Axopatch 200B amplifier (Axon Instruments). Signals were sampled and filtered at 10 kHz and 2 kHz, respectively. For voltage-clamp recordings, families of current-voltage relations were generated by holding the cell at −100 mV and stepping from −50 to 60 mV in 5 mV increments for 1000 ms before returning to $V_h$. For current-clamp recordings, action potentials were induced with current steps from −50 to 125 pA with 25 pA increments for 1000 ms. All recordings were performed at room temperature Immunostaining Immunofluorescent labeling of human cells followed standard protocols. Briefly, cells were fixed in 4% paraformaldehyde (Electron Microscopy Sciences), blocked in 10% normal donkey serum (Jackson ImmunoResearch) for 1 hr. Primary antibody was applied overnight at 4° C. Appropriate conjugated AlexaFluor (Molecular Probes, Life Technologies) secondary antibodies were used (488, 594, 647). Hoechst 33342 (Life Technologies) was used as a nuclear stain for some studies. Imaging of cells on plastic surfaces was with an inverted epifluorescent microscope (Eclipse Ti, Nikon Instruments). These images were visualized and processed with the NIS-Elements AR software package (Nikon). Imaging of cells on glass surfaces was with a multispectral spinning disk confocal microscope (Ultraview Perkin Elmer; Zeiss Axiovert 200 inverted microscope; 100× Zeiss 1.4 NA oil immersion lens). These images were visualized and processed with the Volocity software package (Perkin Elmer).

Rat Primary Cortical Cultures

Embryos were harvested by cesarean section from anesthetized pregnant Sprague-Dawley rats at embryonic day 18. Cerebral cortices were isolated and dissociated with Accumax (Innovative Cell Technologies, Inc) digestion for 20 min at 37° C. and triuration with Pasteur pipette. Poly-ornithine and lamine-coated 96 well plates or 8 well-chambered coverglass (Lab-Tek; 70378-81) were seeded with 4×10$^4$ or 8×10$^4$ cells respectively in neurobasal medium (Life Technologies) supplemented with B27 (Life Technologies), 0.5 mM glutamine, 25 μM β-mercaptoethanol, penicillin (100 IU/ml) and streptomycin (100 μg/ml). One third of the medium was changed every 3 to 4 days. As a surrogate marker of cell viability, cellular ATP content was measured using the ViaLight Plus kit (Lonza).

Virus Production pLENTI6/V5 DEST (Life Technologies) lentivirus expression vector was used to generate lentivirus encoding LacZ, αSyn$^{A53T}$ and Synoviolin. Lentiviral expression vectors encoding eYFP (20945) and RFP (22909) under the synapsin promoter were obtained from Addgene. Lentiviral constructs were packaged into virus via lipid-mediated transient transfection of the expression constructs and packaging plasmids (pMD2.G and psPAX2) to 293 cells. Lentivirus was purified and concentrated using Lenti-X Maxi Purification kit and LentiX Concentrator (Clontech) according to the manufacturer's protocol. Lentivirus titer was determined using QuickTiter Lentivirus titer kit (Lentivirus-Associated HIV p24; Cell Biolabs) according to the manufacturer's protocol.

AAV2 encoding either mKate2 or C-terminally mKate2-tagged αSyn$^{A53T}$ under the synapsin promoter was produced by University of North Carolina, Chapel Hill Gene Therapy Core.

Viral Transduction to Rat Primary Cortical Cultures and Human Neural Cells

For lentiviral transduction, rat cortical cultures were transduced with various multiplicities of infection (MOI) of virus at day in vitro (DIV) 5. For AAV2, rat primary cultures were infected at DIV 5 with 5000 genome copies/cell. Cells were imaged 2 weeks post infection.

To label live human iPS neurons with synapsin-driven markers, NPCs at ~50-70% confluence were infected MOI 5 with lentivirus expressing RFP and eYFP constructs described above. NPC medium was changed daily, and NPCs were allowed to grow to confluence. As described above, neural differentiation was triggered by FGF withdrawal. Markers were clearly visible within 2 weeks of differentiation. For Synoviolin modifier studies, neural cultures at 8-12 week differentiation were transduced with lentivirus expressing Synoviolin at MOI of 1, 2, or 5. Biochemical analysis was performed 10 days after viral transduction.

NAB2 Treatment of Human Neurons

The compound NAB2 was stored at −20° C. as a 20 mM stock in DMSO. Immediately prior to use, it was diluted in ND medium. Maturing human neural cultures (typically at 8-12 weeks of differentiation) were exposed to NAB2 at different concentrations. Medium was fully changed every 2-3 days and cells were analyzed after 1 week of exposure to the compound.

FL2 Nitric Oxide Sensor Experiments in Live Cells

The FL2 sensor used in this study was a non-acidified and non-esterified version of the FL2-related sensors that have been previously published[23,24,53,55]. A working 1 mM solution of FL2 (batch SJL #1768) in DMSO (Sigma 276855) was stable for at least 3 months at −20° C. It was stored in aliquots for single use to avoid freeze/thaw. Direct exposure to light was avoided. Immediately before use, 2 volumes of 1 mM $CuCl_2$ were combined with 1 volume of 1 mM FL2. Neurons grown on chambered coverglass (described above) were washed with pre-warmed HBSS, and then incubated for 30 min (37° C., humidified, 5% CO2) in 10 M dye dissolved in HBSS. After a single wash, cells were incubated in fresh pre-warmed HBSS for an additional 20 minutes. Neurons were imaged for the next 2 hours with a multispectral spinning disk confocal microscope (Ultraview Perkin Elmer; Zeiss Axiovert 200 inverted microscope; 100× Zeiss 1.4 NA oil immersion lens). Images were visualized and processed with the Volocity software package (Perkin Elmer). For reproducible data, we found it critical i) to adhere to these incubation times; ii) to ensure that neural cultures were healthy, and that control and experimental cultures were consistent with each other; iii) to image with a stage-top incubation system to maintain temperature, humidity and $CO_2$. (LiveCell, Pathology Devices).

Human Postmortem Brain 3-NT Immunohistochemistry

Archival formalin-fixed, paraffin embedded brain (frontal cortex) tissue was obtained from the Massachusetts Alzheimer's Disease Research Center and the University of Pennsylvania Center for Neurodegenerative Disease Research. 5 μm tissue sections were immunostained with mouse monoclonal anti-nitrotyrosine antibody (1:500, clone 1A6, Millipore) overnight at 4° C., followed by secondary antibody, Avidin-Biotin Complex incubation (Vectastain ABC Elite Kit, Vector Laboratories, Burlingame, Calif.), and developing with ImmPACT 3,3'-diaminobenzidine peroxidase substrate (Vector Laboratories). Immunostained sections were reviewed by light microscopy.

Human iPS Neuron Lysis and Endo H Digestion

Cells were lysed in buffer containing 20 mM HEPES, 150 mM NaCl, 10% glycerol, 1 mM EGTA, 1.5 mM $MgCl_2$, 1% Triton X-100, pH to 7.4 and protease inhibitor cocktail (Sigma) and protein phosphatase inhibitor cocktail 1 and 2 (Sigma) and incubated in an ice/water slurry for 20 mins, followed by 2 freeze thaw cycles (80° C./37° C., ~1 min each). Supernatent was collected after ultracentrifugation at 100,000×g, 4° C., for 30 min. Protein concentration was determined using BCA assay (Pierce). Endoglycosidase (Endo) H (New England Biolabs) digestion was performed based on the manufacturer's instruction. Briefly, 30~50 μg of samples were assembled in 9 μl reaction volume with 1 μl of denaturing buffer and boiled for 10 min at 100° C. Then 2 μl of G5 buffer, 1 μl of Endo H and 7 μl of $H_2O$ was added to the denatured reaction and incubated in 37° C. for 2 hours.

Western Blot

For protein trafficking, protein samples were denatured in the sample buffer (20 mM Tris Cl pH 6.8, 4% glycerol, 180 mM 2-mercaptoethanol, 0.0003% bromophenol blue and 2% SDS) and run in 10% Tris-glycine gel and wet transferred with 20% MeOH onto PVDF membranes (BioRad). Blots were blocked in 1:1 dilution of Odyssey blocking buffer (Li-Cor Biosences) and PBS for 1 hour at room temperature followed by incubation with primary antibodies in 1:1 dilution of Odyssey blocking buffer (Li-Cor Bioscences) and PBS containing 0.1% of Tween 20 (PBST) at 4° C. overnight with gentle rocking. After three 5 min washes with PBST, blots were incubated with secondary antibodies such as anti-mouse or -rabbit IgG conjugated to IRDye 680 or 800 (1:10,000, Rockland) in 1:1 dilution of Odyssey blocking buffer and PBST for 2 hours at room temperature. After three 5 min washes with PBST and two with water, blots were scanned in Odyssey quantitative fluorescent imaging system (Li-Cor Biosciences) and bands were quantitated using Odyssey Software v 2.1 (Li-Cor biosciences).

For other Western blot, samples were run in either 10 or 4-12% Nupage Bis-Tris gel (Life Technologies) and transferred using iBlot (Life Technologies). Blocking was done with 5% nonfat dry milk in PBST except for the biotinylation detection with αSyn APEX, where 4% bovine serum albumin in PBST was used instead. As for the secondary antibodies and chemiluminescent detection, anti-mouse, rabbit IgG or avidin conjugated to HRP was used with SuperSignal West Pico chemiluminescent substrate (Thermo Scientific).

Biotin Switch Assay

The protocol was modified from Jaffrey and Snyder (2001)[39]. Cells were lysed in 250 mM HEPES, 1 mM EDTA, and 0.1 mM neocuproine, pH 7.7 containing 1% Triton X-100, 0.1% sodium deoxycholate, 0.1% SDS. ~500 μg of protein was used per reaction. Lysate concentrations were adjusted to 0.8 ug/μl by adding lysis buffer. The lysate was blocked with 0.2% MMTS and 2.5% SDS at 50° C. for 20 min with vigorous shaking followed by cold acetone precipitation. The pellets were dissolved in HEPES 250 mM 1% SDS (HENS) buffer. Biotin labeling was performed with 0.25 mM biotin-HPDP (Pierce) and 5 mM ascorbate at room temperature for 1 hr and 30 min followed by cold acetone precipitation. The pellets were washed four times with 70% acetone and resuspended in HENS buffer. Acetone precipitation and washing step was repeated to remove residual free biotin. The pellets were again resuspended in HENS buffer and neutralization buffer (25 mM HEPES, 100 mM NaCl, 1 mM EDTA, 0.5% Triton X-100, pH 7.5) was added. Streptavidin magnetic beads (Pierce) were used to pull down biotinylated proteins in a rotating platform at RT for 1-2 hrs. The beads were washed with washing buffer (neutralization buffer+600 mM NaCl) with rotation for 5 min and this was repeated four times. After the final wash, protein was eluted from biotin bound beads by incubating in elution buffer (10 mM HEPES pH 8.00, 1 mM EDTA, 2% 2-mercaptoethanol) for 1 hour with rocking. Elutes were analyzed by Western blot.

Yeast Strains

Yeast strains used include W303 with αSyn integrated into HIS3 and TRP1 loci (IntTox): MATa can1-100, his3-11,15, leu2-3, 112, trp1-1, ura3-1, ade2-1, pRS303Gal-α-synWTYFPpRS304Ga1-αSynWT-YFP; W303 with αSyn integrated into TRP1 and URA3 loci (HiTox): MATa can1-100, his3-11,15, leu2-3,112, trp1-1 ura3-1, ade2-1, pRS304Ga1-αSynWT-GFP pRS306Ga1-αSynWT-GFP; W303 with one copy of αSyn integrated into TRP1 locus (NoTox αSyn): MATa can1-100, his3-11,15, leu2-3,112 trp1-1, ura3-1,ade2-1, pRS304Ga1-αSynWTGFP; W303 with two copies of empty vector integrated into TRP1 and URA3 loci (2× vector): MATa can1-100, his3-11,15, leu2-3,112, trp1-1, ura3-1, ade2-1, pRS304Ga1 pRS306Ga1.

The yeast strains used for NAB2 experiments were in the w303 background (MAT a can1-100, his3-11,15, leu2-3,112, trp1-1, ura3-1, ade2-1, pdrl::kanMX, pdr3::kanMX). The vector control strain contained empty vector at the trp and ura loci (pRS304Ga1, pRS306GAL). The HiTox αSyn strain contained αSyn-GFP inserted at the trp and ura loci (pRS304GAL-αSyn-GFP, pRS306GAL-αSyn-GFP). Strains were manipulated and media prepared using standard techniques.

Generation of Cox5A and Cox5B Deletion Strains

The yeast strains used were in the w303 pump-deleted background (MAT α can1-100, his3-11,15, leu2-3,112, trp1-1, ura3-1, ade2-1). The αSyn expressing strains used for the Cox5A and Cox5B deletions contains αSyn-GFP or untagged α-syn inserted at the his and trp loci (pRS303GAL-αSyn-GFP, pRS304GAL-αSyn-GFP or pRS303GAL-αSyn, pRS304GAL-αSyn) and the estradiol-inducible GAL4 transactivator on a cen plasmid with the ura locus (pRS316 GAL4[1-93].ER.VP16). Cox5A and Cox5B genomic null strains were generated using PCR-based gene deletion strategy as described in Baudin et al., Nucl. Acids Res. 21, 3329-3330, 1993 and Wach et al., Yeast 10, 1793-1808, 1994. Strains were induced with the addition of estradiol (10 nM) to glucose media.

Propidium Iodide and UPR Reporter Yeast Flow Cytometry

Yeast cells were subjected to flow cytometry for the measurement of UPR induction and cell viability. The UPR reporter, pRS305-SR (David Pincus) was integrated into αSyn expressing yeast strains bearing deletions in Cox5A or Cox5B. The SR is a reporter of Ire1 endonuclease activity. It is expressed from the native HAC1 promoter and identical to the HAC1 mRNA except the first exon is replaced with GFP[56]. Single integrents were identified by qPCR for use in flow cytometry. Briefly, 200 μl of induced cells were incubated with gentle shaking (750 rpm) at 30° C. for 20 minutes using an Eppendorf thermomixer. These cells were transferred to a 96-well plate, where they were examined using an EasyCyte flow cytometer (Guava Technologies). UPR induction was monitored by quantifying GFP fluorescence in the green channel. To monitor cell viability, 2 μg/mL of propidium iodide was added to 200 μL of induced cells and PI-positive cells were identified in the red channel.

| Commercial antibodies | | | |
|---|---|---|---|
| Antibody | Manufacturer | Application | Concentration |
| Mouse anti-α-Synuclein | BD Transduction Laboratories 610786 | Immunofluorescence | 1:500 |
| Mouse anti-Carboxypeptidase Y | Life Technologies A66428 | Western blot | 1:10 000 |
| Mouse anti-GAPDH | Millipore MAB374 | Western blot | 1:3000 |
| Rabbit anti-GCase | Sigma G4171 | Western blot | 1:1000 |
| Rabbit anti-GFAP | Dako Z0334 | Immunofluorescence Flow cytometry | 1:1000 1:2000 |
| Rabbit anti-MAP2 | Millipore AB5622 rabbit | Immunofluorescence | 1:500 |
| Mouse anti-Nestin | Neuromics MO15012 | Immunofluorescence Flow cytometry | 1:100 1:200 |
| Rabbit anti-Nicastrin | Cell Signaling 3632 | Western blot | 1:1000 |
| Rabbit anti-Neuroserpin | Abcam ab46761 | Western blot | 1:1000 |
| Rabbit anti-Nitrotyrosine | Sigma N0409 | Western blot | 1:5000 |
| Mouse anti-Nitrotyrosine (1A6) | Millipore 05-233 | Immunohistochemistry | 1:500 |
| Rabbit anti-Pax6 | Covance PRB278P | Immunofluorescence Flow cytometry | 1:200 1:400 |
| Rabbit anti-Tbr1 | Abcam ab31940 | Immunofluorescence | 1:200 |
| Mouse anti-Tuj1 | Covance MMS-435P | Western blot Flow cytometry | 1:2000 1:1000 |
| Rabbit anti-VGLUT1 | Synaptic systems 135303 | Immunofluorescence | 1:500 |

Example 1

αSyn iPS-Derived Cortical Neurons to Model Cortical Synucleinopathy

Neuropathologically, dementias are associated with the loss of cortical neurons, usually accompanied by the aggregation of specific proteins. For example, aggregation of αSyn in cortical neurons is associated with the dementia that commonly accompanies Parkinson disease (PD), known as Parkinson disease dementia, and the closely related dementia with Lewy bodies. In addition to the characteristic motor manifestations of PD ("parkinsonism"), highly penetrant dominant point-mutations in α-Syn or increased gene copy number are also prominently associated with dementia[1]. These findings establish a causal connection between a-Syn, its associated cortical neuropathology and cognitive dysfunction, and facilitate the creation of animal and cellular models.

A promising cellular model for synucleinopathies involves reprogramming of human adult somatic cells to induced pluripotent stem (iPS) cells and, in turn, the differentiation of these cells into neurons of immediate relevance to patients. We recently created such cells from a female member of the "Contursi kindred" carrying a dominant and highly penetrant A53T point mutation in αSyn. To rigorously control for genetic background effects that can profoundly affect phenotypes, we generated isogenic control cells from this patient by zinc finger-mediated correction of the disease-causing threonine residue back to alanine[2,3]. Here, we utilize these isogenic lines, differentiated into cortical neurons, to discover disease-related phenotypes and distinguish them from genetic background effects.

Here, we present a solution to two other problems that have thwarted the use of human iPS-derived cells in the search for potential disease-modifying agents. First, it has been difficult to establish phenotypes solely attributable to naturally occurring disease-causing genetic mutations. Since disease progression occurs over several decades in man, previous studies have accelerated degenerative phenotypes by exposing cultured neurons to toxins such as oxidative stressors[4-6]. Second, multiple factors hinder the use of these cells in high-throughput screening for genetic and chemical modifiers: the production of these cells is arduous and expensive, the cells change over time in cell culture conditions, and neural differentiation can be inconsistent.

To address these problems, we turned to a budding yeast platform we developed in which αSyn-expression results in highly synchronous and robust toxicity[7,8]. Yeast cells offer the advantage of fundamentally conserved eukaryotic cell biology, unparalleled genetic tractability and amenability to high throughput chemical-compound screening. Importantly, αSyn pathobiology in yeast recapitulates pathologic phenotypes in neurons including focal accumulation of αSyn, mitochondrial dysfunction, oxidative stress, αSyn-mediated vesicle trafficking defects, links to genetic and environmental risk factors, and an exquisite sensitivity to αSyn dosage[7-10]. Our previous unbiased yeast screen of 5500 open reading frames (85% of the yeast proteome) identified robust modifiers of αSyn toxicity. Here, we investigate two of these modifiers in detail. We show that our analysis of their biology in yeast can lead to the discovery of early pathologic phenotypes in Parkinson patient cortical neurons in the absence of exogenous stressors and toxins. Further, we show that a chemical compound identified in a high-throughput yeast screen can correct analogous defects in yeast and patient neurons.

Neuropathologic analysis of A53T patient brains has established prominent neuritic pathology and neuronal loss within deep layers of the cerebral cortex[11,12]. Indeed, this phenotype was confirmed in two affected older siblings of the Contursi kindred patient whose cells we reprogrammed (L. Golbe, personal communication). To generate a model for cortical synucleinopathy, we differentiated her iPS cells into cortical neurons.

Figure 1B:
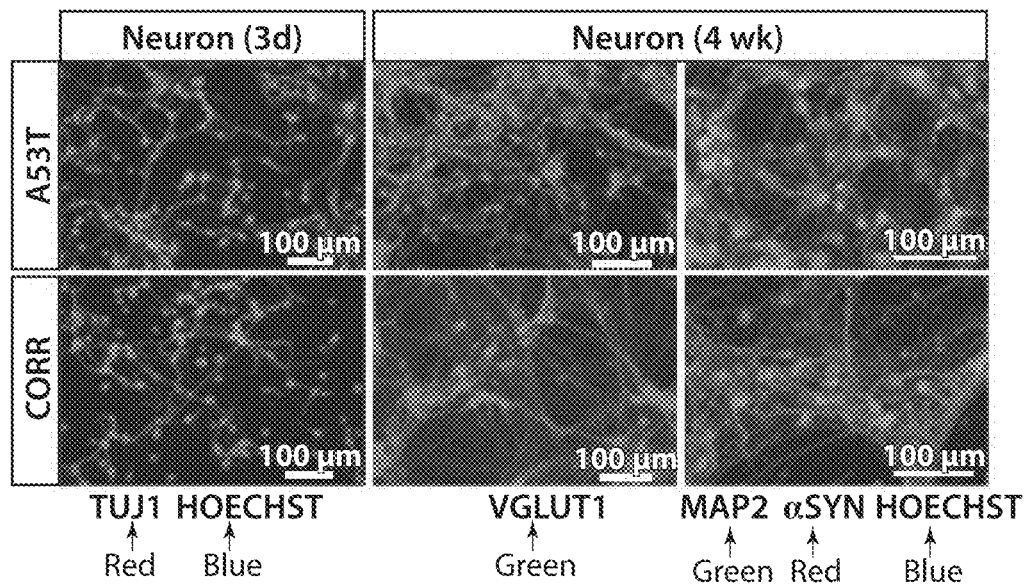
Figure 1C:
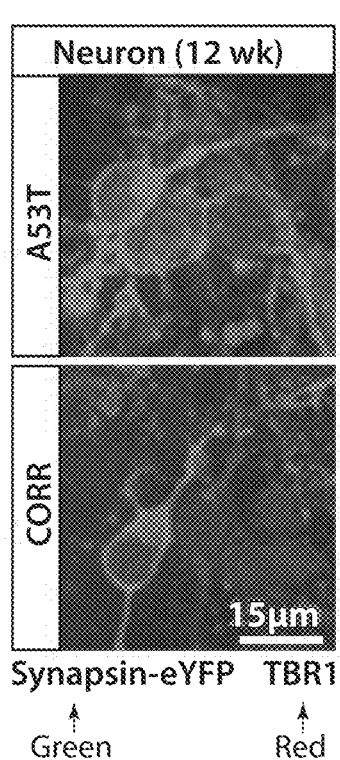
Figure 17A:
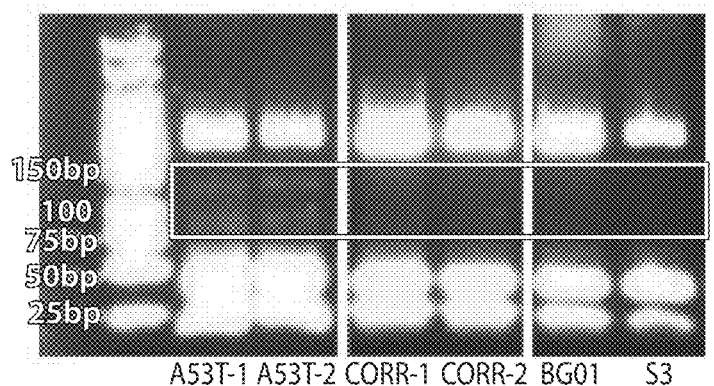
FIG. 17. Genotyping and karyotyping of control and PD iPS cells. αSyn/SNCA locus was PCR-amplified and digested by Tsp45I to verify A53T and corrected lines (A). A53T mutation results in a novel TSP45I site, generating two additional fragments (131 bp and 88 bp). All the lines used were karyotyped routinely and lines that maintained normal karyotype were used for further analysis (B). In the figure "A53T" refers to WIBR-IPS-αSyn$^{A53T}$; "CORR" refers to WIBR-IPS-αSyn$^{A53T\ CORR}$; "S3" refers to WIBR-IPS-αSyn$^{TRPL}$. Note that in the original paper describing the generation of the A53T and CORR iPS lines, the term "SNCA" was used in lieu of "αSyn."
Figure 17B:
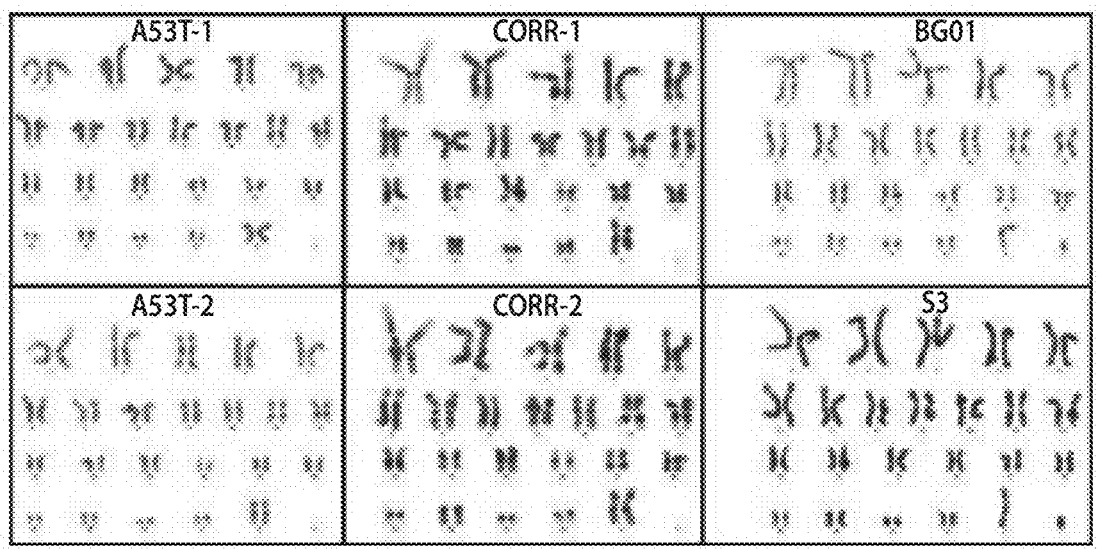
Figure 18A:
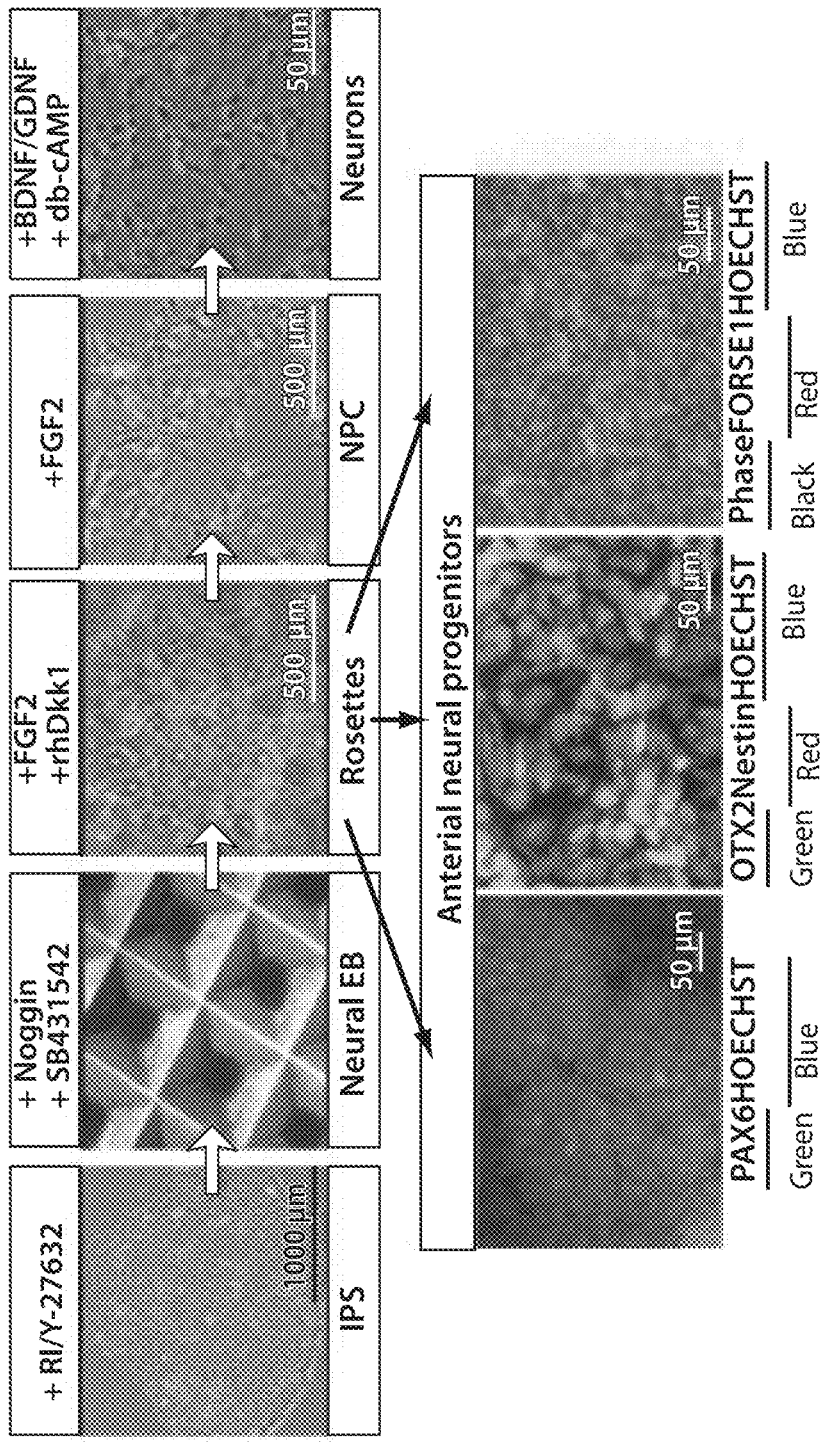
FIG. 18. Neutralization and neural differentiation of iPS cells. (A) iPS cells were single-cell dissociated in the presence of Rock inhibitor (RI/Y-27632). Neutralized embryoid bodies formed under dual SMAD inhibition (Noggin and SB431542) in N2/B27-based medium. Rosettes consisting of neural progenitor cells (NPCs) formed after exposure to fibroblast growth factor (FGF2) and recombinant human Dickkopf-1 (rhDkk-1). Anterior fate was confirmed with markers Pax-6, Forse-1 and Otx2. Dissection and re-plating of rosettes yielded expandable NPC cultures. Withdrawal of FGF2 induced the differentiation of NPCs to neurons. Neurons were aged up to 12 weeks in the presence of brain derived neurotrophic factor (BDNF), glial derived neurotrophic factor (GDNF) and dibutyrl cyclic AMP (db-cAMP). (B) A53T and mutation-corrected iPS neural progenitor cells showed comparable Pax6 and Nestin expression analyzed by flow cytometry. A representative experiment is shown. Note that green fluorescence (Pax6) is represented on the x-axis, and red fluorescence (Nestin) is represented on the y-axis. Double-positive cells appear in the top right quadrant. The first panel shows an unstained population, a control used to determine analysis gates.
Figure 18B:
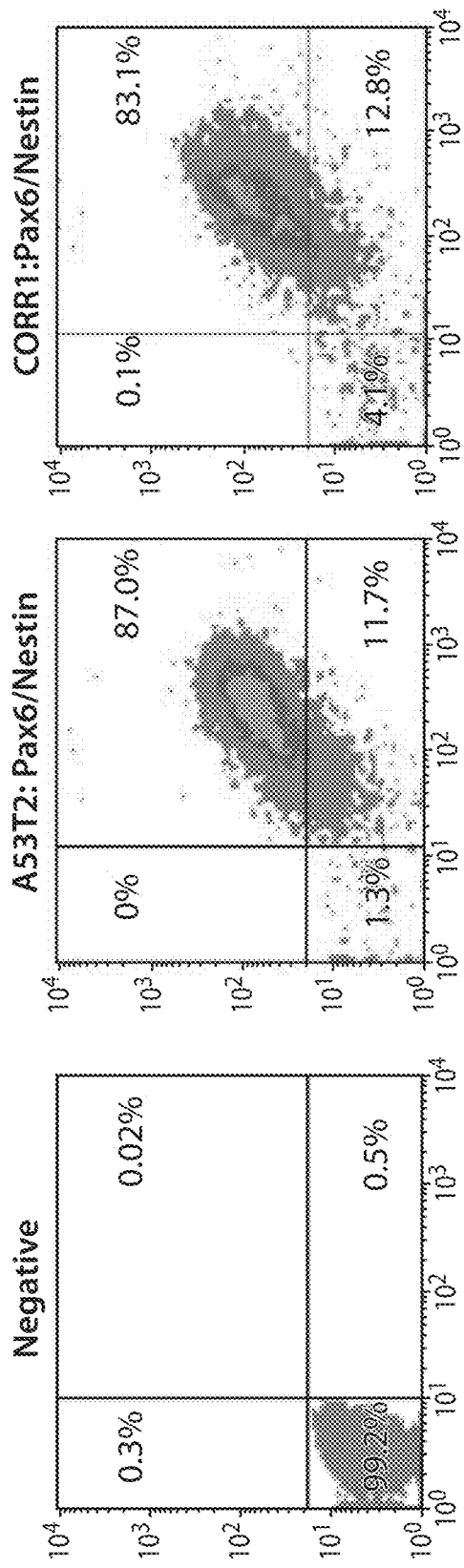

Two mutant A53T iPS cell subclones, and two mutation-corrected subclones (FIG. 1A), were independently passaged up to 90 times and maintained a normal karyotype (FIG. 17). Cortical neuronal differentiation was achieved by integrating previously published protocols[13,14] (FIG. 18A). Neural progenitor cells (NPCs) thus obtained were anterior/forebrain-fated, as demonstrated by the expression of Pax6, Nestin, Forse-1 and Otx-2 (FIGS. 18, A and B). Neural differentiation was then initiated by FGF2 withdrawal, and the postmitotic neuronal identity of these cells was confirmed by elaboration of neuronal processes that were immunopositive for neuron-specific class III beta-tubulin (Tuj1; FIG. 1B). We analyzed these neural cultures over 12 weeks. During this time, the cultures consisted primarily of excitatory glutamatergic neurons mixed with glia (FIG. 1, B; FIG. 19, A to C). By flow cytometry, >90% of Tuj1-positive neurons were consistently VGLUT1 (vesicular glutamate transporter-1)-positive, and the peripheral nervous system marker Peripherin was negligibly expressed (data not shown).

Figure 19A:
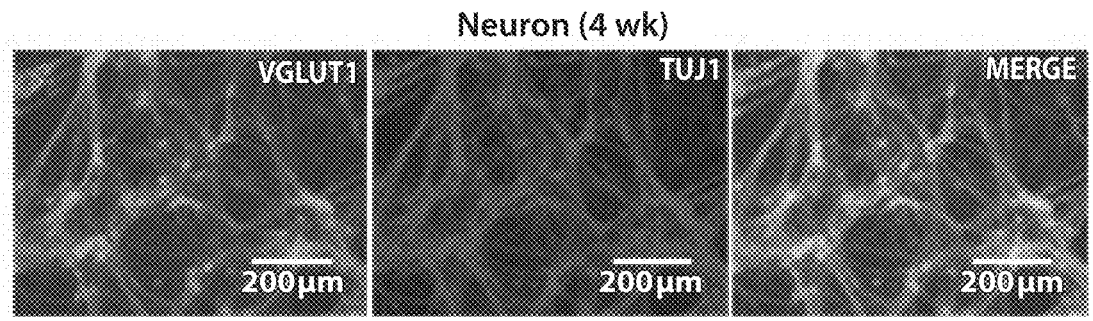
FIG. 19. Further characterization of cortical neuron-enriched cultures differentiated from patient iPS cells. (A-B) Cortical neuronal differentiation protocol for iPS cells generate mixed cultures that include glutamatergic neurons and astrocytes. At 4 weeks neuronal differentiation, cultures were enriched with glutamatergic neurons marked by VGLUT1 that co-localized substantially at this magnification with the neuronal marker, Tuj1 (A). Cultures were mixed with glial cells including astrocytes, marked by glial fibrillary acidic protein (GFAP)(B). (C-F) Analysis of neurons with synapsin promoter-driven markers. Neural progenitor cells (NPCs) were transduced with lentiviruses expressing either eYFP or RFP under the neuron-specific promoter synapsin (D). Higher magnification views of neurons indicated: the distribution of αSyn was both diffuse throughout the cell body and punctate in processes; (C, top) VGLUT1 was characteristically punctate in processes (C, bottom). Functional characterization of live A53T and CORR neurons after 8 weeks of differentiation (co-cultured in the same well or cultured individually) indicated appropriate calcium fluxes with potassium chloride (KCl)-induced depolarization (E). Whole-cell patch clamp recording demonstrated normal sodium and potassium currents with voltage-clamp recording (F, left) and action potentials triggered by 25 pA current injection under current-clamp mode (F, right). These analyses revealed no substantial differences between A53T and CORR neurons.
Figure 19B:
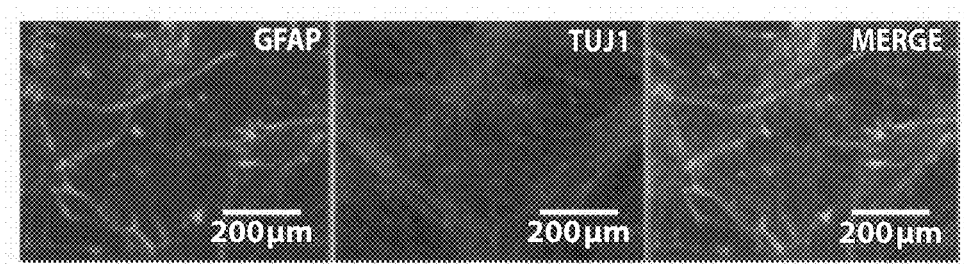
Figure 19C:
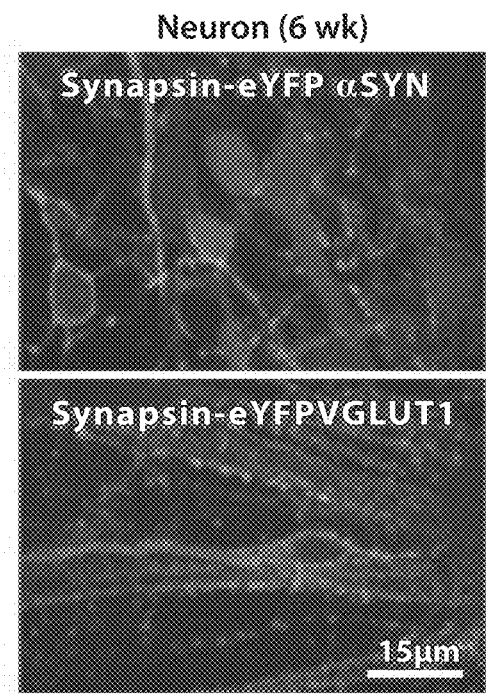
Figure 19D:
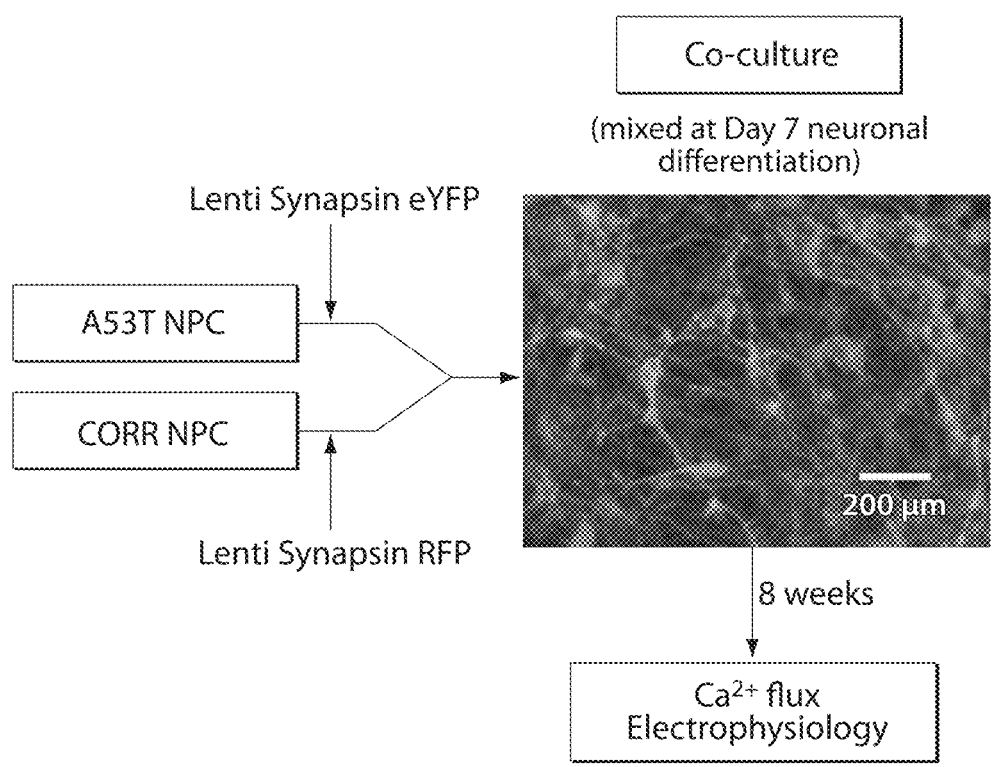
Figure 19E:
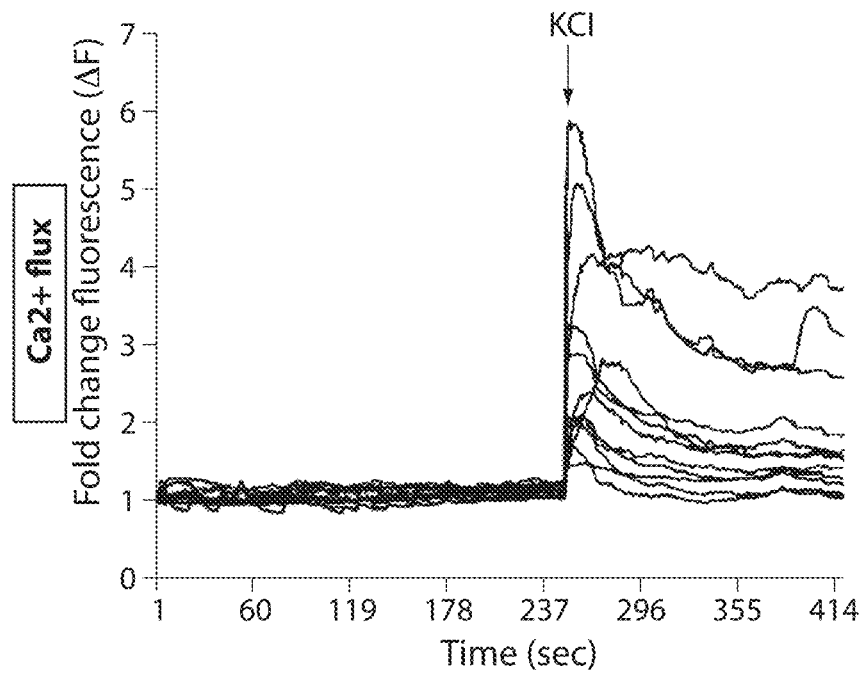
Figure 19F:
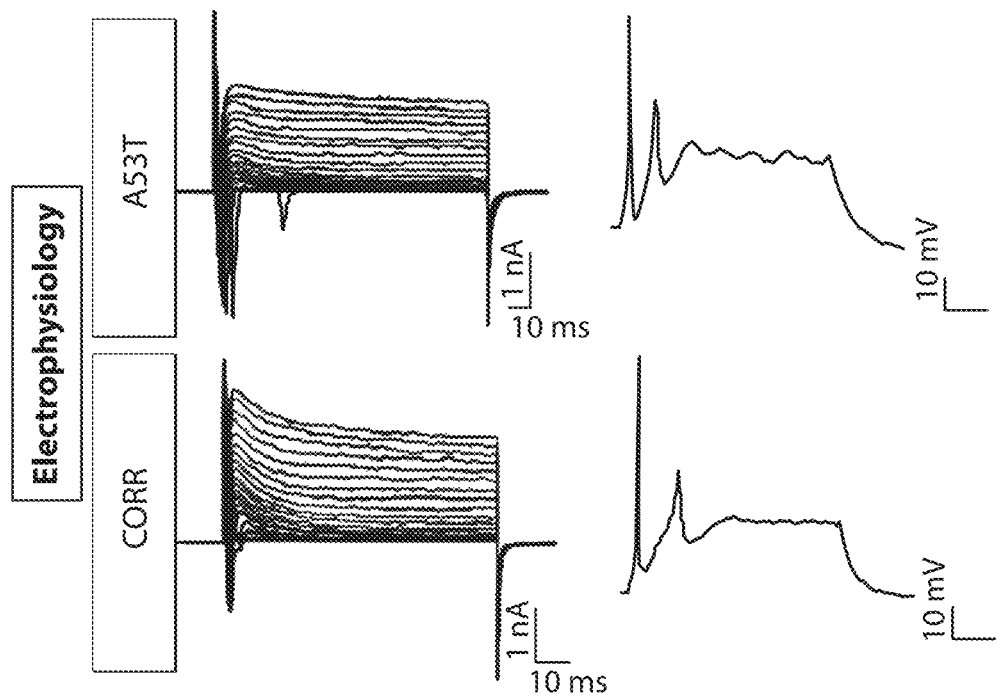

To definitively identify neurons in our cultures, NPCs were infected prior to differentiation with lentiviruses expressing either eYFP or RFP under the control of the pan-neuronal synapsin promoter (FIG. 19D). Co-cultured A53T and corrected neurons were electrically active from around 8 weeks of differentiation. They exhibited similar calcium fluxes and electrophysiology, including action potentials (FIGS. 19, E and F). At 12 weeks of neural differentiation, we found the majority of neurons were immunopositive for Tbr1, a transcription factor characteristic of developing deep cortical layers (FIG. 1C)[15]. Thus, the cells we created provide a relevant substrate for examining early Syn-related cortical pathologies.

Example 2

α-Syn-Induced Nitrosative Stress Conserved from Yeast to Human Cortical Neurons

Figure 2A:
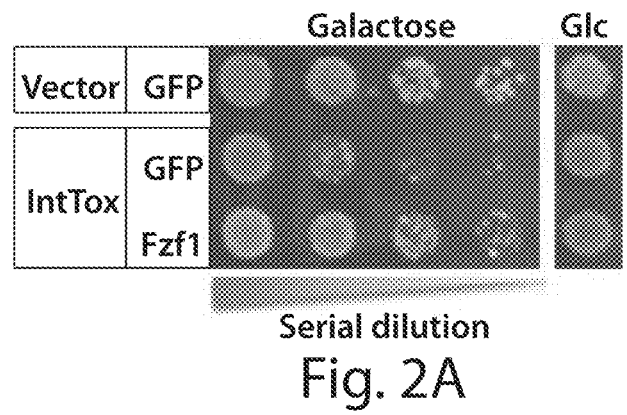
FIG. 2. αSyn toxicity is tied to nitrosative stress in the yeast model. (A) Fzf1 overexpression reduces αSyn toxicity in yeast. Yeast strains were spotted in 5-fold serial dilution to visualize the effect of Fzf1 on cell growth. Transgenes were induced by switching the carbon source from glucose (Glc) to galactose. Glc. spotting shows equivalent number of yeast spotted between the strains. Fzf1 expression ameliorated slow growth caused by αSyn overexpression (IntTox strain). (B) A specific nitrosative stress response occurs in αSyn-expressing yeast strains. Yeast strains were spotted in 5-fold serial dilution to visualize the effect of disease relevant proteins on cell growth as described above. Protein nitration levels in the same strains were measured by Western blotting with an antibody to 3-NT (3-nitrotyrosine). Compared to other proteins causing equivalent toxicity, αSyn-expressing strains showed a dose-dependent increase in nitration levels. 3 strains expressing low (NoTox), intermediate (IntTox) and high (HiTox) levels of αSyn were analyzed[9]. Other neurodegeneration-related models were created by overexpressing Aβ(β-amyloid peptide), Htt72Q (Huntingtin exon 1 with polyglutamine length of 72) or Fus. (C) Fzf1 expression reduces αSyn-induced increase in nitration. (D and E) Manipulating NO levels in yeast alters levels of protein nitration and αSyn-induced toxicity. Cox5A or Cox5B were deleted from αSyn-expressing yeast and αSyn expression was induced using 10 nM of estradiol. The NO-increasing deletion of Cox5A (ΔCox5A) increases protein nitration levels, whereas the NO-decreasing Cox5B deletion (ΔCox5B) reduces protein nitration levels, determined by the 3-NT antibody (D, upper). Toxicity is correspondingly altered, determined by using a spot assay (D, lower) and measuring propidium iodide staining (flow cytometry; E). Data represented as mean±SEM, ***; p<0.001 One way ANOVA with Bonferroni post-hoc test.

Fzf1 is a transcription factor that was identified as a suppressor of αSyn toxicity in our previous unbiased yeast genetic screen (confirmed in FIG. 2A.) Its function as a transcriptional regulator of nitrosative stress responses is well established[16]. Nitrosative stress is induced by reactive nitrogen species (RNS) that include nitric oxide (NO) and related redox forms[17]. RNS can alter cellular processes via post-translational modification of proteins, including nitration of tyrosine (nitrotyrosine) and S-nitrosylation of cysteine residues[17]. We chose Fzf1 as the first modifier for detailed investigation across our platforms because protein S-nitrosylation and nitration are increased in postmortem brain from synucleinopathy patients[18-20]. It has not been previously known, however, if there is a direct causal connection between nitrosative stress and αSyn itself.

Figure 2B:
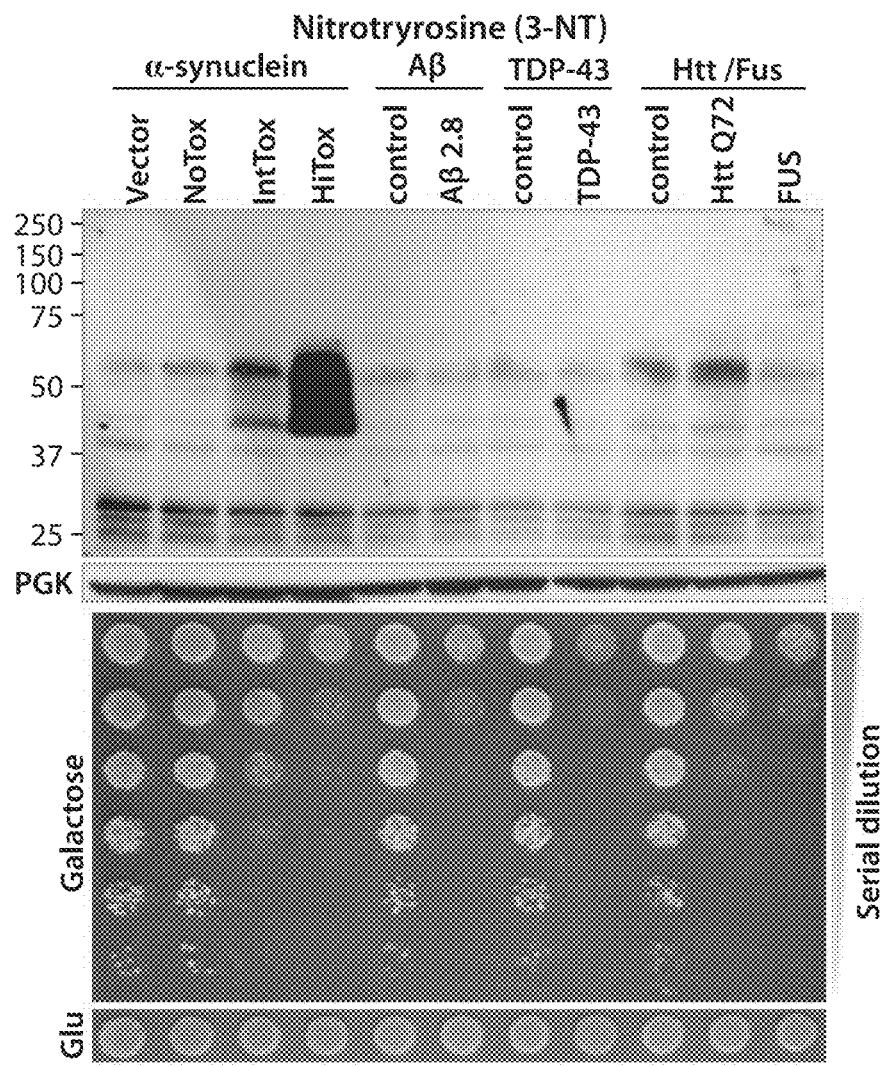

To determine if nitrosative damage occurs to proteins in yeast cells expressing αSyn, we took advantage of an antibody specific for nitrotyrosine. This antibody detects a broad array of proteins in Western analyses of mammalian cells that limits its utility in such cells. In yeast, however, we found minimal background in vector control strains. This allowed us to detect robust protein nitration in response to αSyn (FIG. 2B).

αSyn toxicity is dosage-dependent in both yeast and humans. As previously described, we expressed αSyn at three different levels in yeast—NoTox (low), IntTox (moderate) and HiTox (high)[9]. The level of protein nitration exhibited the same dosage sensitivity as did toxicity (FIG. 2B).

Nitration was a highly specific response to αSyn toxicity in yeast. It was not prominent when other neurodegenerative disease proteins were expressed at equally toxic levels, including Abeta peptide, TDP-43, polyQ-expanded huntingtin, and Fus (FIG. 2B). This finding is consistent with results from our previous genetic screens: Fzf1 suppressed the toxicity of αSyn but not the toxicity of these other proteins (Ref.[21] and our unpublished data).

Figure 2C:
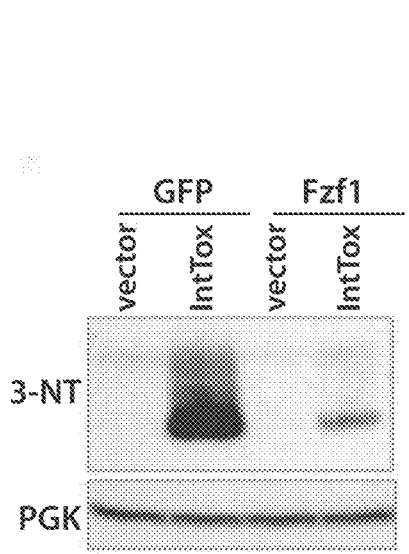
Figure 2D:
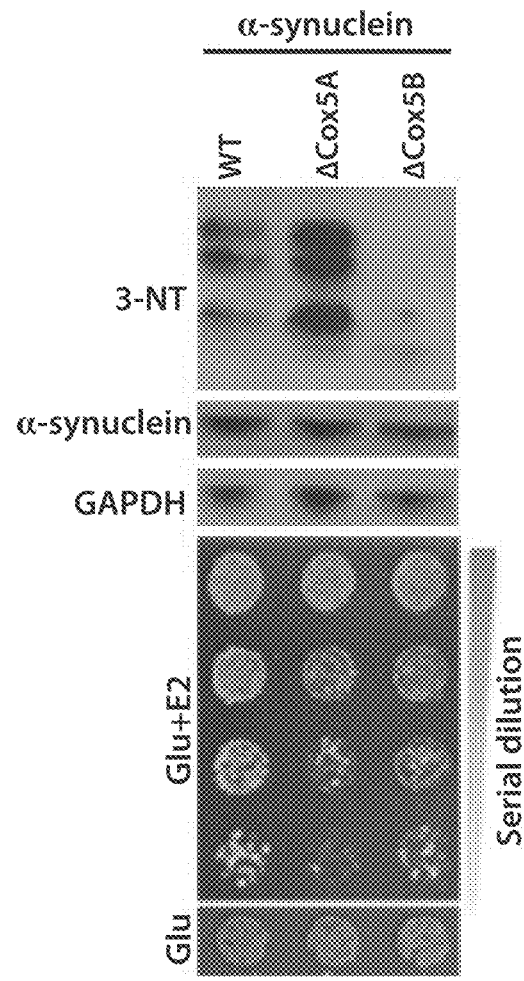
Figure 2E:
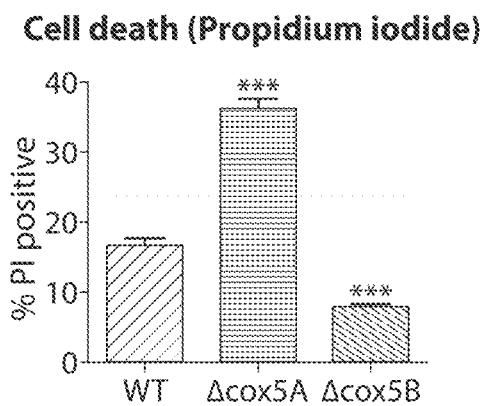

To directly test the link between αSyn and nitrosative stress, we first asked if Fzf1 decreased the unusual protein nitration induced by αSyn. Indeed, nitration was strongly suppressed (FIG. 2C). Next, we asked if altering NO levels in yeast impacted αSyn-induced toxicity. Although NO synthases are broadly conserved across species, yeast cells do not encode a protein in this family. Instead, NO is generated through the mitochondrial respiratory chain. Yeast cells regulate NO production by switching between distinct isoforms of cytochrome c oxidase (COX5). Experimentally, NO production can be manipulated by deletion of the two isoforms: deletion of COX5A increases NO, while the deletion of COX5B decreases it[22]. Indeed, these manipulations increased and decreased nitrotyrosine levels in yeast cells expressing αSyn (FIG. 2D). Commensurately, they increased and decreased toxicity (FIGS. 2, D and E). Thus, nitrosative stress is not simply a result of αSyn toxicity, but is an important contributor to that toxicity.

In mammalian cells, RNS can be detected by chemical sensors. To investigate a possible connection between αSyn and nitrosative stress in neurons we employed FL2, a copper and fluorescein-based sensor that preferentially detects NO over other RNS[23]. We initially optimized the use of FL2 with rat primary cortical neurons. Rat primary cultures offer a highly consistent neuronal model of αSyn toxicity that is of intermediate complexity and, therefore, better suited to assay development than human iPS-derived neurons.

Figure 3A:
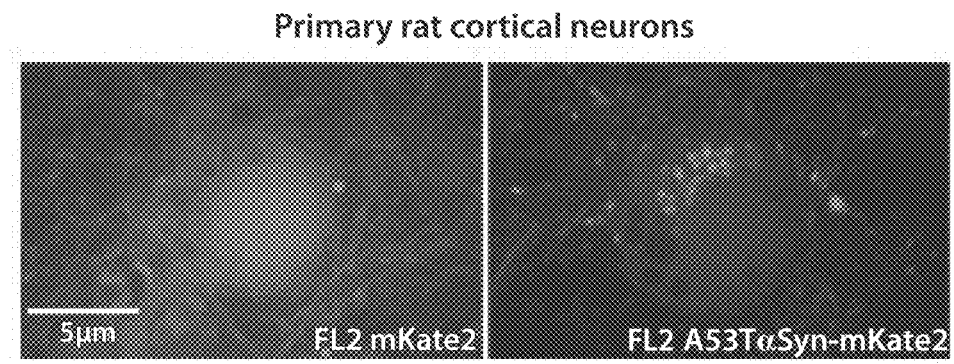
FIG. 3. Nitrosative stress is implicated in rat and human iPS neuron synucleinopathy models, and in the brain of a patient harboring the A53T αSyn mutation. (A-B) αSyn overexpression increases NO levels in rat primary cortical culture. Primary rat cortical cultures were infected with adeno-associated virus2 (AAV2)-encoding mKate2 or A53T αSyn-mKate2 under the synapsin promoter. The distribution of these different mKate2 constructs is quite distinct (see FIG. 21). Cells were loaded with FL2 and imaged live using a confocal microscope. FL2 was quantitated in at least 20 neurons for each condition (B). The same trend was reproduced in three more experiments. (C) Perinuclear FL2 signal partially co-localized with ER tracker in rat neurons. (D) Increased NO levels in human αSyn$^{A53T}$ iPS neurons. Two mutation-corrected (C1 and C2) and two A53T (A1 and A2) iPS cell lines were neutralized. Neural progenitors were transduced with lentivirus encoding RFP under the synapsin promoter. Upon differentiation, neurons were labeled with RFP. At 8 weeks of differentiation, neurons were loaded with FL2 and imaged (for the C1/A1 experiment, n=53 neurons were analyzed and for the C2/A2 pair, n=81 neurons). Note that RFP aggregates are visible at this magnification (E) Postmortem frontal cortex from a patient harboring A53T mutation shows increased 3-NT immunoreactivity. All data represented as mean±SEM, *; p<0.05, ***; p<0.001 (two tail t-test).
Figure 3B:
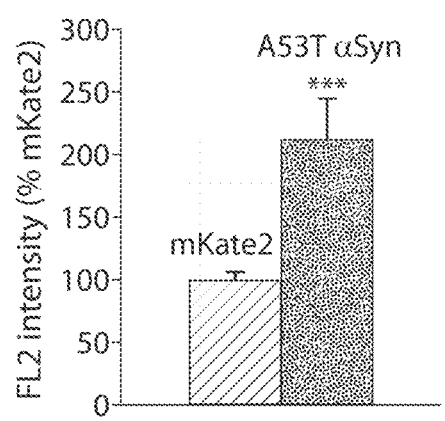
Figure 3C:
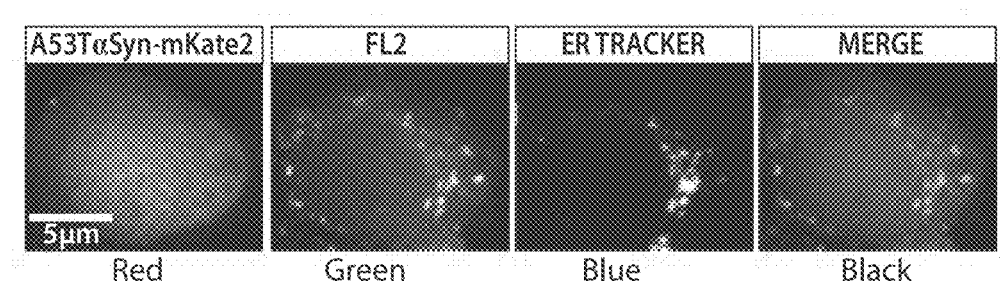
Figure 20:
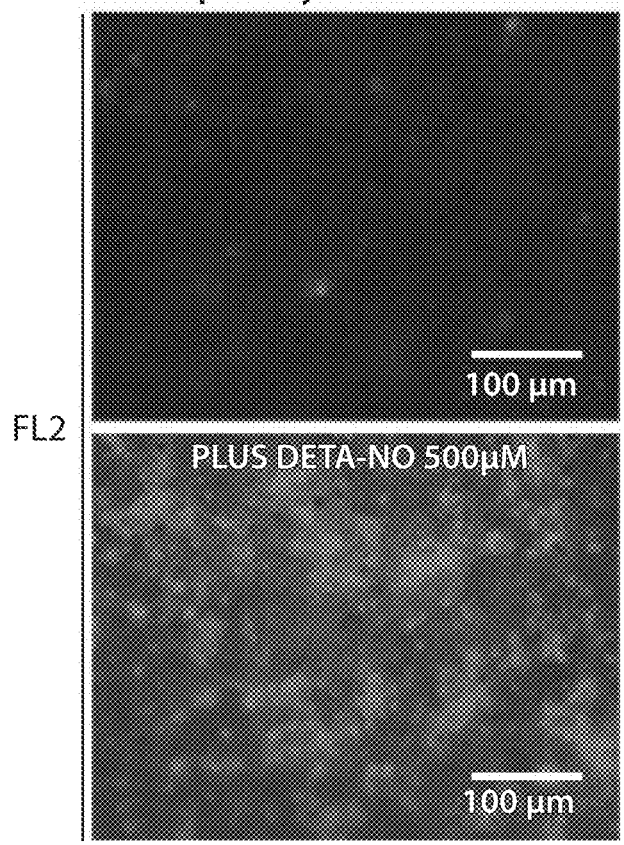
FIG. 20. Optimization of the NO sensor, FL2, using an NO donor, DETA-NONOate. FL2 dye was loaded after exposing primary cortical cultures (DIV 14-21) to 500 μM DETA-NONOate for 30 min. These cultures (lower panel) showed a robust response to DETA-NONOate detected by microscopy. Control cultures exposed to dye without an NO donor are shown in the upper panel. A single representative experiment is shown.
Figure 21:
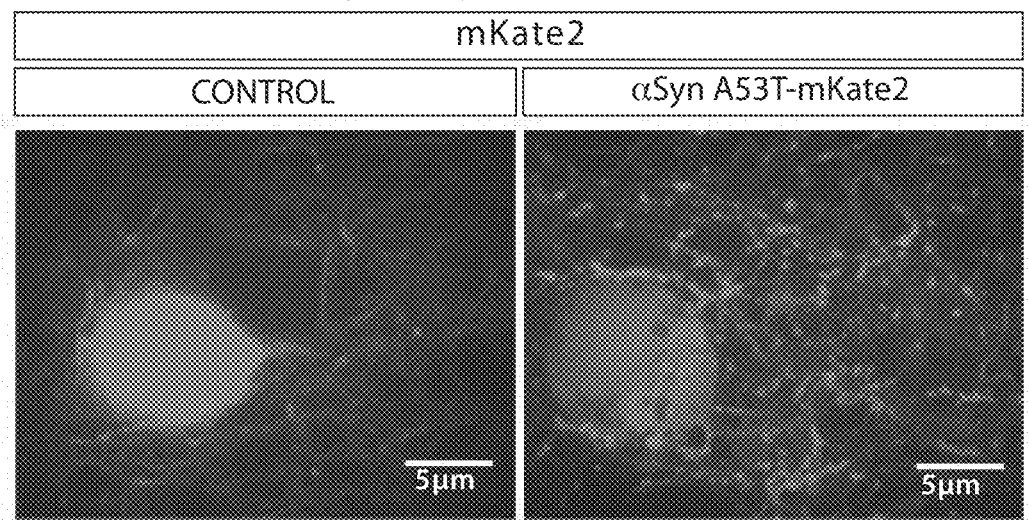
FIG. 21. Distribution of mKate2 in the AAV-transduced rat cortical neuron synucleinopathy model. In control cells, mKate2 is distributed diffusely through the cell body and processes (left). In contrast, mKate2-tagged αSyn is distributed both in the cell body and in punctate foci within processes (right).

We first verified that exposure to a synthetic NO donor, DETA-NONOate, elicited a robust FL2 response (FIG. 20). Next, we infected cultures with adeno-associated virus (AAV) encoding human αSyn[A53T] tagged with mKate2, or mKate2 alone, under the control of the pan-neuronal synapsin promoter. In these cells, exogenously expressed αSyn exhibited the expected punctate localization in neuronal processes, whereas mKate2 alone was diffusely localized (FIG. 21). αSyn overexpression increased the FL2 signal in a striking perinuclear distribution within the cell body (FIGS. 3, A and B). This signal partially co-localized with the endoplasmic reticulum (ER; FIG. 3C). While our yeast data suggested a mitochondrial source for NO, the strong innate affinity of FL2 for mitochondria[24] precluded us from making conclusions about co-localization with this organelle. Moreover, the high density of processes and mixed cell populations in these cultures hindered intensity measurements outside the well-defined neuronal cell body.

Figure 3D:
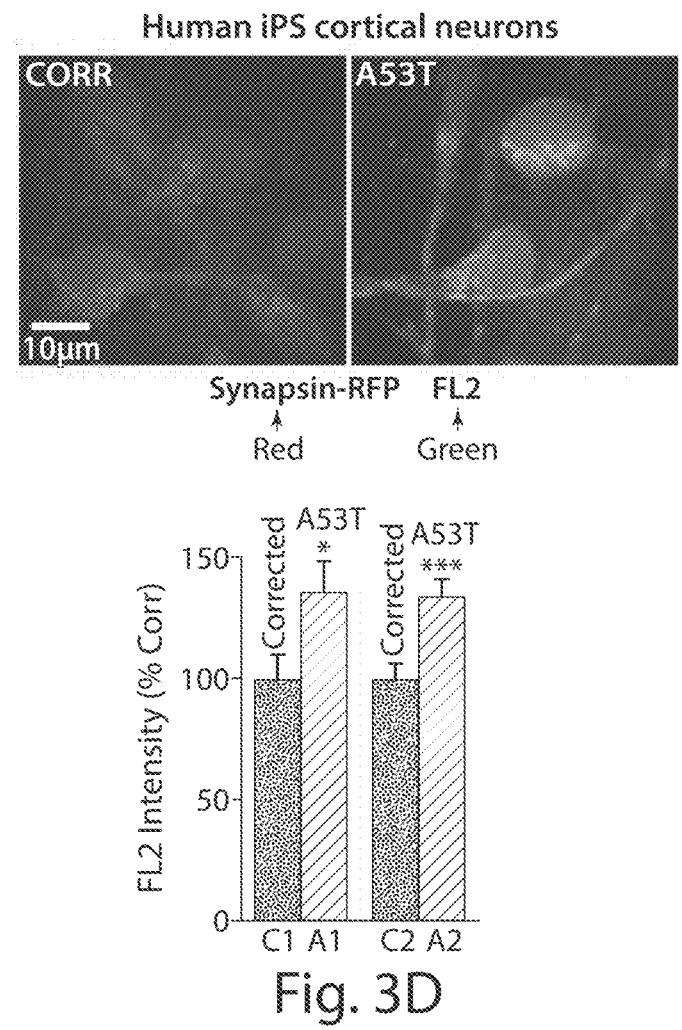
Figure 3E:
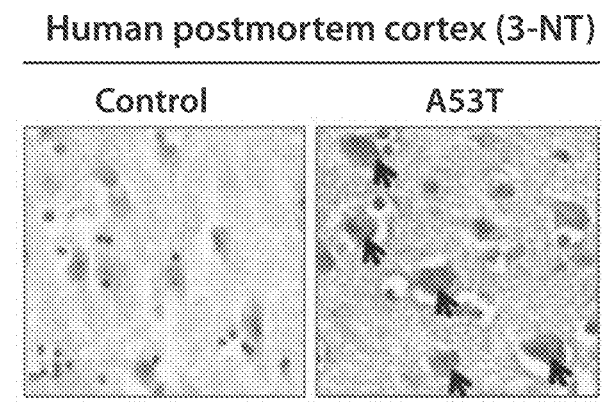

Having optimized conditions in rat neurons, we turned to our Parkinson patient-derived cortical neurons at 8 weeks of differentiation. Two isogenic pairs of A53T and mutation-corrected neurons were differentiated in parallel. The cells had previously been labeled with synapsin-RFP to facilitate the identification of neurons (see FIG. 19D). Intraneuronal FL2 signals increased in A53T neurons compared to corrected neurons, and this was most readily visualized in the cell body (FIG. 3D). Just as in rodent neurons, there was partial co-localization of this signal with an ER marker (not shown).

To determine whether nitrosative stress also occurred in cortical neurons within the brains of A53T patients, we immuno-labeled tissue from the frontal cortex of another subject in the same kindred[25] with an anti-nitrotyrosine antibody1[9]. There was a strong increase in diffuse cytoplasmic nitrotyrosine staining in these cortical neurons and in the neuropil (FIG. 3E), providing a pathologic correlate of our finding in patient iPS-derived cortical neurons.

Figure 4A:
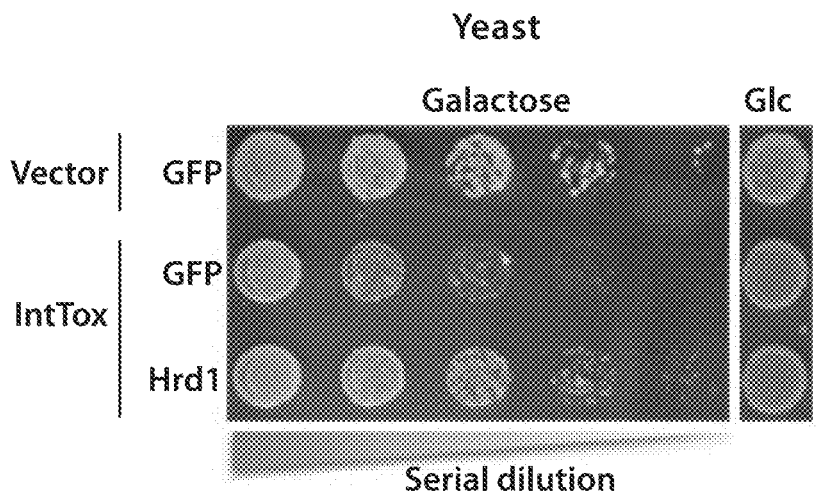
FIG. 4. ERAD substrate accumulation and ER stress from yeast to patient cortical neurons. (A) Over-expression of Hrd1, a modifier identified in a previous unbiased yeast screen, is confirmed to reduce αSyn toxicity in yeast. Yeast strains were spotted in 5-fold serial dilution to visualize the effect of Hrd1 on cell growth. Transgenes were induced by switching the carbon source from glucose (Glc) to galactose. Glc spotting shows the equivalent number of yeast spotted between the strains. Compared to GFP expression, Hrd1 expression ameliorated the slow growth caused by αSyn overexpression (IntTox strain). (B-D) iPS neurons from αSyn$^{A53T}$ (A1, A2), αSyn$^{A53T\text{-}corrected}$(C1, C2) and αSyn$^{triplication}$ (S3) patients were differentiated into cortical neurons and harvested at 4 weeks and 8-12 weeks. As a sex-matched control for the male S3 line, neurons were differentiated from a male human ES line (BGO1). The glycosylation pattern of three proteins trafficked through the ER and Golgi were monitored: GCase (glucocerebrosidase), Nicastrin and Nrspn (neuroserpin). ER or post ER forms of proteins were distinguished based on the sensitivity to Endoglycosidase H (Endo H), which cleaves high mannose moieties of ER proteins. For GCase and Nrspn, Endo H-resistant bands are considered to be post ER form and Endo H-sensitive bands are the ER form. Nicastrin normally presents two major bands, an upper "mature" band and a lower "immature" band. Both bands are sensitive to Endo H, because even the mature band represents a mixture of ER and post-ER forms of the protein. The lowest band in Endo H condition is a completely deglycosylated ER form of Nicastrin[51]. The post ER/ER ratio of Nicastrin was calculated by comparing mature vs deglycosylated ER form. (n=4~6, Con and BGO1 samples were pooled as control, and A53T and S3 lines were pooled as PD samples; data represented as mean±SEM, *; $p<0.05$, ; $p<0.01$; *; $p<0.001$, two tail t-test compared to control samples at each time point). (E) ER stress markers such as BIP and PDI but not CHOP, were increased in PD iPS neurons at 12 weeks. A1 and A1-1 represent independent differentiation experiments of the A1 subclone (n=2-4, mean±SEM, *; $p<0.05$, **; $p<0.01$, two tail t-test compared to corrected). (F) Synoviolin, a mammalian homolog of Hrd1 protects primary rat cortical cultures from αSyn toxicity. Cultures were transduced by lentivirus encoding Synoviolin with varying multiplicity of infection (MOI) and co-transduced with either lenti-αSyn$^{A53T}$ or lenti-LacZ at MOI 15. Cellular ATP content was measured at 2 weeks post-infection to determine cell viability. The same trend was repeated in an independent experiment. Data represented as mean±SEM, *; $p<0.05$, **; $p<0.01$, One way ANOVA with Bonferroni post-hoc test. (G) Synoviolin overexpression reduces accumulation of the ER form of nicastrin in αSyn$^{A53T}$ iPS cortical neurons. Neurons at 8-12 weeks of differentiation were transduced with lenti-Synoviolin at MOI 1, 2, and 5. After 10 days, cells were harvested for Western blot analysis. The baseline A53T level was made equivalent to % control established in FIG. 4C-D to more faithfully depict the biological significance of the change.

Example 3

αSyn-Induced ERAD Substrate Accumulation and ER Stress in Cortical Neurons from Two Parkinson Kindreds We next directed our attention to Hrd1, a gene previously identified as a suppressor of αSyn toxicity in our genome-wide yeast screen[26] (confirmed in FIG. 4A). Hrd1, known as Synoviolin (Syvn1) in mammals, is a highly conserved E3 ubiquitin ligase that plays a critical role in ER-associated degradation, a process through which misfolded proteins are removed from the ER. The recovery of Hrd1 in our screen strongly implicated ERAD dysfunction in our yeast synucleinopathy model. Indeed, we have previously shown in this model that ERAD substrates accumulate[10], and this is accompanied by a transcriptional ER stress response[26] and a defect in ER-to-Golgi trafficking of these substrates[10]. ER stress has also recently been described in a transgenic mouse synucleinopathy model[27].

Turning to our Parkinson patient cortical neurons, we first asked whether ERAD substrates accumulate. We examined three ERAD substrates of high relevance to neurodegeneration: Glucocerebrosidase (GCase), Neuroserpin and Nicastrin. Mutations in GCase, the Gaucher's disease protein, are among the most common risk factors for PD and independently confer risk for cognitive impairment in this disease[28,29]. Additionally, αSyn overexpression impedes the forward trafficking of GCase through the ER[30]. Nicastrin is a component of the Alzheimer disease-related presenilin complex and its knockout causes memory loss and cortical neurodegeneration in mice[31]. Neuroserpin is mutated in a rare form of dementia with cortical neuropathology[32]. We utilized an assay that distinguishes ER and post-ER forms of these proteins, based on the sensitivity of their N-glycosylations to cleavage by the enzyme endoglycosidase H (Endo H). ER forms are sensitive to Endo H, whereas post-ER forms are resistant[30]. The ratio of post-ER to ER forms provides a steady-state measure of changes in ERAD and/or forward vesicle trafficking from the ER.

Figure 22A:
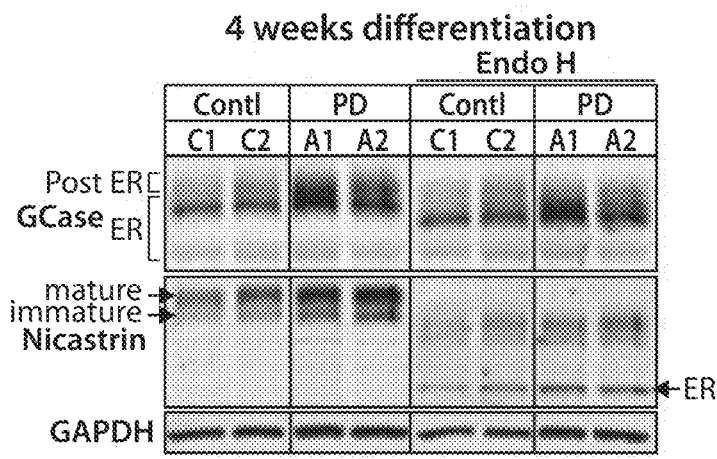
FIG. 22. Accumulation of ERAD substrates, defective forward trafficking through the ER and ER stress in Parkinson patient cortical neurons (these are additional Western blots that were quantitated in FIGS. 4, C and D). iPS neurons from αSyn$^{A53T}$ (A1, A2), αSyn$^{A53T-corrected}$ (C1, C2) and αSyn$^{triplication}$ (S3) patients were differentiated into cortical neurons and harvested at 4 weeks and 8-12 weeks. The glycosylation pattern of three proteins that traffic through the ER and golgi were monitored: GCase (glucocerebrosidase), Nicastrin and Nrspn (neuroserpin). ER or post ER forms of proteins were distinguished based on their sensitivity to Endoglycosidase H (Endo H), which cleaves high mannose moieties of ER proteins. For GCase and Nrspn, Endo H-resistant bands are considered to be post-ER form and Endo H-sensitive bands are the ER form. Nicastrin normally presents two major bands, an upper "mature" band and a lower "immature" band. Both bands are sensitive to Endo H, because even the mature band represents a mixture of ER and post-ER forms of the protein. The lowest band in Endo H condition is a completely deglycosylated ER form of nicastrin. The post-ER/ER ratio of nicastrin was calculated by comparing the mature vs deglycosylated ER form. Quantitation from these samples was combined with that of the samples shown in FIG. 4 to generate the graphs in FIGS. 4, B and C. Note that the neural cultures in (C) were differentiated using a distinct neutralization protocol independent of embryoid body formation, to confirm the phenotype was not protocol-dependent (see Materials and Methods for details).
Figure 22B:
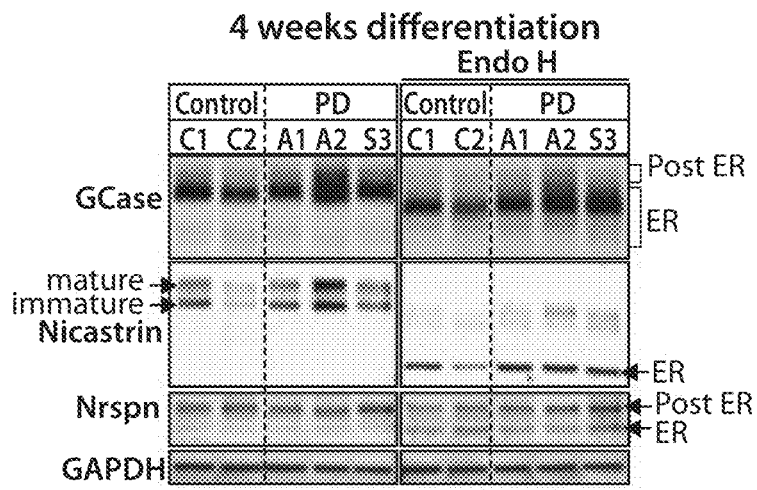
Figure 22C:
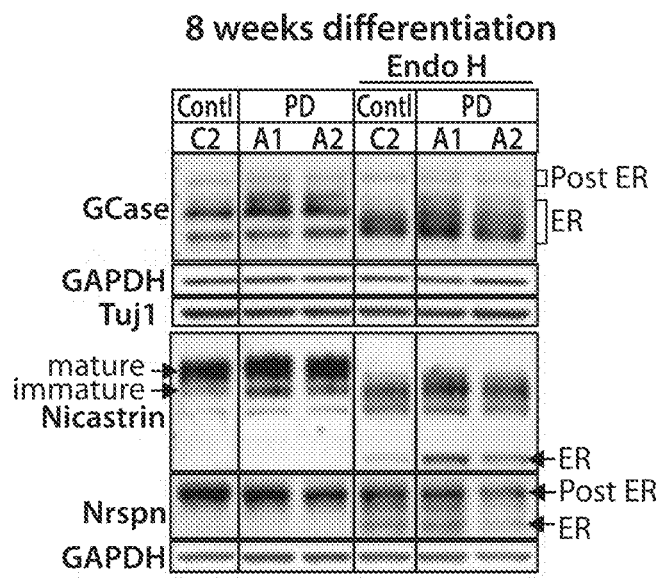

\We analyzed cortical neurons differentiated from our A53T and corrected iPS subclones at 4 weeks and 8-12 weeks of differentiation. ER forms of GCase and Nicastrin accumulated in A53T neurons by 4 weeks of differentiation, and this was more pronounced by 8-12 weeks (FIGS. 4, B and C; FIG. 22). For these two ERAD substrates, there was also a progressive decrease in the ratio of the post-ER/ER forms over time, specific to the A53T cells (FIGS. 4, B and D; FIG. 22). These defects appeared to be substrate-specific because Neuroserpin did not accumulate in the ER, and the ratio of its post-ER/ER forms did not change at the time-points we examined (FIG. 4, B to D and FIG. 22). Notably, levels of neuron-specific markers, including Tuj1, were similar between the lines (FIG. 22C and not shown). These findings were highly consistent in multiple rounds of differentiation, and reproducible between two distinct differentiation protocols (FIG. 22C). Thus, the A53T mutation causes ERAD dysfunction and/or defective trafficking of these proteins out of the ER.

Figure 4B:
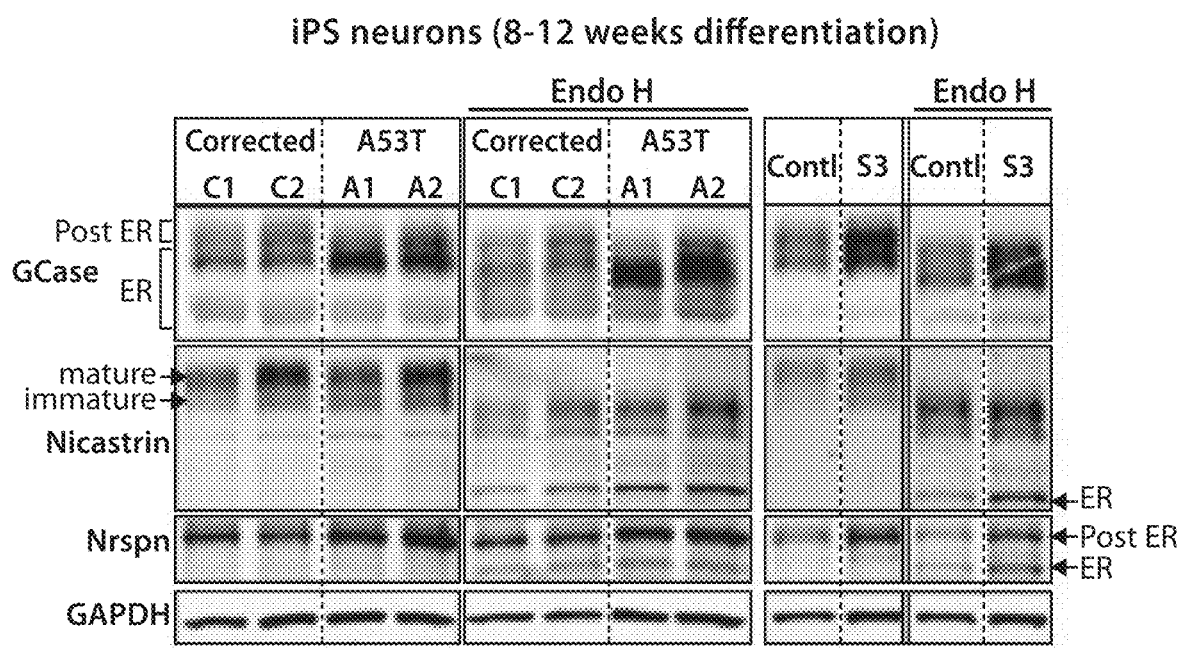
Figure 4C:
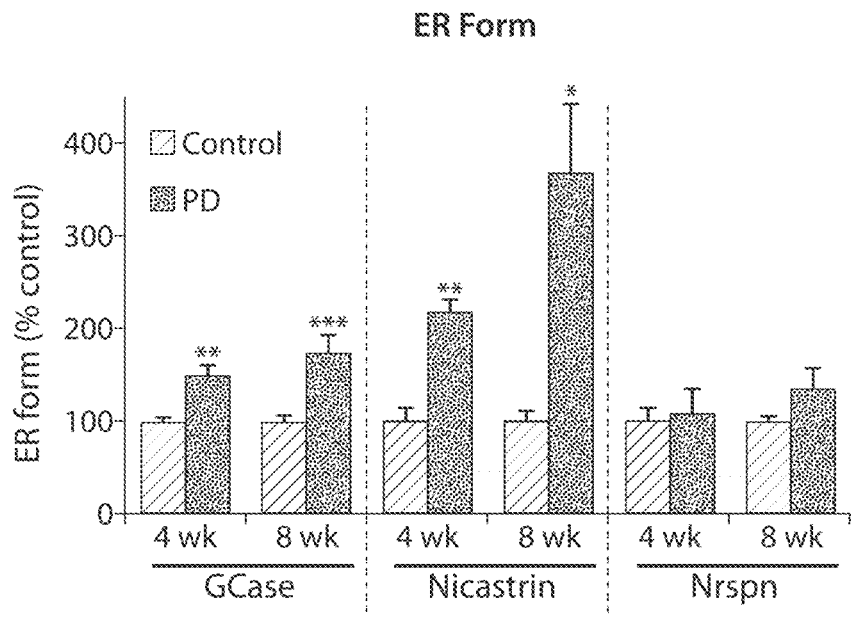
Figure 4D:
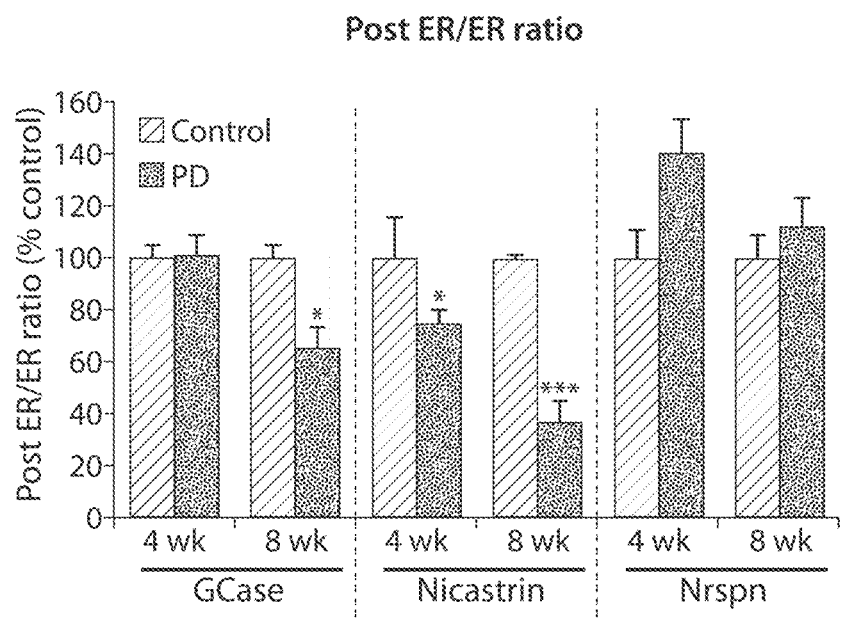
Figure 4E:
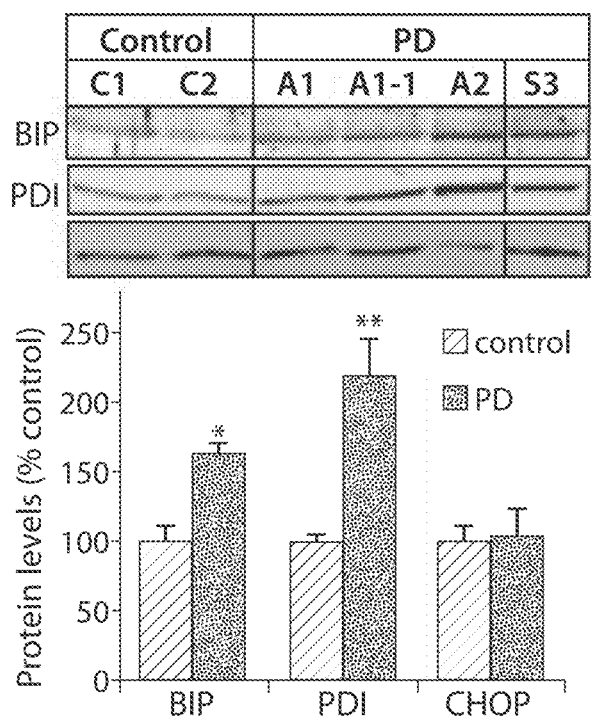

ER stress is an expected consequence of such defects. Indeed, levels of PDI and BIP, two hallmarks of ER stress, increased at 12 weeks of differentiation. However, levels of CHOP, a component of the apoptotic pathway induced by ER stress, did not change. This suggests the observed phenotypes represent an early stage of pathology (FIG. 4E).

To extend our findings beyond patients with the A53T cLSyn mutation we created iPS cells from a male patient of the "Iowa kindred", who harbored a triplication of the wild-type αSyn gene and manifested early cognitive dysfunction in addition to parkinsonism[33]. An EB-based protocol (FIG. 18) was used to neuralize these iPS cells (WIBR-IPS-αSyn$^{TRPL}$; FIG. 17) and generate cortical neurons (not shown). Aged cortical neurons generated from a previously described male human embryonic stem cell line BG01[34] served as a control (FIG. 4B). Indeed, ERAD substrates accumulated (FIG. 4B and FIG. 22A) and ER stress increased (FIG. 4E) in neurons from this patient, closely phenocopying the A53T cells.

Example 5

Figure 4F:
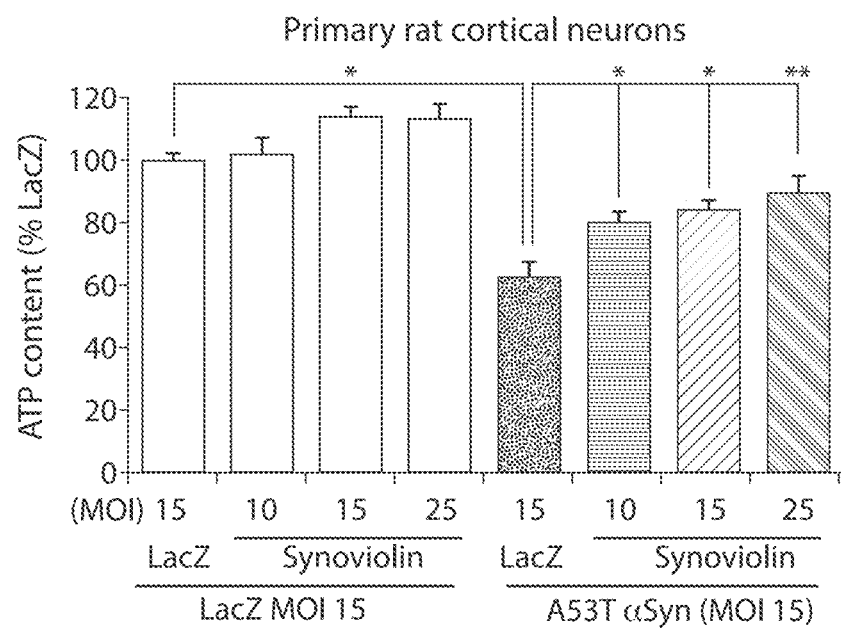
Figure 4G:
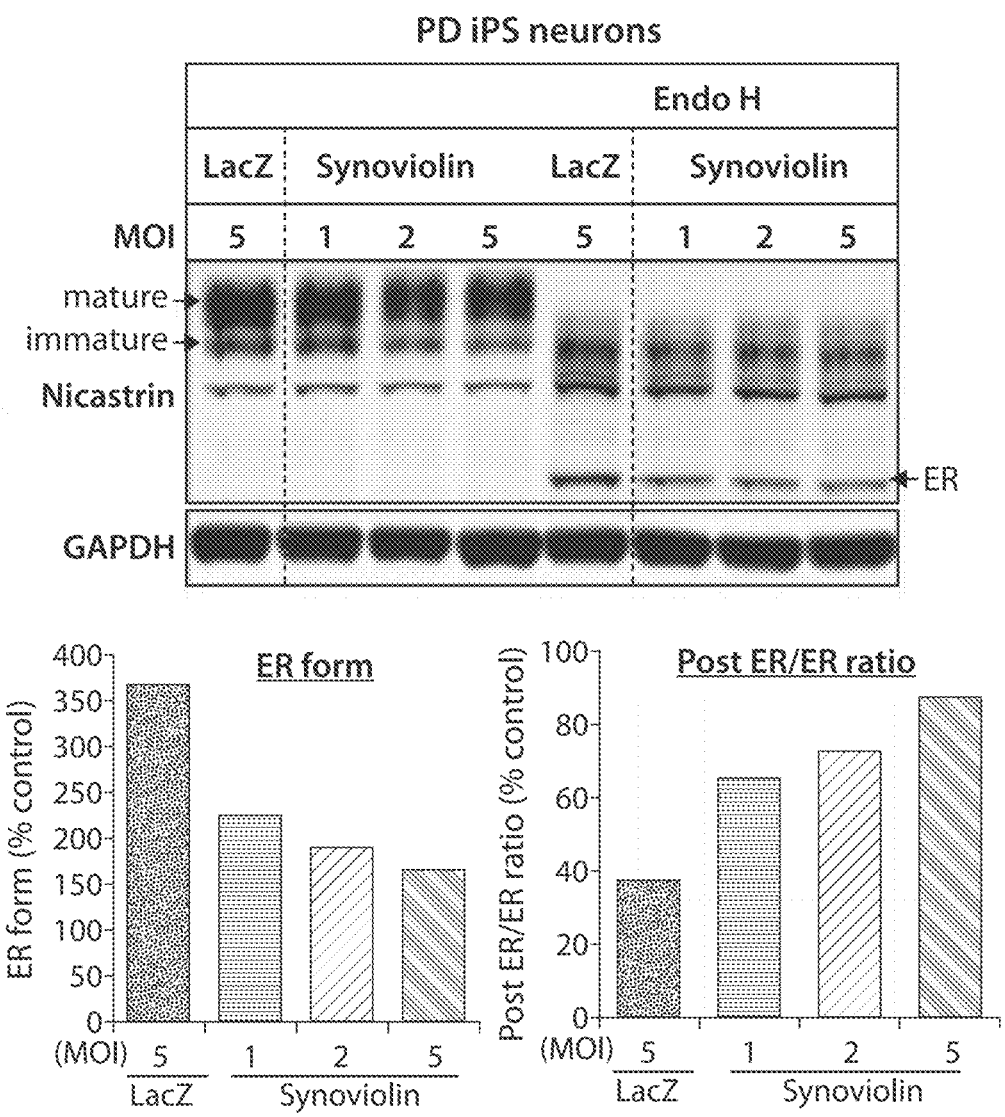

Hrd1/Syvn1 Reverses ERAD Substrate Accumulation in Rodent and Human iPS Cell Synucleinopathy Models As noted above, the yeast modifier of αSyn toxicity, Hrd1, has an excellent mammalian homolog, Syvn1. Having implicated ERAD in cLSyn pathogenesis, we asked whether Syvn1 could reverse pathologic phenotypes in neurons. Indeed, co-expression of Syvn1 rescued αSyn toxicity in primary rat cortical neurons in a dosage-dependent manner (FIG. 4F). Moreover, lentiviral expression of Syvn1 reduced the ER accumulation of Nicastrin in A53T patient cortical neurons without affecting levels of the mature form (FIG. 4G). The effect on GCase was less pronounced (not shown).

Example 6

αSyn-Induced Nitrosative and ER Stress are Causally Connected

A previous bioinformatics approach linking genetic and transcriptional data in yeast had suggested that the transcription factor Fzf1 (see FIG. 2A) induces the ERAD chaperone, Protein disulfide isomerase (PDI) in response to αSyn toxicity[26]. This, together with our finding that NO accumulated near the ER in αSyn-overexpressing neurons (FIG. 3C), prompted us to experimentally investigate a potential connection between nitrosative and ER stress. To do this, we returned to the genetically tractable yeast synucleinopathy model.

Figure 5A:
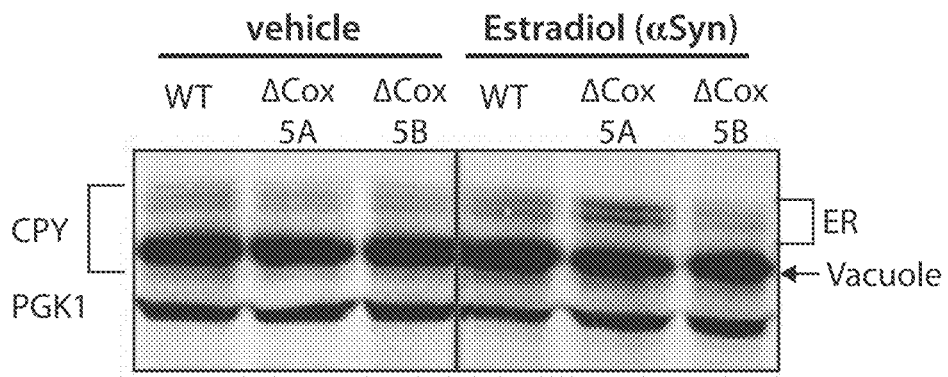
FIG. 5. A connection between αSyn-induced nitrosative stress and ER stress in yeast leads to the identification of abnormal VCP nitrosylation in Parkinson patient neurons. (A-C) Increasing nitric oxide in αSyn-expressing yeast exacerbates the accumulation of the well-characterized ERAD substrate CPY in the ER, and the unfolded protein response (UPR). Note that the baseline levels of the ER form in the WT yeast strain was low (A and B), making it difficult to assess a reduction by the NO-decreasing ΔCoxB. The UPR was measured in these yeast strains using a reporter for Ire1 endonuclease activity, combined with flow cytometry. The NO-increasing ΔCox5A increased the UPR whereas the NO-decreasing ΔCoxB had the opposite effect (C) Data represented as mean±SEM, n=3~4 *; $p<0.05$, **; $p<0.01$, One way ANOVA with Bonferroni post-hoc test (D-E). Biotin switch assay demonstrates increased S-nitrosylation of VCP, but not GAPDH (n=3, mean±SEM, *; $p<0.05$). Neurons from two A53T (A1 and A2) and mutation-corrected controls (C1 and C2) were used in this analysis.
Figure 5B:
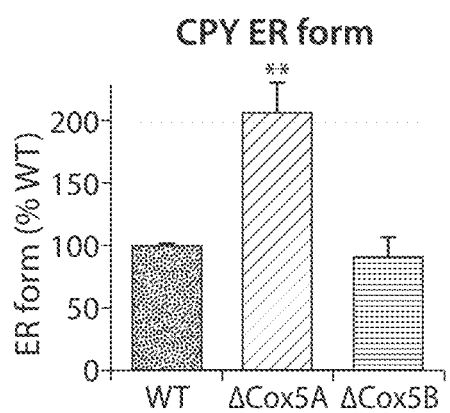
Figure 5C:
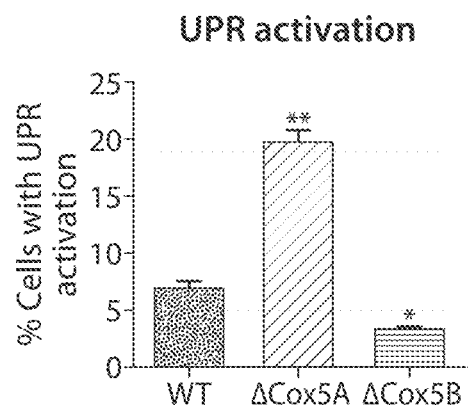

As noted above, manipulating COX5 isoforms can modulate NO levels in yeast in the context of αSyn toxicity (FIGS. 2, D and E). We therefore examined the effect of manipulating COX5 isoforms on the accumulation of immature forms of carboxypeptidase Y (CPY), a well-characterized ERAD substrate that traffics between the ER and vacuole[10]. When NO levels were increased by deleting COX5A, CPY accumulated significantly in the ER (FIGS. 5, A and B). Furthermore, this genetic manipulation robustly increased the unfolded protein response (FIG. 5C), consistent with ERAD dysfunction and ER stress. Conversely, reducing NO levels by deletion of COX5B reduced this response (FIG. 5C). Nitrosative and ER stress are thus intimately related mechanisms of αSyn.

Example 7

Valosin-Containing Protein (VCP) is Nitrosylated in Patient Neurons

S-nitrosylation modulates the function of many proteins by modifying critical cysteines. Nitrosative and ER stress could plausibly be connected through the S-nitrosylation of critical ERAD-related enzymes. Indeed, S-nitrosylation abrogates the function of two such enzymes, PDI[20] and VCP[35,36], and a direct connection between nitrosative and ER stress in PD was previously suggested by the discovery of PDI S-nitrosylation in PD patient brains[20]. VCP, also known as Cdc48 or p97, was of exceptional interest. VCP is an AAA-type ATPase that provides the mechanical force for the extraction of proteins from the ER in ERAD. Importantly, mutations in the gene encoding VCP cause a distinct dementia with prominent cortical pathology[37]. Moreover, VCP co-localizes within αSyn aggregates in synucleinopathies[38]. Accordingly, we asked if the S-nitrosylation of ERAD-related enzymes occurred in Parkinson patient neurons.

Figure 5D:
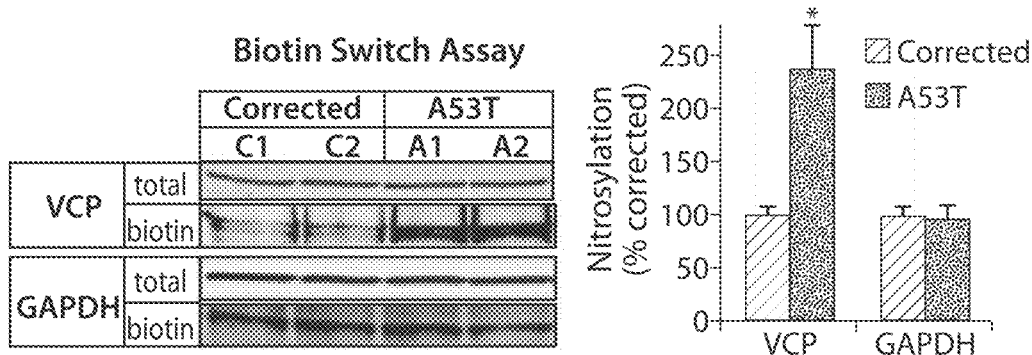

Protein S-nitrosylations are highly unstable, but can be detected in mammalian cells with the so-called "biotin switch" assay. Free thiol groups in total cellular proteins are blocked with an alkylating agent immediately after cell lysis. Nitrosylated thiols escape this blocking step and, in subsequent steps, are converted to biotinylated cysteines. The biotinylated proteins are then collected by binding to streptavidin beads, eluted and identified by Western blotting[39]. When we employed this assay in A53T and mutation-corrected cortical neurons, the PDI yield was insufficient to determine its S-nitrosylation status (not shown). However, the method did reveal a striking increase in S-nitrosylation of VCP in A53T neurons compared to corrected controls (FIG. 5D). In addition, the assay revealed an increase in clathrin heavy chain and Hsc70 S-nitrosylation in A53T patient-derived cortical neurons compared to mutation-corrected control neurons (data not shown). Interestingly, there was no change in the S-nitrosylation status of GAPDH, a protein that shows increased nitrosylation in multiple paradigms of neuronal apoptosis[40].

Example 8

Figure 7:
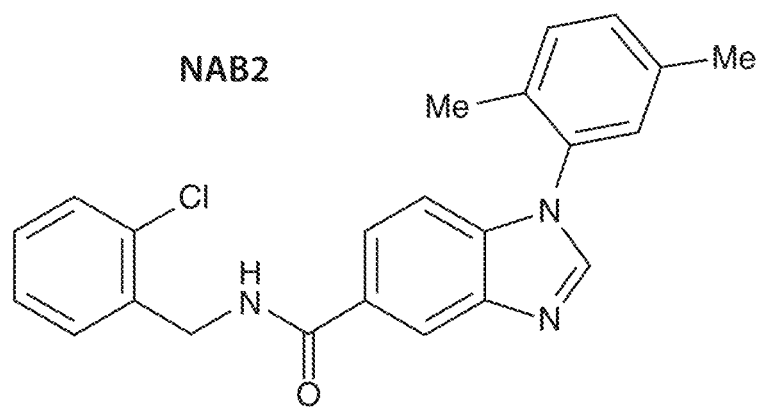
FIG. 7. Structure of NAB2.
Figure 8:
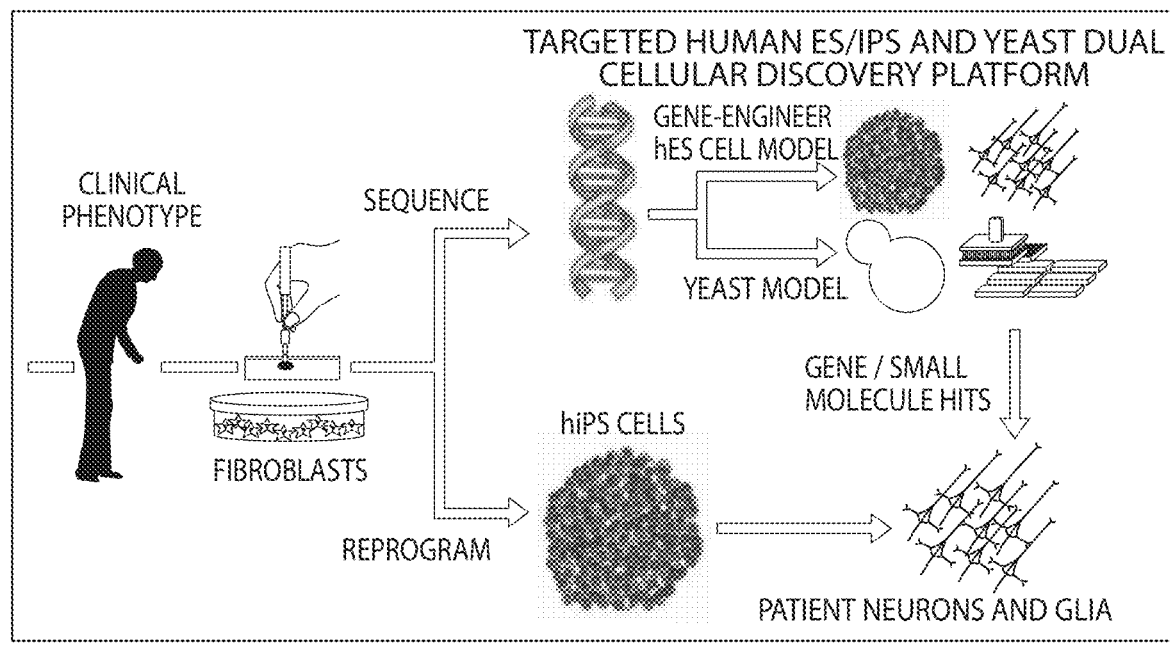
FIG. 8: A yeast and human stem cell discovery platform for neurodegenerative diseases such as parkinsonism-associated disorders and ataxias. A patient is clinically characterized. Skin biopsy enables growth of fibroblasts, from which genomic sequence information and iPS cells can be obtained. Clinical phenotype and genotypic information are used to guide genetic engineering of yeast and human embryonic stem cells, iPS cells, or induced neural stem cells to create models for phenotype identification and high-throughput screening or to guide selection of appropriate model(s) from among existing models. Candidate genetic and small molecule modifiers identified using the models are tested in patient-derived neurons and/or glial cells.

A Small Molecule Modifier Identified in a Yeast Screen Reverses Pathologic Effects in Patient Neurons A powerful aspect of disease modeling in yeast is the ability to conduct unbiased and large-scale small-molecule screens. Having identified highly conserved biological phenotypes in yeast and human neurons, we asked whether a small molecule identified in yeast screens could reverse them. Specifically, we tested an N-arylbenzimidazole (NAB2) recovered in a screen of more than 180,000 small molecules (FIG. 7).

As described in patent application U.S. Ser. No. 61/794, 870, this compound rescues αSyn toxicity in yeast, worm and rodent neuronal synucleinopathy models. Chemical genetic analysis in yeast identified the ubiquitin ligase Rsp5/Nedd4 as an integral component of NAB2's target space (U.S. Ser. No. 61/794,870 and ref 41). Rsp5 and its human homolog NEDD4 have been implicated in protein trafficking and ERAD in both yeast and neurons[42,43]. Indeed, NAB2 reduced the accumulation of CPY in the yeast ER in a dose-dependent manner (FIG. 6A). Strikingly, NAB2 also reduced the specific αSyn-induced increase in protein nitration in yeast (FIG. 6A). Furthermore, in a dose-dependent manner NAB2 increased the post-ER and decreased the immature forms of Nicastrin and GCase in patient neurons from both the Contursi and Iowa kindreds (FIG. 6B and FIG. 23). Finally, as measured by the sensor FL2, NAB2 strongly decreased NO levels in A53T patient neurons without affecting its levels in mutation-corrected controls (FIG. 6C). In addition, overexpression of Nedd4 phenocopied NAB2 in A53T patient neurons (FIG. 6D), reverting nitrosative stress and ERAD substrate accumulation/ER stress.

Figure 24:
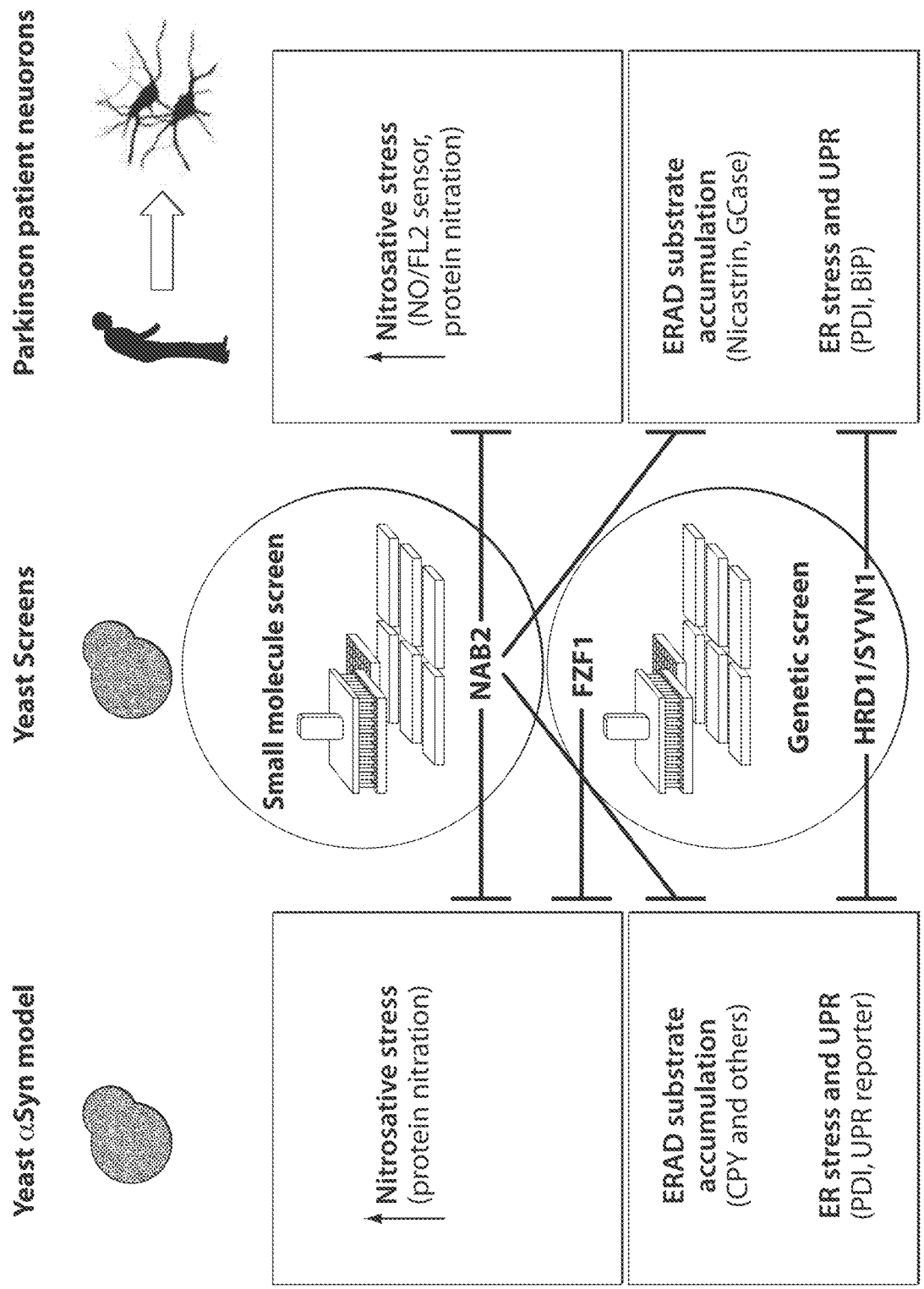
FIG. 24. Yeast and patient iPS neuron dual discovery platform is empowered by the conservation of biology from yeast to human. Previously published chemical (small molecule) and genetic screens in the αSyn yeast model shed light on cellular pathways perturbed by αSyn in yeast, and guided the effort to identify early disease-relevant phenotypes in Parkinson patient iPS neurons. In this figure, we focus on modifiers and phenotypes related to the current study. Key genetic suppressors of αSyn toxicity, when overexpressed, included the Fzf1 transcription factor, a master regulator of the nitrosative stress response in yeast, and Hrd1/Synoviolin1 (Syvn1), a critical ERAD-related ubiquitin ligase. The corresponding phenotypes identified included an increase in nitrosative stress; ERAD substrate accumulation; ER stress and the unfolded protein response (UPR). Assays used to identify these phenotypes in yeast and patient neurons are summarized parenthetically. The genetic modifier Hrd1/Syvn1 and small molecule NAB2 inhibit αSyn-related toxicities in both yeast cells and patient cortical neurons.

In this study we leverage the tractability of yeast cells with the relevance of patient iPS cell-derived neurons to establish a broadly applicable and practical discovery pipeline for neurodegenerative diseases (FIG. 24). Our approach is empowered by the extraordinary conservation of αSyn toxicity across a billion years of evolution. We coordinated three cellular platforms, each with distinct strengths. Yeast cultures provide genetically and epigenetically uniform populations of cells for highly synchronous induction of αSyn. This enabled the identification of early phenotypes and large-scale unbiased genetic and small molecule screening. Primary rat cortical cultures, virally transduced to overexpress αSyn, provide highly consistent and temporally synchronized cultures for neuronal assay development. Human iPS-derived neurons provide a direct link to patients, and, particularly when compared to suitable control cells (e.g., mutation-corrected control cells), allow for exploration of phenotypes in the context of complex human pathobiology. Validation in human neurons, in turn, motivates detailed mechanistic studies in simpler model systems.

Directed principally by genetic modifiers recovered in yeast screens, we identified phenotypes in patient-derived cortical neurons in the absence of stressors that could, therefore, be solely attributable to the disease-causing mutation. Our mechanistic studies in yeast linked nitrosative stress to ER stress, and both of these pathologic processes to αSyn. Identifying this connection paved the way for the identification of VCP nitrosylation in patient neurons. Yeast cells don't have NO synthase. Without wishing to be bound by any theory, because the cellular pathology we have explored for αSyn is so extraordinarily conserved, it is possible that αSyn-induced nitrosative stress in neurons may also depend on the mitochondrial respiratory chain as it does in yeast. Our genetic and biochemical data in yeast suggest that the particular type of nitrosative stress we have uncovered is highly specific to αSyn. Moreover, our data in Parkinson patient neurons also point to this specificity because GAPDH, a protein S-nitrosylated in multiple other paradigms of neurotoxicity[40] was not abnormally S-nitrosylated in these cells.

In addition, the cross-species platform enabled the discovery of genes and small molecules that reverted pathologic phenotypes from yeast to human cells[41]. While we focused on αSyn in this study, other neurodegenerative diseases have also been modeled in yeast[9]. Distinct proteotoxicities are induced by the β-amyloid and TDP-43, each with remarkable parallels between yeast and human genetic modifiers[47,48]. Our approach is amenable to application to these and other neurodegenerative diseases characterized by proteotoxicity.

Example 9

Generation of Doxycycline-Inducible Transgenic αSyn-Overexpressing hESc Lines

Figure 11A:
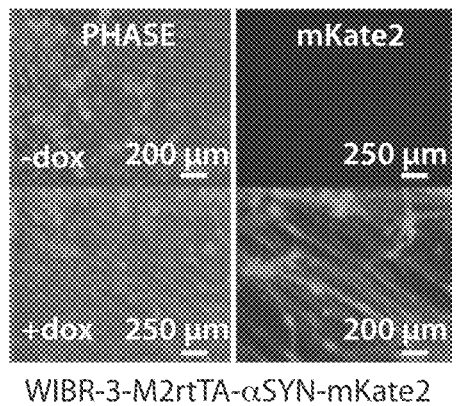
FIG. 11: (A) WIBR-3 hESC line double-targeted with M2rtTA and αSyn-mKate2 transgene, differentiated to DA neuron-enriched cultures. There is robust induction of αSyn-mKate2 with doxycycline (2 ug/mL 7 days). (B) DA neuron-enriched cultures (differentiation d30) from PD patient (A53T), midbrain DA identity indicated by tyrosine hydroxylase (TH) and FOXA2 with Hoechst nuclear stain. >95% of cells were FOXA2+; ~33% cells were FOXA2+/TH+(>1000 cells quant).

TALENs directed to the AAVS1 "safe harbor" locus of the PPP1R12C gene (Hockemeyer, D., et al. (2011) Nature Biotechnology 29 (8): 731-4) were designed to target two hESc lines listed on the NIH Embryonic Stem Cell Registry (WIBR-1, WIBR-3). In a sequential targeting, one allele was targeted with the M2rtTA tetracycline transactivator (CAAGS promoter), and the other allele with αSyn-WT (untagged or mKate2-tagged) transgene under the TetR responsive promoter. Multiple clones were obtained for both constructs. Targeted hESC and neurons (FIG. 11A) robustly turn on αSyn expression with doxycycline exposure, allowing comparisons to be made on identical neuronal cultures, ±doxycycline.

Example 10

Figure 11B:
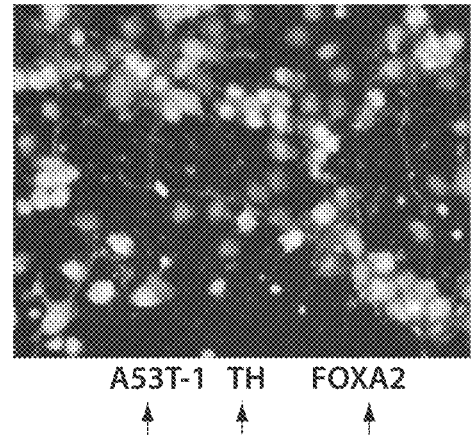
Figure 12:
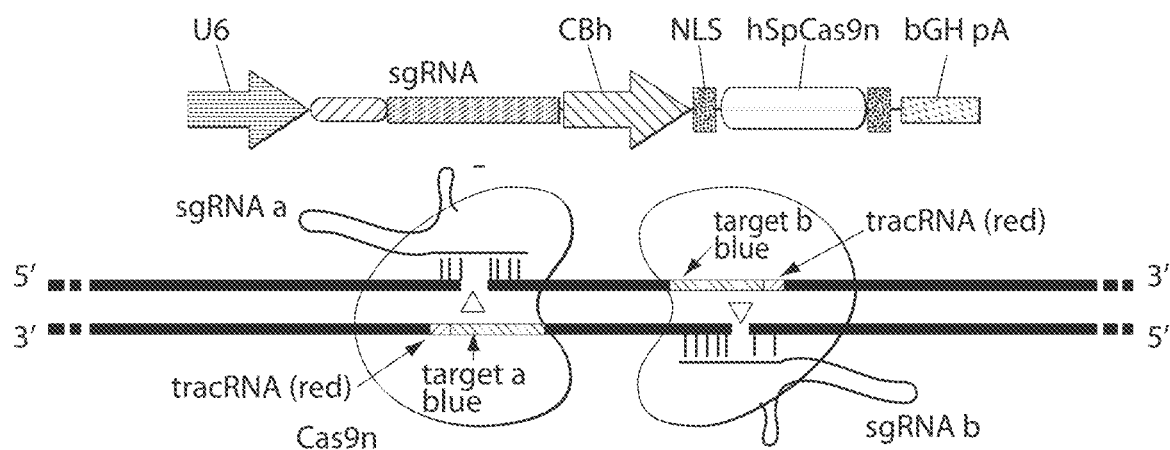
FIG. 12. Schematic diagram of an exemplary CRISPR-based strategy useful for genome-editing. The depicted targeting construct consists of single guide RNA (sgRNA) that includes the "spacer" sequence homologous to the target (blue) and a tracRNA (red), and also encodes a mutated nuclease (Cas9n) such that that only a single strand of DNA can be cut. Two such constructs are expressed (lower panel) in the hESC to create a "double-nick" (two single-stranded breaks in close proximity). DNA (for example, containing a desired point mutation) with homologous flanking sequences can then be introduced through homologous recombination. See Ran, F. A. et al. Double Nicking by RNA-Guided CRISPR Cas9 for Enhanced Genome Editing Specificity. Cell 154, 1380-1389 (2013).

Generation of Dopaminergic (DA) Neurons from iPS Cells Containing a PD-Associated Mutation Midbrain DA neurons are typically affected in PD and other disorders associated with parkinsonism. iPS cells were generated from a PD patient with an A53T mutation as described above. Large numbers of midbrain-type dopaminergic neurons double positive for tyrosine hydroxylase (TH) and FOXA2, were generated using a floor plate protocol described in Kriks, S., et al., (2011), Nature, Vol. 480, pp. 547-553 by aging the iPS cells for 12 weeks (FIG. 11B). These DA neurons provide a relevant model for PD and may be used, for example, to identify phenotypes (e.g., corresponding to yeast phenotypes) or assess candidate therapeutic agents.

Example 11

Deleting Yeast Homolog of a Second Parkinsonism Gene in a Yeast Synucleinopathy Model Exacerbates Toxicity Mutations in human VPS35 have been identified (by others) in patients with certain forms of PD. The effect of VPS35 deletion in a yeast synucleinopathy model (yeast expressing wild type α-Syn) was assessed. As shown in FIG. 13(A), deletion of VPS35 enhances αSyn toxicity but has no effect in the control strain. Re-introducing wild type yeast (y) or human (h) VPS35 into a VPS35-deficient αSyn strain restores viability, as shown in the right panel of FIG. 13. Introducing a human gene with a disease-relevant point mutation D620N does not (FIG. 13, right panel), underscoring the homology and relevance of the system with regard to this interaction. Glucose (Glu) to galactose (Gal) induces αSyn and VPS35 transgene expression in these strains.

REFERENCES

1. Goedert, M., Spillantini, M. G., Del Tredici, K. & Braak, H. 100 years of Lewy pathology. *Nat Rev Neurol* 9, 13-24 (2013).
2. Soldner, F. et al. Generation of isogenic pluripotent stem cells differing exclusively at two early onset Parkinson point mutations. *Cell* 146, 318-331 (2011).

3. Urnov, F. D., Rebar, E. J., Holmes, M. C., Zhang, H. S. & Gregory, P. D. Genome editing with engineered zinc finger nucleases. *Nat Rev Genet* 11, 636-646 (2010).
4. Nguyen, H. N. et al. LRRK2 mutant iPSC-derived DA neurons demonstrate increased susceptibility to oxidative stress. *Cell stem cell* 8, 267-280 (2011).
5. Byers, B. et al. SNCA Triplication Parkinson's Patient's iPSC-derived DA Neurons Accumulate α-Synuclein and Are Susceptible to Oxidative Stress. *PLoS ONE* 6, e26159 (2011).
6. Cooper, O. et al. Pharmacological rescue of mitochondrial deficits in iPSC-derived neural cells from patients with familial Parkinson's disease. *Sci Transl Med* 4, 141ra90 (2012).
7. Gitler, A. D. et al. Alpha-synuclein is part of a diverse and highly conserved interaction network that includes PARK9 and manganese toxicity. *Nat Genet* 41, 308-315 (2009).
8. Outeiro, T. F. & Lindquist, S. Yeast cells provide insight into alpha-synuclein biology and pathobiology. *Science* 302, 1772-1775 (2003).
9. Khurana, V. & Lindquist, S. Modelling neurodegeneration in *Saccharomyces cerevisiae: why cook with baker's yeast? Nat Rev Neurosci* 11, 436-449 (2010).
10. Cooper, A. A. et al. Alpha-synuclein blocks ER-Golgi traffic and Rab1 rescues neuron loss in Parkinson's models. *Science* 313, 324-328 (2006).
11. Spira, P. J., Sharpe, D. M., Halliday, G., Cavanagh, J. & Nicholson, G. A. Clinical and pathological features of a Parkinsonian syndrome in a family with an Ala53Thr alpha-synuclein mutation. *Ann Neurol* 49, 313-319 (2001).
12. Markopoulou, K. et al. Clinical, neuropathological and genotypic variability in SNCA A53T familial Parkinson's disease. Variability in familial Parkinson's disease. *Acta Neuropathol* 116, 25-35 (2008).
13. Chambers, S. M. et al. Highly efficient neural conversion of human ES and iPS cells by dual inhibition of SMAD signaling. *Nat Biotechnol* 27, 275-280 (2009).
14. Kim, J.-E. et al. Investigating synapse formation and function using human pluripotent stem cell-derived neurons. *Proc Natl Acad Sci USA* 108, 3005-3010 (2011).
15. Saito, T. et al. Neocortical Layer Formation of Human Developing Brains and Lissencephalies: Consideration of Layer-Specific Marker Expression. *Cerebral Cortex* 21, 588-596 (2011).
16. Sarver, A. & DeRisi, J. Fzf1p regulates an inducible response to nitrosative stress in *Saccharomyces cerevisiae. Mol Biol Cell* 16, 4781-4791 (2005).
17. Stamler, J. S., Singel, D. J. & Loscalzo, J. Biochemistry of nitric oxide and its redox-activated forms. *Science* 258, 1898-1902 (1992).
18. Giasson, B. I. et al. Oxidative damage linked to neurodegeneration by selective alpha-synuclein nitration in synucleinopathy lesions. *Science* 290, 985-989 (2000).
19. Gómez-Tortosa, E. et al. Patterns of protein nitration in dementia with Lewy bodies and striatonigral degeneration. *Acta Neuropathol* 103, 495-500 (2002).
20. Uehara, T. et al. S-Nitrosylated protein-disulphide isomerase links protein misfolding to neurodegeneration. *Nature* 441, 513-517 (2006).
21. Treusch, S. et al. Functional links between Aβ toxicity, endocytic trafficking, and Alzheimer's disease risk factors in yeast. *Science* 334, 1241-1245 (2011).
22. Castello, P. R. et al. Oxygen-regulated isoforms of cytochrome c oxidase have differential effects on its nitric oxide production and on hypoxic signaling. *Proc Natl Acad Sci USA* 105, 8203-8208 (2008).
23. Pluth, M. D., Tomat, E. & Lippard, S. J. Biochemistry of Mobile Zinc and Nitric Oxide Revealed by Fluorescent Sensors. *Annu. Rev. Biochem.* 80, 333-355 (2011).
24. McQuade, L. E. et al. Visualization of nitric oxide production in the mouse main olfactory bulb by a cell-trappable copper(II) fluorescent probe. *Proc Natl Acad Sci USA* 107, 8525-8530 (2010).
25. Kotzbauer, P. T. et al. Fibrillization of alpha-synuclein and tau in familial Parkinson's disease caused by the A53T alpha-synuclein mutation. *Exp Neurol* 187, 279-288 (2004).
26. Yeger-Lotem, E. et al. Bridging high-throughput genetic and transcriptional data reveals cellular responses to alpha-synuclein toxicity. *Nat Genet* 41, 316-323 (2009).
27. Colla, E. et al. Endoplasmic reticulum stress is important for the manifestations of α-synucleinopathy in vivo. *J Neurosci* 32, 3306-3320 (2012).
28. Alcalay, R. N. et al. Cognitive performance of GBA mutation carriers with early-onset PD: the CORE-PD study. *Neurology* 78, 1434-1440 (2012).
29. Bendikov-Bar, I. & Horowitz, M. Gaucher disease paradigm: from ERAD to comorbidity. *Hum Mutat* 33, 1398-1407 (2012).
30. Mazzulli, J. R. et al. Gaucher disease glucocerebrosidase and α-synuclein form a bidirectional pathogenic loop in synucleinopathies. *Cell* 146, 37-52 (2011).
31. Tabuchi, K., Chen, G., Siidhof, T. C. & Shen, J. Conditional forebrain inactivation of nicastrin causes progressive memory impairment and age-related neurodegeneration. *J Neurosci* 29, 7290-7301 (2009).
32. Ying, Z., Wang, H., Fan, H. & Wang, G. The endoplasmic reticulum (ER)-associated degradation system regulates aggregation and degradation of mutant neuroserpin. *Journal of Biological Chemistry* 286, 20835-20844 (2011).
33. Singleton, A. B. et al. alpha-Synuclein locus triplication causes Parkinson's disease. *Science* 302, 841 (2003).
34. Mitalipova, M. et al. Human embryonic stem cell lines derived from discarded embryos. *STEM CELLS* 21, 521-526 (2003).
35. Astier, J. et al. Nitric oxide inhibits the ATPase activity of the chaperone-like AAA+ ATPase CDC48, a target for S-nitrosylation in cryptogein signalling in tobacco cells. *Biochem J* 447, 249-260 (2012).
36. Noguchi, M. et al. ATPase activity of p97/valosin-containing protein is regulated by oxidative modification of the evolutionarily conserved cysteine 522 residue in Walker A motif. *J Biol Chem* 280, 41332-41341 (2005).
37. Guinto, J. B., Ritson, G. P., Taylor, J. P. & Forman, M. S. Valosin-containing protein and the pathogenesis of frontotemporal dementia associated with inclusion body myopathy. *Acta Neuropathol* 114, 55-61 (2007).
38. Mizuno, Y., Hori, S., Kakizuka, A. & Okamoto, K. Vacuole-creating protein in neurodegenerative diseases in humans. *Neuroscience Letters* 343, 77-80 (2003).
39. Jaffrey, S. R. & Snyder, S. H. The biotin switch method for the detection of S-nitrosylated proteins. Sci STKE 2001, pl1 (2001).
40. Hara, M. R., Cascio, M. B. & Sawa, A. GAPDH as a sensor of NO stress. Biochim Biophys Acta 1762, 502-509 (2006).
41. Tardiff, D. F. et al. Phenotypic screening and chemical genetics reveals a 'druggable' Rsp5/Nedd4 network that ameliorates alpha-synuclein toxicity. (Submitted)

42. Haynes, C. M., Caldwell, S. & Cooper, A. A. An HRD/DER-independent ER quality control mechanism involves Rsp5p-dependent ubiquitination and ER-Golgi transport. *J Cell Biol* 158, 91-101 (2002).
43. Donovan, P. & Poronnik, P. Nedd4 and Nedd4-2: Ubiquitin ligases at work in the neuron. *Int J Biochem Cell Biol* 1-5 (2012).doi:10.1016/j.bioce1.2012.12.006
44. Macleod, D. A. et al. RAB7L1 Interacts with LRRK2 to Modify Intraneuronal Protein Sorting and Parkinson's Disease Risk. *Neuron* 77, 425-439 (2013).
45. Su, L. J. et al. Compounds from an unbiased chemical screen reverse both ER-to-Golgi trafficking defects and mitochondrial dysfunction in Parkinson's disease models. *Disease Models and Mechanisms* 3, 194-208 (2010).
46. Soper, J. H., Kehm, V., Burd, C. G., Bankaitis, V. A. & Lee, V. M.-Y. Aggregation of α-synuclein in *S. cerevisiae* is associated with defects in endosomal trafficking and phospholipid biosynthesis. *J Mol Neurosci* 43, 391-405 (2011).
47. Elden, A. C. et al. Ataxin-2 intermediate-length polyglutamine expansions are associated with increased risk for ALS. *Nature* 466, 1069-1075 (2010).
48. Treusch, S., Cyr, D. M. & Lindquist, S. Amyloid deposits: protection against toxic protein species? *Cell Cycle* 8, 1668-1674 (2009).
49. Egawa, N. et al. Drug screening for ALS using patient-specific induced pluripotent stem cells. *Sci Transl Med* 4, 145ra104 (2012).
50. Israel, M. A. et al. Probing sporadic and familial Alzheimer's disease using induced pluripotent stem cells. *Nature* 482, 216-220 (2012).
51. Yang, D. S. Mature Glycosylation and Trafficking of Nicastrin Modulate Its Binding to Presenilins. *Journal of Biological Chemistry* 277, 28135-28142 (2002).
52. Soldner, F. et al. Parkinson's disease patient-derived induced pluripotent stem cells free of viral reprogramming factors. *Cell* 136, 964-977 (2009).
53. Kim, J.-E. et al. Investigating synapse formation and function using human pluripotent stem cell-derived neurons. 1-6 (2011).doi:10.1073/pnas.1007753108
54. Shi, Y., Kirwan, P. & Livesey, F. J. Directed differentiation of human pluripotent stem cells to cerebral cortex neurons and neural networks. *Nat Protoc* 7, 1836-1846 (2012).
55. Lim, M. H. Preparation of a copper-based fluorescent probe for nitric oxide and its use in mammalian cultured cells. *Nat Protoc* 2, 408-415 (2007).
56. Pincus, D. et al. BiP Binding to the ER-Stress Sensor Ire1 Tunes the Homeostatic Behavior of the Unfolded Protein Response. *PLoS Biol* 8, e1000415 (2010).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method of identifying a candidate therapeutic agent for treatment of a neurodegenerative disease comprising:
   (a) identifying an agent by screening for an agent in yeast cells that express a toxicity-inducing level of a neurodegeneration associated protein, wherein the agent is identified when it reduces the toxicity induced by the neurodegeneration associated protein in the yeast cells;
   (b) contacting a human neuron or glial cell that has a genotype associated with the neurodegenerative disease with the agent identified in step (a);
   (c) measuring the level of a phenotype associated with the neurodegenerative disease in the neuron or glial cell, wherein the phenotype is also observable in the yeast cells that express the toxicity-inducing level of the neurodegeneration associated protein;
   (d) identifying the agent as a candidate therapeutic agent for treatment of the neurodegenerative disease if the level of the phenotype is reduced as compared with the level of the phenotype in the neuron or glial cell in the absence of the agent; and
   (e) identifying a target of the candidate therapeutic agent in yeast cells by performing a genetic screen, wherein the genetic screen comprises contacting the candidate therapeutic agent with (1) a library of over-expression yeast strains covering most genes in the yeast genome; (2) a library of yeast containing at least 100,000 random transposon-insertions; (3) a library of yeast harboring spontaneous genomic point mutations arising from at least $10^5$ cells; or (4) a library of yeast containing deletions of non-essential genes in the yeast genome.

2. The method of claim 1, wherein the neurodegeneration associated protein comprises an alpha-synuclein protein, TDP-43 protein, FUS protein, A-beta protein, or polyglutamine-expanded protein.

3. The method of claim 1, wherein the neurodegenerative disease is a synucleinopathy, TDP-43 proteinopathy, FUS-opathy, Alzheimer's disease, or a polyglutamine expansion disease.

4. The method of claim 1, wherein:
   (i) the neuron or glial cell is not engineered to have an extra copy of a gene encoding neurodegeneration associated protein and has not been derived or cultured in the presence of an agent that enhances the phenotype;
   (ii) the phenotype is detectable in the yeast cells expressing the toxicity-inducing level of the neurodegeneration associated protein and in the absence of the agent;
   (iii) the phenotype is detectable in a neuron or glial cell derived from an iPS cell derived from a human subject who has the neurodegenerative disease, wherein the neuron or glial cell is not engineered to have an extra copy of a gene encoding the neurodegeneration associated protein and has not been derived or cultured in the presence of an agent that enhances the phenotype;
   (iv) the neurodegeneration associated protein comprises an alpha-synuclein protein, and the phenotype comprises nitrosative stress, mitochondrial dysfunction, defective endoplasmic reticulum-associated degradation (ERAD), or impaired ER-to-Golgi trafficking; or
   (v) the neuron or glial cell is derived from a human subject who has the neurodegenerative disease.

5. The method of claim 1, wherein the neuron or glial cell has a disease-associated mutation in the gene encoding the neurodegeneration associated protein, and wherein the phenotype is not detectable in an isogenic mutation-corrected neuron.

6. The method of claim 1, wherein contacting the neuron or glial cell with the agent comprises contacting a central nervous system (CNS) cell culture comprising the neuron with the agent.

7. The method of claim 1, wherein the neuron is a cortical neuron or dopaminergic neuron.

8. The method of claim 1, wherein step (c) comprises measuring the level of at least two phenotypes associated with the neurodegenerative disease in the neuron or glial cell; and step (d) comprises determining that the agent inhibits at least two of the phenotypes.

9. The method of claim 1, further comprising:
   (f) generating an analog of a candidate therapeutic agent identified in step (d); and
   (g) testing the ability of the analog to reduce toxicity induced by the neurodegeneration associated protein in a yeast cell or testing the ability of the analog to inhibit the phenotype in a neuron or glial cell that has a genotype associated with the neurodegenerative disease, wherein the analog is identified as a candidate therapeutic agent for treating the disease if the analog reduces toxicity induced by the neurodegeneration associated protein in the yeast cell or reduces the phenotype in the neuron or glial cell.

10. The method of claim 1, wherein the agent that is identified in step (a) is from a small molecule library.

11. The method of claim 1, further comprising administering a candidate therapeutic agent identified in step (d) or an analog thereof to a mammalian subject that has the neurodegenerative disease or is at increased risk of developing the neurodegenerative disease.

12. The method of claim 1, wherein the neuron or glial cell was derived from a human subject in need of treatment for the neurodegenerative disease.

13. The method of claim 12, further comprising administering a candidate therapeutic agent identified in step (d) to the subject.

14. The method of claim 1, wherein:
   (i) the neuron or glial cell is derived from a subject who has a mutation in or at least one extra copy of a gene that encodes the neurodegeneration associated protein; or (ii) the neuron or glial cell is genetically engineered to have a mutation in or at least one extra copy of a gene that encodes the neurodegeneration associated protein.

15. The method of claim 1, wherein the glial cell is an oligodendrocyte.

16. The method of claim 1, wherein step (e) comprises identifying in the genetic screen one or more genetic alterations that allow growth of the yeast cells at growth-suppressing concentrations of the agent.

17. The method of claim 16, further comprising (f) validating the candidate therapeutic agent identified in step (d) by conducting a screen of the candidate therapeutic agent in yeast cells in which expression of the target is increased or reduced.

18. The method of claim 1, wherein step (e) further comprises analyzing a genetic network comprising yeast genes identified in the genetic screen, or analyzing a genetic network comprising human homologs of said yeast genes.

19. The method of claim 1, wherein step (e) comprises selecting yeast cells for genetic alterations that allow growth at high concentrations of the candidate therapeutic agent.

20. The method of claim 1, further comprising identifying yeast that exhibit increased ability to survive in the presence of toxic concentrations of the agent and determining the genes that are overexpressed or mutated in such yeast.

\* \* \* \* \*